United States Patent [19]
Suzuki et al.

[11] Patent Number: 5,977,132
[45] Date of Patent: *Nov. 2, 1999

[54] PROLACTIN PRODUCTION INHIBITORY AGENT

[75] Inventors: Nobuhiro Suzuki; Hirokazu Matsumoto; Shuichi Furuya, all of Ibaraki, Japan

[73] Assignee: Takeda Chemical Industries, Ltd., Osaka, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/762,125

[22] Filed: Dec. 9, 1996

[30] Foreign Application Priority Data

Dec. 8, 1995 [JP] Japan ................. 7-345046

[51] Int. Cl.$^6$ ................. A61K 31/47
[52] U.S. Cl. ................. 514/301
[58] Field of Search ................. 514/301

[56] References Cited

U.S. PATENT DOCUMENTS

| | | | |
|---|---|---|---|
| 3,755,372 | 8/1973 | Irmscher et al. | 260/345.2 |
| 5,744,479 | 4/1998 | Furuya et al. | . |
| 5,807,869 | 9/1998 | Furuya et al. | . |
| 5,817,819 | 10/1998 | Furuya et al. | . |

FOREIGN PATENT DOCUMENTS

| | | |
|---|---|---|
| 0 443 568 | 8/1991 | European Pat. Off. . |
| 0 520 423 | 12/1992 | European Pat. Off. . |
| 0 640 606 | 3/1995 | European Pat. Off. . |
| 2 006 505 | 8/1971 | Germany . |
| 293 824 | 9/1991 | Germany . |
| 1-213284 | 8/1989 | Japan . |
| 2-225485 | 9/1990 | Japan . |
| 89/02432 | 3/1989 | WIPO . |
| 94/20460 | 9/1994 | WIPO . |
| WO 9420459 | 9/1994 | WIPO . |
| 95/28405 | 10/1995 | WIPO . |

OTHER PUBLICATIONS

Sixteenth Edition—The Merck Manual of Diagnosis and Therapy, Berkow et al., 1992.
Stedman's Medical Dictionary, 26th Edition, pp. 57–58.
Endocrine Effects and Pharmacokinetic Characteristics of a Potent New Gonadotropin–Releasing Hormone Antagonist (Ganirelix) with Minimal Histamine–Releasing Properties: Studies in Postmenopausal Women; Jaron Rabinovici et al.,vol. 75. No. 5, pp. 1220–1225. Journal of Clinical Endocrinologoy and Metabolism, Acta Endocrinologica (Copenh) 1991, 124; 98–105.
Effects of a novel gonadotropin–releasing hormone antagonist (ORG 30850) on gonadotropin and prolactin secretion by rat pituitary cells in culture; Paul Franchimont et al.
Chemical Abstracts, "Thieno Compounds", vol. 106, (1987), p. 658.
R. Boehm et al., Pharmazie, vol. 41, (1986), H.9.
P. M. Gilis et al., "Synthesis and Antibacterial Evaluation of 4,7–dihydro–4–oxothieno[2,3–b]pyridine–5–carboxylic acids", Eur. J. Med. Chem. (1978), pp. 265–269.
N. Tamaki et al., Prolactine Producing Adenoma, Nihon Risho, vol. 51, No. 10, (1993), pp. 173–178.
Clinical Neuroscience, vol. 8, No. 4, (1990), pp. 74:428–77:431.{partial translation}.

*Primary Examiner*—Keith D. MacMillan
*Attorney, Agent, or Firm*—Foley & Lardner

[57] ABSTRACT

The prolactin production inhibition agent of the present invention containing a condensed cyclic compound, which is characterized by containing a condensed bicyclic structure of an optionally substituted homo or hetero 5- to 7-membered ring with an optionally substituted homo or hetero 5- to 7-membered ring, or a salt thereof, can be used, as a medicine, for the prophylaxis or therapy of diseases accompanied with an excess prolactin production or diseases having enhanced reactivity with prolactin, or is useful for inhibiting puerperal lactation, and also useful as a prophylactic or therapeutic agent of galactorrhea, hyperprolactinemic ovulation disturbance, amenorrhea-galactorrhea syndrome, prolactinoma, and besides, interbrain tumor, and acromegaly, pituitary gigantism.

11 Claims, No Drawings

PROLACTIN PRODUCTION INHIBITORY AGENT

This application claims priority to Japanese Patent Application Japan 345046-1995, filed Dec. 8,1995.

TECHNICAL FIELD

The present invention relates to a prolactin production inhibitory composition containing a condensed cyclic compound, especially containing at least a condensed bicyclic structure, or a salt thereof; a method for treating a mammal suffering from hyperprolactinemia; and a use of a condensed cyclic compound for producing a prolactin production inhibitory composition for treating a mammal suffering from hyperprolactinemia.

BACKGROUND ART

Prolactin, which is produced and secreted from anterior lobe of the pituitary gland, shows a variety of actions including the actions on mammary glands to play an important role for starting and maintenance of lactation, the actions on water-electrolyte metabolism, the actions on reproductive glands, the actions on the immune system and the actions on brain function. The prolactin-producing cells of the pituitary gland are recognized to have clearly characteristic properties. For example, peptide hormones so far known as various pituitary hormone secretion/production stimulating hormones secreted from hypothalamus are clearly observed to act preferentially and specifically on specified pituitary hormone secretion/production cells of the anterior lobes of the pituitary gland. Typically, while gonadotropic hormone releasing hormone, sometimes referred to as GnRH (gonadotropin releasing hormone): lutenizing hormone-releasing hormone (LH-RH), acts preferentially and specifically on the cells which secrete/produce, for example, follicle stimulating hormone (FSH) and lutenizing hormone (LH) in the anterior lobe of pituitary, no observational studies have been reported that the GnRH acts on the cells which produce/secrete prolactin, also known as an anterior pituitary hormone, to cause secretion of prolactin. Therefore, cells which produce/secrete gonadotropins and prolactin are considered to have, among anterior pituitary hormone secreting/producing cells, entirely different characteristic features. From the viewpoints as above, for controlling the prolactin production/secretion, the drug to be used therefor should at least act on pituitary prolactin-producing cells which can be clearly distinguished from other peptide hormone secretion/production cells of pituitary.

As diseases caused by excess production and secretion of prolactin, hyperprolactinemia has been known, which shows clinical symptoms such as suppression of reproductive function and galactorrhea (cf. Clinical Neuroscience, Vol.8, No.4, 1990, Chugai Igakusha; Nihon Rinsho, Vol.51, No.10, 1993, Nihon Rinshosha). As causes of this hyperprolactinemia, prolactin-secreting pituitary tumor (prolactinoma) is frequently observed, and, besides, functional hyperprolactinemia due to paracrisis of prolactin-inhibiting factor or drug-induced hyperprolactinemia have been known (cf. Clinical Neuroscience, Vol.8, 1990, Chugai Igakusha; Nihon Rinsho, Vol.51, No.10, 1993, Nihon Rinshosha). Furthermore, prolactin takes part also in puerperal lactation and galactorrhea.

Hyperprolactinemia is treated principally by surgical operation and drug treatment. As the drug for treatment, a dopamine agonistic one such as bromocriptine is used, leaving several problems still to be solved. First of all, bromocriptine therapy is not a complete cure, and, after suspension of the administration, the prolactin levels rise up again and the recurrence and progression of the disease are observed. And, undesirable side effects, including digestive symptoms such as nausea, vomiting and constipation, postural hypotension and headache, are observed. Further, among prolactin adenomas, there exist bromocriptine-resistant ones. For solving these problems, development of a novel agent of suppressing prolactin-production has been desired.

Condensed bicyclic compounds, for example, a thieno[2,3-b]pyridine derivative and a thieno[2,3-d]pyrimidine derivative, are known to have an excellent gonadotropic hormone-releasing hormone antagonistic activity (PCT International Publication No. WO95/28405). On the other hand, while the pituitary prolactin-producing cells have so far been considered to be clearly distinguished from other pituitary peptide hormone secreting/producing cells, especially FSH- or LH-secreting/producing cells, among peptide pituitary hormone secretion/production stimulating hormone actually secreted from hypothalamus, none of such hormone as acting on prolactin-producing cells to cause secretion of prolactin while showing simultaneously activity on gonadotropin secreting/producing cells has been known. Circumstances being such as above, development of a novel agent of suppressing prolactin-production from an independent viewpoint has been required as well.

Furthermore, for treating diseases/disturbances due to hyperprolactin, use of a prolactin inhibitory agent acting specifically on prolactin-producing cells has a possibility of curing completely hyperprolactinemia and of reducing undesirable side-effects. Therefore, a highly stable and orally administrable prolactin-inhibiting agent, which is capable of directly suppressing or inhibiting the prolactin-production of pituitary prolactin-producing/secreting cells, especially a non-peptide prolactin inhibitory agent, is ardently desired.

SUMMARY OF THE INVENTION

The present invention is to provide an excellent prolactin production inhibitory agent. The present inventors, while taking the above circumstances into consideration, have made diligent efforts for finding out a compound usable as the prolactin-inhibiting agent, resulting in finding that condensed bicyclic compounds, especially, a thieno[2,3-b] pyridine derivative and a thieno[2,3-d]pyrimidine derivative, have an excellent prolactin production inhibitory activity. Based on this finding, the present inventors have studied further to complete this invention.

DETAILED DESCRIPTION OF THE INVENTION

The present invention provides a pharmaceutical composition of a prolactin production inhibitory agent containing a condensed cyclic compound, especially containing at least a condensed bicyclic structure, or a salt thereof. The present invention also provides a method for treating a mammal suffering from hyperprolactinemia. The present invention further provides a use of a condensed cyclic compound for producing a prolactin inhibitory composition for treating a mammal suffering from hyperprolactinemia.

More specifically, the present invention provides:
(1) A method for treating a mammal suffering from hyperprolactinemia, which comprises administering an effective amount of a composition, which comprising a condensed cyclic compound containing at least a condensed bicyclic structure of an optionally substituted homo or hetero 5- to 7-membered ring with an optionally substituted homo or hetero 5- to 7-membered ring, or a salt thereof, and a carrier, excipient or diluent therefor to the mammal, (2) A method according to the item (1), wherein the condensed cyclic compound is represented by the formula:

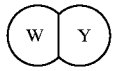

wherein ring W stands for an optionally substituted homo or hetero 5- to 7-membered cyclic group, and ring Y stands for an optionally substituted homo or hetero 5- to 7-membered cyclic group, (3) A method according to the item (2), wherein ring W is a group represented by the formula:

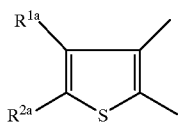

wherein each of $R^{1a}$ and $R^{2a}$ stand for a hydrogen atom or a group bonded through a carbon atom, a nitrogen atom, an oxygen atom or a sulfur atom, (4) A method according to the item (2), wherein ring W is a group represented by the formula:

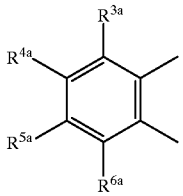

wherein each of $R^{3a}$, $R^{4a}$, $R^{5a}$ and $R^{6a}$ stand for a hydrogen atom or a group bonded through a carbon atom, a nitrogen atom, an oxygen atom or a sulfur atom, (5) A method according to the item (2), wherein ring Y is any one of the groups represented by the formula:

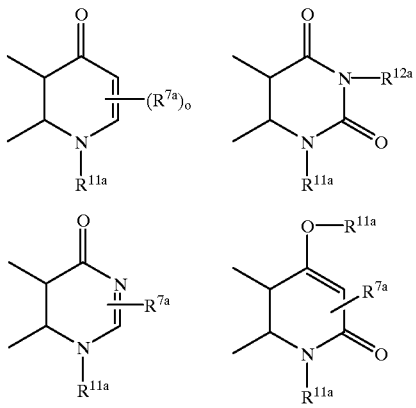

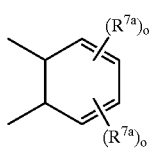 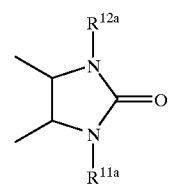

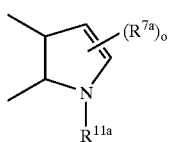 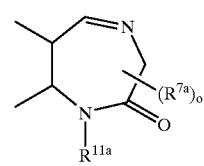

and

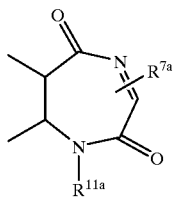

wherein the respective groups shown by $R^{7a}$ independently stand for a hydrogen atom or a group bonded through a carbon atom, a nitrogen atom, an oxygen atom or a sulfur atom; $R^{11a}$ and $R^{12a}$ independently stand for a hydrogen atom or an optionally substituted hydrocarbon residue; and o denotes an integer of 1 to 2, (6) A method according to the item (2), wherein ring Y is a group represented by the formula:

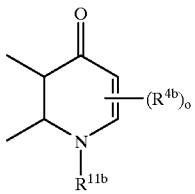

wherein groups shown by $R^{4b}$ independently stand for a hydrogen atom or a group bonded through a carbon atom, a nitrogen atom, an oxygen atom or a sulfur atom; $R^{11b}$ stands for an optionally substituted hydrocarbon residue; and o denotes an integer of 1 to 2; or a group represented by the formula:

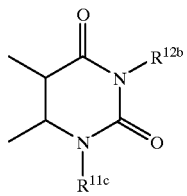

wherein each of $R^{11c}$ and $R^{12b}$ independently stand for a hydrogen atom or a group bonded through a carbon atom (7) A method according to the item (1), wherein the condensed cyclic compound is a compound of the formula:

(X)

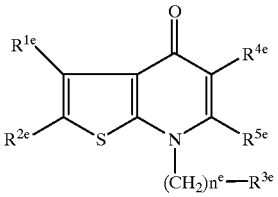

wherein each of $R^{1e}$ and $R^{2e}$ are a hydrogen atom or a group bonded through a carbon atom, a nitrogen atom, an oxygen atom or a sulfur atom,
$R^{3e}$ is an optionally substituted homo- or hetero-cyclic ring,
$R^{4e}$ is a hydrogen atom, a group bonded through a carbon atom, a group bonded through a nitrogen atom, an oxygen atom or a sulfur atom or an optionally substituted heterocyclic group,
$R^{5e}$ is a hydrogen atom or a group bonded through a carbon atom,
n is an integer of 0 to 3; or
a compound of the formula:

(XX)

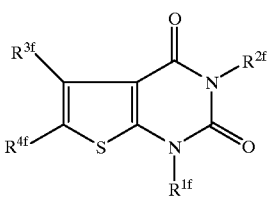

wherein $R^{1f}$ is (1) a hydrogen atom, (2) a group bonded through a carbon atom or (3) a group of the formula:

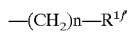

wherein $R^{1f'}$ is a group bonded through a carbon atom or an optionally substituted homo- or hetero-cyclic group and n is an integer of 0 to 3,
$R^{2f}$ is a hydrogen atom or a group bonded through a if carbon atom, each of $R^{3f}$ and $R^{4f}$ are a group bonded through a carbon atom; or a compound of the formula:

(XXX)

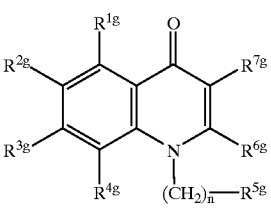

wherein each of $R^{1g}$, $R^{2g}$, $R^{3g}$, $R^{4g}$, $R^{6g}$ and $R^{7g}$ are a hydrogen atom or a group bonded through a carbon atom, a nitrogen atom, an oxygen atom or a sulfur atom,
$R^{5g}$ is a group bonded through a carbon atom or an optionally substituted homo- or hetero-cyclic ring, n is an integer of 0 to 3, with the proviso that all of the groups $R^{1g}$, $R^{2g}$, $R^{3g}$, $R^{4g}$, $R^{6g}$ and $R^{7g}$ are not hydrogen atoms simultaneously, (8) A method according to the item (1), wherein the condensed cyclic compound is a compound represented by the formula:

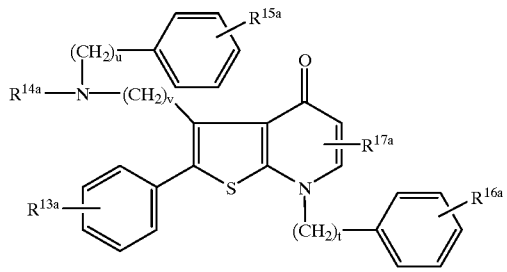

wherein $R^{13a}$ stands for 1 to 5 substituents and independently stands for a hydrogen atom, an alkyl group, an alkoxy group, a halogen atom or an alkanoylamino group; $R^{14a}$ stands for a hydrogen atom or an alkyl group; $R^{15a}$ stands for 1 to 5 substituents and independently stands for a hydrogen atom, a halogen atom, an alkyl group, an alkoxy group or an alkylthio group; $R^{16a}$ stands for 1 to 5 substituents and independently stands for a hydrogen atom, an alkyl group, a halogen atom or an alkoxy group; $R^{17a}$ stands for one or two substituents and independently stands for an optionally esterified or amidated carboxyl group, an alkylcarbonyl group, an arylcarbonyl group or an optionally substituted alkyl group; and each of v, t and u denote an integer of 1 to 4, (9) A method according to the item (1), wherein the condensed cyclic compound is a compound represented by the formula:

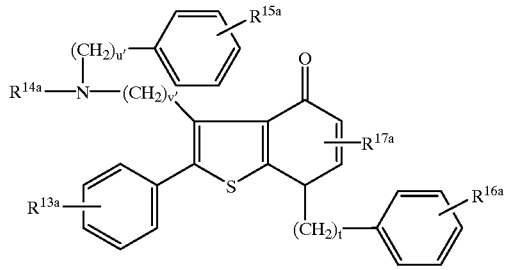

wherein $R^{13b}$ stands for 1 to 3 substituents and independently stands for hydrogen atom, a $C_{1-6}$ alkoxy group or an alkanoylamino group, $R^{14b}$ stands for a hydrogen atom or a $C_{1-6}$ alkyl group, $R^{15b}$ stands for 1 to 3 substituents and independently stands for a hydrogen atom or a halogen atom, $R^{16b}$ stands for 1 to 3 substituents and independently stands for a hydrogen atom, a halogen atom or a $C_{1-6}$ alkoxy group, $R^{17b}$ stands for 1 to 2 substituents and independently stands for a carboxyl group which may optionally be esterified or amidated or an alkylcarbonyl group, and each of v', t' and u' denote an integer of 1 to 3.

(10) A method according to the item (1), wherein the condensed cyclic compound is 4,7-dihydro-3-(N-methyl-N-benzylaminomethyl)-7-(2-methoxybenzyl)-2-(4-methoxyphenyl)-4-oxo-thieno[2,3-b]pyridine-5-carboxylic acid ethyl ester or its salt,

(11) A method according to claim 1, wherein the condensed cyclic compound is 2-(4-acetylaminophenyl)-4,7-dihydro-3-(N-methyl-N-benzylaminomethyl)-7-(2-methoxybenzyl)-4-oxo-thieno[2,3-b]pyridine-5-carboxylic acid ethyl ester or its salt,

(12) A method according to the item (1), wherein the condensed cyclic compound is 5-n-butyryl-4,7-dihydro-3-(N-methyl-N-benzylaminomethyl)-7-(2-fluorobenzyl)-2-(4-methoxyphenyl)-4-oxo-thieno[2,3-b]pyridine or its salt,

(13) A method according to the item (1), wherein the condensed cyclic compound is 5-benzoyl-4,7-dihydro-3-(N-methyl-N-benzylaminomethyl)-7-(2-fluorobenzyl)-2-(4-methoxyphenyl)-4-oxo-thieno[2,3-b]pyridine or its salt,

(14) A method according to the item (1), wherein the condensed cyclic compound is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine or its salt,

(15) A method according to the item (1), wherein the condensed cyclic compound is 7-(2,6-difluorobenzyl)-4,7-dihydro-3-(N-methyl-N-benzylaminomethyl)-5-isobutyryl-2-(4-propionylaminophenyl)-4-oxo-thieno[2,3-b]pyridine or its salt,

(16) A method according to the item (1), wherein the condensed cyclic compound is 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine or its salt,

(17) A method according to the item (1), wherein the composition comprises a condensed cyclic compound or a salt thereof and a medicine selected from the group consisting of a steroidal or non-steroidal anti-androgenic agent or anti-estrogenic agent, a somatostatin-acceptor agonist and an antitumor agent,

(18) A method according to the item (1), wherein the composition is administered to a mammal suffering from prophylactic•therapeutic agent for galactorrhea, hyperprolactinemic ovulation disturbance, amenorrhea-galactorrhea syndrome, prolactinoma or interbrain tumor,

(19) A method according to the item (1), wherein the composition is administered as an agent of suppressing puerperal galactorrhea, and

(20) A pharmaceutical composition for a treatment of a mammal suffering from hyperprolactinemia, which comprises a condensed cyclic compound containing at least a condensed bicyclic structure of an optionally substituted homo or hetero 5- to 7-membered ring with an optionally substituted homo or hetero 5- to 7-membered ring, or a salt thereof, and a carrier, excipient or diluent therefor.

In the above condensed cyclic compound, W ring denotes an optionally substituted homo or hetero 5- to 7-membered ring. As the homo or hetero 5- to 7-membered ring of W ring, it is exemplified by 5- to 7-membered homo or heterocyclic ring which may have one or more, preferably one to two, of a nitrogen atom, a sulfur atom or an oxygen atom. The preferable examples include homo or hetero 5- to 6-membered ring.

As the preferable examples of the 5- to 7-membered homo or heterocyclic ring of the W ring, mention is made of the following rings:

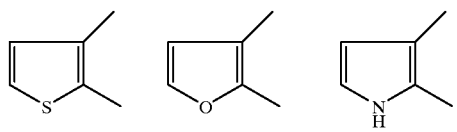

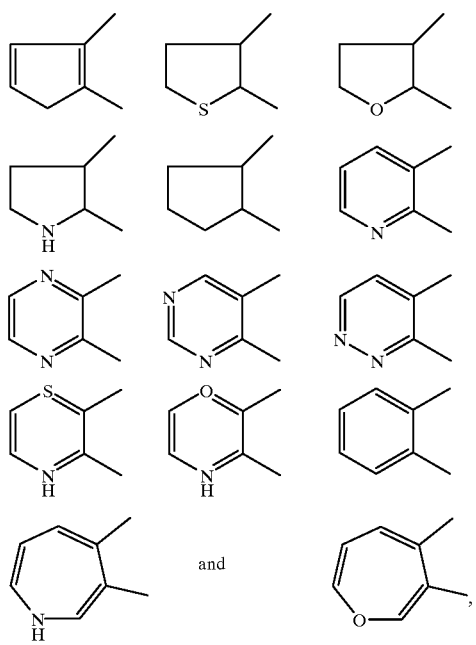

Among these, more preferable examples include:

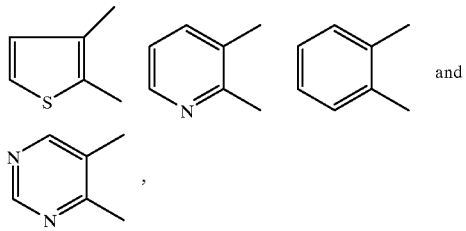

Among these, further more preferable examples include:

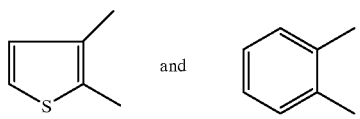

As the W ring, most preferable examples include a group of the formula:

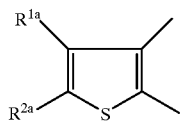

wherein each of $R^{1a}$ and $R^{2a}$ stand for a hydrogen atom or a group bonded through a carton atom, a nitrogen atom, an oxygen atom or a sulfur atom, or a group of the formula:

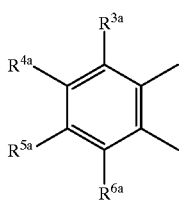

wherein each $R^{3a}$, $R^{4a}$, $R^{5a}$ and $R^{6a}$ stand for a hydrogen atom or a group bonded through a carbon atom, a nitrogen atom, an oxygen atom or a sulfur atom.

In the above condensed cyclic compound, Y ring denotes an optionally substituted homo or hetero 5- to 7-membered ring. As the homo or hetero 5- to 7-membered ring of Y ring, it is exemplified by 5- to 7-membered homo or heterocyclic ring which may have one or more, preferably one to two, of a nitrogen atom, a sulfur atom or an oxygen atom. The preferable examples include homo or hetero 5- to 6-membered ring, more preferably 6-membered ring.

As the preferable examples of the 5- to 7-membered homo or heterocyclic ring of the Y ring, mention is made of the following rings:

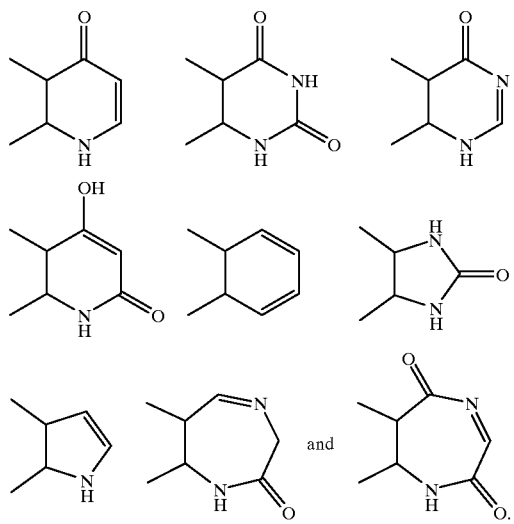

Among these, more preferable examples include the following groups:

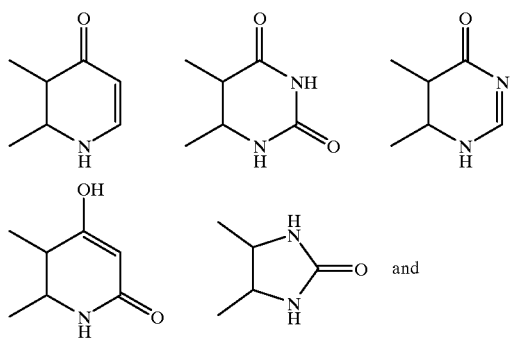

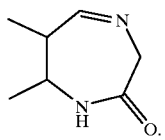

Further preferable examples include the following groups:

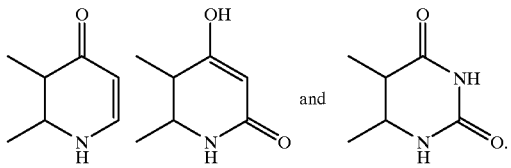

Most preferable examples of the Y ring include the following structure:

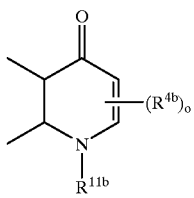

wherein groups shown by $R^{4b}$ independently stand for a hydrogen atom or a group bonded through a carbon atom, a nitrogen atom, an oxygen atom or a sulfur atom; $R^{11b}$ stands for an optionally substituted hydrocarbon group; and o denotes an integer of 1 to 2; or a group represented by the formula:

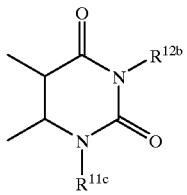

wherein each $R^{11c}$ and $R^{12b}$ independently stand for a hydrogen atom or a group bonded through a carbon atom.

The substituents to the condensed cyclic group a include a halogen atom, a group bonded through a carbon atom, a nitrogen atom, an oxygen atom or a sulfur atom, or a heterocyclic group.

Examples of the compound employed in the present invention include 4-oxothieno[2,3-b]pyridine derivative of the formula (X):

(X)

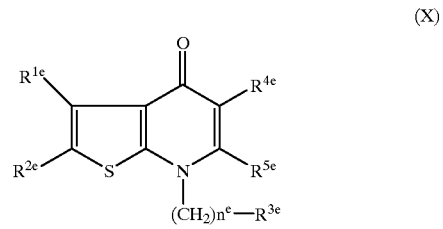

wherein each $R^{1e}$ and $R^{2e}$ are a hydrogen atom, a group bonded through a carbon atom, a nitrogen atom, an oxygen atom or a sulfur atom, $R^{3e}$ is an optionally substituted homo- or hetero-cyclic group, $R^{4e}$ is a hydrogen atom, a group bonded through a carbon atom, a nitrogen atom, an oxygen atom or a sulfur atom or an optionally substituted heterocyclic group, $R^{5e}$ is a hydrogen atom or a group bonded through a carbon atom n is an integer of 0 to 3;

2,4(1H,3H)-dioxothieno[2,3-d]pyrimidine derivative of the formula (XX):

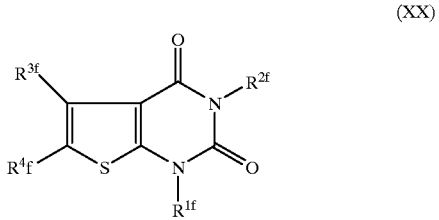

(XX)

wherein $R^{1f}$ is (1) a hydrogen atom, (2) a group bonded through a carbon atom or (3) a group of the formula:

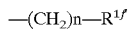

—(CH$_2$)n—$R^{1f'}$ wherein $R^{1f'}$ is a group bonded through a carbon atom or an optionally substituted homo- or hetero-cyclic group and n is an integer of 0 to 3, $R^{2f}$ is a hydrogen atom or a group bonded through a carbon atom, each of $R^{3f}$ and $R^{4f}$ are a group bonded through a carbon atom; or quinoline derivatives of the formula (XXX):

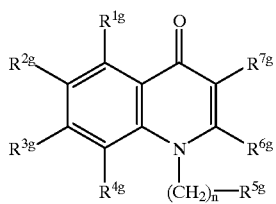

(XXX)

wherein each $R^{1g}$, $R^{2g}$, $R^{3g}$, $R^{4g}$, $R^{6g}$ and $R^{7g}$ are a hydrogen atom or a group bonded through a carbon atom, a nitrogen atom, an oxygen atom or a sulfur atom, $R^{5g}$ is a group bonded through a carbon atom or an optionally substituted homo- or hetero-cyclic group, and n is an integer of 0 to 3, with the proviso that the $R^{1g}$, $R^{2g}$, $R^{3g}$, $R^{4g}$, $R^{6g}$ and $R^{7g}$ are not simultaneously hydrogen atoms. The group bonded through a carbon atom, a nitrogen atom, an oxygen atom or a sulfur atom and the optionally substituted homo- or hetero-cyclic group have the same meanings as defined above.

The group bonded through a carbon atom represented in the formula includes, for example, (1) a hydrocarbon residue, (2) an acyl group, (3) a carbamoyl group, and (4) a heterocyclic group which bonds through carbon atom of the heterocyclic group. Each of these groups may optionally be substituted. Furthermore, as the group bonded through a carbon atom, (5) an optionally esterified or amidated carboxyl group, (6) a cyano group and (7) an amidino group are mentioned.

The optionally esterified carboxyl group includes a group of the formula: —COO—$R^{21}$, wherein $R^{21}$ is a hydrogen atom, a hydrocarbon residue or a heterocyclic group. Each of these hydrocarbon residue and heterocyclic group may optionally be substituted.

The optionally amidated carboxyl group includes a group of the formula; —CO—NR$^{22}$R$^{23}$, wherein $R^{22}$ is a hydrogen atom, a hydrocarbon residue, a heterocyclic group or a group bonded through a sulfur atom. $R^{23}$ represents a hydrogen atom or a hydrocarbon residue. $R^{22}$ and $R^{23}$ may form a 5 to 8 membered cyclic amino group together with the neighboring nitrogen atom or may form a nitrogen-containing heterocyclic group together with a neighboring nitrogen atom. Each of these hydrocarbon residue, heterocyclic group, cyclic amino group, nitrogen-containing heterocyclic group may optionally be substituted. The optionally amidated carboxyl group may have-one to 3 substituents as those of the substituents on the hydrocarbon residue mentioned below.

Examples of the group bonded through a nitrogen atom include (1) a nitro group, (2) a group of the formula: —NR$^{24}$R$^{25}$, wherein $R^{24}$ represents a hydrogen atom, a hydrocarbon residue, a hydrocarbon residue-oxy group, an acyl group, a hydroxyl group, a heterocyclic group, condensed homo-bicyclic group or a group of the formula: —SO$_p$—$R^{26}$, wherein p denotes an integer of 0 to 2, and $R^{26}$ represents a hydrocarbon residue, $R^{25}$ represents a hydrogen or a hydrocarbon residue, and the group —NR$^{24}$R$^{25}$ may form a cyclic amino group or a nitrogen-containing heterocyclic group. Each of these hydrocarbon residue, hydrocarbon residue-oxy group, acyl group, hydroxyl group, heterocyclic group and cyclic amino group may optionally be substituted. The group bonded through a nitrogen atom may have one to 3 substituents as those of the substituents on the hydrocarbon residue mentioned below.

Examples of the group bonded through an oxygen atom include a group of the formula: —O—$R^{27}$, wherein $R^{27}$ is a hydrogen atom, a hydrocarbon residue, an acyl group or a heterocyclic group. Each of these hydrocarbon residue, acyl group and heterocyclic group may optionally be substituted.

Examples of the group bonded through a sulfur atom include a group of the formula: —S(O)$_{te}$—$R^{28}$, wherein $R^{28}$ is a hydrogen atom, a hydrocarbon residue or a heterocyclic group, and te denotes an integer of 0 to 2. Each of these hydrocarbon residue and heterocyclic group may be optionally substituted.

The hydrocarbon residue in the hydrocarbon residue which may optionally be substituted and the hydrocarbon residue-oxy group which may optionally be substituted described above includes a hydrocarbon residue having one to 20 carbon atoms. As examples of the $C_{1-20}$ hydrocarbon residue, mention is made of (1) $C_{1-15}$ alkyl, e.g. methyl, ethyl, n-propyl, isopropyl, n-butyl, isobutyl, sec-butyl, t-butyl, pentyl, hexyl, heptyl, octyl, nonyl, decyl, undecyl, dodecyl, tridecyl, tetradecyl, pendadecyl, etc, and among others, with $C_{1-10}$ alkyl or $C_{1-6}$ alkyl being preferable; (2) $C_{3-10}$ cycloalkyl, e.g. cyclopropyl, cyclobutyl, cyclopentyl, cyclohexyl, cycloheptyl, cyclooctyl, cyclononyl, etc, and among others, with $C_{3-6}$ cycloalkyl being preferable; or $C_{7-20}$ bicycloalkyl, e.g. bicyclo[2,2,1]heptyl, bicyclo[2,2,2] octyl, bicyclo[3,2,1]octyl, bicyclo[3,2,1]nonyl, bicyclo[4,2, 1]nonyl, bicyclo[4,3,1]decyl; (3) $C_{2-10}$ alkenyl, e.g. vinyl, allyl, isopropenyl, 1-butenyl, 2-butenyl, 3-butenyl, 2-methylallyl, butadienyl, hexatrienyl, 3-octenyl, etc, and among others, with $C_{2-6}$ alkenyl being preferable, (4) $C_{2-10}$ alkynyl, e.g. ethynyl, 2-propynyl, isopropynyl, butynyl, t-butynyl, 3-hexynyl, etc, and among others, with $C_{2-6}$ alkynyl being preferable; (5) $C_{3-10}$ cycloalkenyl, e.g. cyclopropenyl, cyclopentenyl, cyclohexenyl, etc, among others, with $C_{3-6}$ cycloalkenyl being preferable; (6) $C_{6-14}$ aryl e.g. phenyl, 1- or 2-naphthyl, anthryl, phenanthryl, acenaphthyl, anthracenyl, etc., among others, with phenyl and naphthyl, being preferable; and (7) $C_{7-20}$ aralkyl, e.g. benzyl, phenethyl, phenylpropyl, benzhydryl, trityl, etc, and among others, with benzyl and phenethyl being preferable.

The substituents which said hydrocarbon residue may optionally have include (1) halogen, (2) nitro, (3) nitroso, (4) cyano, (5) a hydroxyl group which may optionally be substituted by (i) $C_{1-6}$ alkyl, which may optionally be substituted by hydroxyl, $C_{1-6}$ alkoxy, $C_{1-3}$ alkoxy-$C_{1-3}$ alkoxy, $C_{1-3}$ alkylthio, hydroxy-$C_{1-3}$ alkoxy, $C_{1-6}$ alkyl-carbonyl, carboxyl, carbamoyl, $C_{1-6}$ alkyl-carbamoyl, 5 to 8 membered nitrogen-containing heterocyclic group, $C_{6-10}$ aryl, $C_{7-13}$ aralkyl, nitro, or halogen, (ii) $C_{1-4}$ acyl, (iii) $C_{7-20}$ arakyl, which may optionally be substituted by halogen, $C_{1-3}$ alkoxy, $C_{1-6}$ alkyl, $C_{6-14}$ aryl, $C_{7-13}$ aralkyl or nitro, (iv) $C_{6-14}$ aryl, which may optionally be substituted by $C_{1-6}$ alkyl, $C_{6-14}$ aryl, $C_{7-13}$ aralkyl, $C_{1-3}$ alkoxy-$C_{1-6}$ alkoxy, nitro or halogen, (v) $C_{2-6}$ alkenyl, (vi) $C_{3-7}$ cycloalkyl, (vii) $C_{1-3}$ alkoxy-carbonyl, (viii) mono- or di-$C_{1-6}$ alkyl-amino, (ix) $C_{2-6}$ alkenyl-amino, (x) $C_{1-3}$ alkoxy-carbonyl, (xi) $C_{1-6}$ alkyl-carbonyl, (xii) $C_{3-6}$ cycloalkyl-oxycarbonyl, (xiii) $C_{6-14}$ aryl-carbonyl, (xiv) $C_{7-20}$ aralkyl-carbonyl, (xv) $C_{6-14}$ aryl-oxycarbonyl, (xvi) trifluorosulfonyl, (xvii) pyranyl, (xviii) furanyl or (xix) tri($C_{1-4}$ alkyl)silyl, e.g. trimethylsilyl, triethylsilyl, (6) a group of the formula: —S(O)f—$R^{31}$, wherein f is an integer of 0 to 2, $R^{31}$ represents a hydrogen atom or a hydrocarbon residue which may optionally be substituted or an amino group optionally be substituted with mono- or di-$C_{1-4}$ alkyl, the hydrocarbon residue has the same meaning as defined above, among others, $C_{1-20}$ alkyl especially $C_{1-6}$ alkyl, $C_{6-14}$ aryl, $C_{7-20}$ aralkyl are preferable, and as examples of the substituent to the hydrocarbon residue, mention is made of halogen, nitro, cyano, hydroxy, oxo, thioxo, carboxyl, cyano-$C_{6-14}$ aryl, halogeno-$C_{6-14}$ aryl, etc, (7) an optionally substituted amino group, which is represented by the formula: —NR$^{32}$R$^{33}$, wherein each of R$^{32}$ and R$^{33}$ independently are (i) hydrogen, (ii) $C_{1-6}$ alkyl, (iii) $C_{1-6}$ acyl, (iv) a carbamoyl group optionally be substituted with mono- or di-$C_{1-4}$ alkyl, $C_{1-4}$ alkylthio or $C_{6-14}$ aryl, (v) $C_{1-8}$ alkanoyl, (vi) $C_{6-14}$ aryl, (vii) $C_{1-4}$ alkylthio, (viii) $C_{1-4}$ alkylsulfonyl, (ix) $C_{1-4}$ alkylsulfinyl or (x) a cyclic amino group or a nitrogen-containing heterocyclic group which is mentioned below or a group bonded through a nitrogen atom as described above, (8) a group of the formula: —CO—$R^{34}$ wherein $R^{34}$ denotes (i) hydrogen, (ii) hydroxyl, (iii) $C_{1-10}$ alkyl, (iv) $C_{1-6}$ alkoxy which may be substituted with $C_{6-14}$ aryl which may optionally be substituted with halogen, nitro, $C_{6-14}$ aryl, (V) $C_{3-6}$ cycloalkyl, (vi) $C_{6-14}$ aryl, (vii) $C_{6-14}$ aryloxy, (viii) $C_{7-20}$ aralkyl, (ix) $C_{7-20}$ aralkyloxy, (x) an optionally substituted amino group as defined item (7) above, (xi) an optionally susbstituted amino-oxy group represented by the formula: —O—NR$^{32}$R$^{33}$, wherein R$^{32}$ and R$^{33}$ have the same meaning as defined above, (xii) 5- to 8-membered heterocyclic group, or (xiii) 5- to 8-membered heterocyclic-oxy group, especially, $C_{1-10}$ acyl is preferable, (9) a 3- to 9-membered heterocyclic group containing 1 to 4 hetero-atom(s) selected from oxygen (O), sulfur (S) and nitrogen (N) as ring members, the heterocyclic group being optionally substituted, for example, by (i) halogen, (ii) $C_{1-4}$ alkyl, (iii) $C_{1-3}$ alkoxy, (iv) $C_{1-4}$ alkylthio or (v) phenoxy which may optionally be substituted by a halogen, (10) sulfo, (11) $C_{6-14}$ aryl, e.g. phenyl, naphthyl, anthryl, phenanthryl, acenaphthyl, anthracenyl, etc, which may optionally be substituted with one to 4 of (a) hydroxyl, (b) amino, (c) mono- or di-$C_{1-6}$ alkylamino, e.g. methylamino, ethylamino, propylamino, dimethylamino, diethylamino, etc, (d) $C_{1-6}$ alkoxy, (e) halogen or (f) cyano, (12) $C_{3-7}$ cycloalkyl, (13) $C_{1-6}$ alkylenedioxy, e.g. methylenedioxy, ethylenedioxy, propylenedioxy, 2,2-dimethylenedioxy, etc, (14) oxo, (15) thioxo, (16) $C_{1-15}$ alkyl, (17) $C_{2-10}$ alkynyl, (18) $C_{3-10}$ cycloalkyl, (19) $C_{2-10}$ alkenyl, e.g. vinyl, allyl, isopropenyl, 1-butenyl, 2-butenyl, butadienyl, hexatrienyl, etc., and among others, $C_{2-6}$ alkenyl is preferable, (20) $C_{5-7}$ cycloalkenyl, (21) $C_{7-20}$ aralkyl, (22) amidino, (23) azido, (24) —B(OH)$_2$, (25) epoxy(—O—), (26) phosphono, (27) dihydroxyboryl, (28) a group of the formula: —A—$R^{35}$, wherein A is a spacer group and $R^{35}$ denotes a $C_{1-10}$ alkyl group, (29) phthaloyl, (30) a group bonded through a sulfur atom as described above, (31) hexamethylenetetraamino, (32) indanyl and (33) phthalimide.

The above substituents on the hydrocarbon residue may further have substituents. Such substituents includes (1) hydroxy, (2) amino, (3) mono- or di-$C_{1-4}$ alkyl-amino, e.g. methylamino, ethylamino, propylamino, dimethylamino, diethylamino, etc, (4) $C_{1-4}$ alkoxy, (5) $C_{1-6}$ alkyl optionally be substituted with halogen, (6) $C_{6-14}$ aryl which may optionally be substituted with halogen or cyano, (7) $C_{7-13}$ aralkyl, (8) $C_{1-6}$ alkoxy-carbonyl, (9) 5- to 8-membered heterocyclic group, (10) $C_{1-10}$ acyl, (11) carboxyl, (12) $C_{1-6}$ alkoxy-carbonyl, (13) $C_{6-14}$ aryl-carbonyl, (14) $C_{1-6}$ alkylendioxy, (15) sulfamoyl, (16) carbamoyl, (17) $C_{1-4}$ alkylthio, (18) $C_{1-4}$ alkylsulfinyl, (19) $C_{1-4}$ alkylsulfonyl, (20) halogen, (21) nitro, (22) mercapto or (23) cyano. The number of the substituents is preferably 1 to 4, and more preferably 1 to 2.

When the above hydrocarbon residue is cycloalkyl, cycloalkenyl, alkynyl, aryl or aralkyl, each of the group may have one to three of $C_{1-6}$ alkyl, as a substituent. The $C_{1-6}$ alkyl group may further substituted by one to three of hydroxy, oxo, $C_{1-3}$ alkoxy, $C_{1-3}$ acyl, $C_{1-3}$ alkylthio, halogen or carbamoyl.

As examples of the substituted $C_{1-6}$ alkyl, mention is made of (1) formyl, i.e. methyl is substituted by oxo, (2) carboxyl, i.e. methyl is substituted by oxo and hydroxy, (3) $C_{1-6}$ alkoxy-carbonyl, i.e. methyl is substituted by oxo and alkoxy, e.g. methoxycarbonyl, ethoxycarbonyl, t-butoxycarbonyl, (4) hydroxy-$C_{1-6}$ alkyl, e.g. hydroxymethyl, hydroxyethyl, hydroxypropyl, hydroxybutyl, (5) $C_{1-3}$ alkoxy-$C_{1-6}$ alkyl, e.g. methoxymethyl, ethoxyethyl, ethoxybutyl, propoxymethyl, propoxyhexyl.

In the above optionally substituted hydrocarbon residue, the number of the substituent(s) is preferably 1 to 6, more preferably 1 to 5, still more preferably 1 to 3 and most preferably 1 to 2. The number of the substituent(s) which is substituted on the substituent is preferably 1 to 3, more preferably 1 or 2.

As the acyl group in the optionally substituted acyl group, mention is made of an acyl group of hydrocarbon-carbonyl or hydrocarbon-oxy-carbonyl, which is derived from $C_{1-24}$ aliphatic carboxylic acid.

Further examples of the acyl group include formyl, $C_{1-10}$ alkyl-carbonyl, e.g. acetyl, propionyl, butyryl, isobutyryl, valeryl, isovaleryl, pivaloyl, hexanoyl, heptanoyl, octanoyl, $C_{1-13}$ alkoxy-carbonyl, $C_{6-14}$ aryl-carbonyl, e.g. benzoyl, naphthylcarbonyl, anthracenylcarbonyl, $C_{6-14}$ aryloxy-carbonyl, e.g. phenoxycarbonyl, $C_{7-20}$ aralkyl-carbonyl, e.g. benzylcarbonyl, and $C_{7-19}$ aralkyloxy-carbonyl, e.g. benzyloxycarbonyl, $C_{3-10}$ cycloalkyl-carbonyl, e.g. cyclopropylcarbonyl, cyclobutylcarbonyl, cyclopentylcarbonyl, cyclohexylcarbonyl, $C_{2-6}$ alkenyl-carbonyl, e.g. vinylcarbonyl, butenylcarbonyl, butadienylcarbonyl, hexatrienylcarbonyl. Among others, $C_{1-10}$ acyl is preferable, As substituents in the optionally substituted acyl, mention is made of these in the optionally substituted hydrocarbon residue. The substituents on the $C_{1-10}$ acyl group are the same as those on the hydrocarbon residue.

As the $C_{1-13}$ alkoxy in $C_{1-13}$ alkoxy-carbonyl, examples are straight-chain or branched $C_{1-13}$ alkoxy. As straigh-chain alkoxy, it is preferable $C_{1-9}$ straight-chain alkoxy, e.g. methoxy, ethoxy, propoxy, butoxy, pentoxy, neopentyloxy, hexyloxy, octyloxy. As the branched alkoxy group, mention is made of $C_{3-13}$ branched alkoxy groups, e.g. isopropoxy, isobutoxy, sec-butoxy, tert-butoxy, isopentoxy, sec-pentyloxy, tert-pentyloxy, 3-pentyloxy, isohexyloxy, sec-hexyloxy, tert-hexyloxy, isooctyloxy, sec-octyloxy, tert-octyloxy, cyclopentyloxy, cyclopropyloxy, cyclobutyloxy, cycloheptyloxy, 2-indanyloxy, 4-piperidinyloxy, tetrahydro-4H-pyra-4-nyloxy. As the branched alkoxy group, among them, $C_{3-7}$ branched alkoxy groups are preferable.

Examples of the optionally substituted carbamoyl group include a carbamoyl group which may optionally be substituted by an optionally substituted $C_{1-20}$ hydrocarbon residue or a cyclic amino group. As an optionally substituted $C_{1-20}$ hydrocarbon residue, mention is made of those described hereinbefore. Concrete examples of the substituted carbamoyl include mono- or di-$C_{1-15}$ alkyl-carbamoyl, e.g. methylcarbamoyl, ethylcarbamoyl, hexylcarbamoyl, dimethylcarbamoyl, methylethylcarbamoyl. The substituents on the carbamoyl group are the same as those on the hydrocarbon residue.

As the heterocyclic group in the optionally substituted heterocyclic group which bonds with the constitutive carbon atom, mention are made of 3 to 9, preferably 5 to 8, membered heterocyclic groups which have one to 4 hetero atoms selected from an oxygen atom, sulfur atom and nitrogen atom than carbon atom; and condensed heterobi- or tri-cyclic groups composed of the above heterocyclic group and other ring groups.

Examples of the heterocyclic groups include (1) 5-membered cyclic groups containing, besides the carbon atom, 1 to 4 hetero-atoms selected from an oxygen atom, sulfur atom and nitrogen atom, such as thienyl, furyl, pyrrolyl, pyrrolinyl, oxazolyl, thiazolyl, pyrazolyl, pyrazdinyl, pyrazolidinyl, imidazolyl, imidozolinyl, imidazolidinyl, isoxazolyl, isothiazolyl, 1,2,4-oxadiazolyl, 1,3,4-oxadiazolyl, furazanyl, 1,2,4-thiadiazolyl, 1,2,3-thiadiazolyl, 1,2,5-thiadiazolyl, 1,2,3-triazolyl, 1,2,4-triazolyl, triazinyl, triazolidinyl, and 1H- or 2H-tetrazolyl; (2) 6-membered cyclic groups containing, besides, carbon atom, 1 to 4 hetero-atoms selected from an oxygen atom, sulfur atom and nitrogen atom, as exemplified by pyridyl, pyrimidinyl, thiomorpholinyl, morpholinyl, triazinyl, pyrrolidinyl, piperazinyl, piperidinyl, piperadino, pyranyl, thiopyranyl, 1,4-oxadinyl, 1,4-thiazinyl, 1,3-thiazinyl, piperazinyl, triazinyl, oxotriazinyl, pyridazinyl and pyrazinyl; (3) condensed bicyclic or tricyclic groups containing, besides carbon atom, 1 to 4 hetero-atoms selected from oxygen atom, sulfur atom and nitrogen atom, as exemplified by benzofuranyl, isobenzofuranyl, benzothiazolyl, 1,2-benzoisothiazolyl, benzo[b]thienyl, benzoxazolyl, 1H-benzotriazolyl, 1,2-benzoisoxazolyl, tetrazolo[1,5-b] pyridazinyl, triazolo[4,5-b]pyridazinyl, benzoimidazolyl, quinolyl, isoquinolyl, cinnolinyl, phthaladinyl, quinazolyl, quinoxalinyl, quinolizinyl, indolidinyl, indolyl, isoindolyl, 1H-indazolyl, quinolizinyl, 1,8-naphthylidinyl, purinyl, pteridinyl, dibenzofuranyl, carbazolyl, α-carbolinyl, β-carbolinyl, γ-carbolinyl, acridinyl, phenoxazinyl, phenanthridinyl, chromanyl, benzoxadinyl, phenazinyl, phenothiazinyl, phenoxathiinyl, phenoxazinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-tiazolo[4,3-a]pyridyl, 1,2,4-triazolo[4,3-b]pyridazinyl; (4) 3-membered heterocyclic group such as oxirane, aziridino; and (5) 4-membered heterocyclic group such as azetidinyl. The heterocyclic group may be a hydrogen additive form.

Examples of the substituents, which the heterocyclic group may have include (1) $C_{1-6}$ alkyl, (2) $C_{2-6}$ alkenyl, (3) $C_{2-6}$ alkynyl, (4) $C_{3-6}$ cycloalkyl, (5) $C_{5-7}$ cycloalkenyl, (6) $C_{7-11}$ aralkyl, (7) $C_{6-14}$ aryl, (8) $C_{1-6}$ alkoxy, (9) $C_{6-14}$ aryloxy, e.g. phenoxy, (10) $C_{1-6}$ alkanoyl, e.g. formyl, acetyl, propionyl, n-butyryl and isobutyryl, (11) $C_{6-14}$ arylcarbonyl, e.g. benzoyl, (12) $C_{1-6}$ alkanoyloxy, e.g. formyloxy, acetyloxy, propionyloxy, n-butyryloxy and isobutyryloxy, (13) $C_{6-14}$ aryl-carbonyloxy, e.g. benzoyloxy, (14) carboxyl, (15) $C_{1-6}$ alkoxy-carbonyl, e.g. methoxycarbonyl, ethoxycarbonyl, n-propoxycarbonyl, isopropoxycarbonyl, n-butoxycarbonyl, isobutoxycarbonyl and tert-butoxycarbonyl, (16) carbamoyl, (17) N-mono-$C_{1-4}$ alkylcarbamoyl, e.g. N-methylcarbamoyl, N-ethylcarbamoyl, N-propylcarbamoyl, N-isopropylcarbamoyl and N-butylcarbamoyl, (18) N,N-di-$C_{1-4}$ alkyl-carbamoyl, e.g. N,N-dimethylcarbamoyl, N,N-diethylcarbamoyl, N,N-dipropylcarbamoyl and N,N-dibutylcarbamoyl, (19) cyclic aminocarbonyl, e.g. 1-aziridinylcarbonyl, 1-azetidinylcarbonyl, 1-pyrrolidinylcarbonyl, 1-piperidinylcarbonyl, N-methylpiperazinylcarbonyl and morpholinocarbonyl, (20) halogen, (21) mono- or tri-halogeno-$C_{1-4}$ alkyl, e.g. chloromethyl, dichloromethyl, trifluoromethyl and trifluoroethyl, (22) oxo, (23) amidino, (24) imino, (25) amino, (26) mono- or di- $C_{1-4}$ alkylamino, e.g. methylamino, ethylamino, propylamino, isopropylamino, butylamino, dimethylamino, diethylamino, dipropylamino, diisopropylamino and dibutylamino, (27) 3- to 6-membered cyclic amino group containing, besides the carbon atom and one nitrogen atom, 1 to 3 hetero-atoms selected from oxygen atom, sulfur atom and nitrogen atom, e.g. aziridinyl, azetidinyl, pyrrolidinyl, pyrrolinyl, pyrrolyl, imidazolyl, pyrazolyl, imidazolidinyl, piperidino, morpholino, dihydropyridyl, pyridyl, N-methylpiperazinyl and N-ethylpiperazinyl, (28) $C_{1-6}$ alkanoylamino, e.g. formamido, acetamido, trifluoroacetamido, propionylamido, butyrylamido and isobutyrylamido, (29) benzamido, (30) carbamoylamino, (31) N- $C_{1-4}$ alkylcarbamoylamino, e.g. N-methylcarbamoylamino, N-ethylcarbamoylamino, N-propylcarbamoylamino, N-isopropylcarbamoylamino and N-butylcarbamoylamino, (32) N,N-di-$C_{1-4}$ alkylcarbamoylamino, e.g. N,N-dimethylcarbamoylamino, N,N-diethylcarbamoylamino, N,N-dipropylcarbamoylamino and N,N-dibutylcarbamoylamino, (33) $C_{1-3}$ alkylenedioxy, e.g. methylenedioxy and ethylenedioxy, (34) —B(OH)$_2$, (35) hydroxyl, (36) epoxy (—O—), (37) nitro, (38) cyano, (39) mercapto, (40) sulfo, (41) sulfino, (42) phosphono, (43) dihydroxyboryl, (44) sulfamoyl, (45) $C_{1-6}$ alkylsulfamoyl, e.g. N-methylsulfamoyl, N-ethylsulfamoyl, N-propylsulfamoyl, N-isopropylsulfamoyl and N-butyl sulfamoyl, (46) di-$C_{1-6}$ alkylsulfamoyl, e.g. N,N-dimethylsulfamoyl, N,N-diethylsulfamoyl, N,N-dipropylsulfamoyl and N,N-dibutylsulfamoyl, (47) $C_{1-6}$ alkylthio, e.g. methylthio, ethylthio, propylthio, isopropylthio, n-butylthio, sec-butylthio and tert-butylthio, (48) phenylthio, (49) $C_{1-6}$ alkylsulfinyl, e.g. methylsulfinyl, ethylsulfinyl, propylsulfinyl and butylsulfinyl), (50) phenylsulfinyl, (51) $C_{1-6}$ alkylsulfonyl, e.g. methylsulfonyl, ethylsulfonyl, propylsulfonyl and butylsulfonyl, and (52) $C_{6-14}$ arylsulfonyl, e.g. phenylsulfonyl. The number of the substituents ranges from 1 to 6, preferably 1 to 3.

Examples of the above-mentioned optionally substituted heterocyclic groups which bond through a carbon atom include 5- to 8-membered cyclic groups or the condensed hetero bi- or tri-cyclic group containing, besides carbon atom, 1 to 4 hetero-atoms such as oxygen atom, sulfur atom and nitrogen atom. Examples of (1) 5-membered cyclic groups containing, besides carbon atom, 1 to 4 hetero-atoms selected from oxygen atom, sulfur atom and nitrogen atom which bond through a carbon atom include 2- or 3-thienyl, 2- or 3-furyl, 2-or 3-pyrrolyl, 2- or 3-pyprolinyl, 2-, 4- or 5-oxazolyl, 2-, 4- or 5-thiazolyl, 3-, 4- or 5-pyrazolyl, 2- or 3- pyrrolidinyl. 2-, 4- or 5-imidazolyl, 2-imidazolinyl, 2-imidazolidinyl, 3, 4- or 5-isoxazolyl, 3-, 4- or 5-isothiazolyl, 3- or 5-(1,2,4-oxadiazolyl), 3- or 4-furazanyl, 2-, 5- or 6-(1,3,4-oxadiazolyl), 3- or 5-(1,2,4-thiadiazolyl), 2- or 5-(1,3,4-thiadiazolyl), 4- or 5-(1,2,3-thiadiazolyl), 3- or 4-(1,2,5-thiadiazolyl), 2- or 5-(1,2,3-triazolyl), 3- or 5-(1,2,4-triazolyl), and 5-(1H- or 2H-tetrazolyl). Examples of 6-membered cyclic groups containing, besides, carbon atom, 1 to 4 hetero-atoms selected from oxygen atom, sulfur atom or nitrogen atom which bond through a carbon atom include 2-, 3- or 4-pyridyl, 2-, 4- or 5-pyrimidinyl, 2- or 3-thiomorpholinyl, 2- or 3-morpholinyl, 2- or 4-triazinyl, 2-, 3- or 4-piperidinyl, 2- or 3-piperazinyl, 2- or 3-pyranyl, 2- or 3-thiopyranyl, 2- or 3-(1,4-oxadinyl), 2- or 3-(1,4-thiazinyl), 1- or 4-(1,3-thiazinyl), 3- or 6-triazinyl, 3- or 4-pyridazinyl, 2- or 3-pyrazinyl and 3- or 4-pyridazinyl. Examples of condensed hetero bicyclic or tricyclic groups containing, besides carbon atom, 1 to 4 hetero-atoms selected from oxygen atom, sulfur atom and nitrogen atom which bonds through a carbon atom include benzofuranyl, isobenzofuranyl, benzothiazolyl, 1,2-benzoisothiazolyl, benzo[b]thienyl, benzoxazolyl, 1H-benzotriazolyl, 1,2-benzoisoxazolyl, tetrazolo[1,5-b]pyridazinyl, triazolo[4,5-b]pyridazinyl, benzoimidazolyl, quinolyl, isoquinolyl, cinnolinyl, phthaladinyl, quinazolyl, quinoxalinyl, indolidinyl, indolyl, isoindolyl, 1H-indazolyl, quinolizinyl, 1,8-naphthylidinyl, purinyl, pteridinyl, dibenzofuranyl, carbazolyl, α-carbolinyl, β-carbolinyl, γ-carbolinyl, acridinyl, phenoxazinyl, phenanthridinyl, chromanyl, benzoxadinyl, phenazinyl, phenothiazinyl, phenoxathiinyl, phenoxazinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2-4-tiazolo[4,3-a]pyridyl, 1,2,4-triazolo[4,3-b]pyridazinyl. The substituents on the heterocyclic groups which bond through a carbon atom are the same as those on the heterocyclic group above-mentioned.

Preferable examples of the cyclic amino group is are a 3 to 8-membered cyclic amino group.

As examples of the 3 to 8 membered cyclic amino groups containing nitrogen atom, i.e. cyclic amino group or nitrogen atom-containing heterocyclic group, mention is made of aziridinyl, azetidinyl, pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, azepinyl, hexamethyleneamino, oxazolidino, morpholino, thiazolidino, thiomorpholino, phthalimido. As more preferable cyclic amino groups, mention is made of 5 to 6-membered ring such as pyrolidinyl, pyrazolinyl, pyrazolyl, piperidinyl, piperazinyl, morpholino and thiomorpholino.

The nitrogen-containing heterocyclic groups are preferably 5 to 7-membered heterocyclic groups and the condensed bicyclic group. The nitrogen-containing heterocyclic groups and the condensed bicyclic group are exemplified by pyrrolyl, pyrazolyl, thiazolyl, isothiazolyl, oxazolyl, isoxazolyl, imidazolyl, triazolyl, tetrazolyl, furazanyl, pyridyl, pyrimidinyl, pyridazynyl, oxadiazolyl, morpholinyl, thiomorpholinyl, pyrrolidinyl, pyrrolinyl, pyrazolidinyl, pyrazolinyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneaminyl, oxazolidinyl, thiazolidinyl, indolyl, indazolyl, purinyl, quinolyl. The heterocyclic group includes hydrogen additive forms. As more preferable heterocyclic groups, mention is made of 5 to 6 membered heterocyclic groups. In particular, pyrrolidinyl, pyrazolinyl, pyrazolyl, piperidinyl, piperazinyl, morpholinyl and thiomorpholinyl are preferable.

The cyclic amino groups and the nitrogen-containing heterocyclic group may be substituted. The examples of the substituents includes (1) $C_{1-6}$ alkyl, (2) $C_{6-14}$ aryl, (3) $C_{7-13}$ aralkyl, (4) $C_{1-6}$ alkyl-carbonyl, (5) $C_{6-14}$ aryl-carbonyl, (6) $C_{1-6}$ alkoxy-carbonyl. As the preferable substituent, mention is made of $C_{1-6}$ alkyl, more preferably $C_{1-3}$ alkyl.

Examples of the homocyclic group in the optionally substituted homocyclic groups include 3- to 10-membered cyclic hydrocarbon groups consisting of carbon atoms, for example, $C_{6-10}$ aryl, e.g. phenyl, naphthyl; $C_{3-7}$ cycloalkyl, e.g. cyclopropyl, cyclobutyl, cyclopentyl, cyclohexyl and cycloheptyl; and $C_{3-7}$ cycloalkenyl, e.g. cyclopropenyl, cyclobutenyl, cyclopentenyl, cyclohexenyl and cycloheptenyl. As the homo bicyclic group, mention is made of indanyl and indenyl. Among the homocyclic group, those having 3 to 7 carbon atoms are preferable.

Examples of the substituents which the homocyclic groups may have, include (1) $C_{1-15}$ alkyl (and among others $C_{1-6}$ alkyl being preferable) which may optionally be substituted by a halogen, (2) $C_{3-10}$ cycloalkyl, (3) $C_{2-10}$ alkenyl, (4) $C_{2-10}$ alkynyl, (5) $C_{3-10}$ cycloalkyl, (6) $C_{6-10}$ aryl, (7) $C_{7-19}$ aralkyl, (8) nitro, (9) hydroxyl, (10) mercapto, (11) oxo, (12) thioxo, (13) cyano, (14) carbamoyl, (15) carboxyl, (16) $C_{1-5}$ alkoxy-carbonyl (e.g. methoxycarbonyl and ethoxycarbonyl), (17) sulfo, (18) halogen, (19) $C_{1-6}$ alkoxy, (20) $C_{6-}$, aryloxy, e.g. phenoxy, (21) $C_{1-6}$ acyloxy, e.g. acetoxy, propionyloxy, (22) $C_{1-6}$ alkylthio, e.g. methylthio, ethylthio, n-propylthio, isopropylthio, n-butylthio and t-butylthio, (23) $C_{6-10}$ arylthio, e.g. phenylthio, (24) $C_{1-6}$ alkylsulfinyl, e.g. methylsulfinyl and ethylsulfinyl, (25) $C_{6-10}$ arylsulfinyl, e.g. phenylsulfinyl, (26) $C_{1-6}$ alkylsulfonyl, e.g. methylsulfonyl and ethylsulfonyl, (27) $C_{6-10}$ arylsulfonyl, e.g. phenylsulfonyl, (28) amino, (29) $C_{1-6}$ acylamino, e.g. acetylamino and propylamino, (30) mono- or di- $C_{1-4}$ alkylamino, e.g. methylamino, ethylamino, n-propylamino, isopropylamino, n-butylamino, dimethylamino and diethylamino, (31) $C_{3-8}$ cycloalkylamino, e.g. cyclopropylamino, cyclobutylamino, cyclopentylamino and cyclohexylamino, (32) $C_{6-10}$ arylamino, e.g. anilino, (33) $C_{1-6}$ alkanoyl, e.g. formyl, acetyl and hexanoyl, (34) $C_{1-6}$ alkanoyl-oxy, e.g. acetyloxy, propionyloxy, (35) $C_{6-10}$ aryl-carbonyl, e.g. benzoyl, and (36) 5- to 6-membered heterocyclic groups containing, besides carbon atom, 1 to 4 hetero-atoms selected from oxygen, sulfur and nitrogen (e.g. 2- or 3-thienyl, 2- or 3-furyl, 3-,4- or 5-pyrazolyl, 2-,4- or 5-thiazolyl, 3-,4- or 5-isothiazolyl, 2-,4- or 5-oxazolyl, 3-,4- or 5-isoxazolyl, 2-,4- or 5-imidazolyl, 1,2,3- or 1,2,4-triazolyl, 1H or 2H-tetrazolyl, 2-,3- or 4-pyridyl, 2-,4- or 5-pyrimidyl, 3- or 4-pyridazinyl, quinolyl, isoquinolyl and indolyl. The number of substituents ranges from 1 to 6, preferably from 1 to 3, more preferably from 1 to 2.

In the formulae, n is preferably 1.

In the above definitions, as the examples of halogen, mention is made of fluorine, chlorine, bromine, iodine.

As examples of $C_{1-6}$ alkyl, mention is made of methyl, ethyl, n-propyl, isopropyl, n-butyl, isobutyl, s-butyl, t-butyl, pentyl, isopentyl, neopentyl, hexyl.

$C_{1-4}$ alkyl is exemplified by methyl, ethyl, n-propyl, isopropyl, n-butyl, isobutyl, t-butyl. $C_{1-3}$ alkyl is exemplified by methyl, ethyl, n-propyl, isopropyl.

As examples of $C_{2-10}$ alkenyl, mention is made of vinyl, allyl, propenyl, 2-methylallyl, isopropenyl, 2-butenyl, 3-butenyl, butadienyl, hexatrienyl, 3-octenyl. Examples of $C_{2-6}$ alkenyl are vinyl, allyl, propenyl, isopropnyl, butenyl and hexatrienyl. Examples of $C_{2-4}$ alkenyl are vinyl, allyl, isopropenyl and butenyl.

As example of the $C_{2-10}$ alkynyl, mention is made of ethynyl, 1-propynyl, 2-propynyl, propargyl, and 3-hexynyl. $C_{2-6}$ alkynyl and $C_{2-4}$ alkynyl is exemplified by ethynyl, 1-propynyl, 2-propynyl.

$C_{3-10}$ cycloalkyl is exemplified by cyclopropyl, cyclobutyl, cyclopentyl, cyclohexyl, cycloheptyl, cyclooctyl, cyclononyl. $C_{3-8}$ cycloalkyl is exemplified by cyclopropyl, cyclobutyl, cyclopentyl, cyclohexyl, cycloheptyl, cyclooctyl. $C_{3-7}$ cycloalkyl is exemplified by cyclopropyl, cyclobutyl, cyclopentyl, cyclohexyl, cycloheptyl. $C_{3-6}$ cycloalkyl is exemplified by cyclopropyl, cyclobutyl, cyclopentyl, cyclohexyl.

Examples of $C_{3-7}$ cycloalkenyl are cyclopropenyl, cyclobutenyl, cyclopentenyl, cyclohexenyl, and examples of $C_{5-7}$ cycloalkenyl are cyclopentyl, cyclohexenyl.

$C_{6-14}$ aryl is exemplified by phenyl, naphthyl, anthryl, phenanthryl, acenaphthyl, anthracenyl. Examples of $C_{6-10}$ aryl are phenyl and naphthyl. Especially phenyl is most preferable.

$C_{7-20}$ aralkyl and $C_{7-19}$ aralkyl are exemplified by benzyl, phenethyl, benzhydryl, trithyl. $C_{7-15}$ aralkyl and $C_{7-13}$ aralkyl are benzyl, phenethyl, benzhydryl. Examples of $C_{7-11}$ aralkyl and $C_{7-10}$ aralkyl are benzyl, α-methylkenyl and phenethyl.

$C_{1-6}$ alkoxy is exemplified by methoxy, ethoxy, propoxy, isopropoxy, n-butoxy, isobutoxy, s-butoxy, t-butoxy, pentyloxy, isopentyloxy, neopentyloxy, hexyloxy, $C_{1-4}$ alkoxy is exemplified by methoxy, ethoxy, propoxy, isopropoxy, n-butoxy, isobutoxy, s-butoxy, t-butoxy. $C_{1-3}$ alkoxy is exemplified by methoxy, ethoxy, propoxy, isopropoxy.

$C_{1-6}$ acyl is exemplified by a $C_{1-6}$ alkanoyl group of the formula: —CO—$R^{36}$, wherein $R^{36}$ is hydrogen or $C_{1-6}$ alkyl (e.g. methyl, ethyl, propyl, isopropyl, n-butyl, isobutyl, s-butyl, t-butyl, pentyl).

$C_{1-4}$ acyl is exemplified by a $C_{1-4}$ alkanoyl group of the formula: —CO—$R^{37}$, wherein $R^{37}$ is hydrogen, methyl, ethyl, propyl, isopropyl.

$C_{1-8}$ alkanoyl is exemplified by formyl, acetyl, propionyl, butyryl, isobutyryl, valeryl, isovaleryl, octanoyl.

As the spacer group shown by the symbol "A", mention is made of, for example, chemical bond, $C_{1-4}$ alkylene (e.g. methylene, ethylene), $C_{2-6}$ alkenylene (e.g. vinylene, butadienylene); a group of the formula: —$(CH_2)m'$ $NR^{38}$— in which m' is an integer of 0 to 3 and $R^{38}$ is hydrogen, $C_{1-6}$ alkyl; a group of the formula: —CO—; a group of the formula: —$CONR^{38'}$- in which $R^{38'}$ is hydrogen, $C_{1-6}$ alkyl, $C_{3-7}$ cycloalkyl, $C_{6-14}$ aryl or a heterocyclic group; a group of the formula: —$S(O)m"$—, wherein m" is an integer of 0 to 2; —O—; —S—; a group of the formula —$NR^{38'}S(O)m'''$ in which m''' is an integer of 0 to 2, $R^{38'}$ is of the same meaning as defined above.

In the compound of the formula (X), preferable examples include a compound of the formula (XI):

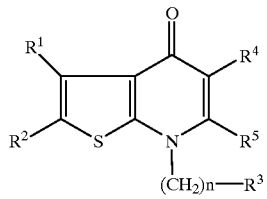

(XI)

wherein $R^1$ and $R^2$ are each independently hydrogen or a group bonded through a carbon atom, a nitrogen atom, an oxygen atom or a sulfur atom;

$R^3$ is an optionally substituted homo- or hetero-cyclic group;

$R^4$ is (1) hydrogen, (2) formyl, (3) cyano, (4) a lower alkyl group substituted by a group bonded through a sulfur atom, an optionally substituted hydroxyl group, or an optionally substituted hydrocarbon residue, (5) a carbonyl group substituted with an optionally substituted hydrocarbon residue, or (6) an optionally esterified or amidated carboxyl group;

$R^5$ is hydrogen or a group bonded through a carbon atom; n is an integer of 0 to 3;

Each of $R^1$, $R^2$, $R^3$ and $R^5$ are of the same meanings as each of $R^{1e}$, $R^{2e}$, $R^{3e}$ and $R^{5e}$.

Examples of the groups bonded through sulfur atom, shown by $R^4$, include mercapto, each optionally substituted alkylthio, alkylsulfinyl, cycloalkylthio, arylthio, aralkylthio and heterocyclic thio groups. The alkyl, cycloalkyl, aryl, aralkyl and heterocyclic groups, in the said alkylthio, alkylsulfinyl, cycloalkylthio, arylthio, aralkylthio and heterocyclic thio groups, are of the same meaning as defined above.

The substituents, which the said group bonded through sulfur atom may have, are of the same meaning as that of the substituents which the above-mentioned optionally substituted groups bonded through nitrogen atom may have.

As the ester group in the optionally esterified carboxyl group shown by $R^4$, mention is made of, for example, alkyl, cycloalkyl, aryl, aralkyl and heterocyclic groups, and these are of the same meaning as defined above.

Examples of the amidated carboxyl groups shown by $R^4$ include "a group bonded through a nitrogen atom"-carbonyl group, wherein the group bonded through a nitrogen atom has the same meaning as defined above.

As the lower alkyl in the substituted lower alkyl shown by $R^4$, mentioned is made of, for example, $C_{1-6}$ alkyl such as methyl, ethyl, propyl, i-propyl, butyl, i-butyl, s-butyl, pentyl, hexyl and the like. The group bonded through a sulfur atom is as the same meaning as defined above.

The optionally substituted hydrocarbon residue in the lower alkyl group substituted with an optionally substituted hydrocarbon residue of $R^4$ has the same meaning as defined above.

As substituents in the optionally substituted hydroxyl, use is made of, for example, $C_{1-6}$ alkyl (e.g. methyl, ethyl, n-propyl, i-propyl, n-butyl and tert-butyl) optionally having 1 to 4 substituents selected from halogen (e.g. chlorine, bromine and fluorine), $C_{6-10}$ aryl (e.g. phenyl and naphthyl), $C_{7-12}$ aralkyl (e.g. benzyl and phenylethyl) and nitro; $C_{6-10}$ aryl (e.g. phenyl and naphthyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl, phenethyl) and nitro; $C_{7-12}$ aralkyl (e.g. benzyl, phenylethyl and naphtylmethyl) optionally having 1 to 4 substituents selected from halogen, (e.g. chlorine, bromine and fluorine), $C_{1-6}$ alkyl (e.g. methyl, ethyl and and n-propyl), $C_{6-10}$ aryl (e.g. phenyl and naphthyl), $C_{7-12}$ aralkyl (e.g. benzyl and phenethyl) and nitro; $C_{1-6}$ alkyl-carbonyl (e.g. acetyl and propionyl) optionally having 1 to 3 substituents selected from formyl, halogen (e.g. chlorine, bromine and fluorine), $C_{1-6}$ alkyl (e.g. methyl, ethyl and n-propyl), $C_{6-10}$ aryl(e.g. phenyl and naphthyl), $C_{7-12}$ aralkyl (e.g. benzyl and phenylethyl) and nitro; $C_{6-10}$ aryloxy-carbonyl (e.g. phenyloxycarbonyl and naphthyloxycarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl(e.g. phenyl and naphthyl), $C_{7-12}$ aralkyl (e.g. benzyl and phenylethyl)and nitro; $C_{6-10}$ aryl-carbonyl (e.g. benzoyl and naphthylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenylethyl) and nitro; $C_{7-12}$ aralkyl-carbonyl (e.g.benzylcarbonyl and phenethylcarbonyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) and nitro; and pyranyl, furanyl or tri ($C_{1-4}$ alkyl) silyl (e.g. trimethylsilyl and triethylsilyl) optionally having 1 to 4 substituents selected from halogen (e.g. chlorine, bromine and fluorine), $C_{1-6}$ alkyl (e.g. methyl, ethyl and n-propyl), $C_{6-10}$ aryl (e.g. phenyl and naphthyl), $C_{7-12}$ aralkyl (e.g. benzyl and phenethyl) and nitro.

As the hydrocarbon residue in the carbonyl group substituted by the hydrocarbon residue, shown by $R^4$, mention is made of, for example, saturated or unsaturated hydrocarbon residues having up to 25 carbon atoms. Examples of them include alkyl (e.g. $C_{1-8}$ alkyl such as methyl, ethyl, propyl, isopropyl, butyl, isobutyl, sec-butyl, t-butyl, pentyl, isopentyl, hexyl and heptyl), cycloalkyl (e.g. $C_{3-6}$ cycloalkyl such as cyclopropyl, cyclobutyl, cyclopentyl and cyclohexyl), alkoxyalkyl (e.g. $C_{1-3}$ alkoxy-$C_{1-6}$ alkyl such as methoxymethyl, ethoxymethyl, ethoxybutyl and propoxyhexyl), alkenyl (e.g. $C_{2-6}$ alkenyl such as vinyl, butenyl, butadienyl and hexatrienyl), aryl (e.g. $C_{6-14}$ aryl such as phenyl, naphthyl and anthracenyl) and aralkyl (e.g. $C_7zo_0$ aralkyl such as benzyl, benzhydryl and trityl). As the substituents, mention is made of the same substituents on the above group bonded through a carbon atom.

$R^1$ and $R^2$ (desirably $R^1$) are preferably such ones as either one of them being a group of the formula:

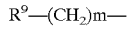
$R^9$—$(CH_2)m$— wherein $R^9$ is a group bonded through nitrogen atom, and m is an integer of 0 to 3 and the other one (desirably $R^2$) being a group represented by the general formula:

$R^{10}$—A— wherein $R^{10}$ is an optionally substituted phenyl group and A is spacer group.

The optionally substituted group bonded through nitrogen atom, shown by the above-mentioned $R^9$, is of the same meaning as described above. The optionally substituted group bonded through nitrogen atom is preferably a group of the formula: —$NR^{39}R^{40}$ wherein $R^{39}$ is an alkyl group and $R^{40}$ is an aralkyl group.

Examples of the substituents in optionally substituted phenyl group shown by the above-mentioned $R^{10}$ include halogen (fluorine, chlorine, bromine and iodine), $C_{1-8}$ alkyl (e.g. methyl, ethyl, propyl, isopropyl, butyl, isobutyl, sec-butyl, tert-butyl, pentyl, isopentyl and neopentyl) optionally substituted with 1 to 3 halogen atoms (fluorine, chlorine, bromine and iodine), $C_{1-8}$ alkoxy (e.g. methoxy, ethoxy, propoxy, isopropoxy, butoxy and isobutoxy) optionally substituted with 1 to 3 halogen atoms (e.g. fluorine, chlorine, bromine and iodine), $C_{1-8}$ alkylthio (e.g. methylthio, ethylthio, propylthio, isopropylthio, butylthio, sec-butylthio, tert-butylthio, pentylthio, isopentylthio and neopentylthio) optionally substituted with 1 to 3 halogen atoms (fluorine, chlorine, bromine and iodine), $C_{1-6}$ alkanoylamino (e.g. formylamino, acetylamino, propionylamino, butyrylamino, isobutyrylamino, valerylamino, isovalerylamino), $C_{1-6}$ alkanoyloxy (e.g. formyloxy, acetoxy and propionyloxy), hydroxyl, carboxyl, $C_{1-6}$ alkoxy-carbonyl (e.g.methoxycarbonyl, ethoxycarbonyl and t-butoxycarbonyl), cyano, nitro, amino, and mono- or di-$C_{1-6}$ alkylcarbamoyl (e.g. methylcarbamoyl, ethylcarbamoyl and dimethylcarbamoyl). The number of substituents ranges from 1 to 5, preferably 1 to 3.

As the spacer group shown by the symbol "A", mention is made of those as defined above, e.g. a chemical bond or methylene.

$R^3$ is preferably a group of the formula:

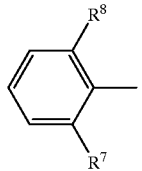

wherein $R^7$ is hydrogen, halogen or a group bonded through a carbon, nitrogen, oxygen or sulfur atom, and $R^8$ is hydrogen, halogen, nitro, cyano or optionally substituted aliphatic hydrocarbon residue which may optionally be substituted with a group bonded through carbon, oxygen, nitrogen or sulfur atom.

The above-mentioned optionally substituted groups bonded through carbon, nitrogen, oxygen or sulfur atom, shown by $R^7$ are of the same meaning as defined above.

Examples of the optionally substituted aliphatic hydrocarbon residue, in the optionally substituted aliphatic hydrocarbon residue bonded through oxygen, nitrogen or sulfur atom shown by the above-mentioned $R^8$, include $C_{1-15}$ alkyl (e.g. methyl, ethyl, propyl, isopropyl, butyl, isobutyl, s-butyl, pentyl, hexyl, heptyl, octyl, nonyl, decyl, undecyl, dodecyl, tridecyl, tetradecyl and pentadecyl), $C_{3-8}$ cycloalkyl (e.g. cyclopropyl, cyclobutyl, cyclopentyl and cyclohexyl), $C_{2-10}$ alkenyl (e.g. vinyl, allyl, 2-methylallyl, 2-butenyl, 3-butenyl and 3-octenyl), $C_{2-10}$ alkynyl (e.g. ethynyl, 2-propynyl and 3-hexynyl) and $C_{1-6}$ alkoxy (e.g. methoxy, ethoxy, propoxy and butoxy). Examples of the substituents, which the said hydrocarbon group may have, include nitro, hydroxyl, oxo, thioxo, cyano, carbamoyl, carboxyl, $C_{1-4}$ alkoxycarbonyl (e.g. methoxycarbonyl and ethoxycarbonyl), sulfo, halogen (fluorine, chlorine, bromine and iodine), $C_{1-4}$ alkoxy (e.g. methoxy, ethoxy, propoxy, isopropoxy, butoxy, isobutoxy, s-butoxy and t-butoxy), $C_{1-4}$ alkylthio (e.g. methylthio, ethylthio, n-propylthio, isopropylthio, n-butylthio and t-butylthio), amino, $C_{1-6}$ alkanoylamino (e.g. acetylamino and propionylamino), mono- or di- $C_{1-4}$ alkylamino (e.g. methylamino, ethylamino, n-propylamino, isopropylamino, n-butylamino, dimetylamino and diethylamino), $C_{1-4}$ alkanoyl (e.g. formyl, acetyl and propionyl), 5- or 6-membered heterocyclic groups containing, besides carbon atoms, 1 to 4 heteroatoms selected from oxygen, sulfur and nitrogen, as exemplified by 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H or 2H-tetrazolyl, 2-, 3- or 4-pyridyl, 2-, 4- or 5-pyrimidyl, 3- or 4-pyridazinyl, quinolyl, isoquinolyl and indolyl, which may optionally have 1 to 4 substituents selected from (a) halogen (e.g. fluorine, chlorine, bromine and iodine) and (b) $C_{1-4}$ alkyl (e.g. methyl, ethyl, propyl and isopropyl), and $C_{1-6}$ haloalkyl (e.g. difluoromethyl, trifluoromethyl, trifluoroethyl and trichloroethyl). Number of the substituents ranges from 1 to 4, preferably 1 to 3.

$R^4$ is preferably a carbonyl group substituted with an optionally substituted hydrocarbon residue.

$R^5$ is preferably a hydrogen atom.

The compound (XI) is preferably such ones as a compound represented by the formula:

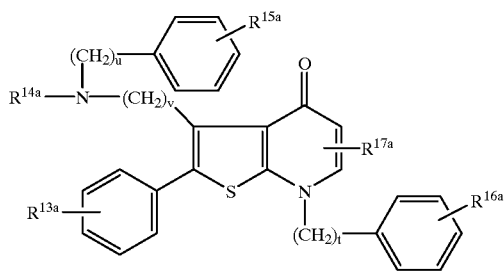

wherein $R^{13a}$ stands for 1 to 5 substituents and independently stand for a hydrogen atom, an alkyl group, an alkoxy group, a halogen atom or an alkanoylamino group; $R^{14a}$ stands for a hydrogen atom or an alkyl group; $R^{15a}$ stands for 1 to 5 substituents and independently stand for a hydrogen atom, a halogen atom, an alkyl group, an alkoxy group or an alkylthio group; $R^{16a}$ stands for 1 to 5 substituents and independently stand for a hydrogen atom, an alkyl group, a halogen atom or an alkoxy group; $R^{17a}$ stands for one or two substituents and independently stands for an optionally esterified or amidated carboxyl group, an alkylcarbonyl group, an arylcarbonyl group or an optionally substituted alkyl group; and each v, t and u denote an integer of 1 to 4; or a compound represented by the formula:

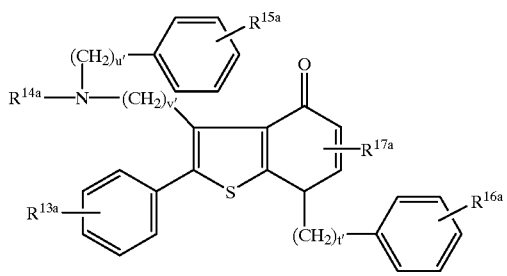

wherein $R^{13b}$ stands for 1 to 3 substituents and independently stand for hydrogen atom, a $C_{1-6}$ alkoxy group or alkanoylamino, $R^{14b}$ stands for hydrogen atom or a $C_{1-6}$ alkyl group, $R^{15b}$ stands for 1 to 3 substituents and independently stand for a hydrogen atom or a halogen atom, $R^{16b}$ stands for 1 to 3 substituents and independently stand for a hydrogen atom, a halogen atom or a $C_{1-6}$ alkoxy group, $R^{17b}$ stands for 1 to 2 substituents and independently stand for a carboxyl group which may optionally be esterified or amidated or a alkylcarbonyl group, and each v', t' and u' denote an integer of 1 to 3 $R^{17a}$ or $R^{17b}$ is preferably bonded at 5-position.

Especially preferable examples of the compound (XI) include 4,7-dihydro-3-(N-methyl-N-benzylaminomethyl)-7-(2-methoxybenzyl)-2-(4-methoxyphenyl)-4-oxo-thieno[2,3-b]pyridine-5-carboxylic acid ethyl ester or its salt, 2-(4-acethylaminophenyl)-4,7-dihydro-3-(N-methyl-N-benzylaminomethyl)-7-(2-methoxybenzyl)-4-oxo-thieno[2,3-b]pyridine-5-carboxylic acid ethyl ester or its salt, 5-n-butyryl-4,7-dihydro-3-(N-methyl-N-benzylamino-methyl)-7-(2-fluorobenzyl)-2-(4-methoxyphenyl)-4-oxo-thieno[2,3-b]pyridine or its salt, 5-benzoyl-4,7-dihydro-3-(N-methyl-N-benzylaminomethyl)-7-(2-fluorobenzyl)-2-(4-methoxyphenyl)-4-oxo-thieno[2,3-b]pyridine or its salt, 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine or its salt. 7-(2,6-difluorobenzyl)-4,7-dihydro-3-(N-methyl-N-benzylaminomethyl)-5-isobutyryl-2-(4-propionylaminophenyl)-4-oxo-thieno[2,3-b]pyridine or its salt, and 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine or its salt.

In the compound of the formula (X), a preferable examples include also a compound of the formula (XII):

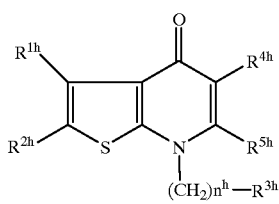

(XII)

wherein each of $R^{1h}$ and $R^{2h}$ are hydrogen or a group bonded through a carbon atom, a nitrogen atom, an oxygen atom or a sulfur atom, $R^{3h}$ is an optionally substituted homo-or hetero-cyclic group, $R^{4h}$ is an optionally substituted heterocyclic group or a group bonded through a hetero atom, $R^{5h}$ is hydrogen or a group bonded through a carbon atom, $n^h$ is an integer of 0 to 3.

$R^{1h}$, $R^{2h}$, $R^{3h}$ and $R^{5h}$ are of the same meanings as each of $R^{1e}$, $R^{2e}$, $R^{3e}$ and $R^{5e}$.

The optionally substituted heterocyclic group of $R^{4h}$ is of the same meaning as in $R^{4e}$.

Examples of the group bonded through a hetero atom includes a group bonded through a nitrogen atom of $R^{4h}$, a group bonded through an oxygen atom and a group bonded through a sulfur atom. Those groups are the same as defined in $R^{4e}$.

In the compound (XII), preferred examples of $R^{1h}$ are a group bonded through a carbon atom or a group bonded through a nitrogen atom. As the group bonded through a carbon atom, mention is made of an optionally substituted $C_{1-20}$ hydrocarbon residue, especially, an optionally substituted $C_{1-10}$ alkyl group or an optionally substituted $C_{1-6}$ alkyl group. As substituents in the optionally substituted $C_{1-20}$ hydrocarbon residue of $R^{1h}$, mention is made of (1) halogen, (2) nitro, (3) cyano, (4) an optionally substituted amino, (5) an optionally substituted hydroxyl group, (6) a group of the formula: —S(O)$t^h$—R$^{6h}$ (wherein $t^h$ denotes an integer of 0 to 2, and $R^{6h}$ is a hydrogen atom or an optionally substituted hydrocarbon residue.) A more preferable example of $R^{1h}$ is substituted amino-alkyl such as N,N-disubstituted aminoalkyl. The most preferable example of $R^{1h}$ is N-aralkyl-N-alkylaminoalkyl, especially N-$C_{7-11}$ aralkyl-N-$C_{1-6}$ alkylamino-$C_{1-6}$ alkyl.

As the preferable example of $R^{2h}$, mention is made of a group bonded through a carbon atom, especially an optionally substituted $C_{1-20}$ hydrocarbon residue, more especially an optionally substituted $C_{6-14}$ aryl group. As the preferable examples of the substituents, mention is made of (1) an optionally substituted amino, (2) an optionally substituted hydroxyl group, (3) an optionally substituted carbamoyl, (4) an optionally substituted carboxyl, (5) an optionally substituted alkenyl, (6) acyl or (7) nitro.

The preferable substituents in the optionally substituted aryl, include (1) an alkoxy group, (2) an alkylcarbonyl group, (3) an alkylaminocarbonyl group, (4) an optionally substituted alkenyl, whose preferable substituent includes alkylcarbonyl or alkylaminocarbonyl, or (5) an optionally substituted amino, whose preferable substituent includes an alkyl group or an alkyl group which is substituted by alkanoyl, alkanoyl or hydroxy. Especially, an alkanoylamino group or an alkoxy group is more preferable.

As the preferable group of $R^{2h}$, mention is made of a $C_{6-14}$ aryl group which may optionally be substituted with a group selected from the group consisting of (i) nitro, (ii) $C_{1-6}$ alkoxy and (iii) amino which may optionally be substituted $C_{1-6}$ alkanoyl.

As the preferable example of $R^{3h}$, mention is made of an optionally substituted homo-cyclic group, more preferably, an optionally substituted $C_{6-14}$ aryl group.

The substituents in the optionally substituted homo-cyclic group, mention is made of (1) halogen, (2) nitro, (3) an optionally substituted hydroxyl group, (4) a group of the formula: —S(O)$t^h$—R$^{6h}$ (wherein $t^h$ denotes an integer of 0 to 2, and $R^{6h}$ is a hydrogen atom or an optionally substituted hydrocarbon residue).

As more preferable group of $R^3$, mention is made of an aryl group substituted by one or two halogens. As the aryl group, phenyl is most preferable. The most preferable group of $R^3$ is a phenyl group substituted by fluorine.

As the preferable example of the heterocyclic group in the optionally substituted heterocyclic group of $R^{4h}$, mention is made of an optionally substituted 3- to 8-membered heterocyclic group, especially an optionally substituted 5- to 8-membered heterocyclic group having at a least one nitrogen atom in a ring, and more preferably 5- to 6-membered heterocyclic group having at least one nitrogen atom in a ring. As the preferred examples of the heterocyclic ring, mention is made of oxazolyl, isoxazolyl, thiazolyl, imidazolyl, triazolyl, oxoimidazolyl, thiazinyl. Among others, isoxazoly is most preferred.

Preferred examples of the substituent to the heterocyclic group are (1) halogen, (2) nitro, (3) an optionally substituted hydroxyl group, (4) a group of the formula: —S(O)m$^h$-R$^{6h}$ (wherein m denotes an integer of 0 to 2, and $R^{6h}$ is a hydrogen atom or an optionally substituted hydrocarbon residue), (5) an optionally substituted amino, or (6) a $C_{1-10}$ hydrocarbon residue.

Preferred examples of the substituents on the optionally substituted amino group, the optionally substituted hydroxyl group or the optionally substituted mercapto group of $R^{4h}$ are (1) $C_{1-10}$ hydrocarbon residue which may optionally be substituted by $C_{1-6}$ alkoxy-carbonyl or carbamoyl, (2) $C_{1-10}$ acyl group, or (3) a group of the formula: —S(O)$t^h$—R$^{6h}$ wherein $t^h$ denotes an integer of 0 to 2, and $R^{6h}$ is a hydrogen atom or an optionally substituted hydrocarbon residue.

Preferably $R^{4h}$ is (1) a 5- or 6-membered heterocyclic group which has one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxycarbonyl or carbamoyl, (ii) $C_{1-6}$ alkanoyl and (iii) $C_{1-6}$ alkylsulfonyl, (3) a group of the formula: —S(O)$t^h$—R$^{6h'}$, wherein t is an integer of 0 to 2 and $R^{6h}$ is $C_{1-6}$ alkyl, or (4) an amino group which may optionally be substituted with $C_{1-6}$ alkanoyl.

As the group $R^{5h}$, a hydrogen atom or a hydrocarbon residue is preferable, especially, a hydrogen atom or $C_{1-20}$ hydrocarbon atom is more preferable. Among others, hydrogen atom or $C_{1-10}$ alkyl is more preferable. Hydrogen atom is most preferable.

More preferable examples of the compound (XII) include a compound of the formula (XII), wherein $R^{1h}$ is an alkyl group which may optionally be substituted with halogen or N-$C_{7-13}$ aralkyl-N-$C_{1-6}$ alkylamino, $R^{2h}$ is a $C_{6-14}$ aryl group which may optionally be substituted with a group selected from the group consisting of (i) nitro, (ii) $C_{1-6}$ alkoxy and (iii) amino which may optionally be substituted with $C_{1-6}$ alkanoyl, $R^{3h}$ is a mono- or di-halogeno-$C_{6-14}$ aryl group, $R^{4h}$ is (1) a 5- or 6-membered heterocyclic group which has at least one nitrogen atom and one oxygen atom and which is bonded through a carbon atom, (2) a hydroxyl group which may optionally be substituted with a group selected from the group consisting of (i) $C_{1-6}$ alkyl which may optionally be substituted with $C_{1-6}$ alkoxy-carbonyl or carbamoyl, (ii) $C_{1-6}$ alkanoyl and (iii) $C_{1-6}$ alkylsulfonyl, (3) a group of the formula: —S(O)$t^h$—R$^{6h'}$, wherein $t^h$ is an integer of 0 to 2 and $R^{6h'}$is $C_{1-6}$ alkyl, or (4) an amino group which may optionally be substituted with $C_{1-6}$ alkanoyl, $R^{5h}$ is a hydrogen atom and $n^h$ is 1.

In the formula (XII), $n^k$ is preferably 1.

Concrete examples of these groups are the same as those mentioned above.

In the compound of the formula (X), preferable examples include a compound of the formula (XIII):

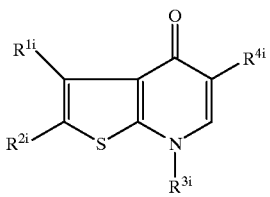 (XIII)

wherein $R^{1i}$ stands for a group represented by the formula:

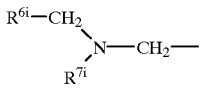

(wherein $R^{6i}$ stands for (1) phenyl group which may optionally be substituted with fluorine, bromine, sulfamoyl, methylthio or nitro, (2) 2- or 3-pyridyl group, (3) 3-indolyl group optionally substituted with methyl, (4) propyl group or (5) butylcarbamoyl group, and $R^{7i}$ stands for methyl group) or hexamethylenetetraaminomethyl group, $R^{2i}$ stands for phenyl group substituted with methoxycarbonylvinyl, ethoxycarbonylvinyl, carboxyvinyl, benzoylvinyl, acetylvinyl, propionylvinyl, isobutyrylamino, propionylamino, 3-oxobutylamino, 3-oxopentylamino, 2-hydroxycyclohexylamino, trifluoroacetylamino, 2-hydroxypropylamino, 2-hydroxybutylamino, 2-hydroxyisobutylamino, N-ethyl-N-trifluoroacetylamino, methylamino, ethylamino, propylamino, butylamino, isobutylamino, diethylamino, 1-pyrrolidinylamino, ethanesulfonamide or acetonyloxy, $R^{3i}$ stands for 2-fluorobenzyl group or 2,6-difluorobenzyl group, and $R^{4i}$ stands for (1) acyl group or (2) a $C_{1-6}$ alkyl group optionally substituted with hydroxy or alkylcarbonyloxy, or salts thereof.

Preferable examples of the group shown by $R^{1i}$ in the compound (XIII) of this invention include N-methyl-N-benzylaminomethyl.

The number of substituents in $R^{2i}$ and $R^{4i}$ in the compound (XIII) of this invention ranges from 1 to 6, preferably 1 to 3, more preferably 1 to 2.

Preferable examples of the group shown by $R^{2i}$ in the compound (XIII) of this invention include phenyl group substituted with groups represented by the formula $R^{10i}$—$R^{9i}$— ( wherein $R^{9i}$ stands for vinyl group and $R^{10i}$ stands for methoxycarbonyl, ethoxycarbonyl, carboxyl, benzoyl, acetyl or propionyl), groups represented by the formula $R^{11i}$—NH— (wherein $R^{11i}$ stands for 3-oxobutyl, 3-oxopentyl or 2-hydroxycyclohexyl) or groups represented by the formula $R^{12i}$—O— (wherein $R^{12i}$ stands for acetonyl).

Preferable examples of acyl shown by $R^{4i}$ in the compound (XIII) of this invention include groups represented by the formula —CO—$R^{8i}$ (wherein —$R^{8i}$ stands for optionally substituted hydrocarbon residue or optionally substituted heterocyclic group).

Example of the hydrocarbon residue are those as defined in the above.

Examples of substituents of the hydrocarbon residue include nitro, hydroxy, oxo, thioxo, cyano, sulfo, carbamoyl, carboxyl, halogen (e.g. fluorine, chlorine, bromine, iodine), $C_{1-6}$ alkoxy (e.g. methoxy, ethoxy, propoxy, isopropoxy and butoxy), $C_{1-3}$ alkoxy-$C_{1-6}$ alkoxy, amino, mono- or di-$C_{1-6}$ alkylamino (e.g. methylamino, ethylamino, propylamino, dimethylamino and diethylamino), $C_{1-6}$ alkyl-carbonyl, $C_{1-6}$ alkyl-carbonyloxy (e.g. acetoxy and ethyl carbonyloxy), $C_{1-6}$ alkyl-thio, $C_{1-6}$ alkyl-sulfonyl, $C_{1-6}$ alkyl-sulfinyl, benzoyl, phenoxy, alkylenedioxy and heterocyclic groups described below. The number of substituents ranges from 1 to 6, preferably 1 to 3, more preferably 1 to 2.

Examples of the heterocyclic groups are those as defined in the above.

Examples of substituents of the heterocyclic groups include $C_{1-6}$ alkyl (e.g. methyl, ethyl, propyl, isopropyl, butyl, isobutyl, sec-butyl and tert-butyl), $C_{2-6}$ alkenyl (e.g. vinyl, 1-methylvinyl, 1-propenyl and allyl), $C_{2-6}$ alkynyl (e.g. ethynyl, 1-propynyl and propargyl), $C_{3-6}$ cycloalkyl (e.g. cyclopropyl, cyclobutyl, cyclopentyl and cyclohexyl), $C_{5-7}$ cycloalkenyl (e.g. cyclopentenyl and cyclohexenyl), $C_{7-11}$ aralkyl (e.g. benzyl, α-methylbenzyl and phenethyl), $C_{6-14}$ aryl (e.g. phenyl and naphthyl), $C_{1-6}$ alkoxy (e.g. methoxy, ethoxy, propoxy, iso-propoxy, n-butoxy, isobutoxy, sec-butoxy and tert-butoxy), $C_{6-14}$ aryloxy (e.g. phenoxy), $C_{1-6}$ alkanoyl (e.g. formyl, acetyl, propionyl, n-butyryl and iso-butyryl), $C_{6-14}$ aryl-carbonyl (e.g. benzoyl), $C_{1-6}$ alkanoyloxy (e.g. formyloxy, acetyloxy, propionyloxy, n-butyryloxy and iso-butyryloxy), carboxyl, $C_{1-6}$ alkoxy-carbonyl (e.g. methoxycarbonyl, ethoxycarbonyl, n-propoxycarbonyl, isopropoxycarbonyl, n-butoxycarbonyl, isobutoxycarbonyl and tert-butoxycarbonyl), carbamoyl group, halogen (fluorine, chlorine, bromine, iodine), oxo, amino, mono- or di-$C_{1-4}$ alkylamino (e.g. methylamino, ethylamino, propylamino, isopropylamino, butylamino, dimethylamino, diethylamino, dipropylamino, diisopropylamino and dibutylamino), $C_{1-6}$ alkanoylamino (e.g. formamide, acetamide, trifluoroacetamide, propionylamide, butyrylamide and isobutyrylamide), carbamoylamino, N-$C_{1-4}$ alkyl carbamoylamino (e.g. N-methylcarbamoylamino, N-ethylcarbamoylamino, N-propylcarbamoylamino, N-isopropylcarbamoylamino and N-butylcarbamoylamino), nitro, cyano, mercapto, sulfo, sulfino, phosphono, sulfamoyl, $C_{1-6}$ alkylsulfamoyl (e.g. N-methylsulfamoyl, N-ethylsulfamoyl, N-propylsulfamoyl, N-isopropylsulfamoyl and N-butylsulfamoyl), di-$C_{1-6}$ alkylsulfamoyl (e.g. N,N-dimethylsulfamoyl, N,N-diethylsulfamoyl, N,N-dipropylsulfamoyl and N,N-dibutylsulfamoyl), $C_{1-6}$ alkylthio (e.g. methylthio, ethylthio, propylthio, isopropylthio, n-butylthio, sec-butylthio and tert-butylthio), $C_{1-6}$ alkylsulfinyl (e.g. methylsulfinyl, ethylsulfinyl, propylsulfinyl and butylsulfinyl) and $C_{1-6}$ alkylsulfonyl (e.g. methylsulfonyl, ethylsulfonyl, propylsulfonyl and butylsulfonyl). The number of substituents ranges from 1 to 6, preferably 1 to 3, more preferably 1 to 2.

Preferable examples of the hydrocarbon residue shown by $R^{8i}$ in the above-mentioned —CO—$R^{8i}$ include optionally substituted $C_{6-14}$ aryl groups and optionally substituted $C_{1-6}$ alkyl groups.

Preferable examples of substituents in the optionally substituted $C_{6-14}$ aryl groups include alkyl, alkoxy, alkoxyalkoxy, alkylenedioxy, phenoxy, hydroxyl, alkylcarbonyloxy, mono- or di-alkylamino and alkylthio.

Examples of substituents in the optionally substituted $C_{1-6}$ alkyl groups include hydroxy, halogen, nitro, cyano, alkoxycarbonyl, alkoxy or groups represented by the formula —S(O)$p^i$—$R^{7i}$ (wherein $p^i$ denotes an integer of 0 to 2, $R^{7i}$ stands for alkyl), and alkylenedioxy.

Preferable examples of the heterocyclic groups shown by $R^{8i}$ include thienyl, furyl, pyrrolyl, pyridyl, pyrimidinyl, thiazolyl, imidazolyl, triazolyl, isoxazolyl, isothiazolyl, morpholinyl, oxoimidazonyl, pyrrolidinyl, piperidinyl and thiazinyl. Especially, thienyl is preferable.

Preferable examples of substituents of the said heterocyclic groups include $C_{1-6}$ alkyl, $C_{1-6}$ alkoxy, carboxyl, $C_{1-6}$ alkxoy-carbonyl, carbamoyl group, halogen, oxo, amino, mono- or di-$C_{1-4}$ alkylamino, nitro, cyano, mercapto, sulfo, sulfino, phosphono, sulfamoyl and $C_{1-6}$ alkylthio.

More preferable examples of the group —CO—$R^{8i}$ include (1) benzoyl group substituted with alkoxy, alkoxyalkyl, alkylenedioxy, phenoxy, hydroxy, alkylcarbonyloxy, mono- or di-alkylamino, or alkylthio, (2) alkylcarbonyl group substituted with alkylenedioxy or (3) thienylcarbonyl group.

Preferable examples of $C_{1-6}$ alkyl groups, shown by $R^{4i}$, optionally substituted with hydroxyl or alkylcarbonyloxy include alkyl groups substituted with hydroxy or acetyloxy, and, further, 2-hydroxyisobutyl and 2-acetoxyisobutyl are preferable.

In the above definitions, as alkylenedioxy group, mention is made of, for example, $C_{1-3}$ alkylenedioxy groups, which are exemplified by methylenedioxy, ethylenedioxy and propylenedioxy.

As alkyl group in the above definitions, $C_{1-6}$ alkyl groups are preferable, which are exemplified by methyl, ethyl, n-propyl, isopropyl, n-butyl, isobutyl, sec-butyl, tert-butyl, pentyl, isopentyl and hexyl. Among them, $C_{1-3}$ alkyl groups are more preferable.

As alkoxy group in the above definitions, mention is made of $C_{1-6}$ alkoxy groups, which are exemplified by methoxy, ethoxy, propoxy, isopropoxy, butoxy, isobutoxy, sec-butoxy, tert-butoxy, pentyloxy, isopentyloxy, neopentyloxy and hexyloxy. Among them, $C_{1-3}$ alkoxy groups are preferable.

In the compound of the formula (X), preferable examples include a compound of the formula (XIV):

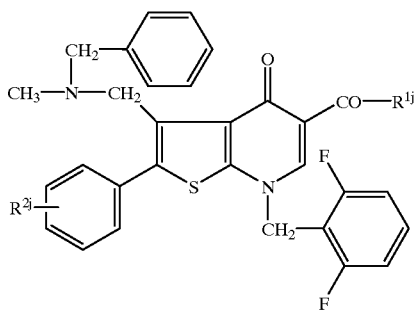

(XIV)

wherein $R^{1j}$ stands for an optionally substituted branched alkoxy group or hydroxy group, and $R^{2j}$ stands for $C_{1-8}$ alkanoylamino group, or a salt thereof.

In the above formula, preferable examples of the branched alkoxy group in the optionally substituted branched alkoxy group shown by $R^{1j}$ include $C_{3-13}$ branched alkoxy groups (e.g. isopropoxy, sec-butoxy, tert-butoxy, isopentoxy, sec-pentyloxy, tert-pentyloxy, 3-pentyloxy, isohexyloxy, sec-hexyloxy, tert-hexyloxy, isooctyloxy, sec-octyloxy, tert-octyloxy, cyclopentyloxy, cyclopropyloxy, cyclobutyloxy, cycloheptyloxy, 2-indanyloxy, 4-piperidinyloxy, tetrahydro-4H-pyra-4-nyloxy). As the branched alkoxy group, among them, $C_{3-7}$ branched alkoxy groups are preferable, and isopropoxy, sec-butoxy, 3-pentyloxy or 2,4-dimethyl-3-pentyloxy are especially preferable.

The branched alkoxy group may optionally have substituents, as exemplified by $C_{1-4}$ alkyl, halogen, amino, mono- or di-$C_{1-4}$ alkylamino, $C_{1-4}$ alkoxy and $C_{3-7}$ cycloalkyl. Among them, $C_{1-4}$ alkyl and halogen are preferable. As the $C_{1-4}$ alkyl in $C_{1-4}$ alkyl and mono- or di-$C_{1-4}$ alkylamino, mention is made of, for example, methyl, ethyl, propyl, isopropyl, n-butyl, isobutyl, s-butyl and t-butyl. Among them, $C_{12}$ alkyl is preferable. As the halogen, mention is made of fluorine, chlorine, bromine and iodine. Among them, fluorine and chlorine are preferable. Examples of the $C_{1-4}$ alkoxy include methoxy, ethoxy, propoxy, isopropoxy, butoxy and isobutoxy. Among them, methoxy and ethoxy are preferable. Examples of the $C_{3-7}$ cycloalkyl include cyclopropyl, cyclobutyl, cyclopentyl and cyclohexyl. Among them, cyclohexyl is preferable. The number of these substituents ranges from 1 to 3, preferably 1 or 2.

Specific examples of the optionally substituted branched alkoxy groups include those represented by the formula —O—$R^{3j}$, wherein $R^{3j}$ is for example isopropyl, sec-butyl, tert-butyl, isopentyl, sec-pentyl, tert-pentyl, 3-pentyl, isohexyl, sec-hexyl, tert-hexyl, isooctyl, sec-octyl tert-octyl, 1,3-difluoro-2-propyl, 2,6-dimethyl-1-cyclohexyl, 3,5-dimethyl-1-cyclohexyl, cyclopentyl, cyclopropyl, 4-methyl-1-cyclohexyl, cyclobutyl, cycloheptyl, 4-ethylcyclohexyl, 2-indanyl, 4-piperidinyl, N-methyl-4-piperidinyl, N-ethyl-4-piperidinyl, tetrahydro-4H-pyra-4-nyl, 1,3-bis(dimethylamino)-2-propyl, 1,3-dimethoxy-2-propyl, 4-amino-1-cyclohexyl or dicyclohexylmethyl.

Preferable examples of $R^{1j}$ include $C_{3-7}$ branched alkoxy groups optionally substituted with $C_{1-4}$ alkyl or halogen, and, isopropoxy optionally substituted with halogen is especially preferable.

In the above formula, examples of the $C_{1-8}$ alkanoylamino group shown by $R^{2j}$ include formylamino, acetylamino, propionylamino, butyrylamino, isobutyrylamino and octanoylamino. As the alkanoylamino group shown by $R^{2j}$, $C_{3-5}$ alkanoylamino is preferable, isobutyrylamino being especially preferable.

$R^{2j}$ is preferably phenyl having one or two substituents, and, phenyl group having one substituent at the 4-position is especially preferable.

The compound of the formula (X), preferable examples include a compound of the formula (XV):

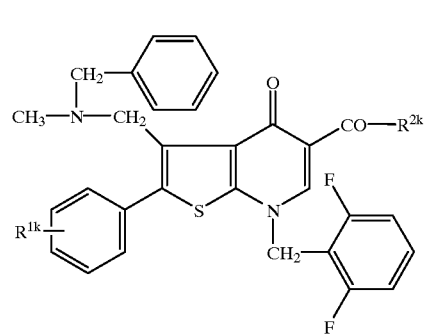

(XV)

wherein $R^{1k}$ stands for an alkoxy group substituted with a group selected from (i) halogen, (ii) cycloalkyl and (iii) alkenyl optionally substituted with alkyl, and $R^{2k}$ stands for alkyl group, aryl group or an optionally substituted alkoxy group, or a salt thereof.

In the above formula, as the alkoxy group in the substituted alkoxy group with a group selected from (i) halogen, (ii) cycloalkyl and (iii) alkenyl optionally substituted with alkyl, $C_{1-6}$ alkoxy group is preferable, as exemplified by methoxy, ethoxy, propoxy, isopropoxy, butoxy, isobutoxy, sec-butoxy, tert-butoxy, pentoxy and hexyloxy. Among them, $C_{1-3}$ alkoxy group is preferable, and methoxy is especially preferable.

In $R^{1k}$ of the above formula, as the substituent halogen on the alkoxy group, fluorine, chlorine, bromine and iodine are mentioned. Among them, fluorine is preferable. As the substituent cycloalkyl on the alkoxy group, $C_{3-10}$ cycloalkyl is preferable, which is exemplified by cyclopropyl, cyclobutyl, cyclopentyl, cyclohexyl, cycloheptyl, cyclooctyl and cyclononyl. Among them, $C_{3-6}$ cycloalkyl is preferable, and cyclopropyl is especially preferable. As the alkenyl group optionally substituted with the substituent alkyl on the alkoxy group, $C_{2-10}$ alkenyl is preferable, which is exemplified by vinyl, allyl, 1-butenyl, 2-butenyl butadienyl, isopropenyl, hexatrienyl and 3-octenyl. Among them, $C_{2-6}$ alkenyl group is preferable, and $C_{2-4}$ alkenyl group is especially preferable. As the alkyl in the alkenyl group optionally substituted with alkyl, $C_{1-3}$ alkyl is preferable, which is exemplified by methyl, ethyl propyl and isopropyl, methyl being especially preferable. Preferable examples of the alkenyl group substituted with alkyl include 2-methyl allyl.

As $R^{1k}$, a $C_{1-3}$ alkoxy group substituted with a group selected from (i) halogen, (ii) $C_{3-10}$ cycloalkyl and ii)$C_{2-10}$ alkenyl is preferable, and, further, vinyl-$C_{1-3}$ alkoxy is preferable, allyloxy being especially preferable.

The number of substituents in $R^{1k}$ is preferably 1 to 3, especially 1 to 2.

As the alkyl group shown by $R^{2k}$, $C_{1-6}$ alkyl group is preferable, exemplified by methyl, ethyl, n-propyl, isopropyl, butyl, isobutyl, sec-butyl, tert-butyl, pentyl and hexyl. Among them, $C_{1-3}$ alkyl is preferable, especially $C_3$ alkyl group (n-propyl, isopropyl) being preferable.

As the aryl group shown by $R^{2k}$, $C_{6-14}$ aryl group is preferable, exemplified by phenyl, naphthyl, anthryl, phenanthryl and anthracenyl.

As the alkoxy group in optionally substituted alkoxy group shown by $R^{2k}$, straight-chain or branched $C_{1-9}$ alkoxy group is preferable, exemplified by methoxy, ethoxy, propoxy, isopropoxy, butoxy, isobutoxy, sec-butoxy, tert-butoxy, pentoxy, isopentyloxy, sec-pentyloxy, tert-pentyloxy, 3-pentyloxy, neopentyloxy, hexyloxy, isohexyloxy, sec-hexyloxy, tert-hexyloxy, octyloxy, isooctyloxy, sec-octyloxy and tert-octyloxy. Among them, $C_{3-7}$ alkoxy group is preferable, and $C_3$ alkoxy group (n-propoxy, isopropoxy) being especially preferable.

As substituent in the optionally substituted alkoxy group shown by $R^{2k}$, mention is made of halogen, alkoxy, alkyl and cycloalkyl. The halogen is exemplified by fluorine, chlorine, bromine and iodine. Among the, fluorine and chlorine are preferable. As alkoxy, $C_{1-4}$ alkoxy is preferable, exemplified by methoxy, ethoxy, propoxy, isopropoxy, butoxy, isobutoxy, sec-butoxy and tert-butoxy. Among them, methoxy is especially preferable. As the alkyl, $C_{1-4}$ alkyl is preferable, exemplified by methyl, ethyl, n-propyl, isopropyl, butyl, isobutyl, sec-butyl and tert-butyl. Among them, methyl is especially preferable. As cycloalkyl, $C_{3-8}$ cycloalkyl is preferable, exemplified by cyclopropyl, cyclopentyl, cyclohexyl, cycloheptyl and cyclooctyl. Examples of substituted alkoxy include cyclopentyloxy, cyclopropyloxy, cyclobutyloxy, cycloheptyloxy, 2-indanyloxy and 4-piperidinyloxy, tetrahydro-4H-pyra-4-nyloxy.

As $R^{2k}$, (1) $C_{1-3}$ alkyl, (2) $C_{6-14}$ aryl group or (3) $C_{3-7}$ alkoxy group optionally substituted with halogen, $C_{1-3}$ alkyl or $C_{1-3}$ alkoxy is preferable. Among them, isopropyl, phenyl or isopropoxy are especially preferable.

The number of substituents in the group shown by $R^{2k}$ is preferably 1 to 3, especially 1 to 2.

Preferable $R^{2k}$ is phenyl group having 1 to 2 substituents, especially phenyl group having one substituent at the 4-position is preferable.

In the compound of the formula (XX), preferable examples include a compound of the formula (XXI):

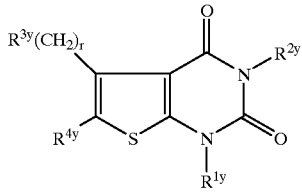

(XXI)

wherein $R^{1y}$ is hydrogen, an alkyl group or a group of the formula:

$Q-(CH_2)p^y-$ in which Q is (1) an aryl group which may be substituted by one or more of (i) halogen, (ii) nitro, (iii) cyano, (iv) amino, (v) an optionally substituted carboxyl, (vi) alkylenedioxy and (vii) a group of the formula: $-A^y-R^{5y}$ in which $A^y$ is a chemical bond or a spacer group and $R^{5y}$ is an alkyl group, (2) an optionally substituted cycloalkyl group or (3) an optionally substituted heterocyclic group, and $p^y$ is an integer of 0 to 3;

$R^{2y}$ is hydrogen, an alkyl group which may be substituted by alkoxy, an optionally substituted aryl group, an optionally substituted aralkyl group or an optionally substituted cycloalkyl group;

$R^{3y}$ is an optionally substituted amino group; r is an integer of 0 to 3; and $R^{4y}$ is an optionally substituted aryl group; or a salt thereof.

In the formula (XXI), as the alkyl group shown by $R^{1y}$, $R^{5y}$ and alkyl which may be substituted by alkoxy shown by $R^{2y}$, mention is made of, for example, $C_{1-6}$ alkyl (e.g. methyl, ethyl, propyl, isopropyl, butyl, sec-butyl, t-butyl, pentyl, hexyl). Among these, alkyl group having one to three carbon atoms is preferable.

As the aryl group shown by Q or in the optionally substituted aryl group shown by $R^{2y}$ and $R^{4y}$, mention is made of, for example, mono cyclic- or condensed polycyclic-aromatic hydrocarbon residues. Preferable example of them includes $C_{6-14}$ aryl such as phenyl, naphthyl, anthryl, phenanthryl, acenaphthylenyl and the like. Among these, phenyl, 1-naphthyl and 2-naphthyl are more preferable.

The number of substituents on the aryl group is one or more, preferably one to three. Examples of the substituents on the aryl group shown by $R^{2y}$ and $R^{4y}$ include (1) $C_{1-6}$ alkyl (e.g. methyl, ethyl, n-propyl, isopropyl, n-butyl, isobutyl, pentyl, hexyl. The alkyl may be substituted by alkyl-carbonyl or alkoxy-carbonyl), (2) an optionally substituted alkenyl group such as $C_{2-6}$ alkenyl (e.g. vinyl, allyl, 1-butenyl, 2-butenyl), which may be substituted by one or more of $C_{1-10}$ acyl or $C_{1-6}$ alkoxy-carbonyl, (3) $C_{2-6}$ alkynyl (e.g. ethynyl, propargyl, 2-butynyl, 5-hexynyl), (4) $C_{3-7}$ cycloalkyl (e.g. cyclopropyl, cyclobutyl, cyclopentyl, cyclohexyl), (5) $C_{6-14}$ aryl (e.g. phenyl, naphthyl) which may be substituted by one or more of (i) halogen, (ii) alkyl, (iii) alkoxy which may be further substituted by alkoxy, (iv) nitro, (v) cyano, (vi) a group $-S(O)n^y-R^{6y}$ wherein $n^y$ is an integer of 0 to 2 and $R^{6y}$ shows alkyl or amino, (vii) amino, (viii) acyl, (ix) carbamoyl, (x) carboxy and (xi) hydroxy, (6) heterocyclic group, for example, 5- to 9-membered aromatic heterocyclic group having 1 to 4 hetero atoms selected from a nitrogen atom, an oxygen atom and a sulfur atom (e.g. furyl, thienyl, pyrrolyl, thiazolyl, imidazolyl, pyrazolyl, pyridyl), or 3- to 9-membered non-aromatic heterocyclic group having 1 to 4 hetero atoms selected from a nitrogen atom, an oxygen atom and a sulfur atom (e.g. oxiranyl, azetidinyl, oxetanyl, thietanil, pyrrolidinyl, tetrahydrofuryl, thioranyl, piperidinyl, tetrahydropyranyl, morpholinyl, thiomorpholinyl, piperazinyl), these heterocyclic group may be substituted by one or more of (i) halogen, (ii) alkyl, (iii) amino, (iv) acyl, (v) carbamoyl, (vi) carboxy, (vii) nitro, (viii) hydroxy, (ix) alkoxy and (x) a group of the formula: —S(O)n$^y$—R$^{6y}$ in which ny is an integer of 0 to 2 and R$^{6y}$ is alkyl group, (7) C$_{7-13}$ aralkyl (e.g. benzyl, phenethyl, benzhydryl) which may be substituted by one or more of halogen, (8) an optionally substituted amino group such as a group of the formula:

wherein R$^{11y}$ denotes hydrogen; alkyl, e.g. C$_{1-6}$ alkyl which may be substituted by hydroxy; acyl (e.g. C$_{1-6}$ alkyl-carbonyl, formyl; arylcarbonyl) which may be substituted by one or more of halogen or alkoxy; optionally substituted alkoxy group as mentioned below; C$_{3-7}$ cycloalkyl which may be substituted by one or more of hydroxy; a group of the formula: —S(O)n$^y$—R$^{6y}$ in which n$^y$ is an integer of 0 to 2 and R$^{6y}$ is alkyl group and R$^{12y}$ denotes hydrogen or C$_{1-6}$ alkyl, (9) a group of the formula:

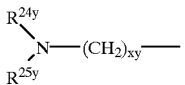

wherein R$^{24y}$ is hydrogen, alkyl group or aryl group, R$^{25y}$ is hydrogen or alkyl group and R$^{24y}$ and R$^{25y}$ may form an optionally substituted 5 to 7 membered cyclic amino group containing the adjacent nitrogen atom and xy is an integer of 0 to 3, (10) amidino, (11) acyl (e.g. C$_{1-8}$ alkanoyl such as formyl, acetyl, propionyl, butyryl, octanoyl; C$_{1-8}$ alkoxy-carbonyl such as methoxycarbony, ethoxycarbonyl, propoxycarbonyl, butoxycarbonyl; C$_{6-14}$ aryl-carbonyl such as benzoyl; C$_{8-11}$ aralkylcarbonyl such as benzylcarbonyl; C$_{7-12}$ aralkyloxy-carbonyl such as benzyloxycarbonyl) which may be optionally substituted by one or more of substituents (e.g. halogen, alkylthio, alkoxy, oxo, hydroxy), (12) an optionally substituted carbamoyl group, e.g. carbamoyl, N-monosubstituted carbamoyl {e.g. N-(C$_{1-7}$ alkyl)carbamoyl such as methylcarbamoyl, ethylcarbamoyl, propylcarbamoyl, isopropylcarbamoyl}, N,N-disubstituted carbamoyl [e.g. N,N-di(C$_{1-6}$ alkyl)carbamoyl such as dimethylcarbamoyl, diethylcarbamoyl, N-ethyl-N-methylcarbamoyl, N-propyl-N-methylcarbamoyl}, (13) sulfamoyl, (14) N-monosubstituted sulfamoyl {e.g. N-(C$_{1-6}$ alkyl)sulfamoyl such as methylsulfamoyl, ethylsulfamoyl, propylsulfamoyl}, (15) N,N-disubstituted sulfamoyl {e.g. N,N-di(C$_{1-6}$ alkyl)sulfamoyl such as dimethylsulfamoyl, diethylsulfamoyl}, (16) carboxy, (17) C$_{1-3}$ alkoxy-carbonyl (e.g. methoxycarbonyl, ethoxycarbonyl, propoxycarbonyl), (18) hydroxyl, (19) an optionally substituted alkoxy group, e.g. C$_{1-6}$ alkoxy (e.g. methoxy, ethoxy, propoxy, isopropoxy, butoxy, isobutoxy, sec-butoxy, t-butoxy, pentyloxy, hexyloxy) which may have one or more of substituent (e.g. C$_{1-6}$ alkanoyl which is the same as above, C$_{1-3}$ alkyl, halogen, C$_{1-3}$ alkylthio, C$_{1-3}$ alkoxy, oxo, hydroxy, C$_{3-7}$ cycloalkyl which is the same as above), (20) C$_{2-4}$ alkenyloxy (e.g. vinyloxy, allyloxy), (21) C$_{3-7}$ cycloalkyloxy (e.g. cyclopropyloxy, cyclopentyloxy, cyclohexyloxy), (22) C$_{7-13}$ aralkyloxy (e.g. benzyloxy, benzhydryloxy), (23) C$_{6-14}$ aryloxy (e.g. phenyloxy, naphthyloxy), (24) mercapto, (25) C$_{7-13}$ aralkylthio (e.g. benzylthio, benzhydrylthio), (26) C$_{6-14}$ arylthio (e.g. phenylthio, naphthylthio), (27) a group of the formula: —S(O)n$^y$—R$^{6y}$ in which n$^y$ is an integer of 0 to 2 and R$^{6u}$ is alkyl group (e.g. methylthio, ethylthio, propylthio, methylsulfinyl, ethylsulfinyl, propylsulfinyl, methylsulfonyl, ethylsulfonyl, propylsulfonyl), (28) C$_{1-3}$ alkylenedioxy (e.g. methylenedioxy, ethylenedioxy, propylenedioxy), (29) sulfo, (30) cyano, (31) azide, (32) nitro, (33) nitroso, (34) halogen (e.g. fulorine, chlorine, bromine iodine), and the like.

As the cycloalkyl in the optionally substituted cycloalkyl shown by Q of R$^{1y}$ and R$^{2y}$, mention is made of, for example, C$_{3-10}$ cycloalkyl and C$_{3-10}$ bicycloalkyl. The preferable examples of them include cyclopropyl, cyclobutyl, cyclopentyl, cyclohexyl, cycloheptyl, cyclooctyl, bicyclo[2,2,1]heptyl, bicyclo[2,2,2]octyl, bicyclo[3,2,1]octyl, bicyclo[3,2,1]nonyl, bicyclo[4,2,1]nonyl, bicyclo[4,3,1]decyl. Among these, cyclopentyl and cyclohexyl are more preferable. The substituents are of the same meaning as defined in the substituents which aryl, shown by R$^{2y}$ and R$^{4y}$, may have. Preferred examples of the substituents are alkyl, alkoxy or halogen.

As the heterocyclic group in the optionally substituted heterocyclic group shown by Q of R$^{1y}$, mention is made of, for example, 5- to 13-membered aromatic heterocyclic group having one to four hetero atom(s) selected from an oxygen atom, a sulfur atom and a nitrogen atom; or saturated or unsaturated non-aromatic heterocyclic group.

Examples of the aromatic heterocyclic group include an aromatic monocyclic heterocyclic group (e.g. furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl), an aromatic condensed-ring heterocyclic group {e.g. benzofuranyl, isobenzofuranyl, benzo[b]thienyl, indolyl, isoindolyl, 1H-indazolyl, benzoimidazolyl, benzoxazolyl, 1,2-benzoisoxazolyl, benzothiazolyl, 1,2-binzoisothiazolyl, 1H-benzotriazolyl, quinolyl, isoquinolyl, cinnolinyl, quinazolinyl, quinoxalinyl, phthalazinyl, naphthylidinyl, purinyl, pteridinyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolizinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidenyl, 1,2-4-tiazolo[4,3-a]pyridyl, 1,2,4-triazolo[4,3-b]pyridazinyl}. Examples of the non-aromatic heterocyclic group include oxylanyl, azetizinyl, oxethanyl, thiethanyl, pyrrolidinyl, tetrahydrofuranyl, thiolanyl, piperidyl, tetrahydropyranyl, morpholinyl, thiomorpholinyl, piperazinyl. Among these, furyl, thienyl, thiazolyl, imidazolyl, pyrazolyl, pyridyl, pyrimidyl, benzofuryl, indolyl and quinolyl are preferable.

The heterocyclic group may have one or more substituents, preferably one to three substituents. The substituents are of the same meaning as defined in the optionally substituted aryl shown by R$^{2y}$ and R$^{4y}$. Preferred examples of the substituents are halogen, alkyl, alkylthio or alkoxy.

As the halogen, as the substituent of the aryl shown by Q, mention is made of fluorine, chlorine, bromine, iodine.

As the substituents of the optionally substituted carboxyl of the aryl group shown by Q, mention is made of alkyl, cycloalkyl, aryl, aralkyl and heterocyclic group which are of the same meaning as defined above and below.

As the lower alkylenedioxy as the substituent of aryl group shown by Q, mention is made of, for example, $C_{1-6}$ alkylenedioxy. Examples of the alkylenedioxy includes methylenedioxy, ethylenedioxy, propylenedioxy, 2,2-dimethylmetylenedioxy.

As the spacer group shown by the symbol "$A^y$", mention is made of, for example, $C_{1-4}$ alkylene (e.g. methylene, ethylene), $C_{2-6}$ alkenylene (e.g. vinylene, butadienylene); a group of the formula: —$(CH_2)cNR^{26y}$— in which c is 0 to 3, $R^{26y}$ is hydrogen, $C_{1-6}$ alkyl (e.g. methyl, ethyl, butyl); a group of the formula: —CO—; a group of the formula: —$CONR^{27y}$— in which $R^{27y}$ is hydrogen, $C_{1-6}$ alkyl (Examples of the alkyl are made of those mentioned above), $C_{3-7}$ cycloalkyl (Examples of the cycloalkyl are made of those mentioned above), $C_{6-14}$ aryl (Examples of the aryl are made of those mentioned above), a heterocyclic group (Examples of the heterocyclic group are made of those mentioned above); a group of the formula: —$S(O)m^y$— wherein $m^y$ is an integer of 0 to 2; —O—; a group of the formula; —$NR^{27y}S(O)m^y$— wherein $m^y$ is an integer of 0 to 2, $R^{27y}$ is of the same meaning as defined in the above.

As the alkoxy which may be the substituent of the alkyl group shown by $R^{2y}$, mention is made of $C_{1-6}$ alkoxy.

As the aralkyl in the optionally substituted aralkyl shown by $R^{2y}$, mention is made of, for example, aryl-alkyl. The aryl is of the same meaning as defined above. Examples of the alkyl include $C_{1-6}$ alkyl such as methyl, ethyl, propyl, butyl, pentyl, hexyl. The substituents on the aralkyl shown by $R^{2y}$ are of the same meaning as defined in the substituents which aryl group shown by $R^{2y}$ and $R^{4y}$ may have.

As the optionally substituted amino group shown by $R^{3y}$, mention is made of, for example, (1) a group of the formula:

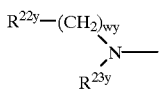

wherein $R^{22y}$ is an alkyl, cycloalkyl, aryl or heterocyclic group and these groups may optionally be substituted, w is an integer of 0 to 3, $R^{23y}$ is hydrogen or an optionally substituted alkyl, or (2) hexamethylenetetraamino. The substituents on the alkyl, cycloalkyl, aryl and heterocyclic groups in the above $R^{22y}$ and $R^{23y}$ are of the same meaning as defined in the substitution on ary group shown by $R^{2y}$ and $R^{4y}$ as mentioned above.

As the preferable spacer group represented by $A^y$ in the definition of the substituents on the aryl group of Q in $R^{1y}$, mention is made of —O— or —$S(O)m^y$— in which $m^y$ is an integer of 0 to 2.

As preferred examples of the above group $R^{1y}$, mention is made of the group of the formula: Q—$(CH_2)p^y$— wherein Q and $p^y$ has the same meaning as defined above.

As preferred examples of the above group $R^{1y}$, mention is made of hydrogen or a group of the formula: —$(CH_2)_pQ'$ wherein Q' denotes an aryl group which may be substituted by halogen, nitro, cyano, amino or a group of the formula: —$A^{y'}$—$R^{5y'}$ (wherein $A^{y'}$ denotes —O— or —S— and $R^{5y'}$ denotes alkyl), and $p^y$ has the same meaning as defined above.

As more preferred examples of the above group $R^{1y}$, mention is made of a group of the formula:

Q—$(CH_2)p^y$— in which Q is an aryl group which may be substituted by one or more of (i) halogen and (ii) a group of the formula: —$A^y$—$R^{5y}$ in which $A^y$ is —O— or —$S(O)m^y$— in which $m^y$ is an integer of 0 to 2 and $R^5$ is alkyl group; and $p^y$ is an integer of 0 to 3.

As still more preferable examples of the group $R^{1y}$, mention is made of $C_{6-14}$ aryl-methyl which may be substituted by halogen or a group —$A^{y''}$—$R^{5y''}$ wherein $A^{y''}$ is —O— or —S— and $R^{5y''}$ is alkyl.

As especially preferable example of the group $R^{1y}$, mention is made of the group Q'''—$(CH_2)p^y$— wherein Q''' is an aryl group which may be substituted by halogen and $p^y$ is an integer of 0 to 3.

As preferred examples of the group $R^{2y}$, mention is made of (1) an alkyl group which may be substituted by alkoxy, (2) an aryl group which may be substituted by one or more of (i) amino, (ii) acyl, (iii) carbamoyl, (iv) carboxy, (v) nitro, (vi) hydroxy, (vii) alkoxy group which may be substituted by alkoxy, (viii) halogen and (iv) a group of the formula: —$S(O)n^y$—$R^{6y}$ in which $n^y$ is an integer of 0 to 2 and $R^{6y}$ is alkyl group, (3) an aralkyl group which may be substituted by halogen or (4) cycloalkyl group.

As more preferred examples of the group $R^{2y}$, mention is made of (1) $C_{1-6}$ alkyl which may be substituted by $C_{1-3}$ alkoxy, (2) $C_{6-14}$ aryl which may be substituted by one or more of amino, acyl, carbomoyl, carboxyl, nitro, hydroxy, $C_{1-3}$ alkoxy, sulfo, halogen and a group of the formula: —$S(O)n^y$—$R^{6y}$ wherein $n^y$ is an integer of 0 to 2 and $R^{6y}$ is $C_{1-3}$ alkyl, or (3) $C_{3-10}$ cycloalkyl.

As further more preferred examples of the group $R^{2y}$, mention is made of (1) an alkyl group which may be substituted by alkoxy, (2) an aryl group which may be substituted by one or more of (i) hydroxy, (ii) alkoxy group which may be substituted by alkoxy, (iii) halogen and (iv) a group of the formula: —$S(O)n^y$—$R^{6y}$ in which $n^y$ is an integer of 0 to 2 and $R^{6y}$ is an alkyl group, (3) aralkyl group or (4) a cycloalkyl group.

As more preferable examples of the group $R^{2y}$, mention is made of (1) $C_{1-6}$ alkyl which may be substituted by $C_{1-3}$ alkoxy, (2) $C_{6-14}$ aryl which may be substituted by one or more of $C_{1-3}$ alkoxy and a group of the formula: —$S(O)n^y$—$R^{6y}$ wherein $n^y$ is an integer of 0 to 2 and $R^{6y}$ is $C_{1-3}$ alkyl, or (3) $C_{3-10}$ cycloalkyl.

As the most preferred examples of the group $R^{2y}$, mention is made of the aryl group which may be substituted by one or more of (1) an alkoxy group which may be substituted by alkoxy, (2) halogen and (3) a group of the formula: —$S(O)n^y$—$R^{5y}$ in which $n^y$ is an integer of 0 to 2 and $R^{5y}$ is an alkyl group.

As preferred examples of the above group $R^{3y}$, mention is made of hexamethylenetetraamino or a substituted amino group of the formula:

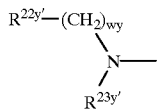

wherein $R^{22y'}$ is (1) an aryl group which may be substituted by one or more of (i) amino, (ii) acyl, (iii) carbamoyl, (iv) carboxy, (v) nitro, (vi) hydroxy, (vii) alkoxy group which may be substituted by alkoxy, (viii) halogen, (ix) alkyl or (x) a group of the formula: —$S(O)n^y$—$R^{6y}$ in which $n^y$ is an integer of 0 to 2 and $R^{6y}$ is alkyl group, (2) heterocyclic group which may be substituted by one or more of (i) amino, (ii) acyl, (iii) carbamoyl, (iv) carboxy, (v) nitro, (vi) hydroxy, (vii) alkoxy, (viii) halogen, (ix) alkyl or (x) a group of the formula: —S(O)n$^y$—R$^{6y}$ in which n$^y$ is an integer of 0 to 2 and R$^{6y}$ is alkyl group, (3) an aralkyl group which may be substituted by halogen, (4) a group of the formula:

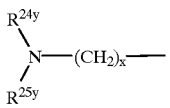

wherein R$^{24y}$ is hydrogen, an alkyl group or an aryl group, R$^{25y}$ is hydrogen or an alkyl group and R$^{24y}$ and R$^{25y}$ may form an optionally substituted 5 to 7 membered cyclic amino group containing the adjacent nitrogen atom and x is an integer of 0 to 3 or (5) an alkyl group which may be substituted by alkylthio, w is an integer of 0 to 3; and R$^{23y'}$ is hydrogen or an alkyl group.

As more preferred examples of the above group R$^{3y}$, mention is made of hexamethylenetetraamino or a group of the formula

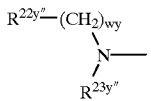

(wherein R$^{22y''}$ denotes (1) alkyl, (2) phenyl which may be substituted by one or more of halogen, nitro, alkyl and a group of the formula: —S(O)n$^y$—R$^{6y}$ wherein n$^y$ is an integer of 0 to 2 and R$^{6y}$ is an alkyl group or an amino group, (3) a heterocyclic group which may be substituted by one or more of halogen and alkyl or (4) N-alkylcarbamoyl, w is an integer of 0 to 3; R$^{23y''}$ denotes hydrogen or alkyl).

As more preferred examples of the above R$^{3y}$, mention is made of a substituted amino group of the formula:

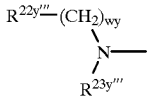

wherein R$^{22y'''}$ is (1) aryl group which may be substituted by alkylthio, (2) heterocyclic group, (3) a group of the formula:

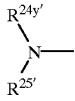

wherein R$^{24y'}$ is hydrogen or alkyl and R$^{25y'}$ is hydrogen or alkyl and R$^{24y'}$ and R$^{25y'}$ may form a 5 to 7 membered cyclic amino group containing the adjacent nitrogen atom or (4) an alkyl group which may be substituted by alkylthio, w is an integer of 0 to 3; and R$^{23y'''}$ is hydrogen or an alkyl group.

As preferred examples of the above group R$^{3y}$, mention is made of a group of the formula:

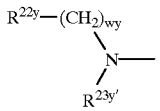

(wherein R$^{22y'}$ is phenyl or pyridyl, these groups being unsubstituted or substituted by a group of the formula: —S(O)n$^y$—R$^{6y}$ in which n$^y$ is an integer of 0 to 2 and R$^{6y}$ is an alkyl group, w is an integer of 0 to 3. R$^{23y'}$ is hydrogen or an alkyl group).

As preferred examples of the group R$^{4y}$, mention is made of the aryl group which may be substituted by one or more of (1) an optionally substituted amino group, (2) acyl, (3) an optionally substituted carbamoyl group, (4) carboxy, (5) nitro, (6) hydroxy, (7) an optionally substituted alkoxy group and (8) an optionally substituted alkenyl group.

As more preferred examples of the above group R$^{4y}$, mention is made of the aryl group which may be substituted by one or more of (1) a group of the formula:

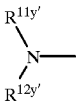

wherein R$^{11y'}$ is (i) hydrogen, (ii) alkyl, (iii) an optionally substituted alkoxy group, (iv) an optionally substituted acyl group or (v) a group of the formula: —S(O)n$^y$—R$^{6y}$ in which n$^y$ is an integer of 0 to 2 and R$^{6y}$ is an alkyl group and R$^{12y'}$ is hydrogen or an alkyl group, (2) acyl, (3) carbamoyl, (4) N-mono or di-alkylcarbamoyl, (5) nitro, (6) alkoxy which may be substituted by one or more of alkoxy, alkanoyl, oxo, hydroxy, cycloalkyl and halogen, (7) alkenyl which may be substituted by alkoxycarbonyl or alkylcarbonyl and (8) alkenyloxy.

Further preferred examples of the above group R$^{4y}$, mention is made of the aryl group which may be substituted by one or more of (1) a group of the formula:

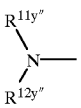

wherein R$^{11y''}$ is (i) hydrogen, (ii) alkyl, (iii) alkoxy which may be substituted by halogen or alkoxy, (iv) formyl, (v) alkanoyl which may be substituted by halogen or alkoxy, (vi) benzoyl or (vii) a group of the formula: —S(O)n$^y$—R$^{6y}$ in which n$^y$ is an integer of 0 to 2 and R$^{6y}$ is an alkyl group and R$^{12y''}$ is hydrogen or alkyl, (2) alkoxy which may be substituted by alkoxy, alkanoyl or cycloalkyl, (3) N-mono or di-alkylcarbamoyl, (4) nitro (5) alkenyl which may be substituted by alkoxycarbonyl or alkylcarbonyl or (6) alkenyloxy.

Further preferred examples of the aryl group in the above optionally substituted aryl R$^{4y}$, mention is made of phenyl. As the preferred examples of the substituents on the aryl group shown by R$^{4y}$, mention is made of amino, acyl, carbamoyl, N-monosubstituted alkylcarbamoyl, carboxyl, nitro, hydroxy, C$_{1-3}$ alkoxy which may be substituted by C$_{1-3}$ alkoxy, a group of the formula:

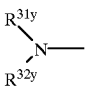

(wherein R$^{31y}$ denotes C$_{1-6}$ alkyl; C$_{1-3}$ alkoxy which may be substituted by C$_{1-3}$ alkoxy; or formyl, R$^{32y}$ denotes hydrogen or C$_{1-6}$ alkyl), or C$_{2-4}$ alkenyl which may be substituted by alkoxy-carbonyl or alkyl-carbonyl.

As a more preferred example of aryl in the optionally substituted aryl of the group R$^{4y}$, mention is made of phenyl.

As more preferred examples of the substituents on the aryl group shown by $R^{4y}$, mention is made of amino; acyl; N-substituted alkylcarbamoyl; nitro; $C_{1-3}$ alkoxy which may be substituted by $C_{1-3}$ alkoxy; a group of the formula;

(wherein $R^{33y}$ denotes $C_{1-6}$ alkyl, $C_{1-3}$ acyl which may be substituted by $C_{1-3}$ alkoxy; $C_{1-3}$ alkoxy which may be substituted by $C_{1-4}$ acyl; benzoyl; or formyl, $R^{34y}$ denotes hydrogen or $C_{1-6}$ alkyl), $C_{2-4}$ alkenyl which may be substituted by $C_{1-3}$ alkoxy-carbonyl or $C_{1-3}$ alkyl-carbonyl.

In the above each groups, the number of the substituents is preferably 1 to 3, r is preferably 1, $p^y$ is preferably 1, and $w^y$ is preferably 1.

As the 5 to 7 membered cyclic amino group containing nitrogen atom, mention is made of pyrrolidinyl, pyrrolinyl, pyrrolyl, pyrazolidinyl, pyrazolinyl, pyrazolyl, imidazolidinyl, imidazolinyl, imidazolyl, 1,2,3-triazinyl, 1,2,3-triazolidinyl, 1,2,3-triazolyl, 1,2,3,4-tetrazolyl, piperidinyl, piperazinyl, hexamethyleneamino, oxazolidino, morpholino, thiazolidino or thiomorpholino. As more preferable cyclic amino group, mention is made of pyrrolidinyl, pyrazolinyl, pyrazolyl, piperidinyl, piperazinyl, morpholino and thiomorpholino.

The cyclic amino group may be substituted. The examples of the substituents includes $C_{1-6}$ alkyl, $C_{6-14}$ aryl, $C_{7-10}$ aralkyl, benzhydryl, $C_{1-6}$ alkyl-carbonyl, $C_{6-14}$ arylcarbonyl, $C_{1-6}$ alkoxy-carbonyl. As the preferable substituent, mention is made of $C_{1-6}$ alkyl, preferably $C_{1-3}$ alkyl.

As the preferable alkyl in the above definition, mention is made of, for example, $C_{1-10}$ alkyl. Examples of the alkyl includes methyl, ethyl, propyl, isopropyl, butyl, isobutyl, sec-butyl, t-butyl, pentyl, isopentyl, neopentyl and hexyl. Among these, alkyl having one to six carbon atoms is more preferable, and alkyl having one to three carton atoms in still preferable.

As the acyl, mention is made of $C_{1-10}$ acyl and the examples of the acyl are for example alkanoyl, arylcarbonyl, aralkyl-carbonyl and aralkyloxy-carbonyl which are mentioned above.

As the preferable acyl and alkanoyl in the above definition, mention is made of alkyl-carbonyl, and alkyl is of the same meaning as defined above.

As the preferable alkoxy in the above adefinition, mention is made of $C_{1-6}$ alkoxy, and examples of the alkoxy includes methoxy, ethoxy, propoxy, isopropoxy, butoxy, isobutoxy, sec-butoxy, t-butoxy, pentyloxy, isopentyloxy, neopentyloxy, hexyloxy. Among these, alkoxy having 1 to 3 carbon atoms is preferable.

As the preferable alkenyl in the above definition, mention is made of $C_{2-4}$ alkenyl. Examples of the alkenyl includes vinyl, allyl, 1-butenyl, 2-butenyl.

As the preferable aryl in the above definition, mention is made of $C_{6-14}$ aryl. Examples of the aryl includes phenyl, naphthyl.

As the preferable aralkyl in the above definition, mention is made of $C_{7-10}$ aralkyl. Examples of the aralkyl includes benzyl, phenethyl.

As the halogen, mention is made of fluorine, chlorine, bromine, iodine.

In the compound of the formula (XXX), preferable examples include a compound of the formula (XXXI):

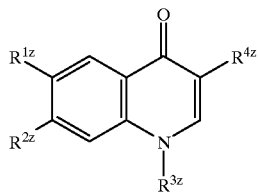

(XXXI)

wherein $R^{1z}$ is a group of the formula:

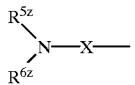

in which $R^{5z}$ is an aralkyl group, $R^{6z}$ is an alkyl group, X is an alkylene group, or an alkyl group which may optionally be substituted by halogen, $R^{2z}$ is an acylaminoaryl group, $R^{3z}$ is a halogenoaralkyl group, $R^{4z}$ is a carboxyl group which may optionally be esterified or amidated, or a salt thereof.

As the aralkyl group of $R^{5z}$ in $R^{1z}$, $C_{7-19}$ aralkyl is preferable, and the $C_{7-19}$ aralkyl is exemplified by benzyl, phenethyl, biphenylylmethyl, benzhydryl. In particular, benzyl is most preferable.

As the alkyl groups $R^{6z}$, a $C_{1-6}$ alkyl group is preferable, and the $C_{1-6}$ alkyl group is exemplified by methyl, ethyl, n-propyl, isopropyl, n-butyl, isobutyl, s-butyl, t-butyl, n-pentyl, isopentyl, neopentyl, hexyl. Among them, $C_{1-3}$ alkyl is preferable.

As the alkylene group of X in $R^{1z}$, $C_{1-6}$ alkylene is preferable, and $C_{1-6}$ alkylene is exemplified by methylene, ethylene, propylene, butylene, pentylene, hexylene. Among them, $C_{1-3}$ alkylene is more preferable.

As the alkyl group in the alkyl group which may optionally be substituted by halogen of $R^{1z}$, it is exemplified by those mentioned above as $C_{1-6}$ alkyl. As the halogen, mention is made of fluorine, chlorine, bromine and iodine. As the preferred alkyl group which has halogen, mention is made of bromomethyl.

As the acylaminoaryl of $R^{2z}$, $C_{1-6}$ acyl amino-$C_{6-14}$ aryl group is preferable. As examples of the $C_{1-6}$ acyl, mention is made of formyl, acetyl, propionyl, butyryl, isobutyryl, valeryl, isovaleryl. As examples of the $C_{6-14}$ aryl, mention is made of phenyl, naphthyl, anthryl.

As the halogenoaralkyl of $R^{3z}$, halogeno-$C_{7-19}$ aralkyl is preferable. As the halogen in the halogenoaralkyl, mention is made of fluorine, chlorine, bromine and iodine. As examples of aralkyl in the halogenoaralkyl, mention is made of benzyl, phenethyl, benzhydryl, in particular, benzyl is most preferable.

As the ester in the esterified carboxyl of $R^{4z}$, $C_{1-6}$ alkyl ester is preferable, and examples of it are methylester, ethylester, n-propylester, isopropylester, n-butylester, isobutylester, s-butylester, t-butylester, n-pentylester, isopentylester, neopentylester, n-hexylester. Among them, ethyl ester is most preferable.

The amidated carboxyl of $R^{4z}$ is exemplified by carbamoyl, methylcarbamoyl, 2-pyridylcarbamoyl, benzylcarbamoyl, isopropylcarbamoyl.

As the more preferable groups in the compound (XXXI), $R^{1z}$ is N-benzyl-N-methylaminomethyl, $R^{2z}$ is propionylaminophenyl or isobutyrylaminophenyl, $R^{3z}$ is difluorobenzyl, and $R^{4z}$ is ethoxycarbonyl.

The compounds (X) to (XV), (XX), (XXI), (XXX) and (XXXI) and their salts which are employed in the present invention can be produced easily by per se known methods, as exemplified by the following production methods.

Production Method 1:

In accordance with the method disclosed by K. Gewald, E. Schinke and H. Bøttcher, Chem. Ber., 99, 94–100 (1966), an adequate ketone or aldehyde having an active methylene (i) is allowed to react with a cyanoacetic acid ester derivative and sulfur to convert into a 2-aminothiophene derivative (ii). More specifically, in the case of using ketone ($R^{1'} \neq H$), a ketone (i) is subjected to heating under reflux together with a cyanoacetic acid ester derivative, in the presence of acetic acid and ammonium acetate, in a proper solvent such as toluene to give an alkylidene cyanoacetic acid ester derivative, which is then heated in an adequate solvent, for example, ethanol in the presence of sulfur and a base to afford a 2-aminothiophene derivative (ii). And, in the case of using aldehyde ($R^{1'}=H$), an aldehyde is heated in a proper solvent, for example, N,N-dimethylformamide, in the presence of a cyanoacetic acid ester derivative, sulfur and a base to give a 2-aminothiophene derivative (ii). The compound (ii) thus obtained is heated, in accordance with the method disclosed by Kuwata et al. (cf. German Patent 2,435,025), with diethyl ethoxymethylenemalonate to give an adduct (iii). The adduct is stirred in a solvent, which does not give undesirable effect on the reaction, e.g. alcohols such as ethanol and methanol, in the presence of a base, e.g. alkali metal hydroxide such as potassium hydroxide and sodium hydroxide, at temperatures ranging from about 10 to 70° C. to give carboxylic acid (iv). Then, the carboxylic acid (iv) thus obtained is subjected to ring-closure reaction by heating in polyphosphoric acid ester (PPE) to give a thieno[2,3-b]pyridine derivative (v). The compound (v) is stirred in a solvent, which does not give undesirable effect on the reaction, e.g. amides such as N,N-dimethylformamide and N,N-dimethylacetamide, in the presence of a halogenated aralkyl derivative and a base, e.g. an organic base such as pyridine and triethylamine, at temperatures ranging from about 10 to 100° C. to give a 4,7-dihydro-4-oxothieno[2,3-b]pyridine-5-carboxylic acid ester derivative shown by the formula (XIa). Then, the compound (XIa) is stirred together with N-bromosuccinimide (NBS) in a solvent, which does not give undesirable effect on the reaction, e.g. halogenated hydrocarbons such as carbon tetrachloride and chloroform, in the presence of α, α',-azobisisobutyronitrile (AIBN), at temperatures ranging from about 30 to 100° C. to give a compound (XIb). Upon necessity, the halogen atom in the compound (XIb) is converted to alkylsulfonyloxy, arylsulfonyloxy. The compound (XIb) is stirred together with various amines (H—$R^9$) in a solvent, which does not give undesirable effect on the reaction, e.g. amides such as N,N-dimethylformamide and N,N-dimethylacetamide, nitrile such as acetonitrile and alcohols such as ethanol, in the presence of a base at temperatures ranging from about 10 to 100° C. to give free form of the compound (XI'), and then the compound is treated with HCl-EtOH to produce the compound (XI'). The Production Method 1 described above is shown in Scheme 1:

Scheme 1

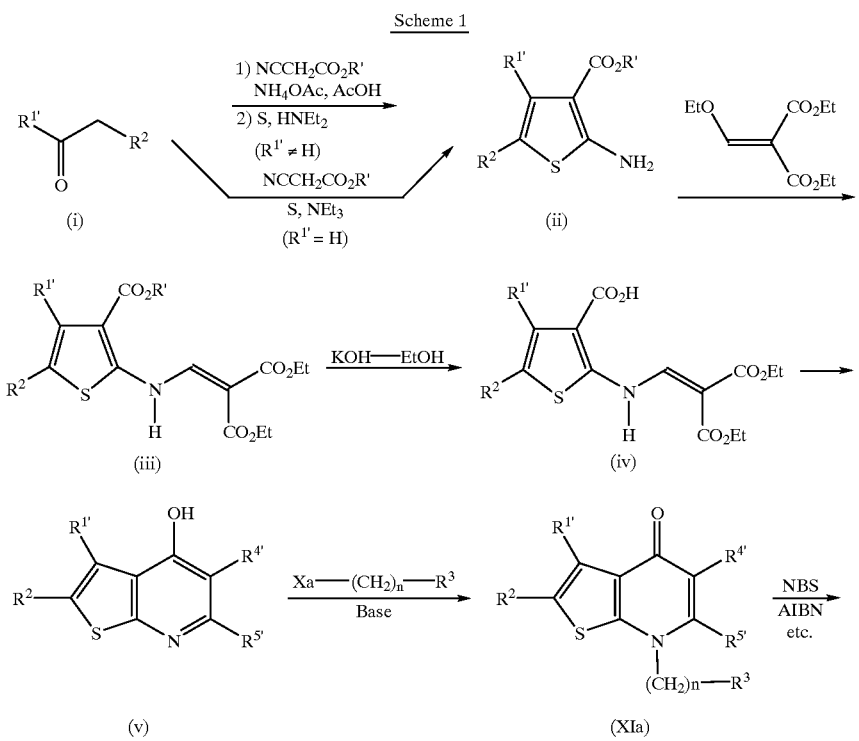

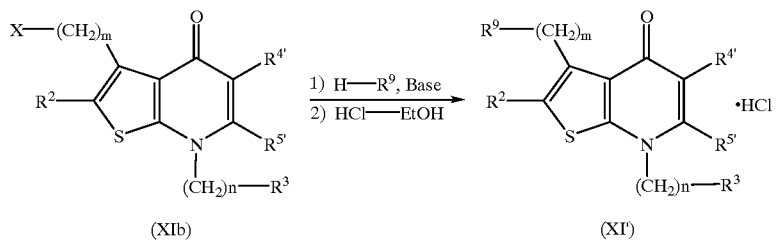

wherein $R^{1'}$ is hydrogen or an optionally substituted alkyl group, R' is an alkyl group, X is a leaving group, Xa is halogen, and $R^2$, $R^3$, $R^9$ and n are of the same meaning as defined above. $R^{4'}$ denotes ethoxycarbonyl. $R^{5'}$ denotes a hydrogen atom. m denotes an integer of 0 to 6.

The alkyl group shown by $R^{1'}$ and R' is of the same meaning as defined above.

As the leaving group shown by X, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen (e.g. iodine, bromine chlorine), alkanoyloxy (e.g. acetoxy), alkylsulfonyloxy (e.g. methanesulfonyloxy), alkyl-arylsulfonyloxy (e.g. p-toluenesulfonyloxy).

The halogen shown by Xa is fluorine, iodine, chlorine, iodine. Among these, bromine is more preferable.

Production Method 2:

In the substantially same manner as in Production Method 1, a 2-aminothiophene derivative (vi) whose 5-position is unsubstituted, which can be synthesized by the method disclosed by Karl Gewald (K. Gewald, Chem. Ber., 98, 3571–3577 (1965); K. Gewald and E. Schinke, Chem. Ber., 99, 2712–2715 (1966)) is allowed to react with diethyl ethoxymethylene malonate under heating, in accordance with the method disclosed by Kuwata et al. German Patent 2,435,025, to give an adduct (vii). The adduct is stirred at temperatures ranging from about 10 to 60° C. in a solvent, which does not affect adversely on the reaction, e.g. alcohols such as ethanol and methanol, in the presence of a suitable base, e.g. alkali metal hydroxide such as potassium hydroxide and sodium hydroxide, to give carboxylic acid (viii). The compound (viii) is subjected to various electrophilic substitution reactions and, depending on cases, to a suitable change of functional groups to introduce the substituent shown by $R^{2''}$, which is then subjected to ring-closure reaction under heating in polyphosphoric acid ester (PPE) to give a thieno[2,3-b]pyridine derivative (ix). As the electrophilic substitution reaction, mention is made of, for example, nitration (fuming nitric acid—concentrated sulfuric acid, sodium nitrate—concentrated sulfuric acid), acylation (acid chloride—aluminum chloride), formylation (phosphorus oxychloride—N,N-dimethylformamide or N-methylformanilide) and halogenation such as bromination (N-bromosuccinimide, bromine-pyridine). The compound (ix) is then processed in the substantially the same manner as in Production Method 1 to produce compounds (XIa'), (XIb') and (XI'). The Production Method 2 is shown in Scheme 2:

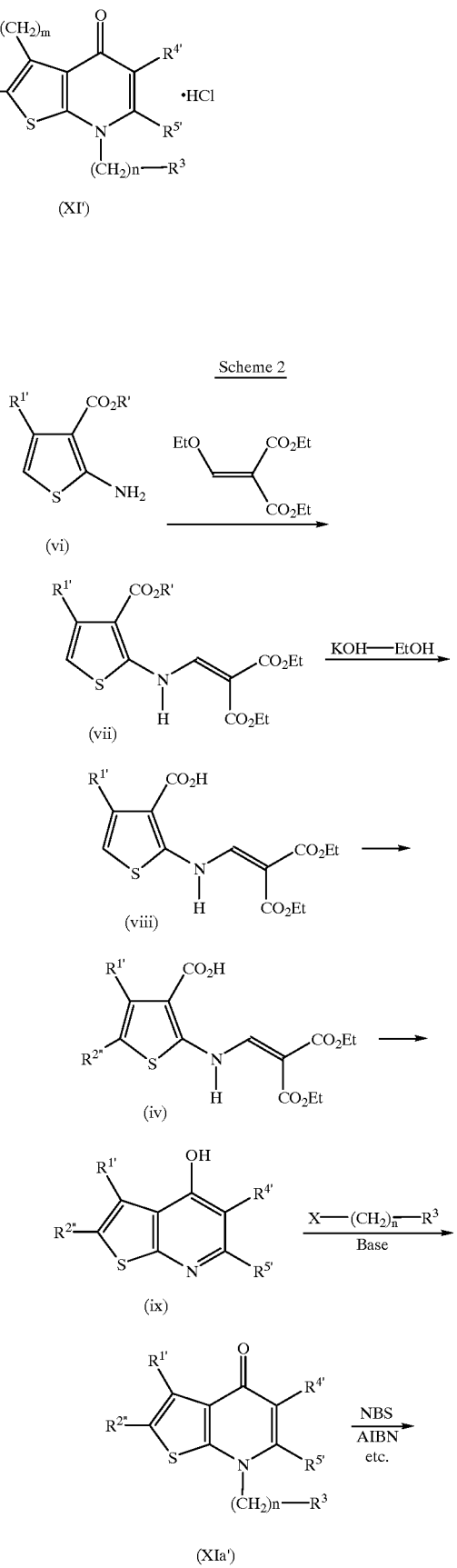

-continued

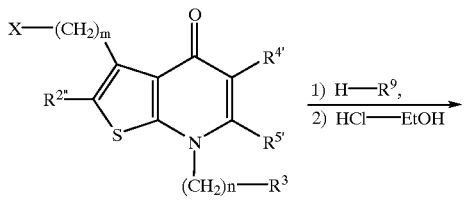

(XIb)

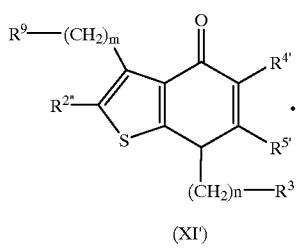

(XI')

wherein each symbol has the same meaning as defined above.

Production Method 3:

An alantonic acid derivative (x) is stirred at temperatures ranging from about 30 to 110° C. together with an equivalent or an excess amount of a compound of the formula: $(CCl_3O)_2CO$ relative to the compound (x) in a solvent which does not adversely affect on the reaction (e.g. ethers such as tetrahydrofuran and 1,4-dioxane) to give an isatoic acid anhydride derivative (xi). Then, a halogenated aralkyl derivative shown by the formula (xii) is stirred at temperatures ranging from about 40 to 130° C. in a solvent, which does not affect adversely on the reaction, (ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide), in the presence of a base (e.g. alkali metal carbonate such as potassium carbonate, alkali metal hydride such as sodium hydride and potassium hydride, and alkali metal alkoxide such as potassium-butoxide), to give a substituted aralkyl derivative (xiii). The aralkyl derivative (xiii) is allowed to react with an equivalent or a little excess amount (e.g. about 1.1 to 1.5 equivalent) of a β-keto-acid ester derivative (xiv) relative to the compound (xiii) at temperatures ranging from 40 to 110° C. in a solvent, which does not affect adversely on the reaction, e.g. ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide, in the presence of a base (e.g. alkali metal carbonate such as potassium carbonate, alkali metal hydride such as sodium hydride and potassium hydride, and alkali metal alkoxide such as potassium-butoxide) to give the compound (Va). The foregoing Production Method 3 is shown in Scheme 3:

Scheme 3

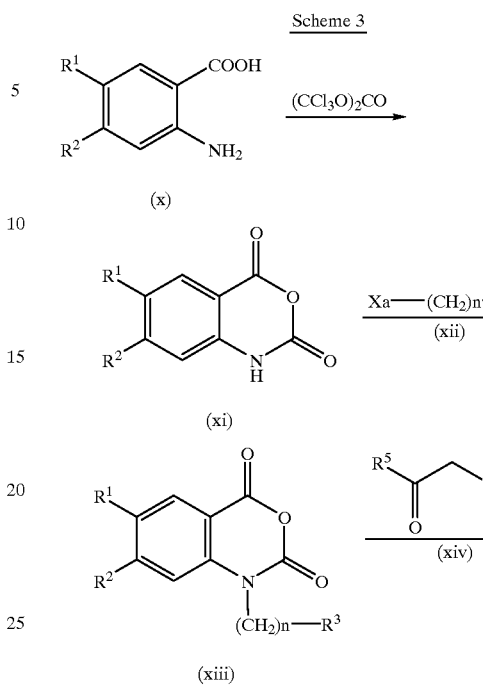

wherein each symbol is of the same meaning as defined above.

Production Method 4:

A pyridine derivative (xv) is stirred, together with equivalent or an excess amount of the compound of the formula: $(CCl_3O)_2CO$ relative to the compound (xv), in a solvent, which does not affect adversely on the reaction, (e.g. ethers such as tetrahydrofuran and 1,4-dioxane), at temperatures ranging from about 30 to 110° C. to give an acid anhydride derivative (xvi). Then, the halogenated aralkyl derivative shown by (xii) is stirred in a solvent, which does not affect adversely on the reaction, (e.g. ethers such as tetrahydrofuran and 1,4-dioxane, aromatic hydrocarbons such as benzene and toluene, amides such as N,N-dimethylformamide and N,N-dimethylacetamide, and alkyl sulfoxides such as dimethyl sulfoxide), at temperatures ranging from about 40 to 130° C. in the presence of a base (e.g. alkali metal carbonate such as potassium carbonate, alkali metal hydride such as sodium hydride and potassium hydride, and alkali metal alkoxide such as potassium-butoxide) to give a substituted aralkyl derivative (xvii). The aralkyl derivative (xvii) is allowed to react with equivalent or a little excess amount (e.g. 1.1 to 1.5 equivalent) of a β-keto-acid ester derivative (xiv) in a solvent, which does not affect adversely on the reaction, (e.g. ethers such as tetrahydrofuran and 1,4-dioxane, aromatic hydrocarbons such as benzene and toluene, amides such as N,N-dimethylformamide and M,N-dimethylacetamide, and alkyl sulfoxides such as dimethyl sulfoxide), in the presence of a base (e.g. alkali metal carbonate such as potassium carbonate, alkali metal hydride such as sodium hydride and potassium hydride and alkali metal alkoxide such as potassium-butoxide), at temperatures ranging from about 40 to 110° C., to give the compound (Vb). The foregoing Production Method 4 is shown by Scheme 4:

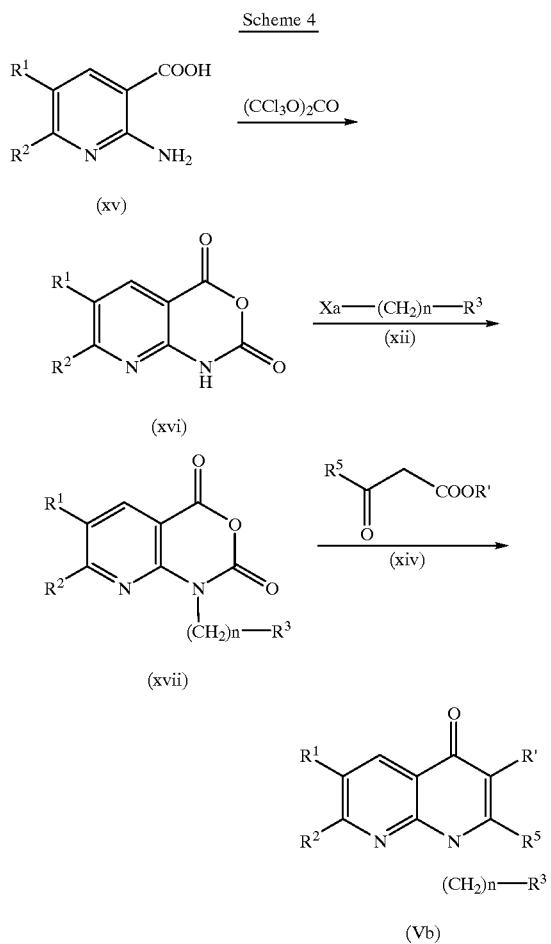

wherein each symbol is of the same meaning as defined above.

Production Method 5:

In a suitable solvent, which does not affect adversely on the reaction, (e.g. ethers such as tetrahydrofuran, ethyl ether and dioxane), 4,7-dihydro-4-oxothieno[2,3-b]pyridine-5-carboxylic acid ester derivative (va) is stirred together with a suitable reducing agent (e.g. lithium aluminum hydride) at temperatures ranging from about 0 to 80° C. to give a 4,7-dihydro-4-oxothieno[2,3-b]pyridine derivative shown by the formula (XIc). The derivative obtained is stirred, together with a suitable oxidizing agent (e.g. manganese dioxide), in a suitable solvent (e.g. dichloroinethane or chloroform) at temperatures ranging from about 10 to 80° C. to give a 5-formyl derivative. The derivative (XId) thus produced is stirred, together with a Grignard's reagent ($R^{25d}$MgXa), at temperatures ranging from about 0 to 80° C. in a solvent, which does not affect adversely on the reaction, (e.g. ethers such as tetrahydrofuran and ethyl ether) to give a corresponding secondary alcohol derivative (XIe). The compound (XIe) is stirred, together with a suitable oxidizing agent (e.g. metal oxide such as manganese dioxide), in a suitable solvent (e.g. halogenated hydrocarbons such as dichloromethane and chloroform) at temperatures ranging from about 10 to 80° C. to give a 5-carbonyl derivative (XIf). The foregoing Production Method 5 is shown in Scheme 5:

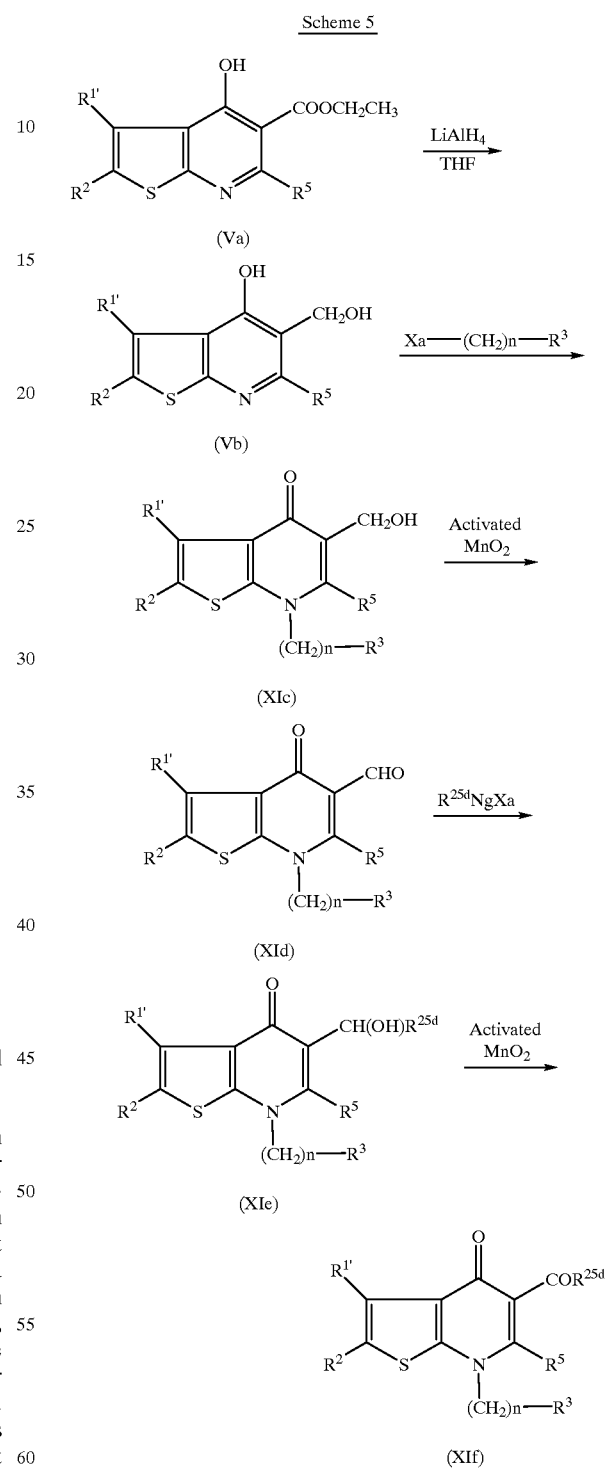

wherein $R^{25d}$ is hydrocarbon residue, and other symbols are of the same-meaning as defined above.

The hydrocarbon residue shown by the above $R^{25d}$ is of the same meaning as the hydrocarbon residue in the carbonyl group substituted with hydrocarbon residue shown by the above-described $R^4$.

Production Method 6:

4,7-Dihydro-4-oxothieno[2,3-b]pyridine-5-carboxylic acid ester derivative (XIa') is stirred at temperatures ranging from about 10 to 100° C., together with an aluminum amide derivative previously produced from a proper aluminum reagent [(e.g. trimethyl aluminum and diisobutyl aluminum hydride (DIBAL)] and amine in a suitable solvent, which does not affect adversely on the reaction, (e.g. halogenated hydrocarbons such as dichloromethane and ethers such as tetrahydrofuran, ethyl ether and dioxane), to give a 4,7-dihydro-4-oxothieno[2,3-b]pyridine-5-carboxylic acid amide derivative (XIa"). The said derivative (XIa") is stirred, together with a Grignard's reagent, in a proper solvent, which does not affect adversely on the reaction, (e.g. tetrahydrofuran and ethyl ether) at temperatures ranging from about −78° C. to 80° C. to give a corresponding ketone derivative (XIf). The foregoing Production Method 6 is shown in Scheme 6:

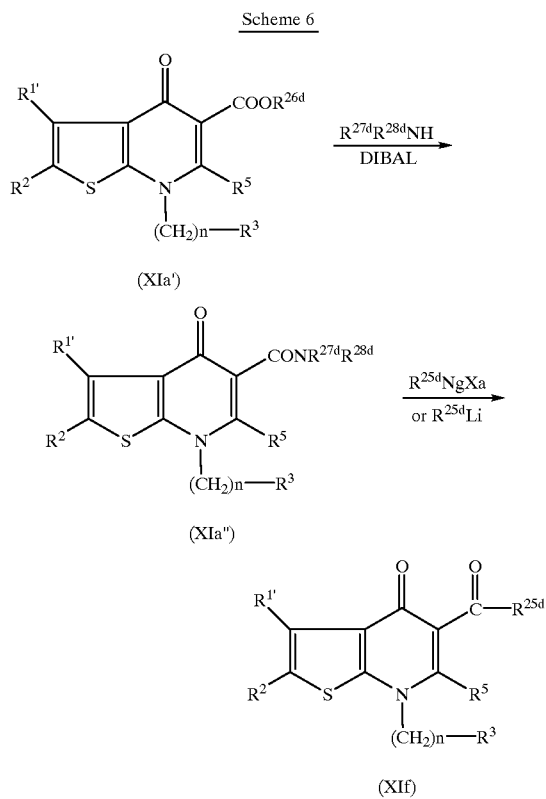

wherein $R^{26d}$ is alkyl or aryl; $R^{27d}$ and $R^{28d}$ are each hydrogen or hydrocarbon residue; and other symbols are of the same meaning as defined above.

The alkyl and aryl shown by the above $R^{26d}$ are of the same meaning as defined above.

The hydrocarbon residue shown by the above $R^{27d}$ and $R^{28d}$ has the same meaning as the hydrocarbon residue in the carbonyl group substituted with hydrocarbon residue shown by the above $R^4$.

Production Method 7:

In a proper solvent, which does not affect adversely on the reaction, e.g. halogenated hydrocarbons such as dichloromethane; ethers such as tetrahydrofuran, ethyl ether and dioxane; and pyridine, a 4,7-dihydro-5-hydroxymethyl-4-oxothieno[2,3-b]pyridine derivative (XIc) is stirred together with a suitable halogenating reagent (e.g. thionyl chloride and methanesulfonyl chloride) at temperatures ranging from about 0 to 100° C. to give a 4,7-dihydro-5-halomethyl-4-oxothieno[2,3-b]pyridine derivative (XIg). The derivative (XIg) is stirred, together with a suitable nucleophilic reagent, in a proper solvent, which does not affect adversely on the reaction, e.g. ethers such as tetrahydrofuran and ethyl ether; and amides such as dimethylformamide, to give a corresponding 5-substituted derivative (XIh). The above Production Method 7 is shown in Scheme 7:

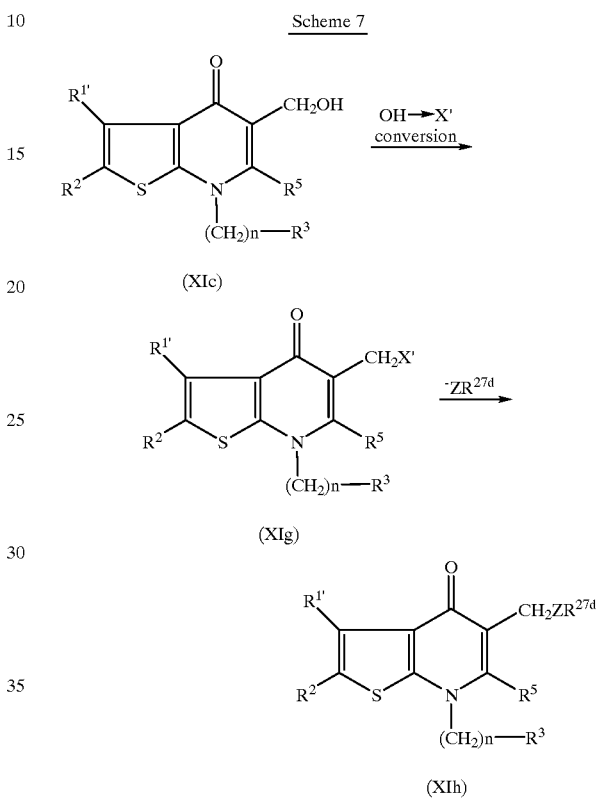

wherein X' is a leaving group, Z is an oxygen atom, a sulfur atom, a group of the formula: —NH or a nitrogen atom substituted with hydrocarbon residue, and other symbols are of the same meaning as defined above.

As the leaving group shown by the above X', mention is made of, for example, groups readily susceptible to substitution reaction by a nucleophilic reagent, e.g. the hydrocarbon residue having a heteroatom with negative electric charge (e.g. oxygen atom, sulfur atom and nitrogen atom) shown by the above $ZR^{27d}$. More specifically, for example, halogen (e.g. chlorine, bromine, iodine), aralkyloxy (e.g. acetoxy), alkylsulfonyloxy (e.g. methanesulfonyloxy) and alkylaryl sulfonyloxy (e.g. p-toluenesulfonyloxy) are mentioned.

The hydrocarbon residue in the nitrogen atom substituted with hydrocarbon residue mentioned above has the same meaning as defined in reference to the hydrocarbon residue in the carbonyl group substituted with hydrocarbon residue shown by the above-mentioned $R^4$.

Production Method 8:

In a proper solvent, which does not affect adversely on the reaction, e.g. ethers such as tetrahydrofuran, ethyl ether and dioxane; and pyridine, 4,7-dihydro-5-formy-4-oxothieno[2,3-b]pyridine derivative (XId) is stirred together with a suitable Wittig reagent at temperatures ranging from about 0 to 100° C. to give a derivative (XIi). The said derivative (XIi) is stirred at temperatures ranging from about 10 to 100°

C. together with a suitable reducing reagent, e.g. hydrogenation using, in hydrogen streams, a catalyst (e.g. palladium-carbon catalyst), in a proper solvent, which does not affect adversely on the reaction (e.g. alcohols such as ethyl alcohol, esters such as acetic acid ethyl ester, ethers such as tetrahydrofuran, ethyl ether and dimethylformamide) to give a corresponding 5-substituted derivative (XIj). The above production method 8 is shown in Scheme 8:

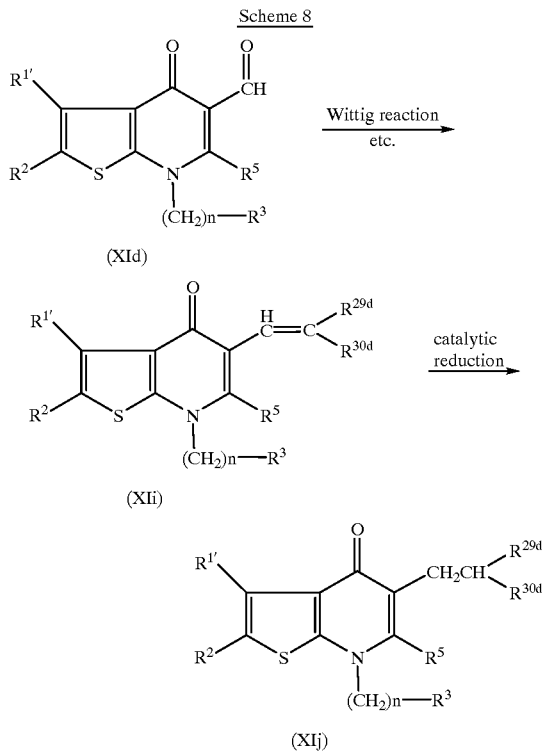

wherein $R^{29d}$ and $R^{30d}$ are each hydrogen or hydrocarbon residue, and other symbols are of the same meaning as defined above.

The hydrocarbon residue shown by the above-mentioned $R^{29d}$ and $R^{30d}$ has the same meaning as the hydrocarbon residue in the carbonyl group substituted with the hydrocarbon residue shown by the above-mentioned $R^4$.

Production Method 9:

In a proper solvent, which does not affect adversely on the reaction, e.g. ethers such as tetrahydrofuran and dioxane; and alcohols such as ethyl alcohol, 4,7-dihydro-4-oxothieno[2,3-b]pyridine-5-carboxylic acid ester derivative (XIf') is subjected to hydrolysis under stirring at temperatures ranging from about 10 to 100° C. by adding an acid (e.g. inorganic acid such as hydrochloric acid) or an alkaline aqueous solution (e.g. 1–4N aqueous solution of alkali metal hydroxide such as sodium hydroxide, potassium hydroxide and lithium hydroxide). The resulting 5-carboxylic acid derivative (XIk) is heated at temperatures ranging from about 50 to 200° C. in a proper solvent, which does not affect adversely on the faction, to give a corresponding decarboxylated derivative (XIn). The foregoing production method 9 is shown by Scheme 9:

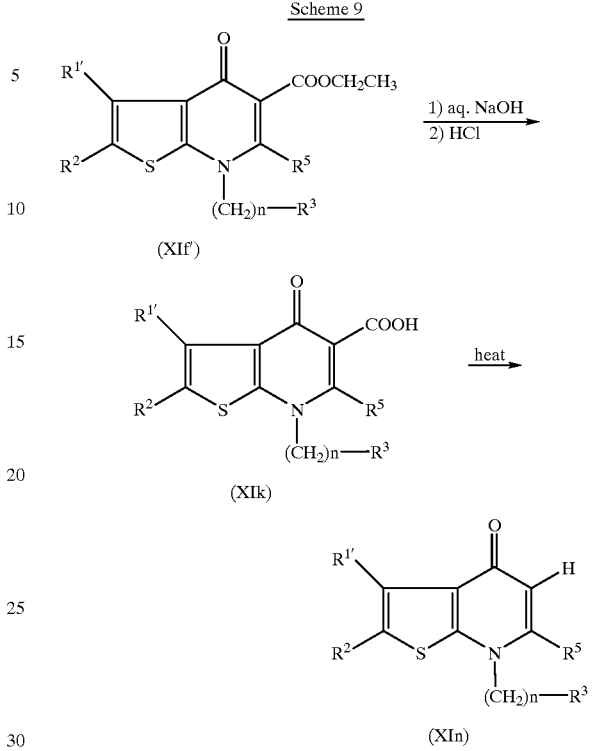

wherein each symbol is of the same meaning as defined above.

Production Method 10:

Starting from the 2-aminothiophene derivative (ii), the urea derivative (II) is produced by, for example, the following method A or B.

1. Method A: The 2-aminothiophene derivative (ii) produced by the method described in Production Method 1 or a salt thereof is allowed to react with an isocyanate derivative. The isocyanate derivative is exemplified by derivatives represented by the formula, $R^{2f}$—NCO (wherein $R^{2f}$ is of the same meaning as defined above). The reaction of the compound (ii) or a salt thereof with the isocyanate derivative is conducted in an solvent which does not adversely affect on the reaction (e.g. tetrahydrofuran, pyridine, dioxane, benzene, dichloromethane, 1,2-dichloroethane, toluene, xylene) at temperatures ranging from about 15 to about 130° C. The isocyanate derivative is employed in an amount of about 1 to 5 equivalents, preferably about 1.1 to 2.5 equivalents, relative to 1 equivalent of the compound (ii). The reaction time ranges from several hours to several days, preferably from about 15 minutes to about two days.

2. Method B: Amine, e.g. a compound represented by the formula $R^{2f}$—NH$_2$ (wherein $R^{2f}$ is of the same meaning as defined above), is subjected to addition reaction to an isocyanate derivative produced by allowing a 2-aminothiophene derivative (ii) or a salt thereof to react with phosgene or an equivalent compound thereof, e.g. diphosgene such as bis(trichloromethyl)carbonate, triphosgene such as trichloromethylchloroformate. The reaction of the compound (ii) or a salt thereof with phosgene or an equivalent compound thereof is conducted in a solvent which does not affect adversely on the reaction (e.g. dioxane, tetrahydrofuran, benzene, toluene, xylene, 1,2-dichloroethane, chloroform) at temperatures ranging from about 40 to 120° C. Phosgene or an equivalent compound thereof is employed in an amount ranging from about 0.5 to 2 equivalents, preferably from about 0.9 to 1.1 equivalent). The reaction time ranges from several minutes to several days, preferably from about 15 minutes to about two days. The addition reaction of amine is conducted in a solvent which does not affect adversely on the reaction (e.g. pyridine, tetrahydrofuran, dioxane, benzene, dichloromethane, 1,2-dichloroethane, toluene, xylene) at temperatures ranging from about 15 to 130° C. Amine is employed in an amount ranging from about 1 to 5 equivalents, preferably from about 1.1 to 3 equivalents. The reaction time ranges from several minutes to several days, preferably from about 15 minutes to about two days.

The compound (xv) or a salt thereof thus produced is processed with a base to cause ring-closure reaction to thereby produce a thieno[2,3-d]pyrimidine derivative (xvi). The ring-closure reaction is conducted in a solvent which does not affect adversely on the reaction. The solvent is exemplified by alcohols such as methanol, ethanol or propanol, and ethers such as dioxane or tetrahydrofuran.

As the base, use is made of, for example, an alkali metal alkoxide such as sodium methylate, sodium ethylate or sodium isopropoxide, and an alkali metal hydride such as sodium hydride.

The amount of the base to be employed ranges from 1 to 5 equivalents, preferably from about 1.5 to 3 equivalents, relative to 1 equivalent of the compound (xv).

The reaction temperature ranges from about 10° C. to the boiling point of the solvent then employed, preferably from about 25° C. to the boiling point of the solvent then employed.

The reaction time ranges from several minutes to several days, preferably from about 10 minutes to two days.

The compound (xvi) and a halogenated aralkyl derivative are stirred, in the presence of a base (e.g. an organic base such as pyridine or triethylamine), in a solvent which does not affect adversely on the reaction (e.g. amides such as dimethylformamide or dimethylacetamide), at about 10 to 100° C., to produce a 2,4-dioxothieno[2,3-d]pyrimidine derivative (IIa). Subsequently, the said compound (IIa) is stirred together with N-bromosuccinimide (NBS) in a solvent which does not affect adversely on the reaction (e.g. halogenated hydrocarbons such as carbon tetrachloride or chloroform), in the presence of α, α'-azobisisobutyronitrile, to thereby produce the compound (IIb). Further, the said compound is stirred together with various amines, in the presence of a base, in a solvent which does not affect adversely on the reaction (e.g. amides such as dimethylformamide or dimethylacetamide, nitrites such as acetonitrile, alcohols such as ethanol), at temperatures ranging from about 10 to 100° C., to thereby produce the compound (II). When necessary, the said compound is made into a corresponding salt with a suitable acid (e.g. hydrochloric acid or oxalic acid).

The foregoing Production Method 10 is shown by Scheme 10:

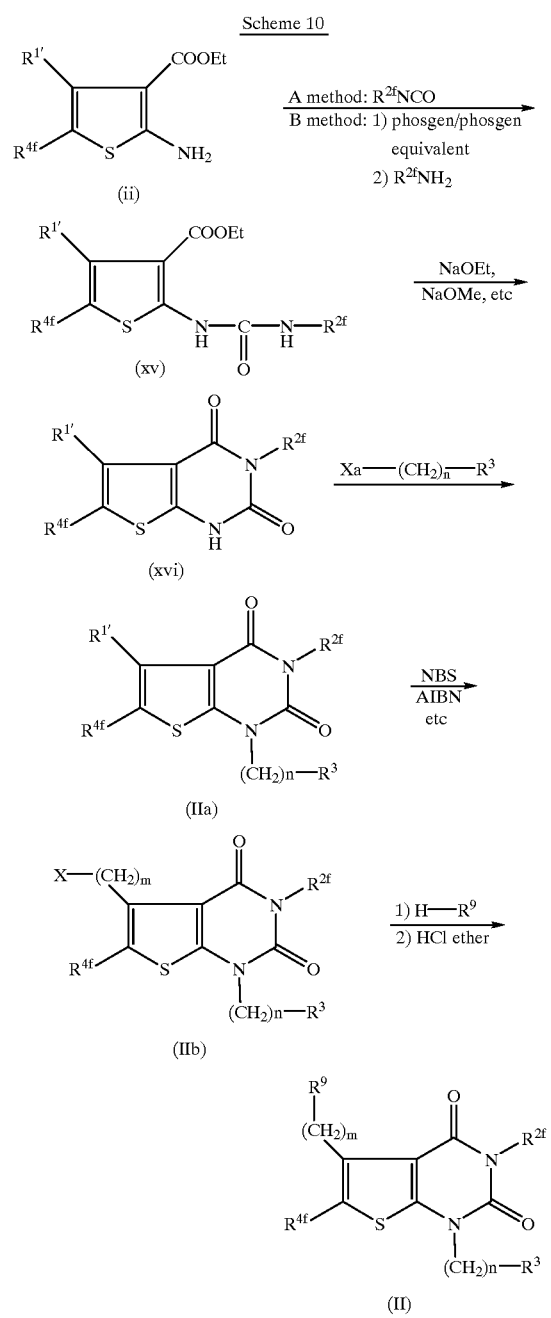

wherein each symbol is of the same meaning as defined above.

Production Method 11:

The amino group of a 2-aminothiophene derivative (xvii) is protected (e.g. Boc), which is stirred, in accordance with the method of German Patent, 2155403 (1972), or the method of Japanese Patent, 73-01664 (1973) together with a halogenated acyl derivative, in the presence of a base, in a solvent which does not affect adversely on the reaction (e.g. amides such as dimethylformamide or dimethylacetamide) at temperatures ranging from about 0 to 100° C. to give a derivative (xviii), which is stirred together with a suitable salt (e.g. lithium iodide) in a suitable solvent (e.g. acetone or methyl ethyl ketone) to give a derivative (xix), which is subjected to substitution reaction with a suitable amine (e.g. ammonia) to give a derivative (xx), which is stirred in a solvent which does not affect adversely on the reaction (e.g. toluene, dimethylformamide, dimethylacetamide, methanol or ethanol), when necessary in the presence of a suitable catalyst (e.g. sodium ethoxide or toluenesulfonic acid) at temperatures ranging from about 30 to 120° C., to cause dehydro-cyclization to thereby produce a derivative (VIIa). The said compound is stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at temperatures ranging from about 10 to 100° C. to give a 2-oxothieno [2,3-e] azepine derivative (VIIb). Subsequently, the said compound (VIIb) is stirred together with N-bromosuccinimide (NBS) in a solvent (e.g. halogenated hydrocarbons including carbon tetrachloride and chloroform), in the presence of α,α'-azobisisobutyronitrile, at temperatures ranging from about 30 to 100° C., to give a compound (VIIc). The said compound is stirred with various amines in the presence of a base, in a solvent which does not affect adversely on the reaction (e.g. amides including dimethylformamide and dimethylacetamide, nitriles including acetonitrile, and alcohols including ethanol) at temperatures ranging from about 10 to 100° C. to give a compound (VIId). When necessary, the said compound is made into a corresponding salt with a suitable acid (e.g. hydrochloric acid or oxalic acid). The foregoing Production Method 11 is shown in Scheme 11:

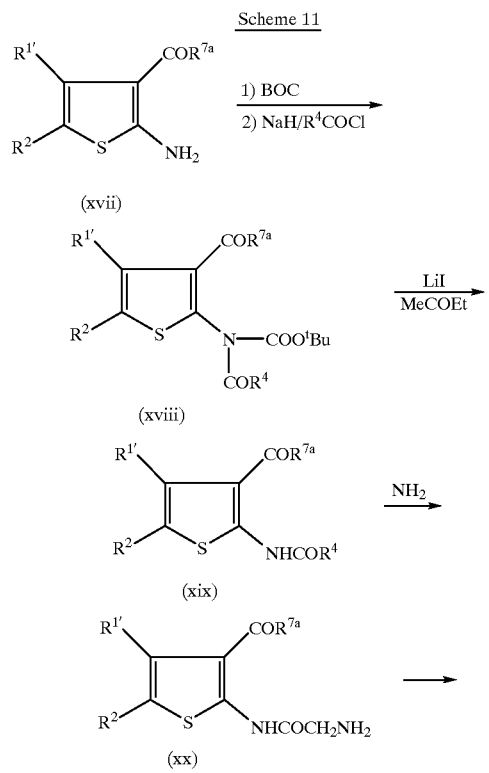

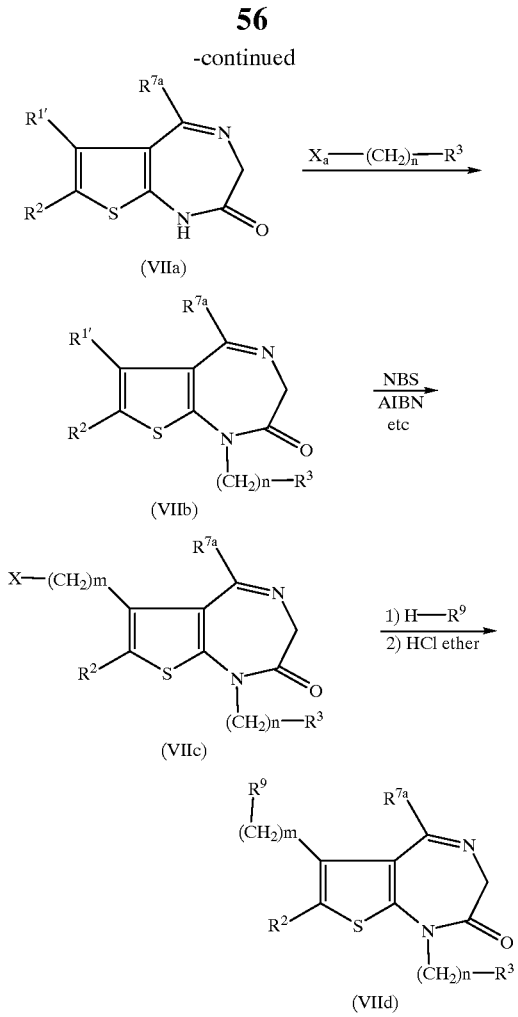

wherein each symbol is of the same meaning as defined above.

Production Method 12:

The amino group of a 2-aminothiophene derivative(ii) producible by the method described in Production Method 1 is protected (e.g. Boc), which is stirred together with a halogenated aralkyl derivative, in the presence of a base (e.g. organic bases including potassium carbonate, pyridine and triethylamine), in a solvent which does not affect adversely on the reaction (e.g. amides including dimethylformamide and dimethylacetamide), at temperatures ranging from about 10 to 100° C., to give a derivative (xxi), which is subjected to alkali hydrolysis with a suitable alkali (e.g. sodium hydroxide) in a suitable solvent (e.g. methanol, tetrahydrofuran), and, the derivative thus produced is stirred together with diphenylphosphorylazide (DPPA) in a solvent which does not affect adversely on the reaction (e.g. toluene, tetrahydrofuran, dimethylformamide, dimethylacetamide, ethanol) at temperatures ranging from about 0 to 100° C., and the resultant is made into a carbamic acid ester derivative (xxii) with a suitable alcohol (e.g. ethanol). The said derivative is stirred, in the presence of a base (e.g. sodium ethoxide), in a solvent which does not affect adversely on the reaction (e.g. dimethylformamide, dimethylacetamide), at temperatures ranging from about 0 to 100° C. to give a 2-oxothieno[2,3-d] imidazol derivative (VIIe). The said compound is stirred together with a halogenated alkyl derivative, in the presence of a base, in a solvent which does not affect adversely on the reaction (e.g. amides including dimethylformamide, dimethylacetamide), at temperatures ranging from about 0 to 100° C. to give a compound (VIIf). Subsequently, the said compound (VIIf) is stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile, at temperatures ranging from about 30 to 100° C. to give a compound (VIIg). The said compound is further stirred, together with various amine, in the presence of a base, in a solvent which does not affect adversely on the reaction (e.g. amides including dimethylformamide and dimethylacetamide, nitrites including acetonitrile, alcohols including ethanol), at temperatures ranging from about 10 to 100° C. to produce a compound (VIIh). The said compound, when necessary, is made into a corresponding salt with a suitable acid (e.g. hydrochloric acid, oxalic acid). The foregoing Production Method 12 is shown in Scheme 12:

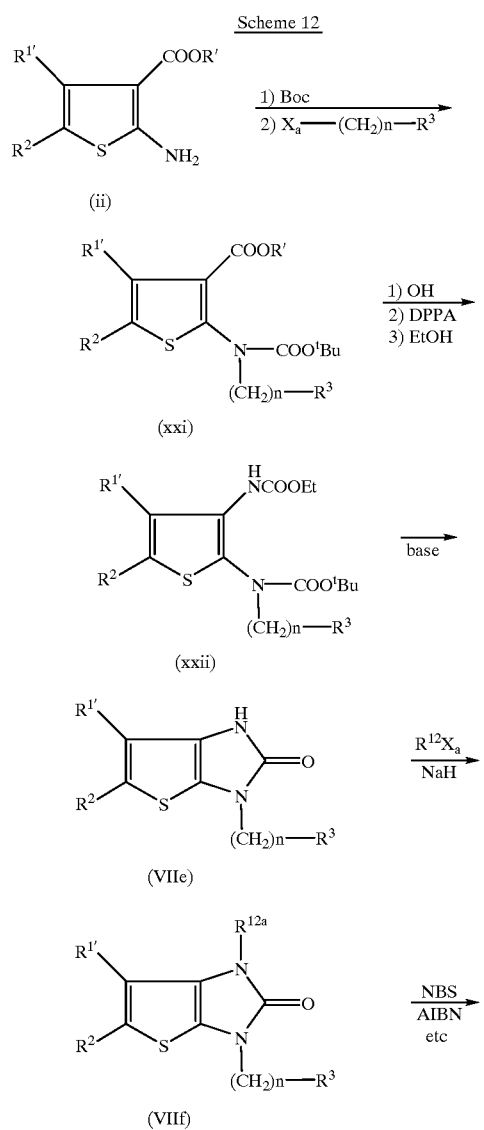

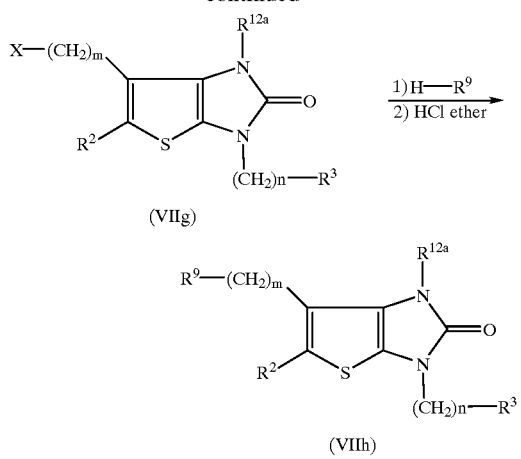

wherein each symbol is of the same meaning as defined above.

Production Method 13:

Starting from a 2-aminothiophene derivative (ii) producible by the method described in Production Method 1 or a salt thereof, 4,5-dihydro-7-hydroxy-5-oxothieno [3,2-b] pyridine-6-carboxylic acid ethyl derivative (VIIj) is produced by the method of J. M. Barker et al. (J. Chem. Res. (M), 1980, 113; J. Chem. Res. (s), 6(1980)). More specifically, the 2-aminothiophene derivative (ii) or a salt thereof is allowed to react with malonic acid ester to give the compound (xxiii), which is stirred, in the presence of a suitable base (e.g. sodium hydride), in a solvent which does not affect adversely on the reaction (e.g. amides including dimethylformamide (DMF) and dimethyl acetamide), at temperatures ranging from about 10 to 100° C. to give the derivative (VIIj). The said derivative (VIIj) is stirred, together with a halogenated aralkyl derivative, in the presence of a base (e.g. organic bases including potassium carbonate, pyridine and triethylamine), in a solvent which does not affect adversely on the reaction (e.g. amides including dimethylformamide and dimethyl acetamide), at temperatures ranging from about 10 to 100° C. to give a derivative (VIIk), and,the said derivative is stirred, together with N-bromosuccinimide (NBS), in a solvent which does not affect adversely on the reaction (e.g. halogenated hydrocarbons including carbon tetrachloride and chloroform), in the presence of α,α'-azobisisobutyronitrile (AIBN), at temperatures ranging from about 30 to 100° C. to give the compound (VIIm). Further, the said compound was stirred, together with various amines, in the presence of a base, in a solvent which does not affect adversely on the reaction (e.g. amides including dimethylformamide and dimethyl acetamide, nitriles including acetonitrile, alcohols including ethanol), at temperatures ranging from about 10 to 100° C. to produce the compound (VIIn). When necessary, the said compound is made into a corresponding salt with a suitable acid (e.g. hydrochloric acid, oxalic acid).The foregoing Production Method 13 is shown in Scheme 13:

Scheme 13

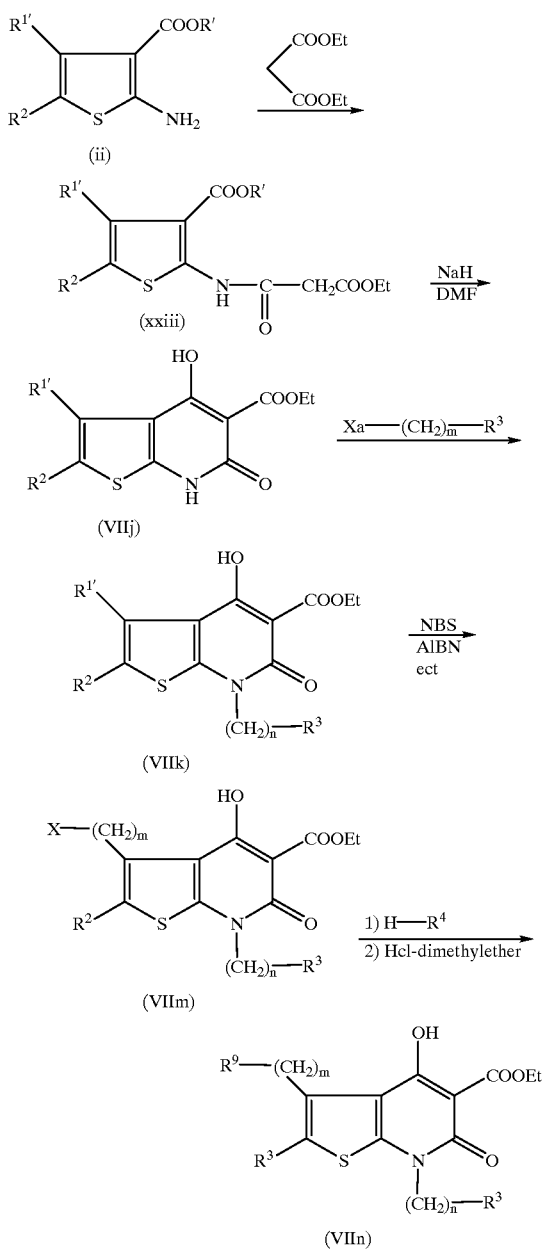

wherein each symbol is of the same meaning as defined above.

Production Method 14:

In a suitable solvent which does not affect adversely on the reaction (e.g. halogenated hydrocarbons including dichloromethane, and ethers including tetrahydrofuran, ethyl ether and dioxane), the 1,4-dihydro-4-oxoquinoline-3-carboxylic acid ester derivative (Va') is stirred, together with an aluminumn amide derivative produced from a suitable aluminum reagent, e.g. trimethyl aluminum, triethyl aluminum or diisobutyl aluminum hydride (DIBAL), and amines, at temperatures ranging from about 10 to 100° C. to give a 1,4-dihydro-4-oxoquinoline-3-carboxylic acid amide derivative (Va"). The said derivative is stirred, together with a Grignard reagent ($R^{14d}MgXa$), in a suitable solvent (e.g. tetrahydrofuran and ethyl ether) at temperatures ranging from 0 to 80° C. to give a corresponding ketone derivative (Vc). The above Production Method 14 is shown in Scheme 14:

Scheme 14

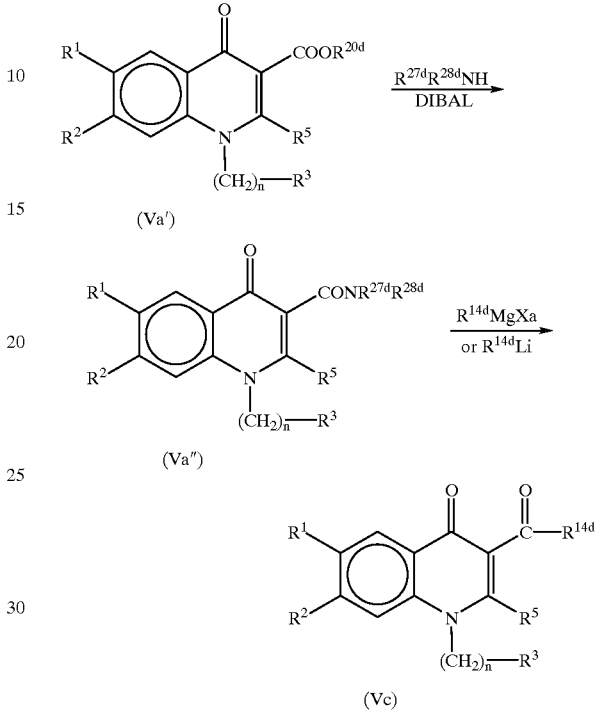

wherein $R^{26d}$ is alkyl or aryl, $R^{27d}$ and $R^{28d}$ are each hydrogen or hydrocarbon residue, and other symbols are of the same meaning as defined in the foregoing.

The alkyl and aryl shown by the above-mentioned $R^{26d}$ is of the same meaning as defined in the foregoing.

The hydrocarbon residues shown by the above-mentioned $R^{27d}$ and $R^{28d}$ are of the same meaning as the hydrocarbon residue in the optionally substituted carbonyl group with a hydrocarbon residue shown by the above-mentioned R'.

Production Method 15:

In a suitable solvent which does not affect adversely on the reaction (e.g. halogenated hydrocarbons including dichloromethane, and ethers including tetrahydrofuran, ethyl ether and dioxane), 1,4-dihydro-4-oxopyrido [2,3-b] pyridine-3-carboxylic acid ester derivative (Vd) is stirred, together with an aluminum amide derivative produced from a suitable aluminum reagent [e.g. trimethyl aluminum, triethyl aluminum and diisobutyl aluminum hydride (DIBAL)] and amines, at temperatures ranging from about 10 to 100° C. to give a 1,4-dihydro-4-oxopyrido[2,3-b]pyridine-3-carboxylic acid amide derivative (Vd'). The said derivative is stirred, together with a Grignard reagent, in a suitable solvent which does not affect go adversely on the reaction (e.g.tetrahydrofuran and ethyl ether), at temperatures ranging from about 0 to 80° C. to give a corresponding ketone derivative (Ve). The Production Method is shown in Scheme 15:

Scheme 15

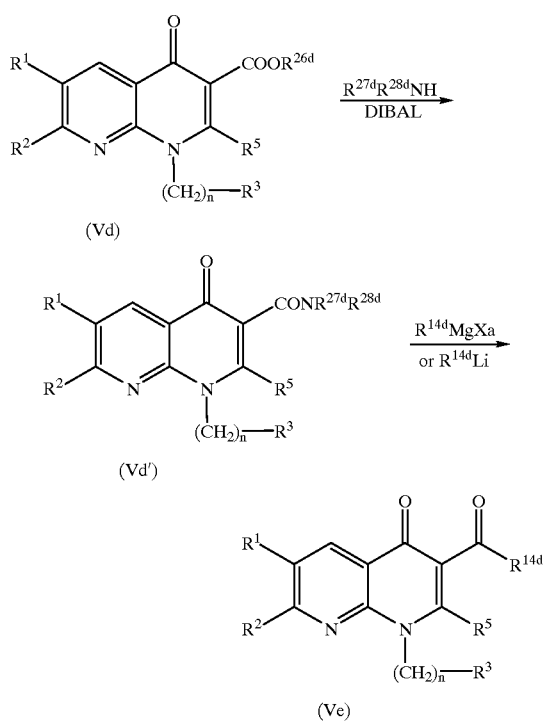

wherein $R^{26d}$ is alkyl or aryl, $R^{27d}$ and $R^{28d}$ are each hydrogen or hydrocarbon residue, and other symbols are of the same meaning as defined above.

The alkyl and aryl shown by the above $R^{26d}$ are of the same meaning as defined above.

The hydrocarbon residue shown by the above $R^{27d}$ and $R^{28d}$ is of the same meaning as the hydrocarbon residue in the carbonyl group optionally substituted with hydrocarbon residue shown by the above-mentioned R'.

Production Method 16:

4,7-Dihydro-2-halogeno-4-oxothieno[2,3-b]pyridine derivative (XIp) is dissolved in a suitable solvent which does not affect adversely on the reaction (e.g. ethers including 1,2-dimethoxyethane, tetrahydrofuran and dioxane and alcohols including ethyl alcohol). To the solution is added, in the presence of equimolar to an excess amount (2 to 10 equivalents) of a suitable base (e.g. sodium carbonate), a suitable aryl boric acid derivative (e.g. phenyl boric acid, 3-methoxyphenyl boric acid and 4-ethoxycarbonyl phenyl boric acid). To the mixture is added, in the streams of an inert gas (e.g. argon gas), a suitable catalyst [e.g. palladium metal including tetrakis (triphenylphosphine) palladium]. The mixture is stirred for a period ranging from several minutes to several hours at temperatures ranging from about 10 to 100° C. Insolubles are removed to leave the desired derivative (XIq). The foregoing Production Method 16 is shown in Scheme 16:

Scheme 16

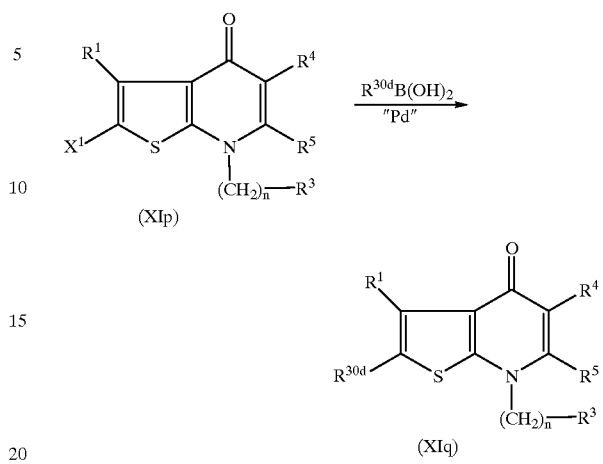

wherein wherein X' is halogen, $R^{30d}$ is an optionally substituted aryl group, and other symbols are of the same meaning as defined above.

Production Method 17:

Production of a derivative which has 2,5-dioxo-4-imidazolidinyl at 5-position is illustrated in Scheme 17, infra:

The formyl derivative (ih), which is obtained in the above Production Method 5 or its similar method, is reacted with a sodium bisulfite in an appropriate solvent, e.g. water, ethanol. The reaction is carried out at 0° C. to 80° C. under stirring to give a sulfuric acid additive (iih).

To the additive (iih) is added a cyano compound, e.g. potassium cyanide, sodium cyanide, in an appropriate solvent, e.g. aqueous ethanol, aqueous tetrahydrofuran, dioxane, in the presence of an equivalent to an excess amount of a base, e.g. ammonium carbonate. The reaction is carried out at 0° C. to 80° C. under stirring, and under refluxing when required, to give an imidazoldiinyl derivative (XIIa).

The foregoing method is shown in Scheme 17. In Scheme 17, all the groups have the same meaning as defined above.

Scheme 17:

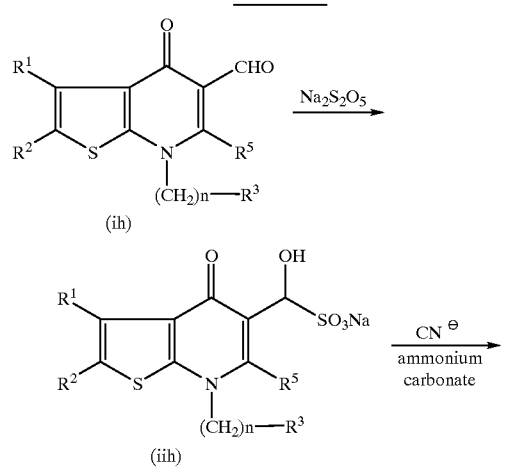

-continued

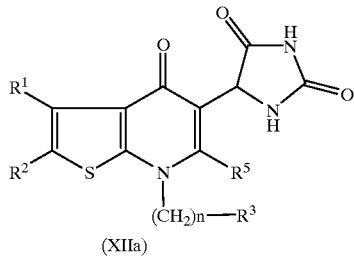

(XIIa)

Production Method 18:

Production of a compound which has an oxazolyl group at 5-position is illustrated in Scheme 18, infra:

The derivative (iiih), which has a formyl group at 5-position, is reacted with an equivalent to excess amount of tosylmethylisoniazide in an appropriate solvent, e.g. methanol, ethanol, in the presence of an equivalent to an excess amount of a base, e.g. potassium carbonate. The reaction is carried out at 0° C. to 80° C. under stirring, and under refluxing when required, to give a derivative (XIIb) which has an oxazolyl group at 5-position.

The foregoing production method is shown in Scheme 18. In scheme 18, other groups have the same meaning as defined above.

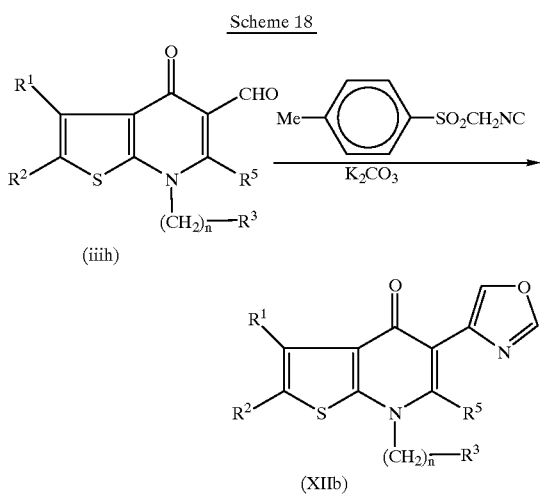

Production Method 19:

Production of a compound having 4-imidazolyl group or 4-thiazolyl group at 5-position is illustrated in Scheme 19, infra:

4,7-Dihydro-5-acyl-4-oxothieno[2,3-b]pyridine derivative (ivh), obtaimed in Production Method 5 or 6, is dissolved in an appropriate solvent, e.g. acetic acid, methanol, tetrahydrofuran, ethylether, dioxane.

To the solution an equivalent to a small excess of halogenating agent, e.g. bromine or iodine, is added dropwise under a room temperature or ice-cooling. The mixture is stirred at a temperature of 0° C. to 80° C. to give an α-haloketon derivative (vh).

α-Haloketon derivative (vh) is dissolved in an appropriate solvent, e.g. methanol, tetrahydrofuran, ethylether, dioxane, dimethylformamide. To the solution is added an equivalent to a small excess amount of amidine derivative under room temperature or ice-cooling. The mixture is stirred at a temperature of 0° C. to 80° C., and the system is heated if required, to give a 4-imidazolyl derivative (XIIc).

The α-haloketone derivative (vh) is reacted with a thiocarbamoyl derivative in an appropriate solvent, e.g. methanol, ethanol, dimethylformamide, dimethylacetamide, at a temperature of about 10° C. to 100° C. under stirring to give a 4-thiazolyl derivative (XIId).

Similar to the above, the α-haloketone derivative is reacted with a thioglycolic acid amide, and then subjected to a ring-closure reaction to give a 1,4-thiazinyl derivative.

The foregoing method of the production of imidazolyl derivative and thiazolyl derivative is shown in Scheme 19. In Scheme 19, $R^{43h}$ denotes hydrogen atom, $C_{1-6}$ alkyl or $C_{6-14}$ aryl. $R^{44h}$ denotes hydrogen atom, $C_{1-6}$ alkyl or $C_{6-14}$ aryl. $R^1, R^2, R^3, R^5$ and n have the same meaning as defined above. Xa denotes a halogen atom.

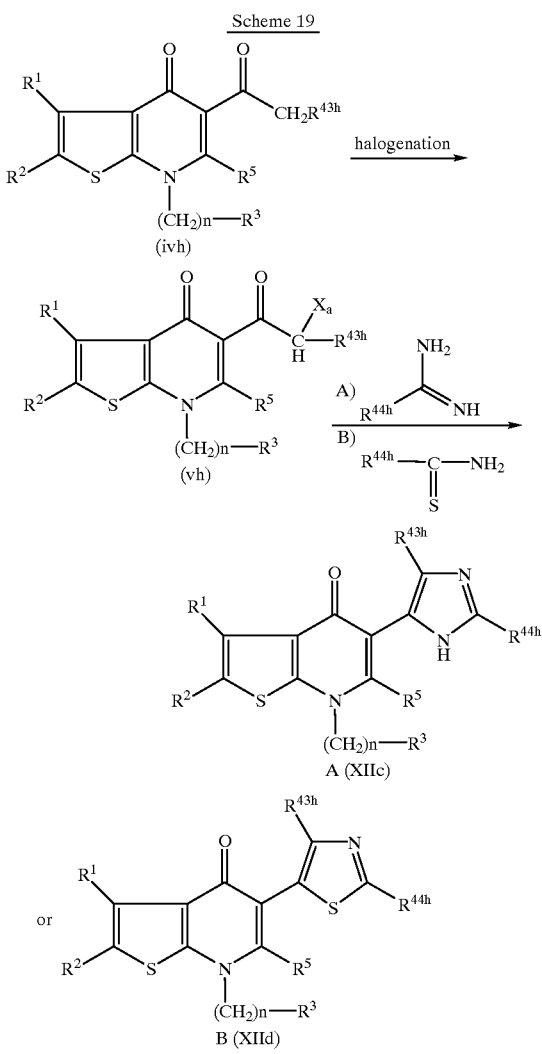

Production Method 20:

Production of a compound having 2-oxazolyl group at 5-position is illustrated in Scheme 10, infra:

4,7-Dihydro-5-carbamoyl-4-oxothieno[2,3-6]pyridine derivative (vih), obtained by the first step in the above Production Method 6, is dissolved in an appropriate solvent, e.g. methanol, ethanol, tetrahydrofuran, dioxane, and to the solution is added an equivalent to a small excess of α-haloketone compound dropwise under room temperature or ice-cooling. The mixture is stirred at 0° C. to 80° C., and refluxed under heating if required, to give a 2-oxazolyl derivative (XIIe).

The foregoing method is shown in Scheme 20. In Scheme 20, $R^{45h}$ denotes hydrogen atom, $C_{1-6}$ alkyl or $C_{6-14}$ aryl. Xa denotes a halogen atom and $R^1$, $R^2$, $R^3$, $R^5$ and n have the same meaning as defined above.

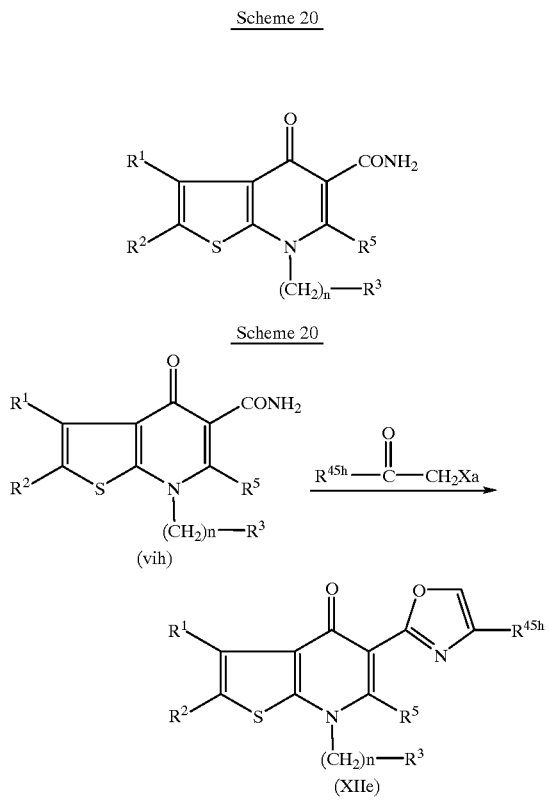

Production Method 21:

Production of a compound having 2-thiazolyl at 5-position is illustrated in Scheme 11, infra:

To a solution of 4,7-Dihydro-5-carbamoyl-4-oxothieno[2,3-b]pyridine derivative (vih) in an appropriate solvent, e.g. toluene, tetrahydrofuran, dioxane, an equivalent amount or a small excess amount of thioamide reagent, e.g. Lawessons reagent, is added under room temperature or ice-cooling. The mixture is stirred at a temperature of 0° C. to 80° C., and subjected to refluxing under heating if required, to give a 4,7-dihydro-5-thiocarbamoyl-4-oxothieno[2,3-b]pyridine derivative (viih).

Said thicarbamoyl derivative (vii h) is dissolved in an appropriate solvent, e.g. methanol, ethanol, tetrahydrofuran, dioxane, and to the solution is added dropwise an equivalent amount to a small excess amount of α-haloketone compound under room temperature or ice-cooling. The mixture is stirred at a temperature of about 0° C. to 80° C., and is subjected to refluxing under heating, to give 2-thiazoly derivative (XIIf).

The foregoing method is shown in Scheme 21. In Scheme 21, $R^{46h}$ denotes hydrogen $C_{1-6}$ alkyl or $C_{6-14}$ aryl. Xa denotes a halogen atom. $R^1$, $R^2$, $R^3$, $R^5$ and n have the same meaning as defined above.

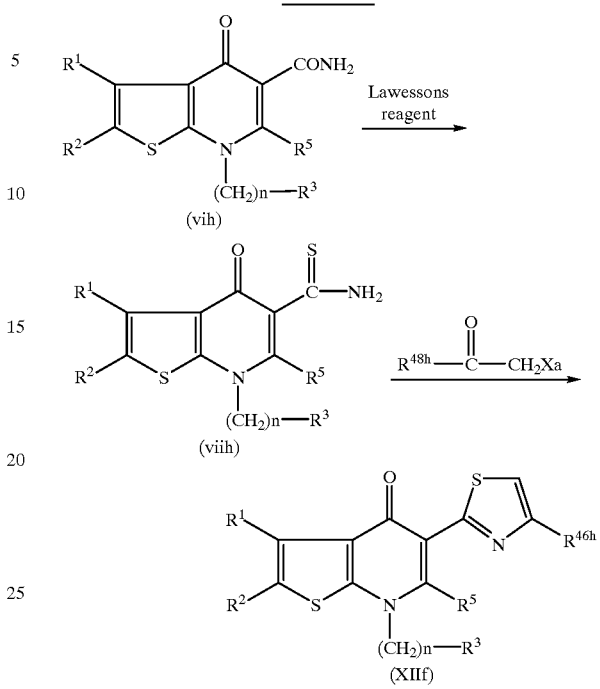

Production Method 22:

Production of a compound having 3-pyrazolyl group at 5-position is illustrated in Scheme 12, infra:

To a solution of 4,7-dihydro-5-acetyl-4-oxothieno[2,3-b]pyrimidine (viiih), obtained by the method of Production Method 6, in an appropriate6 solvent, e.g. methanol, ethanol, tetrahydrofuran, dioxane is added dropwise an excess amount of formyl ethyl ester and a base, e.g. sodium ethoxide, under room temperature or under ice-cooling. The mixture is stirred at a temperature of 0° C. to 80° C. to give an α-formylketone derivative (ixh).

The α-formylketone derivative (ixh) is dissolved in an appropriate solvent, e.g. water, methanol, tetrahydrofuran, dioxano, dimethylformamide. To the solution is added an equivalent to a small excess of hydrazine derivative or its salt under room temperature or ice-cooling. The mixture is stirred at a temperature of about 0° C. to 80° C., and subjected to refluxing under heating if required, to give a 3-pyrazolyl derivative (XIIg).

The foregoing method is shown in Scheme 22. In Scheme 22, $R^1$, $R^2$, $R^3$, $R^5$ and n have the same meaning as defined above.

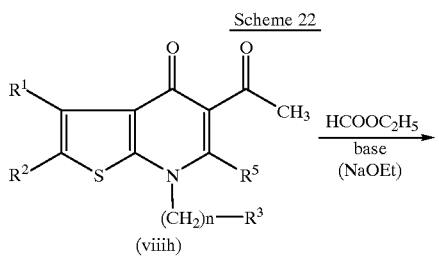

-continued

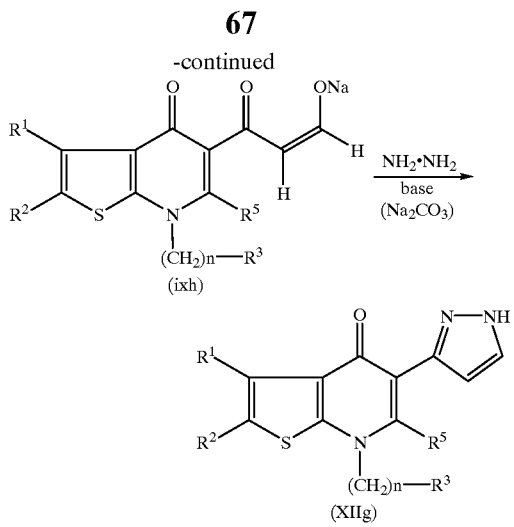

Production Method 23:

Production of a compound having 2-triazolyl at 5-position is illustrated in Scheme 23, infra:

4,7-Dihydro-5-thiocarbamoyl-4-oxothieno[2,3-b]pyrimidine derivative (xh), which is produced in the first process of Production Method 21, is dissolved in an appropriate solvent, e.g. ethyl ether, dimethylformamide, tetrahydrofurane, dioxane, dichloromethane. To the soluion is added an equivalent amount to a small excess amount of methyl iodide at a temperature of 0° C. to 80° C., and the mixture is subjected to refluxing under heating if required, to give a derivative of tetra salt.

To a solution of the derivative in an appropriate solvent, e.g. dimethylformamide, or to the derivative without such solvent, is added an excess amount of formic acid hydrazide under room temperature or ice-cooling.

The mixture is stirred at room temperature to 200° C., to give a 2-triazol derivative (XIIh).

The foregoing method is shown in Scheme 23. In Scheme 23, the groups have the same meaning as defined above.

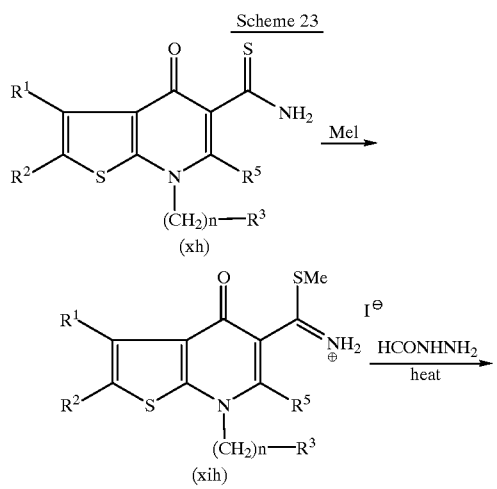

-continued

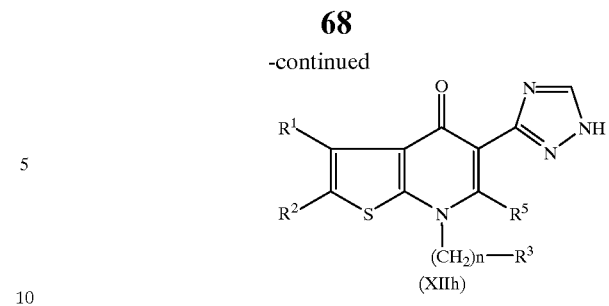

Production Method 24:

Production of a compound having 2-oxazolinyl at 5-position illustrated in SCheme 14, infra:

2,7-Dihydro-4-oxothieno[2,3-b]pyridine-5-carboxylic acid ester (xiih) is added dropwise under ice-cooling to an excess amount of a solution of aluminum amide of ethanol amine in dichloromethane. The mixture is stirred for one to 4 hours at room temperature to produce an amide derivative.

To the solution of the amide derivative in an appropriate solvent, e.g. dichloromethane, ethyl ether, tetrahydrofuran, is added thionyl chloride under ice-cooling.

The mixture is stirred at a temperature of 0° C. to room temperature to give a 2-oxazolinyl derivetive (XIIi).

The foregoing method is shown in Scheme 24. In the Scheme 24, $R^1$, $R^2$, $R^3$, $R^5$ and n have the same meaning as defined above.

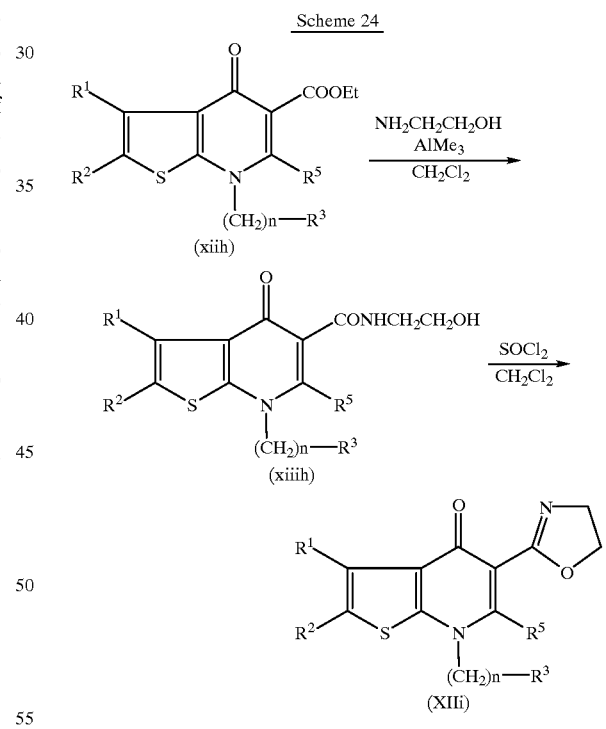

Production Method 25:

Production of the compound wherein $R^{4h}$ is a group bonded through a nitrogen atom is illustrated in Scheme 25, infra:

The compound (xivh), which can be produced by a similar manner of Production Methods 5 or 6, is dissolved in an appropriate solvent, e.g. pyridine. To the solution is added an equivalent to a small excess amount of hydroxylamine derivative or its salt, and the mixture is reacted under room temperature or an elevated temperature, to produce oxime derivative (xvh). The oxime derivative (xvh) is dissolved in an appropriate solvent, e.g. pyridine, and to the solution is added an equivalent to a small excess amount of an acylating agent, e.g. acid halide, acid anhydride, sulfonic acid halide.

The mixture is reacted, under room temperature or under heating for 1 to 12 hours to give a dislocation form (XIIj).

The dislocation form (XIIj) is dissolved in an appropriate solvent, e.g. ethylalcohol, and to the solution is added an alkali, e.g. an sodium hydroxide solution, and the mixture is stirred for about 2 hours to cause an alkali hydrolysis reaction, whereby a primary amino derivative (XIIk) is produced.

The foregoing method is shown in Scheme 25. In Scheme 25, $R^1$, $R^2$, $R^3$, $R^5$ and n have the same meaning as defined above. Ac means acetyl group.

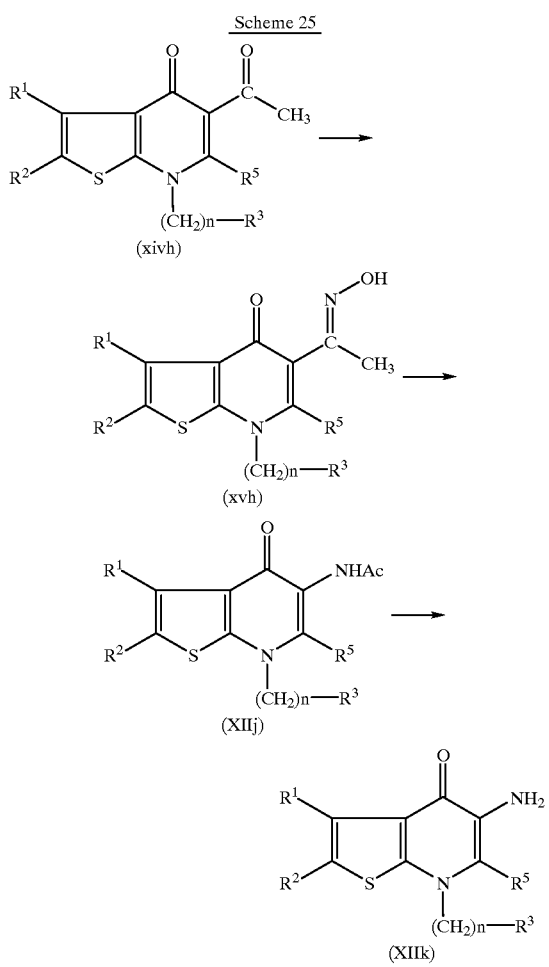

From thus obtained primary amino derivative (XIIk), various derivatives can be produced by alkylation, acylation, sulfonation, imidation and so forth.

Production Method 26:

Production of the compound wherein $R^4$ is a group bonded through an oxygen atom is illustrated in Scheme 26, infra:

The compound (xvih), which can be obtained by the method described in Prodcution Methods 5 or 6, is dissolved in an appropriate solvent, e.g. dichloromethane. To the solution is added a small excess amount, e.g. 1.2 to 1.5 equivalent, of peracids, e.g. chlorobenzoic acid, and the mixture is stirred for 1 to 6 hours to give a dislocation from (XIIm).

The dislocation form (XIIm) is subjected to a reaction by stirring the mixture of the dislocation form (XIIm) with an alkali, e.g. 2N sodium hydroxide solution, in an appropriate solvent, e.g. tetrahydrofuran, under room temperature or under heating, e.g. 40 to 60° C., for 1 to 12 hours, to give an alcoholic derivative (XIIn).

The alcoholic derivative (XIIn) is dissolved in an appropriate solvent, e.g. dimethylformamide, and to the solution are added an alkali, e.g. potassium carbonate, and alkyl halide, e.g. isopropyl bromide, and the mixture is stirred for about one to 24 hours at room temperature to heating, e.g. 40 to 80° C., to give alkoxy derivative (XIIo).

Furthermore, when the alkoxy group is isopropoxy group, the alkoxy derivative is dissolved in an appropriate solvent, e.g. dichloromethane, an excess amount of Lewis acid, e.g. borone trichloride, is added to the solution and the mixture is stirred for one to 6 hours under ice-cooling or room temperature, to give de-alkylated alcoholic derivative (XIIn).

The foregoing methods are shown in Scheme 26. In Scheme 26, $R^1$, $R^2$, $R^3$, $R^5$ and n have the same meaning as defined above. $R^{30h}$ and $R^{4'}$ denote an alkyl group. Xa denotes a halogen atom.

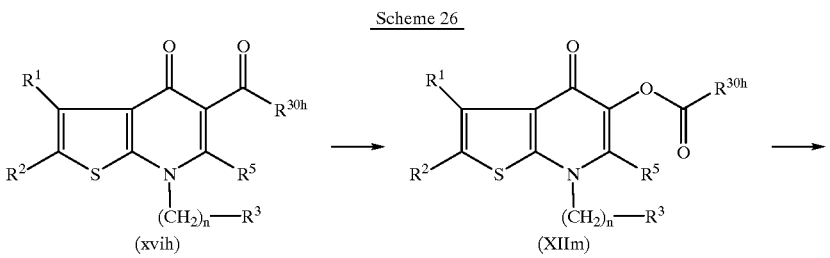

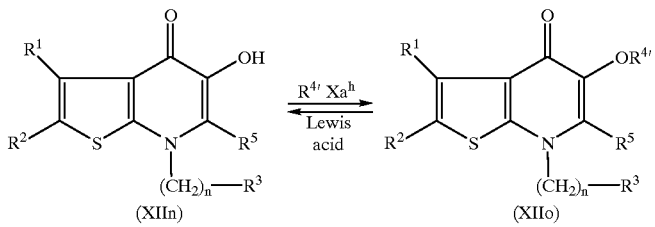

From thus obtained alcoholic derivative (XIIn), various derivatives can be produced by alkylation, acylation, alkenylation, sulfonation and so forth.

Production Method 27:

Production of the compound wherein $R^4$ is a group bonded through a sulfur atom is illustrated in Scheme 27, infra:

At first, thioglycolic acid ester is reacted with an alkali iodide, and then the product is reacted with dimethylaminomethylene compound to give a compound (xviih).

The 2-aminothiophen derivative (xviiih), which is obtained in the above Production Method 1, Scheme 1, is dissolved in an appropriate solvent, e.g. ethyl alcohol, and to the solution is added a base, e.g. an aqueous sodium hydroxide solution, to cause to alkali hydrolysis to give a compound (xixh).

The compound (xixh) is reacted with the compound (xviih) shown above by stirring in an appropriate solvent, or without any solvent, under heating, e.g. 80 to 150° C., for 1 to 6 hours to give an amino substituted derivative (xxh).

The derivative (xxh) is heated, e.g. at 150 to 250° C., in an appropriate solvent, e.g. diphenyl ether, for 30 minutes to 3 hours to give a cyclic form (xxih).

The cyclic form (xxih) is reacted with a compound of the formula: Xa —(CH$_2$)n —R$^3$ by a similar manner as described above in the reaction with a compound of the formula: Xa —(CH$_2$)n —R$^3$ in the Production Method 1, to give a compound (XIIp).

Furthermore, the compound (XIIp) is reacted by stirring with an equivalent to an excess amount of peracid compound, e.g. m-chlorobenzoic acid, in an appropriate solvent, e.g. dichloromethane, under ice-cooling for 5 minutes to about 2 hours to give sulfoxide derivative (XIIq).

The foregoing methods are shown in Scheme 27. In Scheme 17. $R^1$, $R^2$, $R^3$, Xa and n have the same meaning as defined above. $R^{4''}$ denotes an alkyl group.

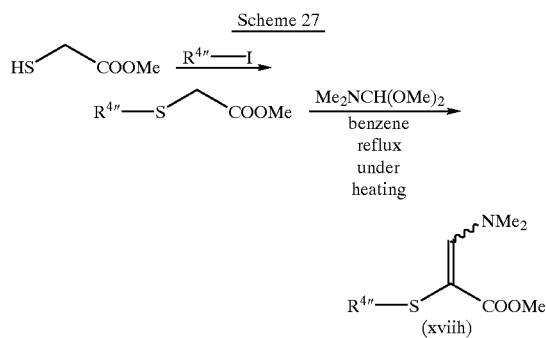

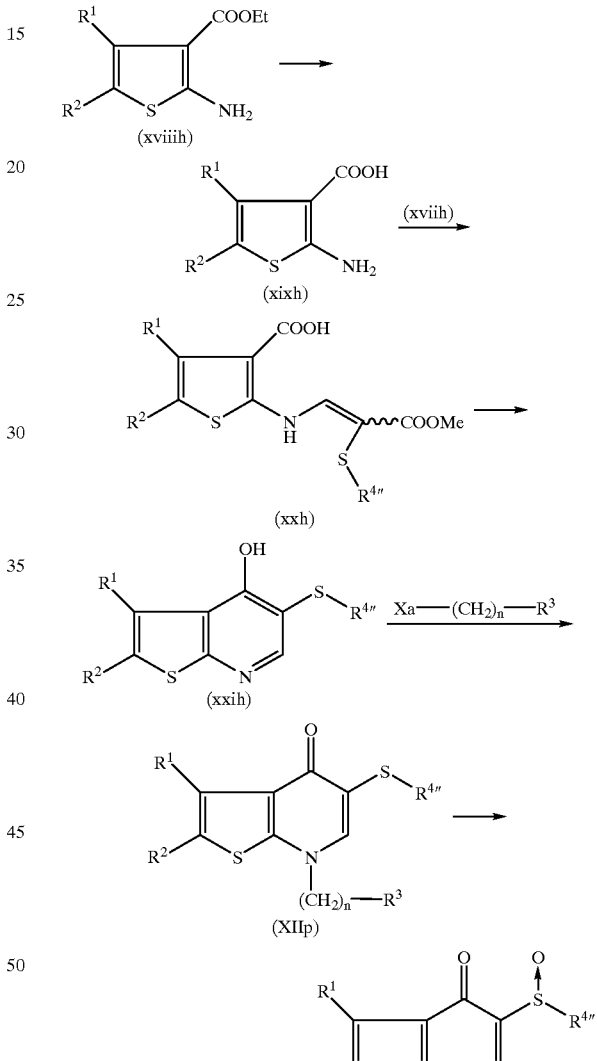

Production Method 28:

Production of the Compound wherein it has a phenyl group substituted by an alkenyl group which may optionally be substituted at 2-position is illustrated in Scheme 28, infra:

4,7-Dihydro-2-(4-aminophenyl)-4-oxothieno[2,3-b] pyrimidine derivative (XIIr) is reacted with diazonizing agent, e.g. sodium nitrite, isoamyl nitrite, in an appropriate proper solvent, e.g. dimethylformamide, dichloromethane, tetrahydrofuran, dioxane, acetenitrile, water, etc, to give a diazonium salt.

To the diazonium salt is added one equivalent to excess amount of an alkenyl derivative, e.g. olephine compound, and palladium catalyst, e.g. bis(dibenzylideneacetone)

The foregoing production method is shown in Scheme 29. In Scheme 29, $R^{35h}$ to $R^{39h}$ denote alkyl group —$R^{40h}$ denotes a group —C($R^{36h}$)—CO—$R^{35h}$ or a group —C(OH)$R^{36h}R^{39h}$. Other groups have the same meaning as defined above.

Scheme 29

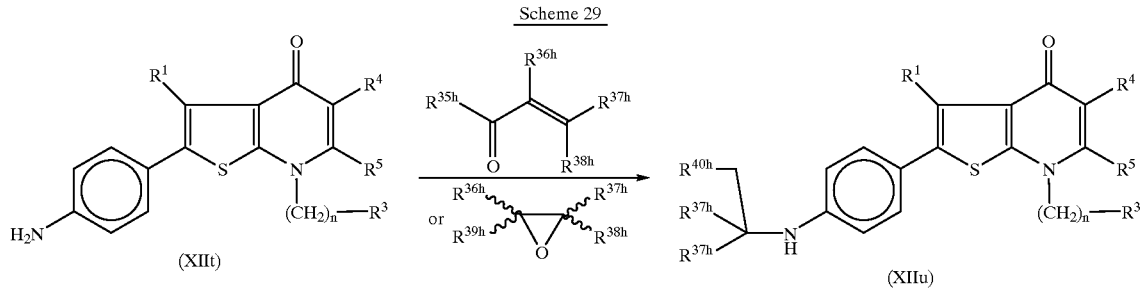

palladium. The reaction is conducted at 0° C. to 80° C. under stirring, to give the desired product, i.e. the compound (XIIs).

The foregoing production method is shown in Scheme 28. In Scheme 28, $R^{32h}$ and $R^{33h}$ independently are an acyl group, $R^{34h}$ denotes a hydrogen atom or $C_{1-6}$ alkyl. Other groups have the same meaning as defined above.

Scheme 28

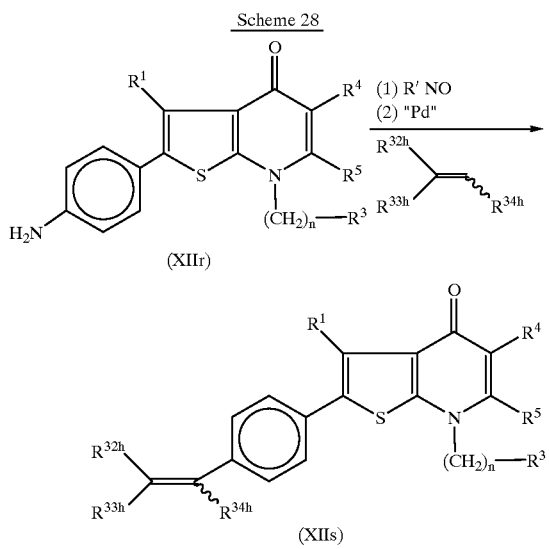

Production Method 29:

Production of a compound which has an aminophenyl group substituted by (1) an optionally substituted alkyl group or (2) an optionally substituted homo-cyclic group is illustrated in Scheme 29, infra:

4,7-Dihydro-2-(4-aminophenyl)-4-oxothieno[2,3-b] pyrimidine derivative (XIIt) is dissolved in an appropriate solvent, e.g. acetic acid, dimethylformamide, dichloromethane, tetrahydrofuran, dioxane. To the solution is added one equivalent to excess amount of Michael acceptor derivative, e.g. acrylic acid ester, or an oxyrane derivative, e.g. epoxy compound. The reaction is carried out at 0° C. to 80° C. under stirring to give the desired compound (XIIu).

Production Method 30:

Production of a compound which has an aminophenyl group substituted by (1) an optionally substituted alkyl or (2) an optionally substituted homo-cyclic group is illustrated in Scheme 20, infra:

4,7-Dihydro-2-(4-aminophenyl)-4-oxothieno[2,3-b] pyrimidine derivative (XIIv) is dissolved in an appropriate solvent, e.g. pyridine, dimethylformamide, dichloromethane, tetrahydrofuran, ethylether, dioxane. To the solution is added one equivalent to one excess amount of acid chloride or acid anhydride, e.g. trifluoroacetic acid anhydride. The reaction is carried out at 0° C. to 80° C. under stirring to give a derivative (XIIw).

The obtained derivative (XIIw) is dissolved in a solvent, e.g. pyridine, dimethylformamide, dichloromethane, tetrahydrofuran, ethylether, dioxane, acetone, and to the solution is added one equivalent to an excess amount of a base, e.g. potassium carbonate, triethylamine, sodium hydrogen, and one equivalent to one excess amount of a halogenated alkyl, e.g. methyl iodide, propyl iodide, benzyl iodide. The reaction is carried out at 0° C. to 80° C. under stirring.

The obtained derivative is subjected to alkali hydrolysis using small excess amount of 1N sodium hydroxide in an appropriate solvent, e.g. tetrahydrofuran, dioxane, ethanol, methanol, acetone, to give the desired derivative (XIIx).

The foregoing method is shown in Scheme 30. In Scheme 30, the group $R^{41h}$ represents $C_{1-6}$ alkyl or trifluoromethyl. The group $R^{42h}$ is an optionally substituted alkyl group or an optionally substituted homo-cyclic group. Other groups have the same meaning as defined above.

Scheme 30

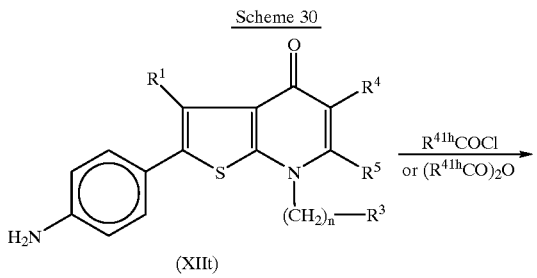

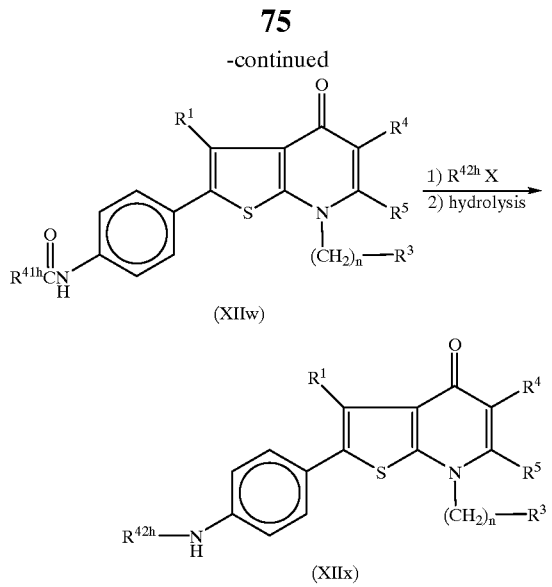

(XIIw)

(XIIx)

Production Method 31: Exchange the group at 3-position:

The group at 3-position of the compound can be exchanged by the following method as illustrated in Scheme 31.

The compound (XIIy) is stirred together with N-bromosuccinimide (NBS) in an appropriate solvent, e.g. halogenated hydrocarbons such as carbon tetrachloride and chloroform, in the presence of α, α-azobisisobutyronitrile (AIBN), at temperatures ranging from about 30 to 100° C. to give a compound (II'), and if required the compound (II') is subjected to a reaction with aliphatic carboxylic acid, alkylsulfonic acid, or alkylarylsulfonic acid to cause a reaction of exchanging the group at 3-position.

The compound (II') is reacted with an equivalent mole to a small excess amount (about 3 mole) of primary or secondary amine, e.g. $R^{1'}$-H to give a compound (III'). The reaction can be carried out in an appropriate solvent which does not adversely effect the reaction. As the solvent, mention is made of amides such as dimethylformamide or dimethylacetamide, nitriles such as acetonitrile, alcohols such as ethanol, and furthermore diethoxyethane, tetrahydrofuran, dioxane, toluene, dichloromethane, chloroform, ethylether, acetone and ethyl acetate can be used. In this reaction, if necessary, a base may be used. As the base, mention is made of a tertiary organic amine, e.g. trimethylamine, triethylamine, diisopropylamine, pyridine, 1,8-diazabicyclic[5,4,0]-7-undecene (DBU), and an inorganic salt, e.g. anhydrous potassium carbonate. The reaction is carried out at a temperature of about 10 to 100° C. The reaction time is about 0.5 to 8 hours. When the reaction is carried out under stirring, the reaction proceeds smoothly.

This reaction gives the compound (III'). The described above is shown in Scheme 21 below:

In Scheme 31, the group $R^{1''}$ denotes a hydrogen atom or a $C_{1-6}$ alkyl group, the group $R'''$ denotes a group bonded through a nitrogen atom, the groups $R^2$, $R^3$, $R^4$, $R^5$ and m have the same meaning as defined above. m denotes an integer of 0 to 6. X denotes a leaving group.

As the leaving group shown by X, mention is made of, for example, a group which is potentially substituted by a nucleophilic reagent such as a hydrocarbon residue having a hetero atom, e.g. an oxygen atom, a sulfur atom, a nitrogen atom, being negatively charged. The preferable examples of the leaving group include halogen, e.g. iodine, bromine chlorine), alkanoyloxy, e.g. acetoxy), alkylsulfonyloxy, e.g. methanesulfonyloxy), alkylarylsulfonyloxy (e.g. p-toluenesulfonyloxy).

Scheme 31

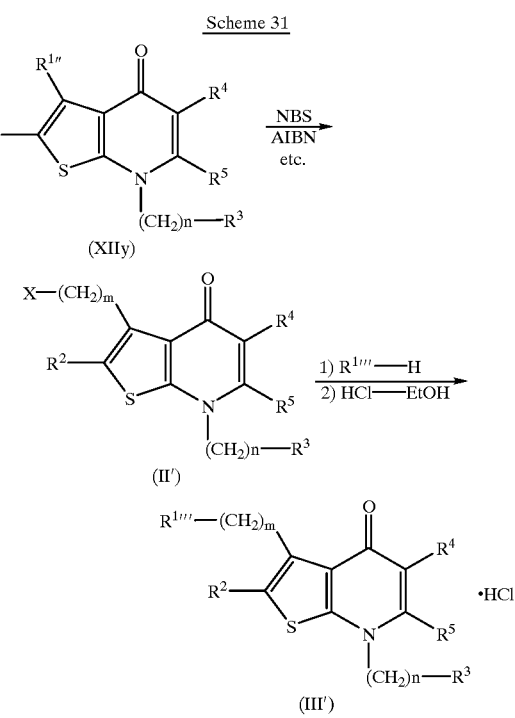

Production Method 32:

A thienopyridine-5-carboxylic acid derivative having an optionally substituted branched alkoxycarbonyl group at the 5-position can be produced by allowing a compound having alkoxycarbonyl group at the 5-position, which is produced by substantially the same method described in PCT International Publication No. WO95/28405, or a salt thereof, to react with a compound represented by the general formula $R^{4j}$—OH, wherein $R^{4j}$ stands for an optionally substituted branched alkoxy group whose specific examples are the same as described in the foregoing or a salt thereof. This reaction is conducted by dissolving the starting compound in an adequate solvent (e.g. isopropyl alcohol and 3-pentyl alcohol), adding to the solution a compound represented by the general formula $Ti(OR^{4j})_4$, wherein $R^{4j}$ stands for a branched alkoxy group, (e.g. isopropyl titanate (titantetraisopropoxide), titanic acid (3-pentyl)) or a salt thereof, and by stirring the mixture at temperatures ranging from about 0 to 120° C., more preferably from about 10 to 20° C., for about 1 to 24 hours, preferably about 1 to 12 hours. Or, the said thienopyridine-5-carboxylic acid derivative can be produced by stirring a compound having carboxyl group at the 5-position in an adequate solvent (e.g. dimethylformamide) in the presence of an adequate agent for converting into acid chloride (e.g. phosphorus oxychloride), a base (e.g. N,N-dimethylaminopyridine) and alcohol (e.g. 2,4-dimethyl-3-pentanol), at room temperature or under heating (about 100° C.), for about 1 to 12 hours.

Production Method 33:

A thienopyridine-5-carboxylic acid of this invention having carboxyl group at the 5-position can be produced by subjecting a compound having alkoxycarbonyl group at the 5-position, which is produced by substantially the same method as that described in the official gazette of International Application WO95/28405 Laid-Open Under PCT, or a salt thereof to hydrolysis. The hydrolysis is conducted by dissolving the starting compound in an adequate solvent which does not exert undesirable influence on the reaction (ethers such as tetrahydrofuran or dioxane, or alcohols such as ethyl alcohol), adding to the solution an acid (e.g. inorganic acid such as hydrochloric acid) or an aqueous alkaline solution (e.g 1–4N aqueous solution of alkali metal hydroxide such as sodium hydroxide, potassium hydroxide or lithium hydroxide), and stirring at temperatures ranging from about 10 to 100° C. for about 1 to 4 hours.

Production Method 34:

The compound (XV) can be produced by allowing a 5-carboxy-4,7-dihydro-4-oxothieno[2,3-b]pyridine derivative, which is produced by a method analogous to the method disclosed in PCT International Publication No. WO95/28405, or a salt thereof to react with a compound represented by the general formula $R^{2k'}$—$Y^{k'}$, wherein $R^{2k'}$ stands for alkyl group having 1 to 3 alkenyl optionally substituted with (i) halogen, (ii) cycloalkyl or (iii) alkyl, and Y stands for halogen atom, or a salt thereof.

This reaction is conducted usually in a solvent, as exemplified by amides such as dimethylformamide, nitriles such as acetonitrile and ethers such as tetrahydrofuran. This reaction is conducted by dissolving the starting compound in any of these solvents and by adding to the solution a compound represented by the general formula $R^{2k}$—$Y^{k}$ (e.g. allyl bromide, cyproprolylmethyl chloride, 1-bromo-2-butene, crotyl bromide (i.e. 1-bromo-2-methyl-2-propene), 1-bromo-3-butene, 2,2,2-trifluoroethyl iodide) or a salt and a basic compound thereof (e.g. potassium carbonate, sodium hydride and triethylamine). The reaction temperature ranges from about 0 to 100° C., preferably from about 0 to 40° C. The reaction time ranges from about 1 to 200 hours, preferably from about 1 to 48 hours. This reaction can be conducted efficiently by stirring.

Production Method 35:

A thienopyridine derivative, which is the compound (XV) wherein $R^{2k}$ stands for an optionally substituted alkoxy group, can be produced through ester exchange by allowing a 5-ethoxycarbonyl-4,7-dihydro-4-oxothieno[2,3-b]pyridine derivative produced by the method analogous to that disclosed in PCT International Publication No. WO95/28405 or a salt thereof to react with a compound represented by the general formula $R^{2k}$—H (wherein $R^{2k}$ is of the same meaning as defined above) or a salt thereof. This reaction is conducted usually in a solvent, as exemplified by alcohols such as isopropyl alcohol. This reaction can be conducted by dissolving the starting compound in any of these solvents and by adding to the solution a compound represented by the general formula Ti($R^{2k}$)4 (e.g. isopropyl titanate, e.g. titan (N) tetraisopropoxide). The reaction temperature ranges from about 0 to 100° C., preferably from about 0 to 40° C. The reaction time ranges from about 1 to 24 hours, preferably from about 1 to 6 hours. This reaction can be conducted efficiently by stirring. Or, the reaction can be conducted by dissolving the compound (I), wherein $R^{2k}$ is carboxyl group, in a solvent (e.g. amides such as dimethylformamide), then by allowing the solution to react with alcohol (e.g. 2,4-dimethyl-3-pentanol). This reaction is conducted by adding, to the reaction system, an acid-chloridation agent such as phosphorus oxychloride and a base such as N,N-dimethylaminopyridine. The reaction is conducted at temperatures ranging from room temperature to about 100° C. under heating. The reaction time ranges from about 1 to 12 hours. This reaction is conducted efficiently by stirring.

Production Method 36:

A thieno[2,3-b]pyridine-5-carboxylic acid derivative, which is the compound (XV) wherein —CO—$R^{2k}$ is carboxyl group, can be produced by subjecting the compound (XV) wherein $R^{2k}$ is alkoxy group or a salt thereof, which is produced by the method disclosed in PCT International Publication No. WO95/28405 or an analogous method thereto, to hydrolysis. The hydrolysis is conducted by adding, to a solution of the starting compound in a solvent, an acid (e.g. inorganic acid such as hydrochloric acid) or an aqueous solution of alkali (e.g. a 1–4N aqueous solution of alkali metal hydroxide such as sodium hydroxide, potassium hydroxide or lithium hydroxide). As the solvent, use is made of, for example, ethers such as tetrahydrofuran or dioxane, and alcohols such as ethyl alcohol. The reaction temperature ranges from about 1 to 100° C. The reaction time ranges from about 1 to 4 hours. The reaction is conducted efficiently by stirring.

The compound (XXI) can be produced by the method of the Production Method 10 or a method shown below, i.e. Production Method 37.

Production Method 37:

In place of the method for producing compound (IIa) from the compound (ii) in the above scheme 13, any per se conventional methods can be employed, for example the following processes for producing the compound (IIa) from the compound (ii). Namely, the compound (ii) is dissolved in an appropriate solvent, e.g. methanol, ethanol, which does not adversely affect the reaction, 2N sodium hydroxide is added, and the mixture is reacted at room temperature to heating (till about 100° C.) for one to 12 hours. The obtained compound wherein —COOEt is converted to —COOH is dissolved in an appropriate solvent, e.g. dioxane, and to the solution is added an equivalent amount of triphosgene and the mixture is reacted at a temperature of 80 to 150° C. for one to 10 hours under stirring. The obtained 1-hydroxy oxazine compound is treated in a manner similar to that of the reaction of the compound (XVI) to the compound (IIa) as mentioned above. Thus obtained oxazine compound to which the group $R^{1y}$ is introduced at 1-position is dissolved in an appropriate solvent, e.g. dichloromethane, to the solution is added an equivalent amount to a small excess amount of an amine, e.g. ammonium, alkylamine, arylamine, and the mixture is reacted at room temperature to heating (till about 100° C.) for 1 to 12 hours under stirring. Then, to the reaction mixture is added triphosgene again and triethylamine as a base, the mixture is reacted at about 100° C. under reflux for 1 to 6 hours, to give a compound of the formula (IIa).

The compound (XXX) and its salt can be produced easily by per se known methods, as exemplified by the Production Method 3, the Production Method 14, or the following procedures.

As the leaving group shown by $X^z$, mention is made of, for example, a group which is potentially substituted by a nucleophilic reagent such as a hydrocarbon residue having a hetero atom (e.g. an oxygen atom, a sulfur atom, a nitrogen atom) being negatively charged. The preferable examples of the leaving group include halogen, e.g. iodine, bromine chlorine, alkanoyloxy, e.g. acetoxy, alkylsulfonyloxy, e.g. methanesulfonyloxy, alkyl-arylsulfonyloxy, e.g. p-toluenesulfonyloxy.

Production Method 38:

To a solution of 3-halogenated aniline derivative (iz) is added an equivalent mole to a small excess amount of ethoxymethylene melonic acid diethylester, the mixture is stirred for one to 4 hours at a temperature of 100° C. to 150° C. to give an additive form (iiz). The additive form (iiz) is dissolved stepwise in an appropriate solvent, e.g. polyphosphoric acid, polyphosphoric acid ester (PPE), Dowtherm, the mixture is stirred at room temperature to heating to give a quinoline derivative (iiiz). The derivative (iiiz) is dissolved in an appropriate solvent, i.e. one which does not adversely affect the reaction, e.g. dimethylformamide, dichloromethane, tetrahydrofuran, ethylether, dioxane, aceton.

To the solution is added one equivalen to a small excess amount of a base, e.g. potassium carbonate, triethylamine, sodium hydrogen, one equivalent to excess amount of halogens alkyl derivative, e.g. methyl iodide, propyl iodide, benzyl iodide, and the mixture is stirred at a temperature of 0° C. to 80° C. to give a quinoline derivative (ivz).

Thus obtained derivative (ivz) or its salt and an equivalent mole to a small excess amount (about 3 mole) of an aryl boric acid derivative, i.e. $R^{III}$—$B(OH)_2$, e.g. $R^{2z}$—$B(OH)_2$, are reacted to give the compound (XXXa) shown in the following Scheme 37. The reaction is carried out in an appropriate solvent which does not adversely affect the reaction. As the solvent, mention is made of dimethoxyethane, tetrahydrofuran, dioxane, benzene, toluene, ethylether, dimethylformamide, dimethylacetamide and ethanol. This reaction is carried out in the presence of a base. As the base, mention is made of inorganic base such as sodium carbonate, sodium hydrogencarbonate, potassium carbonate, potassium hydrogencarbonate, sodium hydroxide, potassium hydroxide, thallium carbonate or an organic base such as triethylamine. In order to proceed the reaction smoothly, a catalytic amount of palladium derivative, e.g. tetrakistriphenylphosphine palladium, may be added to the reaction system. It is preferable to carry out the reaction in a stream of an inert gas, e.g. argon gas, nitrogen gas. The reaction is carried out at room temperature to about 150° C. and it is preferable to carry out the reaction under refluxing. The reaction time is about 1 to 12 hours. This reaction gives the desired product (XXXa).

The foregoing methods are shown in Scheme 32. In Scheme 32, Et denotes ethyl, $Y^z$ denote halogen, whose examples are the same as above, and the other groups have the same meaning as defined above.

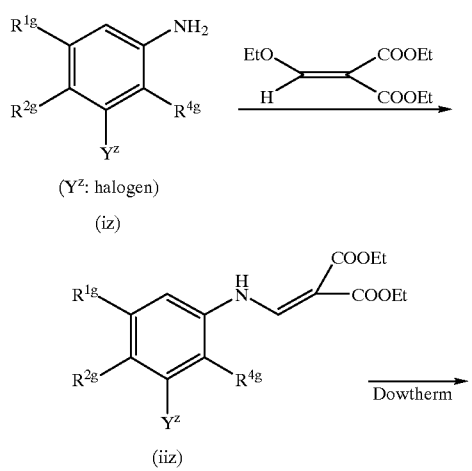

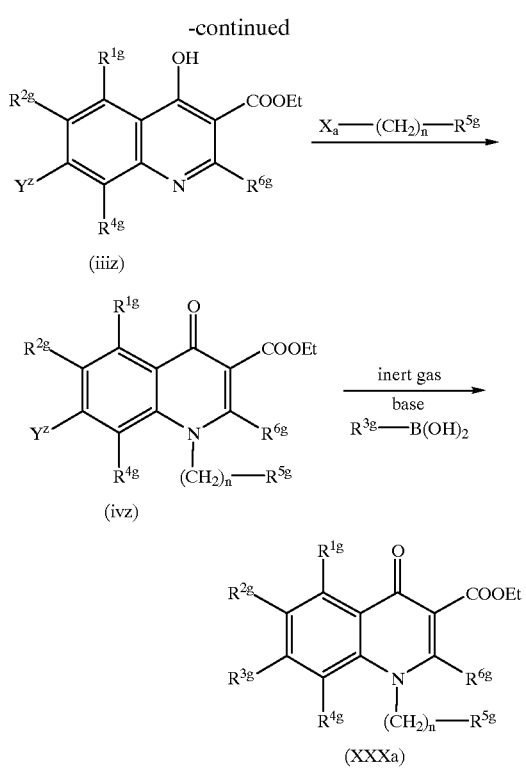

Production Method 39:

Exchange the group at 6-position:

The compound (vz) is stirred together with N-bromosuccinimide (NBS) in an appropriate solvent, e.g. halogenated hydrocarbons such as carbon tetrachloride and chloroform in the presence of α, α'-azobisisobutyronitrile (AIBN), at temperatures ranging from about 30 to 100° C. for 0.5 to 6 hours to give a compound (viz).

The compound (viz), or its salt is reacted with about equivalent mole of an amine of the formula: $R^{1z'}$—H, e.g. the compound shown by the formula: $HNR^{5z}R^{6z}$, to produce the compound (XXXb). The reaction is carried out in an appropriate solvent which does not adversely affect the reaction. As the solvent, mention is made of amides such as dimethylformamide and dimethylacetamide, nitrils such as acetonitrile, alcohols such as ethanol, furthermore in the reaction dimethoxyethane, tetrahydrofuran, dioxane, dichloromethane, acetonitrile, acetone, ethyl acetate can be used as a solvent. The reaction is carried out in the presence of a base such as tertiary organic amine, e.g. triethylamine, trimethylamine, diisopropylethylamine, N-methylmorpholine. The reaction temperature is normally about 10 to 100° C. The reaction time is about 1 to 10 hours. It is preferable to carry out the reaction under stirring.

This reaction gives the compound (XXXb). The production method 2 described above is shown in Scheme 2: In Scheme 2, $R^{1z'}$ denotes an optionally substituted amino group, $Z^z$ is a leaving group. Other groups have the same meaning as defined above.

Scheme 33

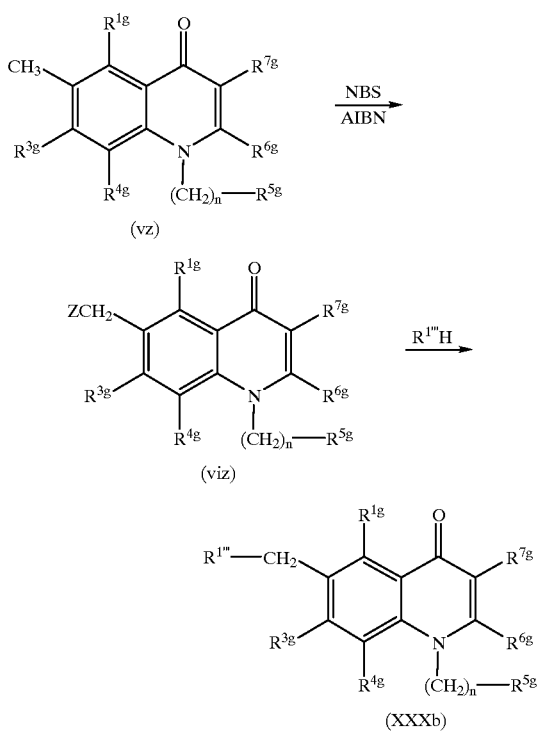

Scheme 34

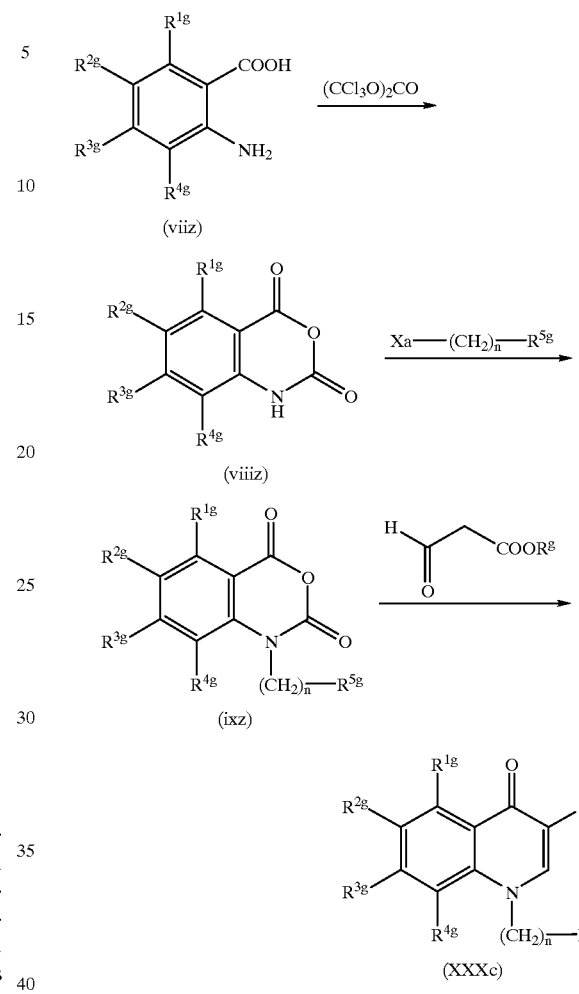

Production Method 40:

An anthranilic acid derivative (viiz) is stirred at temperatures ranging from about 30 to 110° C. together with an equivalent or an excess amount of triphosgene in an appropriate solvent, e.g. ethers such as tetrahydrofuran and 1,4-dioxane, to give an isatoic acid anhydride derivative (viiiz). Then, a halogenated derivative is stirred at temperatures ranging from about 40 to 130° C. in an appropriate solvent, e.g. ethers such as tetrahydrofuran and 1,4-dioxane, aromatic hydrocarbons such as benzene and toluene, amides such as N,N-dimethylformamide and N,N-dimethylacetamide, alkylsulfoxides such as dimethyl sulfoxide, in the presence of a base, e.g. alkali metal carbonate such as potassium carbonate, alkali metal hydride such as sodium hydride and potassium hydride, and alkali metal alkoxide such as potassium-butoxide, to give a substituted derivative (xiz). The derivative (xiz) is allowed to react with an equivalent or a little excess amount, e.g. about 1.1 to 1.5 equivalent, of a β-keto-acid ester derivative relative to the compound at temperatures ranging from 40 to 110° C. in an appropriate solvent, e.g. ethers such as tetrahydrofuran and 1,4-dioxane, aromatic hydrocarbons such as benzene and toluene, amides such as N,N-dimethylformamide and N,N-dimethylacetamide, and alkyl sulfoxide such as dimethyl sulfoxide, in the presence of a base, e.g. alkali metal carbonate such as potassium carbonate, alkali metal hydride such as sodium hydride and potassium hydride, and alkali metal alkoxide such as potassium-butoxide, to give the compound (XXXc). The foregoing Production Method 39 is shown in Scheme 34. In Scheme 34, Xa denotes a leaving group especially halogen, and $R^{g'}$ denotes an alkyl group. Other groups have the same meaning as defined above.

Other methods:

The substituents on the compound can be converted to other substituents by per se known and conventional methods. Examples of the methods are shown below.
(i) The nitro group as the substituent can be converted to an amino group when the starting compound is dissolved in an appropriate solvent, e.g. ethanol, methanol, and (a) to the solution is added palladium-carbon, and the mixture is reacted at room temperature for one to 12 hours under hydrogen atmosphere, or (b) to the solution is added iron powder and hydrochloric acid, and the mixture is reacted at room temperature for one to 12 hours.
(ii) The amino group can be converted to an acylated amino group by dissolving the starting compound in an appropriate solvent, e.g. tetrahydrofuran, dimethylsulfoxide, to the solution is added potassium carbonate, pyridine and triethylamine as a base and acid anhydride or acid halide. The mixture is reacted at a room temperature for one to 10 hours under stirring.
(iii) From an amino compound, a compound having an amino group is converted to alkenyl-amino compound. For example, the starting compound is dissolved in an appropriate solvent, e.g. acetic acid, dimethylformamide, dichloromethane, tetrahydrofuran, dioxane, acetonitrile, to the solution is added diazonizing agent, e.g. sodium nitrite, isoamyl nitrite, to the mixture is added palladium catalyst, e.g. bis(dibenzylideneacetone)palladium and one to excess equivalents of alkenyl derivative, and the mixture is stirred at room temperature to heating (about 80° C.) for one to 12 hours.

(iv) A carbon atom can be introduced to the amino group, for example, to the starting compound in an appropriate solvent, e.g. acetic acid, dimethylformamide, dichloromethane, tetrahydrofuran, dioxane, is added an acrylic acid derivative or oxirane derivative, e.g. epoxide compound. The mixture is stirred at 0 to 80° C. for 6 to 24 hours.

(v) A sulfur atom can be introduced to the amino group in the compound, for example, to the starting compound in an appropriate solvent, e.g. pyridine, dimethylformamide, dichloromethane, tetrahydrofuran, ethylether, dioxane, is added halide of sulfur compound. The mixture is stirred at 0 to 80° C. for 6 to 24 hours.

(vi) The substituent, formyl group, can be converted to methyl group by dissolving a starting compound in an appropriate solvent, e.g. tetrahydrofuran, and to the mixture is added an organic borane, derivative, e.g. dimethylsulfide borane, and the mixture is reacted at room temperature to heating under reflux for a several hours, e.g. one to 3 hours.

(vii) From methoxy derivative, actonyloxy derivative can be prepared by dissolving the starting material in an appropriate solvent, e.g. dichloromethane, and to the solution is added one to excess equivalents of Lewis acid, e.g. aluminium chloride, and thiol compound or sulfide compound, e.g. dimethylsulfide, and the mixture is reacted at ice-cooling to room temperature for one to 10 hours, and then the obtained hydroxy derivative is dissolved in an appropriate solvent, e.g. dimethylformamide, to the solution is added a base, e.g. sodium hydroxide or potassium carbonate, and an alkyl halide. The mixture is reacted at a room temperature for one to 12 hours.

(viii) A methoxy group can be changed to isopropoxy by dissolving the starting material in an appropriate solvent, e.g. dichloromethane, to the solution is added one to excess equivalents of Lewis acid, e.g. aluminum chloride, and thiol compound or sulfide compound, e.g. dimethylsulfide, and the mixture is reacted at room temperature to ice-cooling for one to 10 hours.

(ix) An aminocarbonyl group can be introduced by dissolving a starting compound having halogen atom in an appropriate solvent, e.g. dimethoxyethane, to the solution is added arylborric acid derivative, a base, e.g. sodium carbonate, a palladium compound e.g. tetrakis (triphenylphosphine)palladium(0), as a catalyst and the mixture is refluxed 1 to 6 hours.

(x) An alkylthio compound can be converted to an alkylsulfinyl compound or an alkylsulfonyl compound by reacting a starting compound with an oxidizing agent, e.g. metachloroperbenzoic acid, in an appropriate solvent, e.g. dichloromethane, at ice-cooling to heating. With vigorous heating or by treating with an excess amount of oxidizing agent, an alkylsulfonyl compound is obtained.

(xi) The hydroxyl group in the starting compound can be substituted by various kinds of groups. The reaction is carried out in an appropriate solvent, e.g. dimethylformamide (DMF), acetonitrile, acetone. To the solution of the starting compound is added halide such as alkyl halide, e.g. propyl iodide, isobutyl iodide, ethybromo acetate, or aralkyl halide, e.g. benzylchlolide. The mixture is stirred at 0 to 40° C. for 2 to 18 hours.

For example, in the case of ethyl bromoacetate, the obtained acetic acid ester is hydrolyzed in an adequate solvent and base, e.g. iN NaOH solution in ethyl alcohol, at room temperature for 2 to 12 hours. The acetic acid compound is dissolved in an adequate solvent, e.g. tetrahydrofuran (THF). To the solution is added isobutyl chloroformate in the presence of an adequate base, e.g. $Et_3N$, and the reaction is carried out at 0° C. for 1 to 4 hours. To the solution is added adequate amine derivatives, e.g. methylamine, propylamine, piperidine. The reaction is carried out at 0° C. to room temperature for 1 to 12 hours.

Said starting compound which has a hydroxyl group is produced by acid-hydrolysis of a compound such as one having an alkoxy group. The acid hydrolysis is carried out in a conventional manner such as by adding iN hydrochloric acid in an appropriate solvent such as tetrahydrofuran or alcohol, e.g. methanol, ethanol, at 0° C. to room temperature for one to 10 hours.

(xii) The present compound is an having alkanoyl-phenyl group can be produced by the introduction of a alkanoyl-phenyl group to the halogenated compound. The halogenated compound is obtained by the halogenation reaction with the starting compound. The halogenation is carried out in an adequate solvent, e.g. carbontetrachloride or chloroform. To the solution is added N-bromosuccinimide and catalytic amount of 2,2'-azobis- (isobutyronitrile). The reaction is carried out at 100 to 120° C. for 1 to 4 hours. The introduction reaction of alkanoyl phenyl group is carried out in an appropriate degased solvent, e.g. dimethoxyethane (DME). To the solution is added alkanoyl phenyl borate, palladium compound, e.g. $Pd(PPh_3)_4$(Ph=phenyl) and sodium carbonate (2M, $Na_2CO_3$). The alkanoyl phenyl borate is synthesized by the reaction of alkanoyl phenyl bromide with adequate borate, e.g. (i-PrO)$_3$B(Pro=propyl) in the presence of adequate base, e.g. BuLi (Bu=butyl). The introduction reaction is carried out at room temperature to 120° C. for 1 to 12 hours under inert gas atmosphere.

(xiii) The present compound having alkylphenyl group can be produced by the similar manner as shown in (xii) with alkyl phenyl borates instead of alkanoyl phenyl borates.

Any other group in the compound can be introduced by any known per se known methods.

(xiv) The present compound having alkoxycarbonyl group, can be produced by introducing a cyano group, and then subjecting the obtained compound to esterification.

In the reaction of the introduction of cyano group, the starting compound is dissolved in an appropriate solvent, e.g. dimethylsulfoxide (DMSO), and to the solution is added sodium cyanide. The reaction is carried out at 40 to 60° C. for 2 to 12 hours.

The esterification reaction is carried out in an appropriate solvent such as ethyl alcohol. The reaction is conducted by mixing the starting compound and alcohol solution, e.g. ethyl alcohol, saturated with hydrochloric acid. The reaction is carried out at 80 to 120° C. for 12 to 48 hours.

(xv) The present compound having an alkyl group which is substituted by a sulfonamide group can be synthesized by (i) halogenation of this alkyl group and (ii) nucleophilic substitution of this halogen with a sulfonamide compound in the presence of appropriate base, e.g. sodium hydride.

The halogenation is carried out in an appropriate solvent, e.g. carbon tetrachloride. To the solution is added N-bromosuccinimide or catalytic amount of 2,2'-azobis (isobutyronitrile). The reaction is carried out at 100 to 120° C. for 1 to 4 hours.

The nucleophilic substitution reaction is carried out in an appropriate solvent such as N,N-dimethylformamide (DMF). To the solution is added sodium hydride washed with n-hexane and sulfonamide derivatives, e.g. methanesulfonamide, ethanesulfonamide, benzenesulfonamide. The reaction is carried out at 0 to 40° C. for 1 to 24 hours.

(xvi) The protective group, e.g. methoxymethyl, substituted on the hydroxyl group in the present compound can be removed. The starting compound is dissolved in an appropriate solvent, e.g. ethanol, to the solution is added an acid, e.g. hydrochloric acid, hydrogen chloride in ethanol, under ice-cooling, and the mixture is stirred for 0.5 to 5 hours.

(xvii) An acyl group or an acetonyl group can be introduced to the hydroxyl group in the compound. The starting compound having a hydroxyl group is dissolved in an appropriate solvent, e.g. dichloromethane, dimethylformamide, to the solution is added an appropriate base, e.g. triethylamine, pyridine. To the mixture is further added an excess amount of acid halide, acid chloride or alkyl halide. The mixture is stirred at room temperature for 6 to 24 hours.

(xviii) A carbonyl group in the compound can be converted to a group of the formula: —C(OH)H—. The starting compound having a carbonyl group is dissolved in an appropriate solvent, e.g. methanol, ethanol, and to the solution is added a small excess amount of a reducing agent, e.g. sodium boron hydride. The mixture is stirred at room temperature for 1 to 3 hours.

As salts of the compound used in this invention obtained thus above, physiologically acceptable acid addition salts are preferable. Examples of such salts include those with an inorganic acid, e.g. hydrochloric acid, hydrobromic acid, nitric acid, sulfuric acid and phosphoric acid, or those with an organic acid, e.g. formic acid, acetic acid, trifluoroacetic acid, fumaric acid, oxalic acid, tartaric acid, maleic acid, citric acid, succinic acid, malic acid, methanesulfonic acid, bezenesulfonic acid, and p-toluenesulfonic acid. Further, when the compound has an acid group such as —COOH, the compound may form a salt with an inorganic base, e.g. an alkali metal or alkaline earth metal such as sodium, potassium, calcium and magnesium; ammonia, or an organic base, e.g. trimethylamine, triethylamine, pyridine, picolin, ethanolamine, diethanolamine, triethanolamine, dicyclohexylamine and N,N'-dibenzylethylenediamine.

The compound or salts thereof employed in the present invention and produced thus above can be isolated and purified by conventional separating means such as recrystallization, distillation and chromatography. In the case where the compound is produced in the free form, it can be converted to a salt thereof by a per se conventional means or a method analogous thereto. On the contrary, when it is obtained in the form of a salt, it can be converted to its free form or to any other salt.

In the case where the compound or a salt thereof employed in the present invention is an optically active compound, it can be separated into d-compound and l-compound by means of a conventional optical resolution.

Since the compound or its salt employed in this invention have a prolactin production inhibitory activity and are less toxic, they can safely be used for the prophylaxis or therapy for diseases caused by excess production/secretion of prolactin or enhanced reactivity on prolactin in mammals, e.g. human, monkey, cow, horse, pig, sheep, dog, cat, rabbit, rat and mouse. More specifically, the present composition is useful for inhibiting puerperal lactation, and also useful as a prophylactic or therapeutic agent of galactorrhea, hyperprolactinemic ovulation disturbance, amenorrhea-galactorrhea syndrome, e.g. Chiari-Frommel syndrome, Argonz-del Castillo syndrome, Forbes-Albright syndrome, prolactinoma, interbrain tumor, and acromegaly, pituitary gigantism, especially lactosomatotroph-type acromegaly and pituitary gigantism, and also perkinsonism. According to the experimental observation, the composition of this invention shows an action of inhibiting the production of pituitary hormone which is not the one through the LHRH receptor, i.e. prolactin production inhibiting action, this being worthy of special mention. The composition of this invention act on the pituitary prolactin-producing cells and are considered to be effective for suppressing or inhibiting the prolactin production/secretion, and, they act on other cells including tumor cells producing/secreting prolactin, thus they are considered to be effective for suppressing or inhibiting the prolactin-production/secretion. The composition of this invention act on the lactotolope of pituitary to suppress or inhibit the prolactin production/secretion. And, the composition of this invention are also effective for diseases in which prolactin takes part, for example, prolactin receptor-expressing tumors, and, when these diseases are those dependent on sex hormone, the composition of this invention are especially useful therapeutic agents, because they have a gonadotropic hormone-releasing hormone antagonistic action as well. While these diseases include, for example, breast cancer or prostatic cancer, the usefulness of the composition of this invention is not limited to especially these cancers but covers any diseases in which prolactin participates. Besides, the composition of this invention can be used for the therapy of animal diseases in the field of animal husbandry, and they can be used also for fish. While the composition of this invention can be used singly, they can also be used in combination with a steroidal or non-steroidal antiandrogenic or antiestrogenic agent, a somatostatin-receptor agonistic agent or a chemotherapeutic agent for cancer (e.g adriamycin).

When the present composition of prolactin production inhibitory agent is employed, as prophylactic and therapeutic agents of the above-mentioned diseases, it can be administered orally or parenterally in accordance with per se known means. For example, the condensed cyclic compound or its salt can be mixed with a pharmaceutically acceptable carrier and administered orally as a solid preparation such as tablet, capsule, granule or powder, or parenterally as intravenous, subcutaneous or intramuscular injection, drip injection, external agent, suppository or a sublingually administrable tablet. Further, it can be sublingually, subcutaneously or intramuscularly administered as a prolonged release formulation such as sublingually administrable tablets, or microcapsules. The dosage can vary with, e.g. the degree of affliction, age, sex, body weight and difference of sensitivity of the subject to be administered; the time and intervals of administration, treated dosage forms and kinds of the medicinal preparation; and kinds of the effective components, and dosage of the condensed cyclic compound or its salt ranges usually, though not specifically limited to, from about 0.02 to 20 mg, preferably from about 0.1 to 10 mg, relative to 1 kg body weight of the mammals, which is administered usually once daily or by 2 to 4 divided dosages. The daily dose when used in the field of animal husbandry or fishery varies with the conditions analogous to those mentioned above, it ranges, relative to 1 kg body weight of the subject animal or fish, from about 0.01 to 50 mg, preferably from about 0.1 to 10 mg, once daily or by 2 to 3 divided dosages. When the condensed compound or its salt is used in combination with another agent above-mentioned, the dosage of the another agent is about 0.1 to 1 weight per the condensed compound or its salt.

As the above-mentioned pharmaceutically acceptable carriers, conventional various organic or inorganic carriers are used, and they can be incorporated as excipients, lubricants, binders, disintegrants in solid compositions; and as solvents, solubilisers, suspending agents, isotonizing agents, buffering agents and pain-easing agents in liquid and solid compositions. And, depending on necessity, further additives such as preservatives, anti-oxidants, coloring agents and sweeteners can also be used.

Preferable examples of the above-mentioned excipients include lactose, sugar, D-mannito, starch, crystalline cellulose and light anhydrous silicic acid. Preferable examples of the above-mentioned lubricants include magnesium stearate, calcium stearate, talc and colloid silica. Preferable examples of the above-mentioned binders include crystalline cellulose, sugar, D-mannitol, dextrin, hydroxypropyl cellulose, hydroxypropylmethyl cellulose, polyvinyl pyrrolidone and polyethylene glycol. Preferable examples of the above-mentioned disintegrants include starch, carboxymethyl cellulose, carboxymethyl cellulose calcium, low substituted hydroxypropyl cellulose, cross carmelose sodium, and carboxymethyl starch sodium. Preferable examples of the above-mentioned solvents include water for injection, alcohol, propylene glycol, macrogol, sesame oil and corn oil. Preferable examples of the above-mentioned solubilizers include polyethylene glycol, propylene glycol, D-mannitol, benzyl benzoate, ethanol, tris-aminomethane, cholesterol, triethanolamine, sodium carbonate and sodium citrate. Preferable examples of the above-mentioned suspending agents include surfactants such as stearyl triethanolamine, sodium lauryl sulfate, lauryl aminopropionic acid, lecithin, benzalkonium chloride, benzetonium chloride and monostearic glyceryl ester; and hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose. Preferable examples of the above-mentioned isotonizing agents include sodium chloride, glucose, glycerin, D-mannitol and D-sorbitol. Preferable examples of the above-mentioned buffering agents include buffer solutions such as phosphate, acetate, carbonate and citrate. Preferable examples of the above-mentioned pain-easing agents include benzyl alcohol. Preferable examples of the above-mentioned preservatives include para-hydroxybenzoic acid esters, chlorobutanol, benzyl alcohol, phenethyl alcohol, dehydroacetic acid and sorbic acid. Preferable examples of the above-mentioned anti-oxidants include sulfite and ascorbic acid. Preferable examples of the above mentioned coloring agent include red iron oxide, titanium oxide.

To the condensed cyclic compound or its salt, are added, for example, a suspending agent, a solubilizer, a stabilizer, an isotonizing agent and a preservative, then the mixture is formulated, in accordance with a per se known method, into an intravenous, subcutaneous or intramuscular injection. These injections can be processed into lyophilized preparations, when necessary, by a per se known method.

Examples of the above-mentioned pharmaceutical composition are orally administering agents (e.g. diluted powders, granules, capsules and tablets), injections, drip injections, external agents (e.g. transnasal preparations, percutaneous preparations, etc.), ointments (e.g. rectal ointment, vaginal ointment, etc) and the like.

Such pharmaceutical compositions can be manufactured by a per se known method commonly used in preparing pharmaceutical compositions.

Concretely, the condensed cyclic compound or a salt thereof can be made into injections or dropping injections either in a form of an aqueous injection together with dispersing agents, e.g. Tween 80 (Atlas Powder, U.S.A.), HCO 80 (Nikko Chemicals, Japan), polyethylene glycol, carboxymethylcellulose, sodium alginate, etc., preservatives, e.g. methyl paraben, propyl paraben, benzyl alcohol, etc., isotonizing agents, e.g. sodium chloride, mannitol, sorbitol, glucose, etc., and the like or in a form of an oily injection by dissolving, suspending or emulsifying in plant oil, e.g. olive oil, sesame oil, cotton seed oil, corn oil, etc., propylene glycol and the like.

In preparing a pharmaceutical composition for oral use, the condensed cyclic compound or a salt thereof is molded by compressing, for example, with excipients, e.g. lactose, sucrose, starch, etc., disintegrating agents, e.g. starch, calcium carbonate, etc., binders, e.g. starch, gum arabic, carboxymethylcellulose, polyvinylpyrrolidone, hydroxypropylcellulose, etc., or lubricants, e.g. talc, magnesium stearate, polyethylene glycol 6000, etc., and the like, to prepare tablets or granules. If necessary, the composition is coated by a per se known method with an object of masking the taste, as an enteric coating or for long-acting sustained release. Examples of coating agents therefore are hydroxypropylmethylcellulose, ethylcellulose, hydroxymethylcellulose, hydroxypropylcellulose, polyoxyethylene glycol, Tween 80, pluronic F 68, cellulose acetate phthalate, hydroxypropylmethylcellulose phthalate, hydroxymethylcellulose acetate succinate, Eudragit (a copolymer of methacrylic acid with acrylic acid; manufactured by Rohm, Germany), red oxide of iron and the like. Subcoating layers may be provided between the enteric coating and the core according to per se known methods.

In preparing an external composition, condensed cyclic the compound or a salt thereof is subjected to a per se known method to give a solid, semisolid or liquid agent for external use. For example, the solid preparation is manufactured as follows. The condensed cyclic compound as it is or after adding/mixing fillers, e.g. mannitol, starch, microcrystalline cullulose, etc., thickeners, e.g. natural gums, cellulose derivatives, acrylic acid polymers, etc., and the like thereto/therewith is made into a powdery composition. With respect to the liquid composition, an oily or aqueous suspension is manufactured by the manner nearly the same as in the case of the injection. In the case of a semisolid composition, the preferred one is an aqueous or oily gel or an ointment. Each of them may be compounded with a pH adjusting agent, e.g. carbonic acid, phosphoric acid, citric acid, hydrochloric acid, sodium hydroxide, etc., an antiseptic agent, e.g. p-hydroxybenzoates, chlorobutanol, benzalkonium chloride, etc., and the like.

In the manufacture of an ointment for example, the condensed cyclic compound or a salt thereof can be made into an oily or an aqueous solid, semisolid or liquid ointment. Examples of the oily base material applicable in the above-mentioned composition are glycerides of higher fatty acids, e.g. cacao butter, Witepsols (manufactured by Dynamite-Nobel), etc., medium fatty acids, e.g. Miglyols (manufactured by Dynamite-Nobel), etc., and plant oil, e.g. sesame oil, soybean oil, cotton seed oil, etc., and the like. Examples of the aqueous base material are polyethylene glycols and propylene glycol and those of the base material for aqueous gel are natural gums, cellulose derivatives, vinyl polymers, acrylic acid polymers, etc.

By way of the following Experimental Example, Examples and Reference Examples, the present invention will be described more specifically, but they are not intended to limit the scope of this invention thereto.

Among compounds employed in the following, Compound E-1 is 4,7-dihydro-3-(N-methyl-N- benzylaminomethyl)-7-(2-methoxybenzyl)-2-(4-methoxyphenyl)-4-oxothieno[2,3-b]pyridine-5-carboxylic acid ethyl ester hydrochloride, Compound E-2 is 2-(4-acetylaminophenyl)-4,7-dihydro-3-(N-methyl-N-benzylaminomethyl)-7-(2-methoxybenzyl)-4-oxothieno[2,3-b]pyridine-5-carboxylic acid ethyl ester, Compound E-3 is 5-n-butyryl-4,7-dihydro-3-(N-methyl-N-benzylaminomethyl)-7-(2-fluorobenzyl)-2-(4-methoxyphenyl)-4-oxothieno[2,3-b]pyridine hydrochloride, Compound E-4 is 5-benzoyl-4,7-dihdyro-3-(N-methyl-N-benzylaminomethyl)-7-(2-fluorobenzyl)-2-(4-methoxyphenyl)-4-oxothieno[2,3-b]pyridine hydrochloride, Compound E-5 is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine, and Compound E-6 is 7-(2,6-difluorobenzyl)-4,7-dihydro-3-(N-methyl-N-benzylaminomethyl)-5-isobutyryl-2-(4-propionylaminophenyl)-4-oxo-thieno[2,3-b]pyridine hydrochloride and E-7 is 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine hydrochloride. These compounds are described in PCT International Publication No. WO95/28405.

EXPERIMENTAL EXAMPLE 1

Inhibitory activity of prolactin (PRL) secretion by primary cultured cells of rat pituitary:

Anterior lobes of pituitary glands excised from 40 Wister rats (8-week old, male) were put into a petri dish containing buffer solution A (0.7 mM disodium hydrogenphosphate, 137 mM sodium chloride, 5mM potassium chloride, 25 mM 2-[4-(2-hydroxyethyl)-1-piperazinyl]ethanesulfonic acid (HEPES), 50 μg/ml gentamycin sulfate, pH 7.3), which was once washed with the buffer solution A, then the anterior lobes were divided into four portions. These pituitary fragments were placed into a conical flask containing 30 ml of enzyme solution I [buffer A containing 0.4% collagenase, 0.4% BSA (bovine serum albumin), 10 μg/ml of deoxyribonuclease and 0.2% glucose]. The mixture was incubated for one hour at 37° C. under shaking. The tissue fragments were dispersed by sucking and discharging with a pipette repeatedly. The dispersion was transferred to a centrifugal tube, which was then centrifuged for 6 minutes at 480×g to remove off the supernatant. To the remainder was added 30 ml of enzyme solution II (enzyme solution A containing 0.25% pancreatin), and the mixture was incubated for 8 minutes at 37° C. under shaking, which was mixed with 2 ml of FCS (fetal calf serum). The mixture was again centrifuged for 6 minutes at 480×g, and the supernatant was removed off. The remainder was suspended in 10 ml of a solution I for culture [DMEM (Dulbecco's modified Eagle's medium) containing 10% FCS, 20 mM HEPES, 50U/ml penicilin G, 50 μg/ml streptomycin and 3.7 g/L sodium hydrogencarbonate], which was subjected to filtration with nylon mesh. The filtrate was washed twice with 10 ml each portion of the solution I for culture, followed by allowing the cells to be suspended in the culture solution I at a cell density of 5×10$^5$/ml. One ml each of the cell suspension was added to each well of a 24-well plate, which was incubated for three days in a CO$_2$ incubator at 37° C. under an atmosphere of 5% carbon dioxide—95% air. The cells thus incubated were washed with 2 ml of the solution II for culture (DMEM containing 0.2% BSA, 20 mM HEPES, 50U/ml penicilin G, 50 μg/ml streptomycin and 3.7 g/L sodium hydrogencarbonate), followed by adding 2 ml of the solution II for culture. The mixture was incubated for one hour, then the culture solution was removed off. To each well of the 24-well plate was added 90 μl of fresh solution II for culture, followed by addition of 100 μl of a 20 μM or 100 μM solution of Compound E-1, E-2, E-3 or E-4 dissolved in a 0.2% (v/v) DMSO (dimethyl sulfoxide) (final concentration of the compound being 2 μM or 10 μM). The cultured broth in the absence of the compound was employed as the control. After incubation at 37° C. for 3 hours, 500 μl of the supernatant of the cultured broth was recovered, which was subjected to centrifugation for 8 minutes at 1000×g to collect the supernatant. The concentration of PRL in the supernatant was determined by using the RIA (radio immunoassay) kit (Amersham Inc.).

The inhibiting rate (%) of PRL secretion by each compound was determined by calculating in accordance with the formula:

$$\frac{\text{PRL concentration of the control} - \text{PRL concentration in the presence of the compound}}{\text{PRL concentration of the control}} \times 100$$

As the results, the compound E-1 inhibited the PRL secretion with 34% (final concentration of the compound: 2 μM) and 62% (final concentration of the compound: 10 μM), the compound E-2 inhibited with 12% (final concentration of the compound: 2 μM) and 37% (final concentration of the compound: 10 μM), the compound E-3 inhibited with 52% (final concentration of the compound: 2 μM) and the compound E-4 inhibited with 50% (final concentration of the compound: 2 μM).

The cells left after collecting the supernatant were incubated for one day at 37° C. Then, the cytotoxicity of each compound was examined using MTT [3-(4,5-Dimethyl-2-thiazolyl)-2,5-diphenyl-2H-tetrazolium.Br]. The supernatant of the cultured broth was removed off. Into each well of a 24-well plate was added 500 μl each portion of the solution II for culture containing 1 mg/ml MTT, followed by incubation for one hour at 37° C. The supernatant was removed off, then each 200 μl portion of the pigment extract solution (1% sodium dodecyl sulfate, 0.04 N hydrochloric acid, 86% (v/v) aqueous isopropanol solution) was distributed into each well, then the MTT formazan produced in living cells was extracted. The color development of the extract was quantitatively determined by the absorption at 588 nm.

In any of the above cases, no significant difference was observed in absorbance between the test groups and the control group. Thus, cytotoxicity was not observed in these compounds.

EXAMPLE 1

Using Compound E-1, E-2, E-3, E-4 or E-5 (100 mg), lactose (165 mg), corn starch (25 mg), hydroxy propyl cellulose (9 mg) and magnesium stearate (1 mg), tablets are prepared by a conventional method.

EXAMPLE 2

Using Compound E-6 or E-7 (100 mg), crystalline cellulose (50 mg), low substituted hydroxypropylcellulose-31 (30 mg), hydroxypropylcellulose L (6 mg) and magnesium stearate (1 mg), tablets are prepared by a conventional method.

EXAMPLE 3

Using the compound which is produced in Reference Example 2:16 (100 mg) below mentioned, lactose (150 mg), cross carmelose sodium (30 mg), hydroxypropylcellulose (6 mg) and magnesium stearate (1 mg), tablets are prepared by a conventional method.

EXAMPLE 4

Using the compound which is produced in Reference Example 3:30 (100 mg) below mentioned, lactose (165 mg), corn starch (25 mg), polyvinyl alcohol (4 mg) and magnesium stearate (1 mg), tablets are prepared by a conventional method.

EXAMPLE 5

Using the compound which is produced in Reference Example 4:2 (100 mg), lactose (150 mg), low substituted hydroxypropylcallulose-31 (30 mg), polyvinylpyrrolidone (10 mg) and magnesium stearate (1 mg), tablets are prepared by a conventional method.

EXAMPLE 6

Using the compound which is produced in Reference Example 5:5(1) (100 mg) below mentioned, lactose (150 mg), carboxymethylcellulose calcium (30 mg), hydroxypropylcellulose (6 mg) and magnesium stearate (1 mg), tablets are prepared by a conventional method.

EXAMPLE 7

Using the compound which is produced in Reference Example 6:21 (100 mg) below mentioned, lactose (165 mg), corn starch (25 mg), polyvinyl alcohol (4 mg) and magnesium stearate (1 mg), tablets are prepared by a conventional method.

EXAMPLE 8

Using the compound which is produced in Reference Example 7:6 (100 mg) below mentioned, lactose (165 mg), corn starch (25 mg), polyvinyl alcohol (4 mg) and magnesium stearate (1 mg), tablets are prepared by a conventional method.

EXAMPLE 9

Compound E-1, E-2, E-3, E-4 or E-5 (0.5 g) and mannitol (1 g) are dissolved in distilled water for injection to make the whole volume 100 ml. The solution is subjected to sterilized filtration with 0.22 μm membrane filter (manufactured by Sumitomo Electric Industries, Ltd. or by Zartolius, Inc.), 10 ml each of which is distributed to sterilized vials, followed by lyophilization by a conventional means to give lyophilized injectable solution of 50 mg/vial.

EXAMPLE 10

| | |
|---|---|
| (1) Compound E-1, E-2, E-3, E-4 or E-5 | 100 g |
| (2) Lactose | 234 g |
| (3) Corn starch | 150 g |
| (4) Hydroxypropyl cellulose | 45 g |
| (5) Light anhydrous silicic acid | 1 g |
| total amount | 500 g |

The above (1), (2) and (3) are mixed in a fluidized-bed granulating machine, and an aqueous solution of (4) is sprayed to the mixture in the *an granulating machine to give fine granules. After mixing with the (5), 500 mg each of thus prepared fine granules are packed.

In the following Reference Examples, $^1$H-NMR spectra are taken with the Varian GEMINI 200 (200 MHz) type spectrometer, JEOL LAMBDA300 (300 MHz) type spectrometer or the Brucker AM 500 (500 MHz) type spectrometer, employing tetramethylsilane as the internal standard. All delta values were expressed in ppm.

The symbols used in the present specification have the following meanings:

s: singlet, d: doublet, t: triplet, dt: double triplet, m: multiplet, br: broad

REFERENCE EXAMPLE 1

The compounds shown in the following Tables 1 to 21 are produced in accordance with the methods described in PCT International Publication No. WO95/28405.

TABLE 1

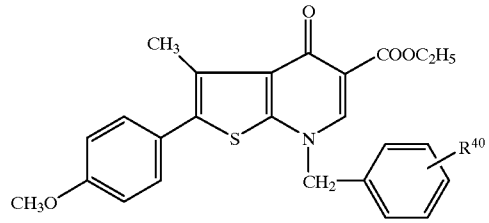

| $R^{40}$ | m.p. (° C.) |
|---|---|
| 2-methoxy | 165–167 |
| hydrogen | 170–172 |
| 3-methoxy | 153–155 |
| 4-methoxy | 132–134 |
| 2-methyl | 199–201 |
| 2-acetoxy | 154–156 |
| 2-methylthio | 152–154 |
| 4-nitro | 98–99 |
| 4-(2-cyanophenyl) | 134–136 |
| 4-(2-t-butoxy-carbonyl)phenyl | 120–122 |

TABLE 2

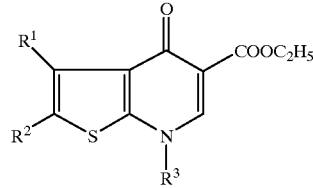

| $R^1$ | $R^2$ | $R^3$ | m.p. (° C.) |
|---|---|---|---|
| methyl | 4-nitro-phenyl | 2-methoxy-benzyl | 194–195 |
| methyl | phenyl | 2-methoxy-benzyl | amorphous |
| phenyl | methyl | 2-methoxy-benzyl | 184–186 |
| methyl | benzyl | 2-methoxy-benzyl | 65–70 |
| methyl | phenyl-acetyl | 2-methoxy-benzyl | 167–170 |
| methyl | 2-methoxy-phenyl | 2-methoxy-benzyl | 194–196 |
| methyl | bromine | 2-methoxy-benzyl | 161–163 |
| methyl | 4-nitro-phenyl | 2-fluorobenzyl | 184–186 |
| methyl | 4-methoxy- | 2-fluorobenzyl | 117–120 |

TABLE 2-continued

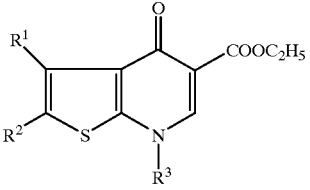

| R¹ | R² | R³ | m.p. (° C.) |
|---|---|---|---|
| | phenyl | | |
| methyl | 4-methoxy-phenyl | 2,6-difluoro-benzyl | amorphous |
| methyl | 4-nitro-phenyl | 2,6-difluoro-benzyl | 215–217 |
| methyl | 4-nitro-phenyl | 2-chloro-6-fluorobenzyl | 211–213 |
| methyl | phenyl | 2,6-difluoro-benzyl | 184–186 |
| methyl | phenyl | 2-chloro-6-fluorobenzyl | 171–173 |
| methyl | 4-methoxy-phenyl | 1-naphthyl | 193–195 |
| methyl | 4-methoxy-phenyl | 2-methoxy-phenethyl | 134–136 |
| methyl | 4-methoxy-phenyl | phenethyl | 182–184 |
| methyl | 4-methoxy-phenyl | 3-phenylpropyl | 147–149 |
| methyl | 4-methoxy-phenyl | cinnamyl | 170–172 |
| methyl | 4-methoxy-phenyl | 3-picolyl | 142–144 |
| methyl | bromine | 2-fluorobenzyl | 211–213 |
| methyl | bromine | 2,6-difluoro-benzyl | 175–176 |

TABLE 3

| R¹ | R² | R³ | R⁴ | m.p. (° C.) |
|---|---|---|---|---|
| methyl | 4-methoxyphenyl | 2-methoxybenzyl | hydroxy-methyl | 153–156 |
| methyl | 4-methoxyphenyl | 2-methoxybenzyl | acetoxy-methyl | 158–159 |
| bromo-methyl | 4-mehoxyphenyl | 2-methoxybenzyl | ethoxy-carbonyl | 200–201 |

TABLE 4

| R¹ | R² | R³ | R⁴ | m.p. (° C.) |
|---|---|---|---|---|
| bromo-methyl | 4-nitrophenyl | 2-methoxy-benzyl | ethoxy-carbonyl | 173–175 |
| bromo-methyl | 4-methoxy-phenyl | 2-methoxy-benzyl | acetoxy-methyl | 131–133 |
| bromo-methyl | phenyl | 2-methoxy-benzyl | ethoxy-carbonyl | 194–196 |
| phenyl | bromomethyl | 2-methoxy-benzyl | ethoxy-carbonyl | amorphous |
| bromo-methyl | benzoyl | 2-methoxy-benzyl | ethoxy-carbonyl | amorphous |
| bromo-methyl | 2-methoxy-phenyl | 2-methoxy-benzyl | ethoxy-carbonyl | amorphous |
| bromo-methyl | bromide | 2-methoxy-benzyl | ethoxy-carbonyl | 174–175 |
| bromo-methyl | 3-methoxy-phenyl | 2-methoxy-benzyl | ethoxy-carbonyl | 83–86 |
| bromo-methyl | 4-nitrophenyl | 2-fluoro-benzyl | ethoxy-carbonyl | 202–204 |
| bromo-methyl | 4-methoxy-phenyl | 2-fluoro-benzyl | ethoxy-carbonyl | amorphous |
| bromo-methyl | 4-nitrophenyl | 2,6-difluoro-benzyl | ethoxy-carbonyl | 200–202 |
| bromo-methyl | 4-nitrophenyl | 2-chloro-6-fluoro-benzyl | ethoxy-carbonyl | 175–177 |
| bromo-methyl | 4-methoxy-phenyl | 2-fluoro-benzyl | 1-acetoxy-ethyl | amorphous |
| bromo-methyl | 4-nitrophenyl | 2,6-difluoro-benzyl | benzoyl | amorphous |
| bromo-methyl | 4-nitrophenyl | 2,6-difluoro-benzyl | isobutyryl | 236–238 |
| bromo-methyl | 4-methoxy-phenyl | 2,6-difluoro-benzyl | isobutyryl | 123–124 |
| bromo-methyl | 4-methoxy-phenyl | 2-fluoro-benzyl | acetyl | 226–228 |
| bromo-methyl | 4-methoxy-phenyl | 2-fluoro-benzyl | propionyl | 186–187 |
| bromo-methyl | 4-methoxy-phenyl | 2-fluoro-benzyl | butyryl | 165–166 |
| bromo-methyl | 4-methoxy-phenyl | 2-fluoro-benzyl | hexanoyl | 168–169 |
| bromo-methyl | 4-methoxy-phenyl | 2-fluoro-benzyl | valeryl | 173–174 |
| bromo-methyl | 4-methoxy-phenyl | 2-fluoro-benzyl | heptanoyl | 146–147 |
| bromo-methyl | 4-methoxy-phenyl | 2-fluoro-benzyl | isovaleryl | 187–189 |
| bromo-methyl | 4-methoxy-phenyl | 2-fluoro-benzyl | benzoyl | 145–147 |
| bromo-methyl | 4-ethoxy-carbonyl-phenyl | 2-methoxy-benzyl | ethoxy-carbonyl | 196–198 |
| bromo-methyl | 4-methoxy-methoxyphenyl | 2-fluoro-benzyl | ethoxy-carbonyl | 115–120 |
| bromo-methyl | 4-diethyl-amino-carbonyl-phenyl | 2-fluoro-benzyl | ethoxy-carbonyl | amorphous |
| bromo-methyl | 4-ethoxy-carbonyl-phenyl | 2,6-difluoro-benzyl | benzoyl | 190–192 |
| bromo- | 4-butoxy- | 2-fluoro- | ethoxyl- | 138–140 |

TABLE 4-continued

[Structure: thieno-pyridinone with R¹, R², R³, R⁴ substituents]

| R¹ | R² | R³ | R⁴ | m.p. (° C.) |
|---|---|---|---|---|
| methyl | phenyl | benzyl | carbonyl | |
| bromo-methyl | 4-methoxy-phenyl | 2-fluoro-benzyl | cyano | 216–218 |

TABLE 5

[Structure: thieno-pyridinone with R¹, COOC₂H₅, 4-methoxyphenyl, N-CH₂-(2-methoxyphenyl)]

| R¹ | m.p. (° C.) |
|---|---|
| benzylaminomethyl | 118–119 (hydrochloride) |
| anilinomethyl | 173–174 |
| phenethylaminomethyl | 148–151 (oxalate) |
| phenylpropylaminomethyl | 116–118 (hydrochloride) |
| N'-methylpiperazinylmethyl | 138–139 |
| N'-phenylpiperazinylmethyl | 189–190 |
| 4-phenylpiperidinomethyl | 165–167 (oxalate) |
| N'-benzylpiperazinylmethyl | 109–110 (oxalate) |
| phthalimidomethyl | 221–223 |
| 1,2,3,4-tetrahydro-isoquinolylmethyl | 156–158 (hydrochloride) |
| benzhydrylaminomethyl | 133–135 (hydrochloride) |
| N-phenyl-N-benzylaminomethyl | 93–95 (hydrochloride) |
| methylaminomethyl | 118–120 (hydrobromide) |
| ethylaminomethyl | 114–116 (hydrobromide) |
| N-benzyl-N-methylaminomethyl | 96–98 (oxalate) |
| N-benzyl-N-methylaminomethyl | 147–152 (hydrochloride) |
| 2-methoxybenzylaminomethyl | 108–110 (hydrochloride) |
| 3-methylbenzylaminomethyl | 110–112 (hydrochloride) |
| 3,4-dimethoxybenzyl-aminomethyl | 129–131 (hydrochloride) |
| 2-phenylimidazo-1-ylmethyl aminomethyl | 130–132 104–106 (hydrobromide) |
| N-benzyl-N-dimethylammonium methyl | 135–137 (bromide) |
| N-methyl-N-(2,3,4-trimethoxybenzyl)aminomethyl | 113–115 (hydrochloride) |
| N-methyl-N-(N-methylindol-3-yl)ethylaminomethyl | 151–153 (hydrochloride) |
| N-methyl-N-phenylpropylaminomethyl | 103–105 (hydrochloride) |
| N-methyl-N-(2-thiomethylbenzyl)aminomethyl | 115–117 (hydrochloride) |
| N-methyl-N-(3,5-trifluoro-methylbenzyl)aminomethyl | 130–132 (hydrochloride) |
| N-methyl-N-(2,6-dichlorobenzyl)aminomethyl | 124–126 (hydrochloride) |
| N-methyl-N-(2-nitrobenzyl)aminomethyl | 139–141 (hydrochloride) |
| t-butylaminomethyl | 126–128 (hydrobromide) |
| dimethylaminomethyl | 117–119 (hydrobromide) |
| N-methyl-N-(2-chlorobenzyl)-aminomethyl | 143–145 (hydrochloride) |
| N-methyl-N-(3-chlorobenzyl)-aminomethyl | 203–205 (hydrochloride) |
| N-methyl-N-(4-chlorobenzyl)aminomethyl | 197–199 (hydrochloride) |
| N-methyl-N-(2-fluorobenzyl)aminomethyl | 120–122 (hydrochloride) |
| dibenzylaminomethyl | 155–157 (hydrochloride) |
| N-hydroxyethyl-N-benzyl-aminomethyl | 112–114 (hydrochloride) |
| N-ethoxycarbonylethyl-N-benzylaminomethyl | 78–80 (hydrochloride) |
| N-benzyl-N-acetamidomethyl | 77–82 (hydrochloride) |
| N-propyl-N-benzylaminomethyl | 103–107 (hydrochloride) |
| N-benzyl-N-phenethylaminomethyl | 105–111 (hydrochloride) |
| 2-indanylaminomethyl | 128–132 (hydrochloride) |
| N-methyl-N-(2-indanyl)aminomethyl | 121–125 (hydrochloride) |
| N-methyl-N-(3-nitrobenzyl)aminomethyl | 209–211 (hydrochloride) |
| N-methyl-N-(4-nitrobenzyl)aminomethyl | 199–201 (hydrochloride) |
| N-methyl-N-(2-phenyl-benzyl)aminomethyl | 112–114 (hydrochloride) |

TABLE 6

[Structure: thieno-pyridinone with R¹, R², R⁴ and N-CH₂-phenyl-R⁴¹]

| R¹ | R² | R⁴¹ | R⁴ | m.p. (° C.) |
|---|---|---|---|---|
| N-benzyl-N-methylamino-methyl | 4-nitro-phenyl | 2-methoxy | ethoxy-carbonyl | 124–126 (hydrochloride) |
| N-benzyl-N-methylamino-methyl | 4-methoxy-phenyl | 2-methoxy | acetoxy-methyl | 108–117 (hydrochloride) |
| N-benzyl-aminomethyl | phenyl | 2-methoxy | ethoxy-carbonyl | 167–169 (hydrochloride) |
| N-benzyl-N-methylamino-methyl | phenyl | 2-methoxy | ethoxy-carbonyl | 117–120 (hydrochloride) |
| phenyl | N-benzyl-aminomethyl | 2-methoxy | ethoxy-carbonyl | 195–97 (hydrochloride) |
| N-benzyl-N-methylamino-methyl | benzoyl | 2-methoxy | ethoxy-carbonyl | 90–95 (hydrochloride) |
| N-benzyl-aminomethyl | 2-methoxy-phenyl | 2-methoxy | ethoxy-carbonyl | 114–118 (hydro- |

TABLE 6-continued

![structure with R1, R2, R4, CH2-phenyl-R41]

| R¹ | R² | R⁴¹ | R⁴ | m.p. (° C.) |
|---|---|---|---|---|
| N-benzyl-N-methylamino-methyl | 2-methoxy-phenyl | 2-methoxy | ethoxy-carbonyl | 119–122 (hydro-chloride) |
| N-benzylamino-methyl | bromine | 2-methoxy | ethoxy-carbonyl | 207–211 (oxalate) |
| N-benzyl-N-methylamino-methyl | bromine | 2-methoxy | ethoxy-carbonyl | 112–116 (oxalate) |
| N-benzyl-N-methylamino-methyl | 3-methoxy-phenyl | 2-methoxy | ethoxy-carbonyl | 115–120 (hydro-chloride) |
| N-benzyl-N-methylamino-methyl | 4-ethoxy-carbonyl-phenyl | 2-methoxy | ethoxy-carbonyl | 122–125 (hydro-chloride) |
| N-benzyl-N-methylamino-methyl | 4-methoxy-phenyl | 2-fluorobenzyl | cyano | 203–206 (hydro-chloride) |

TABLE 7

![structure with CH3, R2, S, N-R3, CON(R42)-R43]

| R² | R³ | R⁴² | R⁴³ | m.p. (° C) |
|---|---|---|---|---|
| 4-methoxy-phenyl | 2-methoxy-benzyl | N-benzyl-piperazinyl | hydrogen | 233–235 |
| 4-methoxy-phenyl | 2-methoxy-benzyl | 3-pyridyl | hydrogen | 214–216 |
| 4-methoxy-phenyl | 2-methoxy-benzyl | dimethyl-aminopropyl | hydrogen | 160–164 |
| 4-methoxy-phenyl | 2-methoxy-benzyl | 3-pyridyl-methyl | hydrogen | 168–170 |
| 4-nitro-phenyl | 2,6-difluoro-benzyl | methyl | methoxy | 223–224 |

TABLE 7-continued

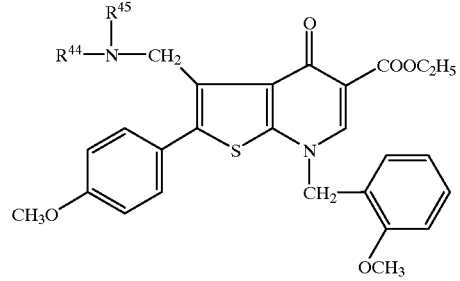

| R² | R³ | R⁴² | R⁴³ | m.p. (° C) |
|---|---|---|---|---|
| phenyl | 2,6-difluoro-benzyl | methyl | methoxy | amorphous |

TABLE 8

![structure with R44-N(R45)-CH2, 4-methoxyphenyl, S, N-CH2-(2-methoxyphenyl), COOC2H5]

| R⁴⁴ | R⁴⁵ | m.p. (° C.) (hydrochloride) |
|---|---|---|
| 2-methoxybenzyl | methyl | 107–109 |
| 2-methylbenzyl | methyl | 120–122 |
| 3-methoxybenzyl | methyl | 74–76 |
| 4-methoxybenzyl | methyl | 126–128 |
| 2,3-dimethoxybenzyl | methyl | 99–101 |
| 2-bromobenzyl | methyl | 141–143 |
| phenethyl | ethyl | 133–135 |
| 2-methoxyphenethyl | methyl | 154–156 |
| 2'-cyanobiphenyl-4-methyl | methyl | 120–122 |
| phenylcarbamoyl | methyl | 89–91 |
| 3-phenyl-2-propenyl | methyl | 152–154 |
| allyl | methyl | 138–140 |
| 3-pyridylmethyl | methyl | 160–162 |
| 1-naphthylmethyl | methyl | 161–163 |
| 2-naphthylmethyl | methyl | 148–150 |
| α-methylbenzyl | methyl | 149–151 |
| 2-hydroxybenzyl | methyl | 178–180 |
| 2-methoxycarbonyl-benzyl | methyl | 129–131 |
| 2-trifluoromethyl-benzyl | methyl | 121–123 |
| 2-thenyl | methyl | 133–135 |

TABLE 9

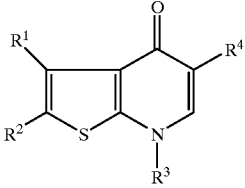

| R¹ | R² | R³ | R⁴ | m.p. (° C.) |
|---|---|---|---|---|
| N-methyl-N-benzylamino-methyl | 4-amino-phenyl | 2-methoxybenzyl | ethoxy-carbonyl | 120–122 |
| N-methyl-N-benzylamino-methyl | 4-methoxy-phenyl | 2-methoxybenzyl | hydroxy-methyl | 135–140 (hydrochloride) |
| N-methyl-N-benzylamino-methyl | 4-methoxy-phenyl | 2-methoxybenzyl | carboxamide (—CO—NH₂) | 152–157 (hydrochloride) |
| N-methyl-N-benzylamino-methyl | 4-methoxy-phenyl | 2-methoxybenzyl | N,N-dimethyl-carboxamide | 136–144 (hydrochloride) |
| N-methyl-N-benzylamino-methyl | 4-methoxy-phenyl | 2-methoxybenzyl | N'-benzyl-piperazino-carbonyl | 168–174 (hydrochloride) |
| N-methyl-N-benzylamino-methyl | 4-methoxy-phenyl | 2-methoxybenzyl | piperidino-carbonyl | 133–142 (hydrochloride) |
| methyl | 3-methoxy-phenyl | 2-methoxybenzyl | ethoxy-carbonyl | amorphous |
| N-methyl-N-benzylamino-methyl | 4-methoxy-phenyl | 2-methyl-thiobenzyl | ethoxy-carbonyl | 118–120 (hydrochloride) |
| N-methyl-N-benzylamino-methyl | 4-methoxy-phenyl | 3-methoxybenzyl | ethoxy-carbonyl | 109–113 (hydrochloride) |
| N-methyl-N-benzylamino-methyl | 4-methoxy-phenyl | 4-methoxybenzyl | ethoxy-carbonyl | 200–204 (hydrochloride) |
| N-methyl-N-benzylamino-methyl | 4-methoxy-phenyl | 2-fluorobenzyl | ethoxy-carbonyl | 203–207 (hydrochloride) |
| N-methyl-N-benzylamino-methyl | 4-methoxy-phenyl | 1-naphthylmethyl | ethoxy-carbonyl | 187–192 (hydrochloride) |
| N-methyl-N-benzylamino-methyl | 4-methoxy-phenyl | 2-naphthymethyl | ethoxy-carbonyl | 122–125 (hydrochloride) |
| N-methyl-N-benzylamino-methyl | 4-methoxy-phenyl | 2-methoxyphenethyl | ethoxy-carbonyl | 76–81 (hydrochloride) |
| N-methyl-N-benzylamino-methyl | 4-methoxy-phenyl | 2-trifluoromethyl-benzyl | ethoxy-carbonyl | 189–194 (hydrochloride) |
| N-methyl-N-benzylamino-methyl | 4-methoxy-phenyl | 2-methoxybenzyl | formyl | 181–185 |
| N-methyl-N-benzylamino-methyl | 4-acetylamino-phenyl | 2-methoxybenzyl | ethoxy-carbonyl | 161–163 |
| N-methyl-N-benzylamino-methyl | 4-formylamino-phenyl | 2-methoxybenzyl | ethoxy-carbonyl | 185–187 |
| methyl | 4-methoxy-phenyl | 2-fluorobenzyl | hydroxy-methyl | 184–185 |
| N-methyl-N-benzylamino-methyl | 4-methoxy-phenyl | 2-fluorobenzyl | hydroxy-methyl | amorphous |

TABLE 10

[Structure shown]

| R¹ | R² | R³ | R⁴ | m.p. (° C.) |
|---|---|---|---|---|
| N-methyl-N-benzylamino-methyl | 4-nitrophenyl | 2-fluorobenzyl | ethoxy-carbonyl | 140–144 |
| N-methyl-N-benzylamino-methyl | 4-nitrophenyl | 2,6-difluoro-benzyl | ethoxy-carbonyl | 145–147 |
| N-methyl-N-benzylamino-methyl | 4-nitrophenyl | 2-chloro-6-fluorobenzyl | ethoxy-carbonyl | 175–177 |
| N-methyl-N-benzylamino-methyl | 4-aminophenyl | 2-fluorobenzyl | ethoxy-carbonyl | 158–160 |
| N-methyl-N-benzylamino-methyl | 4-aminophenyl | 2,6-difluoro-benzyl | ethoxy-carbonyl | 195–196 |
| N-methyl-N-benzylamino-methyl | 4-aminophenyl | 2-chloro-6-fluorobenzyl | ethoxy-carbonyl | 144–146 |
| methyl | 4-methoxy-phenyl | 2-fluorobenzyl | formyl | colorless crystals |

TABLE 11

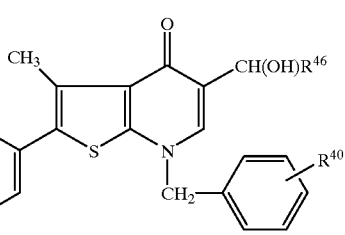

| R⁴⁰ | R⁴⁶ | |
|---|---|---|
| 2-fluoro | methyl | amorphous |
| 2-methoxy | methyl | amorphous |
| 2-fluoro | ethyl | amorphous |
| 2-fluoro | n-propyl | amorphous |
| 2-fluoro | phenyl | amorphous |
| 2-fluoro | isopropyl | amorphous |
| 2-fluoro | n-butyl | amorphous |
| 2-fluoro | sec-butyl | amorphous |
| 2-fluoro | t-butyl | amorphous |
| 2-fluoro | n-pentyl | amorphous |
| 2-fluoro | cyclopentyl | amorphous |
| 2-fluoro | n-hexyl | amorphous |
| 2-fluoro | cyclohexyl | amorphous |
| 2-fluoro | 4-fluorophenyl | amorphous |
| 2-fluoro | benzyl | amorphous |

TABLE 12

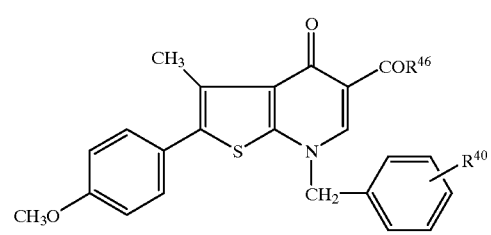

| R⁴⁰ | R⁴⁶ | m.p. (° C.) |
|---|---|---|
| 2-fluoro | methyl | 215–216 |
| 2-methoxy | methyl | 156–157 |
| 2-fluoro | ethyl | 180–181 |
| 2-fluoro | n-propyl | 170–171 |
| 2-fluoro | phenyl | 183–184 |
| 2-fluoro | isopropyl | 173–174 |
| 2-fluoro | n-butyl | 162–163 |
| 2-fluoro | sec-butyl | 132–133 |
| 2-fluoro | t-butyl | 141–144 |
| 2-fluoro | n-pentyl | 145–147 |
| 2-fluoro | cyclopentyl | 182–183 |
| 2-fluoro | n-hexyl | 125–126 |
| 2-fluoro | cyclohexyl | 191–192 |
| 2-fluoro | 4-fluorophenyl | 187–188 |

TABLE 13

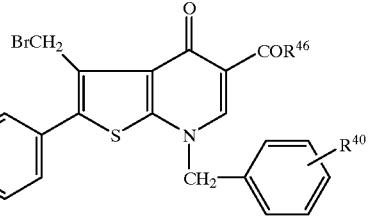

| R⁴⁰ | R⁴⁶ | m.p. (° C.) |
|---|---|---|
| 2-fluoro | methyl | 226–228 |
| 2-methoxy | methyl | 206–208 |
| 2-fluoro | ethyl | 186–187 |
| 2-fluoro | n-propyl | 165–166 |
| 2-fluoro | phenyl | 145–147 |
| 2-fluoro | isopropyl | 123–124 |
| 2-fluoro | n-butyl | 173–174 |
| 2-fluoro | sec-butyl | 146–148 |
| 2-fluoro | t-butyl | 98–99 |
| 2-fluoro | isobutyl | 187–189 |
| 2-fluoro | n-pentyl | 168–169 |
| 2-fluoro | cyclopentyl | 166–167 |
| 2-fluoro | n-hexyl | 146–147 |
| 2-fluoro | cyclohexyl | 169–170 |
| 2-fluoro | 4-fluorophenyl | 135–136 |

TABLE 14

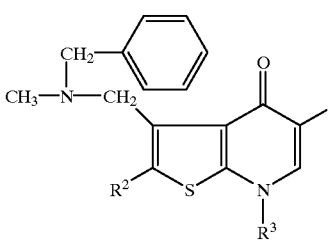

| R² | R³ | R⁴ | m.p. (° C.) |
|---|---|---|---|
| 4-methoxy-phenyl | 2-fluorobenzyl | acetyl | 185–193 |
| 4-methoxy-phenyl | 2-methoxybenzyl | acetyl | 124–130 (hydrochloride) |
| 4-methoxy-phenyl | 2-fluorobenzyl | propionyl | 163–172 (hydrochloride) |
| 4-methoxy-phenyl | 2-fluorobenzyl | n-butyryl | 145–150 (hydrochloride) |
| 4-methoxy-phenyl | 2-fluorobenzyl | benzoyl | 154–161 (hydrochloride) |
| 4-N'-methyl-ureidophenyl | 2-fluorobenzyl | ethoxy-carbonyl | 216–220 |
| 4-acetyl-aminophenyl | 2-fluorobenzyl | ethoxy-carbonyl | 118–120 |
| 4-propionyl-aminophenyl | 2-fluorobenzyl | ethoxy-carbonyl | 221–223 |
| 4-isobutyryl-aminophenyl | 2-fluorobenzyl | ethoxy-carbonyl | 118–192 |
| 4-benzoyl-aminophenyl | 2-fluorobenzyl | ethoxy-carbonyl | 141–143 |
| 4-methane-sulfonamido-phenyl | 2-fluorobenzyl | ethoxy-carbonyl | >300 |

TABLE 15

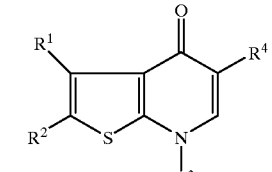

| R¹ | R² | R³ | R⁴ | m.p. (° C.) |
|---|---|---|---|---|
| cyanomethyl | 4-methoxy-phenyl | 2-fluoro-benzyl | ethoxy-carbonyl | oily product |
| ethoxycarbonyl-methyl | 4-methoxy-phenyl | 2-fluoro-benzyl | ethoxy-carbonyl | 199–201 |
| hydroxyethyl | 4-methoxy-phenyl | 2-fluoro-benzyl | ethoxy-carbonyl | amorphous |
| N-methyl-N-benzylamino-ethyl | 4-methoxy-phenyl | 2-fluoro-benzyl | ethoxy-carbonyl | amorphous |
| methyl | 4-methoxy-phenyl | 2-fluoro-benzyl | 1-acetoxy-ethyl | 145–146 |
| N-methyl-N-benzylamino-methyl | 4-methoxy-phenyl | 2-fluoro-benzyl | 1-acetoxy-ethyl | 183–187 |
| N-methyl-N-benzylamino-methyl | 4-nitrophenyl | 2,6-difluoro-benzyl | benzoyl | 197–199 |
| N-methyl-N-benzylamino-methyl | 4-nitrophenyl | 2,6-difluoro-benzyl | isobutyryl | 151–152 |
| N-methyl-N-benzylamino-methyl | 4-ethoxy-carbonyl-phenyl | 2,6-difluoro-benzyl | benzoyl | 175–180 (hydro-chloride) 169–171 (free base) |
| N-methyl-N-benzylamino-methyl | 4-butoxy-phenyl | 2-fluoro-benzyl | ethoxy-carbonyl | 200–202 |
| N-methyl-N-benzylamino-methyl | 4-methoxy-phenyl | 2-fluoro-benzyl | 1-hydroxy-ethyl | 183–187 |

TABLE 16

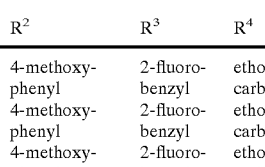

| R² | R³ | m.p. (° C.) |
|---|---|---|
| 4-N'-methyl-ureidophenyl | 2-chloro-6-fluorobenzyl | 199–200 |
| 4-N'-methyl-ureidophenyl | 2-chloro-6-fluorobenzyl | 182–184 |
| 4-propionyl-aminophenyl | 2-chloro-6-fluorobenzyl | 172–173 |
| 4-N'-methyl-ureidophenyl | 2,6-difluoro-benzyl | 214–215 |
| 4-propionyl-aminophenyl | 2,6-difluoro-benzyl | 100–102 |
| 4-N'-methylthio-ureidophenyl | 2,6-difluoro-benzyl | 215–217 |
| 4-(2-methoxy-propionyl- | 2,6-difluoro-benzyl | 110–112 |

TABLE 16-continued

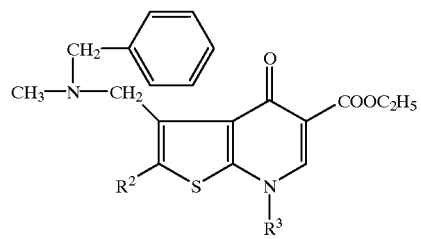

| R² | R³ | m.p. (° C.) |
|---|---|---|
| amino)phenyl | | |
| 4-n-butyryl-aminophenyl | 2-fluoro-benzyl | 203–204 |
| 4-valeryl-aminophenyl | 2-fluoro-benzyl | 206–208 |
| 4-ethoxy-carbonylamino-phenyl | 2-fluoro-benzyl | amorphous |
| 4-N'-methyl-thioureido-phenyl | 2-fluoro-benzyl | 204–205 |
| 4-N'-phenyl-ureidophenyl | 2-fluoro-benzyl | 205–207 |

TABLE 17

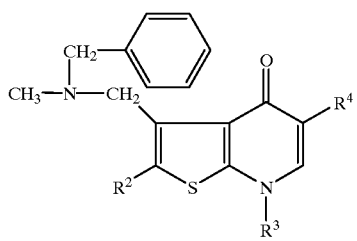

| R² | R³ | R⁴ | m.p. (° C.) |
|---|---|---|---|
| 4-nitro-phenyl | 2,6-difluoro-benzyl | (N-isopropyl)-carboxamide | 200–202 |
| 4-N'-methyl-ureidophenyl | 2,6-difluoro-benzyl | N-isopropyl-N-methylcarboxamide | 133–135 (184–186 as hydrochloride) |
| 4-N'-methyl-ureidophenyl | 2,6-difluoro-benzyl | N-methyl-O-methylhydroxamic acid | 138–140 |
| 4-propionyl aminophenyl | 2,6-difluoro-benzyl | N,N-dimethyl-carboxamide | 110–112 |
| 4-propionyl-aminophenyl | 2,6-difluoro-benzyl | pyrrolidinylamide | 130–132 |
| 4-propionyl-aminophenyl | 2,6-difluoro-benzyl | N',N'-dimethyl-amino-1,3-propylcarboxamide | 90–92 |
| 4-propionyl-aminophenyl | 2,6-difluoro-benzyl | N-methyl-N-butyl-carboxamide | 120–122 |
| 4-N'-methyl-ureidophenyl | 2,6-difluoro-benzyl | N-methyl-N-benzo-carboxamide | 135–137 (179–181 as hydrochloride) |
| 4-N'-methyl-ureidophenyl | 2,6-difluoro-benzyl | N-isopropyl-carboxamide | 148–150 |
| 4-nitro-phenyl | 2,6-difluoro-benzyl | N-methyl-O-methylhydroxamic acid | 100–102 |
| 4-propionyl-aminophenyl | 2,6-difluoro-benzyl | N-isopropyl-carboxamide | 144–146 |
| 4-propionyl-aminophenyl | 2, 6-difluoro-benzyl | N-butyl-carboxamide | 107–109 |
| 4-N'-methyl- | 2-chloro-6- | N-isopropyl- | 172–174 |

TABLE 17-continued

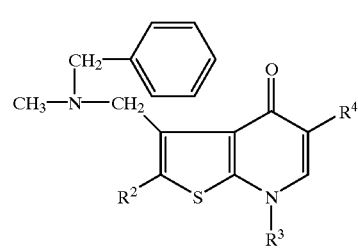

| R² | R³ | R⁴ | m.p. (° C.) |
|---|---|---|---|
| ureidophenyl | fluorobenzyl | carboxamide | |
| 4-propionyl-aminophenyl | 2-chloro-6-fluorobenzyl | N-isopropyl-carboxamide | 120–122 |
| 4-propionyl-aminophenyl | 2-chloro-6-fluorobenzyl | N-butyl-carboxamide | 105–107 |
| 4-acetyl-aminophenyl | 2-fluoro-benzyl | N-isopropyl-carboxamide | 184–186 |
| 4-propionyl-aminophenyl | 2,6-difluoro-benzyl | N-methyl-O-methylhydroxamic acid | amorphous |
| 4-N'-methyl-ureidophenyl | 2,6-difluoro-benzyl | N-methyl-N-(2-pyridyl)-carboxamide | 156–158 (hydrochloride) |
| 4-propionyl-aminophenyl | 2,6-difluoro-benzyl | N-methyl-N-(2-pyridyl)-carboxamide | 148–150 (hydrochloride) |
| 4-N'-methyl-ureidophenyl | 2,6-difluoro-benzyl | N-methyl-N-benzyl-carboxyamide | 125–127 (hydrochloride) |

TABLE 18

| R¹ | R² | R³ | R⁴ | m.p. (° C.) |
|---|---|---|---|---|
| methyl | bromine | 2,6-difluoro-benzyl | N-methyl-O-methyl-hydroxamic acid | 192–194 |
| methyl | 4-nitro-phenyl | 2,6-difluoro-benzyl | benzoyl | 114–116 |
| N-methyl-N-benzyl-aminomethyl | 4-nitro-phenyl | 2,6-difluoro-benzyl | iso-butyryl | 236–238 (hydro-chloride) |
| N-methyl-N-benzyl-aminomethyl | phenyl | 2,6-difluoro-benzyl | iso-butyryl | 204–205 |
| methyl | bromine | 2,6-difluoro-benzyl | benzoyl | 229–230 |
| N-methyl-N-benzyl-aminomethyl | 4-amino-phenyl | 2,6-difluoro-benzyl | benzoyl | 126–128 |
| N-methyl-N-benzyl-aminomethyl | 4-amino-phenyl | 2,6-difluoro-benzyl | isobutyryl | amorphous |

TABLE 19

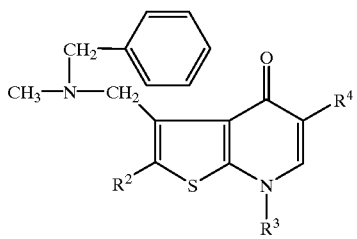

| R² | R³ | R⁴ | m.p. (° C.) (free form) | m.p. (° C.) (HCL salt) |
|---|---|---|---|---|
| 4-propionyl-aminophenyl | 2,6-difluoro-benzyl | benzoyl | 226–228 | 218–220 |
| 4-(N'-methyl-ureidophenyl) | 2,6-difluoro-benzyl | benzoyl | 238–240 | 230–232 |
| 4-propionyl-aminophenyl | 2,6-difluoro-benzyl | iso-butyryl | 201–204 | 207–214 |
| 4-(N'-methyl-ureidophenyl) | 2,6-difluoro-benzyl | iso-butyryl | 207–210 | 222–226 |
| 4-ethane-sulfonamide-phenyl | 2,6-difluoro-benzyl | benzoyl | * | 185–187 |
| 4-isobutyryl-aminophenyl | 2,6-difluoro-benzyl | benzoyl | * | 216–218 |
| 4-(N',N'-dimethyl-ureidophenyl) | 2,6-difluoro-benzyl | benzoyl | * | 180–183 |
| 4-(N'-isopropyl-ureidophenyl) | 2,6-difluoro-benzyl | benzoyl | 245–247 | — |
| 4-pyrrolidine-carboxamidophenyl | 2,6-difluoro-benzyl | benzoyl | * | 176–178 |
| 4-(2,2,2-trifluoro-ethoxy-carboxylamino-phenyl) | 2,6-difluoro-benzyl | benzoyl | * | 232–234 |
| 4-isobutyryl-aminophenyl | 2,6-difluoro-benzyl | iso-butyryl | 188–189 | 192–197 |

*: Salts are prepared from the corresponding free form without measuring the melting point.

TABLE 20

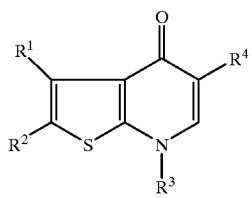

| R¹ | R² | R³ | R⁴ | m.p. (° C.) (HCl salt) |
|---|---|---|---|---|
| N-methyl-N-benzyl-amino-methyl | 4-nitrophenyl | 2,6-difluoro-benzyl | benzoyl | 197–199 |

TABLE 20-continued

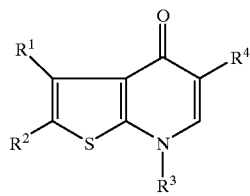

| R¹ | R² | R³ | R⁴ | m.p. (° C.) (HCl salt) |
|---|---|---|---|---|
| N-methyl-N-benzyl-amino-methyl | 4-propionyl-amino-phenyl | 2,6-difluoro-benzyl | iso-butyryl | 207–214 |
| N-methyl-N-benzyl-amino-methyl | 4-(N'-methyl-ureido-phenyl) | 2,6-difluoro-benzyl | iso-butyryl | 222–226 |
| N-methyl-N-benzyl-amino-methyl | 4-propionyl-amino-phenyl | 2,6-difluoro-benzyl | benzoyl | 218–220 |
| N-methyl-N-benzyl-amino-methyl | 4-(N'-methyl-ureido-phenyl) | 2,6-difluoro-benzyl | benzoyl | 230–232 |
| methyl | 4-hydroxy-phenyl | 2-fluoro-benzyl | ethoxy-carbonyl | 225–227 |
| N-methyl-N-benzylamino-methyl | 4-hydroxy-phenyl | 2-fluoro-benzyl | ethoxy-carbonyl | 231–235 |
| methyl | 4-n-butoxy-phenyl | 2-fluoro-benzyl | ethoxy-carbonyl | 119–121 |
| methyl | 4-(4-nitro-benzyloxy-carbonyl)phenyl | 2-fluoro-benzyl | ethoxy-carbonyl | 188–190 |
| methyl | 4-ethoxy-carbonylphenyl | 2,6-difluoro-benzyl | benzoyl | 221–223 |
| methyl | 4-methoxy-methoxyphenyl | 2-fluoro-benzyl | ethoxy-carbonyl | 112–113 |
| methyl | 4-ethoxy-carbonyl-phenyl | 2-methoxy-benzyl | ethoxy-carbonyl | 171–172 |

TABLE 21

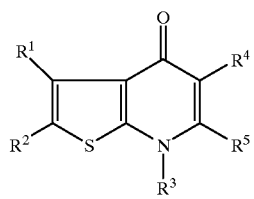

| R¹ | R² | R³ | R⁴ | R⁵ | m.p. (° C.) |
|---|---|---|---|---|---|
| N-methyl-N-benzylaminomethyl | 4-N-ethyl-aminocarbonyl-phenyl | 2,6-difluoro-benzyl | benzoyl | hydrogen | 156–160 (hydrochloride) |
| N-methyl-N-benzyl-aminomethyl | 4-N,N-diethyl aminocarboxy phenyl | 2-fluoro-benzyl | ethoxy-carbonyl | hydrogen | 110–113 (hydrochloride) |
| N-methyl-N-benzyl-aminomethyl | 4-N-propyl-aminocarboxy-phenyl | 2,6-difluoro-benzyl | benzoyl | hydrogen | 153–157 (hydrochloride) |
| N-methyl-N-benzyl-aminomethyl | 4-N-allyl-aminocarboxy-phenyl | 2,6-difluoro-benzyl | benzoyl | hydrogen | 152–156 (hydrochloride) |
| N-methyl-N-benzyl-aminomethyl | 4-methoxy-phenyl | 2-fluoro-benzyl | ethoxy-methyl | hydrogen | 200–204 (hydrochloride) |
| N-methyl-N-benzyl-aminomethyl | 4-methoxy-phenyl | 2-fluoro-benzyl | benzyloxy-methyl | hydrogen | 77–83 (hydrochloride) |
| N-methyl-N-benzyl-aminomethyl | 4-methoxy-phenyl | 2-fluoro-benzyl | ethylthio-methyl | hydrogen | 213–217 (hydrochloride) |
| N-methyl-N-benzyl-aminomethyl | 4-propionyl-aminophenyl | 2,6-difluoro-benzyl | ethoxy-carbonyl | isobutyl | 135–137 (hydrochloride) |
| methyl | 4-methoxy-phenyl | 2-fluoro-benzyl | cyano | hydrogen | 215–216 |
| N-methyl-N-benzyl-aminomethyl | 4-methoxy-phenyl | 2-fluoro-benzyl | ethyl-sulfinyl-methyl | hydrogen | 216–219 (hydrochloride) |

REFERENCE EXAMPLE 2:1

(1) Production of 4,7-dihydro-5-hydroxymethyl-7-(2-fluorobenzyl)-2-(4-methoxyphenyl)-3-methyl-4-oxothieno[2,3-b]pyridine:

The titled compound is produced from 4-hydroxy-5-hydroxymethyl-2-(4-methoxyphenyl)-3-methylthieno[2,3-b]pyridine, which is obtained in PCT International Publication No. WO95/28405 Reference Example 11, 2-fluorobenzyl chloride and potassium iodide. m.p. 159–160° C.

(2) Production of 4,7-dihydro-2-pheny$_{1-3}$-methyl-7-(2,6-difluorobenzyl)-4-oxothieno[2,3-b]pyridine-5-carboxylic acid ethyl ester:

The titled compound is produced by a similar manner as those of the Reference Example 2:1(1). m.p. 184–186° C.

REFERENCE EXAMPLE 2:2

Production of methyl 2-isopropylthioacetate:

The titled compound is produced from thioglycolic acid methyl ester and isopropyl iodide. $^1$H-NMR (CDCl$_3$) δ: 1.26(6H,d,J=6.6 Hz), 3.01–3.09(1H,m), 3.25(2H,s), 3.72 (3H,s).

REFERENCE EXAMPLE 2:3

Production of methyl 2-(N,N-dimethylaminomethylene)-2-isopropylthioacetate:

The titled compound is produced from the compound, which is obtained in Reference Example 2:2, and N,N-dimethylformamidedimethylacetal.

$^1$H-NMR (CDCl$_3$) δ: 1.19(6H,d,J=6.6 Hz), 2.89–2.98(1H, m), 3.26(6H,s), 3.72(3H,s), 7.88(1H,s).

REFERENCE EXAMPLE 2:4

Production of 2-amino-5-phenyl-4-methylthiophene-3-carboxylic acid:

The titled compound is produced from 2-amino-5-phenyl-4-methylthiophene-3-carboxylic acid ethyl ester (13 mg, 50 mmol), which is obtained in PCT International Publication No. WO95/28405 Reference Example 3, and 2N sodium hydroxide solution. Thus obtained compound is used for next reaction step without purification.

REFERENCE EXAMPLE 2:5

Production of methyl (3-carboxy-5-phenyl-4-methylthiophen-2-yl)-aminomethylene-(2-isopropylthio) acetate:

The titled compound is produced from the compound which is obtained in Reference Example 2:4 and the compound which is obtained in Reference Example 2:3. m.p. 119–121° C.

REFERENCE EXAMPLE 2:6

Production of 4-hydroxy-2-phenyl-3-methyl-5-isopropylthiothieno[2,3-b]pyridine:

The titled compound is produced from the compound which is obtained in Reference Example 2:5 and diphenylether.

$^1$H-NMR (CDCl$_3$) δ: 1.30(6H,d,J=6.6 Hz), 2.64(3H,s), 3.07–3.16(1H,m), 7.37–7.54(5H,m), 8.45(1H,s).

REFERENCE EXAMPLE 2:7
Production of 4,7-dihydro-2-(4-methoxyphenyl)-3-methyl-5-(oxazol-5-yl)-7-(2-fluorobenzyl)-4-oxothieno[2,3-b]pyridine:

The titled compound is produced from 4,7-dihydro-2-(4-methoxyphenyl)-3-methyl-5-formyl-7-(2-fluorobenzyl)-4-oxothieno[2,3-b]pyridine which is obtained in PCT International Publication No. WO95/28405 Working Example 28, tosylmethylisocyanide and potassium carbonate. m.p. 235–236° C.

REFERENCE EXAMPLE 2:8
Production of 4,7-dihydro-2-(4-methoxyphenyl)-3-bromomethyl-5-(oxazol-5-yl)-7-(2-fluorobenzyl)-4-oxothieno[2,3-b]pyridine:

The titled compound is produced from the compound which is produced in Reference Example 2:7, N-bromosuccinimide and α, α-azobisisobutyronitrile. m.p. 234–236° C.

REFERENCE EXAMPLE 2:9
Production of 3-(N-benzyl-N-methylaminomethyl)-4,7-dihydro-2-(4-methoxyphenyl)-5-(oxazol-5-yl)-7-(2-fluorobenzyl)-4-oxothieno[2,3-b]pyridine:

The titled compound is production from the compound which is obtained in Reference Example 2:8, ethyldiisopropylamine and N-benzylmethylamine. m.p. 144–150° C.

REFERENCE EXAMPLE 2:10
Production of 4,7-dihydro-2-phenyl-3-methyl-5-acetylamino-7-(2,6-difluorobenzyl)-4-oxothieno[2,3-b]pyridine:

From the compound, which is produced in PCT International Publication No. WO95/28405 Working Example 3(13), O-methyl-N-methylhydroxylamine hydrochloride, and diisopropylethylamine, and trimethyl aluminum in hexane, a compound which is N-methyl-O-hydroxamic acid at 5-position is produced.

From thus obtained compound and methyl magnesium chloride, 4,7-dihydro-2-phenyl-3-methyl-5-acetyl-7-(2,6-difluorobenzyl)-4-oxothieno[2,3-b]pyridine is produced.

A reaction of 4,7-dihydro-2-phenyl-3-methyl-5-acetyl-7-(2,6-difluorobenzyl)-4-oxothieno[2,3-b]pyridine with hydroxylamine hydrochloride, and a reaction thus obtained compound with p-toluensulfonic acid chloride gives the titled compound.

$^1$H-NMR (CDCl$_3$) δ: 2.20(3H,s), 2.70(3H,s), 5.23(2H,s), 6.99(2H,t), 7.3–7.5(6H,m), 8.53(1H,s), 9.11(1H,s).

REFERENCE EXAMPLE 2:11
Production of 4,7-dihydro-2-phenyl-3-methyl-5-amino-7-(2,6-difluorobenzyl)-4-oxothieno[2,3-b]pyridine:

From the compound which is obtained in Reference Example 2:10 and 2N sodium hydroxide, the titled compound is produced.

$^1$H-NMR (CDCl$_3$) δ: 2.71(3H,s), 3.3–4.3(2H,brs), 5.14 (2H,s), 6.98(2H,t), 7.17(1H,s), 7.3–7.5(6H,m).

REFERENCE EXAMPLE 2:12
Production of 4,7-dihydro-2-(4-nitrophenyl)-3-methyl-5-acetoxy-7-(2,6-difluorobenzyl)-4-oxothieno[2,3-b]pyridine:

From 4,7-dihydro-2-phenyl-3-methyl-5-acetyl-7-(2,6-difluorobenzyl)-4-oxothieno[2,3-b]pyridine which is obtained in Reference Example 2:10 and m-chloroperbenzoic acid, the titled compound is produced. m.p. 216–217° C.

REFERENCE EXAMPLE 2:13
Production of 4,7-dihydro-2-(4-nitrophenyl)-3-methyl-5-isopropoxy-7-(2,6-difluorobenzyl)-4-oxothieno[2,3-b]pyridine:

The compound which is obtained in Reference Example 2:12 is subjected to hydrolysis with 1N sodium hydroxide, and from thus obtained compound and isopropyl iodide, the titled compound is produced. m.p. 188–189 ° C.

REFERENCE EXAMPLE 2:14
(1) Using the compound which is obtained in Reference Example 2:13 and by a similar manner as in Reference Example 2:8, the following compound is produced. 4,7-dihydro-2-(4-nitrophenyl)-3-bromomethyl-5-isopropoxy-7-(2,6-difluorobenzyl)-4-oxothieno[2,3-b]pyridine.
Yellow Amorphous.

$^1$H-NMR (CDCl$_3$) δ: 1.31(6H,d), 4.68(1H,m), 5.04(2H,s), 5.27(2H,s), 7.03(2H,t), 7.4–7.5(2H,m), 7.85(2H,d), 8.33 (2H,d).

(2) The compound which is obtained in Reference Example 2:14(1) is used and by a similar manner as in Reference Example 2:9, the following compound is produced. 4,7-dihydro-2-(4-nitrophenyl)-3-(N-benzyl-N-methylaminomethyl)-5-isopropoxy-7-(2,6-difluorobenzyl)-4-oxothieno[2,3-b]pyridine.
Yellow Amorphous.

$^1$H-NMR (CDCl$_3$) δ: 1.33(6H,d), 2.23(3H,s), 3.70(2H,s), 4.23(2H,s), 4.64(1H,m), 5.22(2H,s), 7.01(2H,t), 7.1–7.5(7H, m), 8.11(2H,d), 8.23(2H,d).

(3) The compound which is obtained in Reference Example 2:14(2) is used and by a similar manner as in Reference Example 2:26 below mentioned, the following compound is produced. 4,7-dihydro-2-(4-aminophenyl)-3-(N-benzyl-N-methylaminomethyl)-5-isopropoxy-7-(2,6-difluorobenzyl)-4-oxothieno[2,3-b]pyridine.
Colorless Amorphous.

$^1$H-NMR (CDCl$_3$) δ: 1.30(6H,d), 2.18(3H,s), 3.70(2H,s), 3.92(2H,brs), 4.18(2H,s), 5.16(2H,s), 6.70(2H,d), 6.95(2H, t), 7.1–7.5(7H,m), 7.60(2H,d).

(4) The compound which is obtained in Reference Example 2:14(3) is used and by a similar manner as in Reference Example 2:27 below mentioned, the following compound is produced. 4,7-dihydro-2-(4-isobutyrylaminophenyl)-3-(N-benzyl-N-methylaminomethyl)-5-isopropoxy-7-(2,6-difluorobenzyl)-4-oxothieno[2,3-b]pyridine.
Yellow Amorphous.

$^1$H-NMR (CDCl$_3$) δ: 1.21(6H,d), 1.35(6H,d), 2.42(3H,s), 2.95(1H,m), 3.73(2H,s), 4.25(2H,s), 4.63(1H,m), 5.35(2H, s), 6.99(2H,t), 7.2–7.5(8H,m), 7.69(1H,s), 7.95(2H,d), 9.82 (1H, brs).

REFERENCE EXAMPLE 2:15
Production of 4,7-dihydro-2-(4-isobutyrylaminophenyl)-3-(N-benzyl-N-methylaminomethyl)-5-hydroxy-7-(2,6-difluorobenzyl)- 4-oxothieno[2,3-b]pyridine:

From the compound which is obtained in Reference Example 2:14(4) and boron trichloride, the titled compound is produced.

$^1$H-NMR (CDCl$_3$) δ: 1.25(6H,d), 2.12(3H,s), 2.60(1H,m), 3.63(2H,s), 4.14(2H,s), 5.17(2H,s), 6.98(2H,t), 7.1–7.3(5H, m), 7.3–7.5(2H,m), 7.5–7.9(5H,m).

REFERENCE EXAMPLE 2:16
Production of 4,7-dihydro-2-(4-isobutyrylaminophenyl)-3-(N-benzyl-N-methylaminomethyl)-5-isopropylsulfonyloxy-7-(2,6-difluorobenzyl)-4-oxothieno[2,3-b]pyridine hydrochloride:

From the compound which is obtained in Reference Example 2:15 and isopropylsulfonyl chloride, a free form of the titled compound is produced, and from the free form and hydrogen chloride in ether, the titled compound is produced. m.p. 172–177° C.

REFERENCE EXAMPLE 2:17

Production of 4,7-dihydro-2-(4-isobutyrylaminophenyl)-3-(N-benzyl-N-methylaminomethyl)-5-isobutyryloxy-7-(2,6-difluorobenzyl)-4-oxothieno[2,3-b]pyridine hydrochloride:

From the compound which is obtained in Reference Example 2:15 and isobutyryl chloride, the titled compound is obtained. m.p. 169–172° C.

REFERENCE EXAMPLE 2:18

Production of 4,7-dihydro-2-(4-isobutyrylaminophenyl)-3-(N-benzyl-N-methylaminomethyl)-5-ethoxycarbonylmethoxy-7-(2,6-difluorobenzyl)-4-oxothieno[2,3-b]pyridine and its hydrochloride:

From the compound which is obtained in Reference Example 2:15 and ethyl acetate bromide, the titled compound and its hydrochloride are obtained.
Free Form:
$^1$H-NMR (CDCl$_3$) δ: 1.2–1.3(9H,m), 2.20(3H,s), 2.83(1H,brs), 3.74(2H,s), 4.1–4.2(4H,m), 4.82(2H,s), 5.22(2H,s), 6.97(2H,t), 7.0–7.3(7H,m), 7.39(1H,m), 7.58(1H,brs), 7.83(2H,brs).
Hydrochloride: m.p. 190–194° C.

REFERENCE EXAMPLE 2:19

Production of 4,7-dihydro-2-(4-isobutyrylaminophenyl)-3-(N-benzyl-N-methylaminomethyl)-5-carbamoylmethoxy-7-(2,6-difluorobenzyl)-4-oxothieno[2,3-b]pyridine:

From the free form which is obtained in Reference Example 2:18 and ammonium-ethanol, the titled compound is produced. m.p. 237–238° C.

REFERENCE EXAMPLE 2:20

Production of 4,7-dihydro-2-phenyl-3-methyl-5-isopropylthio-7-(2,6-difluorobenzyl)-4-oxothieno[2,3-b]pyridine:

From the compound which is obtained in Reference Example 2:6 and 2,6-difluorobenzyl chloride, the titled compound is produced. m.p. 129–131° C.

REFERENCE EXAMPLE 2:21

Production of 4,7-dihydro-2-phenyl-3-methyl-5-isopropylsulfinyl-7-(2,6-difluorobenzyl)-4-oxothieno[2,3-b]pyridine:

From the compound which is obtained in Reference Example 2:20 and m-chloroperbenzoic acid, the titled compound is produced. m.p. 217–219° C.

REFERENCE EXAMPLE 2:22

Production of 4,7-dihydro-2-phenyl-3-methyl-5-isopropylsulfonyl-7-(2,6-difluorobenzyl)- 4-oxothieno[2,3-b]pyridine:

The titled compound is obtained as a by-product by the manner of Reference Example 2:21. m.p. 231–233° C.

REFERENCE EXAMPLE 2:23

Production of 4,7-dihydro-2-(4-nitrophenyl)-3-methyl-5-isopropylsulfinyl-7-(2,6-difluorobenzyl)-4-oxothieno[2,3-b]pyridine:

From the compound which is obtained in Reference Example 2:21 and a sodium nitrate solution in conc. sulfuric acid, the titled compound is produced. m.p. 212–214° C.

REFERENCE EXAMPLE 2:24

Production of 4,7-dihydro-2-(4-nitrophenyl)-3-bromomethyl-5-isopropylsulfinyl-7-(2,6-difluorobenzyl)-4-oxothieno[2,3-b]pyridine:

From the compound which is obtained in Reference Example 2:23, N-bromosuccinimide (NBS) and α,α-azobisisobutyronitrile (AIBN), the titled compound is produced. m.p. 176–181° C.

REFERENCE EXAMPLE 2:25

Production of 4,7-dihydro-2-(4-nitrophenyl)-3-(N-benzyl-N-methylaminomethyl)-5-isopropylsulfinyl-7-(2,6-difluorobenzyl)-4-oxothieno[2,3-b]pyridine:

From the compound which is obtained in Reference Example 2:24, ethyldiisopropylamine and N-methylbenzylamine, the titled compound is produced. m.p. 98–103° C.

REFERENCE EXAMPLE 2:26

Production of 4,7-dihydro-2-(4-aminophenyl)-3-(N-benzyl-N-methylaminomethyl)-5-isopropylsulfinyl-7-(2,6-difluorobenzyl)-4-oxothieno[2,3-b]pyridine:

From the compound which is obtained in Reference Example 2:25, iron powder and conc. hydrogen chloride, the titled compound is produced. m.p. 105–115° C.

REFERENCE EXAMPLE 2:27

Production of 4,7-dihydro-2-(4-isobutyrylaminophenyl)-3-(N-benzyl-N-methylaminomethyl)-5-isopropylsufinyl-7-(2,6-difluorobenzyl)-4-oxothieno[2,3-b]pyridine:

From the compound which is obtained in Reference Example 2:26 and isobutyryl chloride, the titled compound is obtained.

$^1$H-NMR (CDCl$_3$) δ: 1.04(6H,d,J=6.8 Hz), 1.27(3H,d,J=6.8 Hz), 1.51(3H,d,J=7.1 Hz), 2.16(3H,s), 2.07–2.67(1H,m), 3.48–3.60(1H,m), 3.68(2H,s), 4.02–4.22(2H,Abq,J=12 Hz), 5.31–5.42(2H,Abq,J=15.0 Hz), 6.99(2H,t,J=8.1 Hz), 7.14–7.45(6H,m), 7.68–7.75(4H,m), 7.86(1H,s), 7.93(1H,s).

REFERENCE EXAMPLE 2:28

Production of 4,7-dihydro-2-(4-isobutyrylaminophenyl)-3-(N-benzyl-N-methylaminomethyl)-5-isopropylsulfinyl-7-(2,6-difluorobenzyl)-4-oxothieno[2,3-b]pyridine hydrochloride:

From the compound which is obtained in Reference Example 2:27 and 1M hydrogen chloride in ether, the titled compound is produced. m.p. 185–187° C.

REFERENCE EXAMPLE 2:29

The following compound is produced by a similar manner as above.

4,7-dihydro-2-(4-isobutyrylaminophenyl)-3-(N-benzyl-N-methylaminomethyl)-5-isopropylsulfonyl-7-(2,6-difluorobenzyl)-4-oxothieno[2,3-b]pyridine.

The compounds shown in the above Reference Examples 2:7 to 2:29 are listed in the following Tables 22 to 24.

TABLE 22

Reference Example No. | R¹
---|---
2:7 | methyl
2:8 | bromomethyl
2:9 | N-benzyl-N-methylaminomethyl

TABLE 23

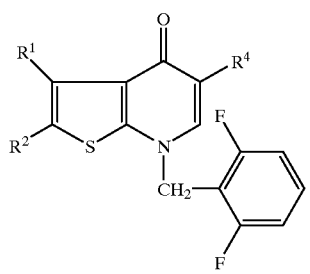

Reference Example No. | R¹ | R² | R⁴
---|---|---|---
2:10 | methyl | phenyl | acetylamino
2:11 | methyl | phenyl | amino
2:12 | methyl | 4-nitrophenyl | acetoxy
2:13 | methyl | 4-nitrophenyl | isopropoxy
2:14(1) | bromomethyl | 4-nitrophenyl | isopropoxy
2:14(2) | N-benzyl-N-methylaminomethyl | 4-nitrophenyl | isopropoxy
2:14(3) | N-benzyl-N-methylaminomethyl | 4-aminophenyl | isopropoxy
2:14(4) | N-benzyl-N-methylaminomethyl | 4-isobutyryl-aminophenyl | isopropoxy
2:15 | N-benzyl-N-methylaminomethyl | 4-isobutyryl-aminophenyl | hydroxy
2:16 | N-benzyl-N-methylaminomethyl | 4-isobutyryl-aminophenyl | isopropyl-sulfonyloxy
2:17 | N-benzyl-N-methylaminomethyl | 4-isobutyryl-aminophenyl | isobutyryloxy
2:18 | N-benzyl-N-methylaminomethyl | 4-isobutyryl-aminophenyl | ethoxycarbonyl-methoxy
2:19 | N-benzyl-N-methylaminomethyl | 4-isobutyryl-aminophenyl | carbamoyl-methoxy
2:20 | methyl | phenyl | isopropylthio
2:21 | methyl | phenyl | isopropyl-sulfinyl

TABLE 24

Reference Example No. | R¹ | R² | R⁴
---|---|---|---
2:22 | methyl | phenyl | isopropylsulfonyl
2:23 | methyl | 4-nitrophenyl | isopropylsulfinyl
2:24 | bromomethyl | 4-nitrophenyl | isopropylsulfinyl
2:25 | N-benzyl-N-methylaminomethyl | 4-nitrophenyl | isopropylsulfinyl
2:26 | N-benzyl-N-methylaminomethyl | 4-aminophenyl | isopropylsulfinyl
2:27 | N-benzyl-N-methylaminomethyl | 4-isobutyryl-aminophenyl | isopropylsulfinyl
2:28 | N-benzyl-N-methylaminomethyl | 4-isobutyryl-aminophenyl | isopropylsulfinyl
2:29 | N-benzyl-N-methylaminomethyl | 4-isobutyryl aminophenyl | isopropylsulfonyl

REFERENCE EXAMPLE 3:1

Production of 4,7-dihydro-7-(2,6-difluorobenzyl)- 2-phenyl-3-methyl-4-oxothieno[2,3-b]pyridine-5-carboxylic acid ethyl ester:

From 4-hydroxy-2-phenyl-3-methylthieno[2,3-b] pyridine-5-canboxylic acid ethyl ester which is produced in PCT International Publication No. WO95/28405 Reference Example 9(1) and 2,6-difluorobenzyl chloride, the titled compound is produced. m.p.171–173° C.

REFERENCE EXAMPLE 3:2

Production of 4,7-dihydro-7-(2,6-difluorobenzyl)-2-(4-nitrophenyl)-3-methyl-4-oxothieno[2,3-b]pyridine-5-carboxylic acid ethyl ester:

From the compound which is produced in Reference Example 3:1, sodium nitrate and conc. sulfuric acid, the titled compound is produced. m.p. 260–261° C.

REFERENCE EXAMPLE 3:3

Production of 3-bromomethyl-4,7-dihydro-7-(2,6-difluorobenzyl)-2-(4-nitrophenyl)-4-oxothieno[2,3-b]pyridine-5-carboxylic acid ethyl ester:

From the compound which is produced in Reference Example 3:2, N-bromosuccinic acid imide and α,α'-azobisisobutyronitrile, the titled compound is produced. m.p. 200–201° C.

REFERENCE EXAMPLE 3:4

Production of 3-(N-benzyl-N-methylaminomethyl)-4,7-dihydro-7-(2,6-difluorobenzyl)-2-(4-nitrophenyl)-4-oxothieno[2,3-b]pyridine-5-carboxylic acid ethyl ester hydrochloride:

From the compound which is produced in Reference Example 3:3, ethyl diisopropylamine and N-benzyl methylamine, the titled compound is produced. m.p. 118–119° C. (hydrochloride).

REFERENCE EXAMPLE 3:5

Production of 3-(N-benzyl-N-methylaminomethyl)-4,7-dihydro-7-(2,6-difluorobenzyl)-2-(4-aminophenyl)-4-oxothieno[2,3-b]pyridine-5-carboxylic acid ethyl ester hydrochloride:

From the compound which is produced in Reference Example 3:4, iron powder and conc. hydrogen chloride, the titled compound is produced. m.p. 195–196° C.

REFERENCE EXAMPLE 3:6
Production of 3-(N-benzyl-N-methylaminomethyl)-4,7-dihydro-7-(2,6-difluorobenzyl)-2-(4-trifluoroacetylaminophenyl)-4-oxothieno[2,3-b]pyridine-5-carboxylic acid ethyl ester:

From the compound which is produced in Reference Example 3:5 and trifluoroacetic anhydride, the titled compound is produced. m.p. 147–149° C.

REFERENCE EXAMPLE 3:7
Production of 3-(N-benzyl-N-methylaminomethyl)-4,7-dihydro-7-(2,6-difluorobenzyl)-2-(4-trifluoroacetylaminophenyl)-4-oxothieno[2,3-b]pyridine-5-(N-methyl-O-methyl)hydroxamic acid:

From N,O-dimethoxyhydroxylamine hydrochloride, diisopropylamine, trimethyl aluminium in hexane and the compound which is produced in Reference Example 3:6, the titled compound is produced.

$^1$H-NMR (300 MHz, CDCl$_3$) δ: 2.15(3H,s), 3.35(3H,s), 3.63(2H,s), 3.73(2H,s), 4.15(2H,s), 5.20(2H,s), 7.00(1H,t), 7.12–7.30(5H,m), 7.42(1H,m), 7.64(2H,d,J=8.7 Hz), 7.72 (1H,s), 7.90(2H,d,J=8.4 Hz). Mass m/z 685(MH)$^+$.

REFERENCE EXAMPLE 3:8

Employing the compound produced in PCT International Publication No. WO95/28405 Working Example 27(2) or the compound produced in the following Reference Example 3:14 as the starting material, substantially the same procedures as in Reference Example 3:6 and 3:7 are conducted to give the compounds set forth in Table 25.

Example 3:8, isopropyl magnesium chloride, while adding to the reaction system tetrabutylammonium bromide to suppress side reactions, to give the titled compound. m.p. 192–197° C. (hydrochloride).

REFERENCE EXAMPLE 3:10
Production of 3-(N-benzyl-N-methylaminomethyl)-4,7-dihydro-7-(2,6-difluorobenzyl)-5-benzoyl-2-(4-methoxyphenyl)-4-oxothieno[2,3-b]pyridine hydrochloride:

From the compound which is obtained in Reference Example 3:8 (Compound 3:8(3)), substantially the same procedure as in Reference Example 3:9 is conducted to produce the titled compound.

REFERENCE EXAMPLE 3:11
Production of 3-(N-benzyl-N-methylaminomethyl)-4,7-dihydro-7-(2,6-difluorobenzyl)-5-isobutyryl-2-(4-methoxyphenyl)-4-oxothieno[2,3-b]pyridine hydrochloride:

From the compound which is produced in Reference Example 3:8 (Compound No. 3:8(3)), substantially the same procedure as in PCT International Publication No. WO95/28405 Working Example 54 is conducted to produce the titled compound.

REFERENCE EXAMPLE 3:12
Production of 4-hydroxy-2-(4-methoxyphenyl)-3-bromomethylthieno[2,3-b]pyridine-5-acetic acid ethyl ester:

From the compound which is produced in PCT International Publication No. WO95/28405 Reference Example 8, substantially the same procedure as in Reference Example 3:3 is conducted to produce the titled compound.

REFERENCE EXAMPLE 3:13
Production of 4-hydroxy-2-(4-methoxyphenyl)-3-(N-benzyl-N-methylaminomethyl)thieno[2,3-b]pyridine-5-acetic acid ethyl ester:

TABLE 25

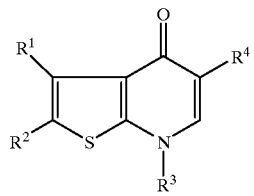

| Ref. Ex. 3:8 Cpd. No. | R$^1$ | R$^2$ | R$^3$ | R$^4$ | m.p. (° C.) |
|---|---|---|---|---|---|
| (1) | N-methyl-N-benzylaminomethyl | 4-isobutyryl-aminophenyl | 2,6-difluorobenzyl | N-methyl-O-methylhydroxamic acid | 152–154 |
| (2) | N-methyl-N-benzylaminomethyl | 4-propionyl-aminophenyl | 2,6-difluorobenzyl | N-methyl-O-methylhydroxamic acid | 139–140 |
| (3) | N-methyl-N-benzylaminomethyl | 4-methoxy-phenyl | 2,6-difluorobenzyl | N-methyl-O-methylhydroxamic acid | |

"N-methyl-O-methylhydroxamic acid" in Table 25 means a group represented by the formula, —CO—N(OCH$_3$)CH$_3$.

REFERENCE EXAMPLE 3:9
Production of 3-(N-benzyl-N-methylaminomethyl)-4,7-dihydro-7-(2,6-difluorobenzyl)-5-isobutyryl-2-(4-isobutyrylaminophenyl)-4-oxothieno[2,3-b]pyridine hydrochloride:

Employing, as the starting material, the compound (Compound No. 3:8(1)) which is produced in Reference From the compound which is produced in Reference Example 3:12, substantially the same procedure as in Reference Example 3:4 is conducted to produce the titled compound.

REFERENCE EXAMPLE 3:14
Production of 4,7-dihydro-7-(2,6-difluorobenzyl)-2-(4-methoxyphenyl)-3-(N-benzyl-N-methylaminomethyl)thieno[2,3-b]pyridine-5-acetic acid ethyl ester:

From the compound which is produced in Reference Example 3:13, substantially the same procedure as in Reference Example 3:1 is conducted to produce the titled compound.

REFERENCE EXAMPLE 3:15
Production of 4,7-dihydro-7-(2,6-difluorobenzyl)-2-(4-hydroxyphenyl)-5-benzoyl-3-(N-benzyl-N-methylaminomethyl)-4-oxothieno[2,3-b]pyridine hydrochloride:

From the compound which is produced in Reference Example 3:10, aluminium chloride and methyl disulfide, the titled compound is produced.

REFERENCE EXAMPLE 3:16
Production of 4,7-dihydro-7-(2,6-difluorobenzyl)-2-(4-hydroxyphenyl)-5-isobutyryl-3-(N-benzyl-N-methylaminomethyl)-4-oxothieno[2,3-b]pyridine hydrochloride:

Employing, as the starting material, the compound which is produced in Reference Example 3:11, substantially the same procedure as in Reference Example 3:15 is conducted to produce the titled compound.

REFERENCE EXAMPLE 3:17
Production of 3-[N-methyl-N-(N-methylindol-3-ylmethyl)aminomethyl-4,7-dihydro-7-(2,6-difluorobenzyl)-5-isobutyryl-2-(4-isobutyrylaminophenyl)-4-oxothieno[2,3-b]pyridine hydrochloride:

Employing the compound which is produced in Reference Example 3:2, 5-(N-methyl-O-methyl)hydroxamic acid is produced. Thus obtained compound is made into 5-isobutyryl compound and thus obtained compound is converted to 4-aminophenyl. The resultant compound is subjected to acylation (introduction of isobutyryl group) then to bromination of the methyl at 3-position to give 3-bromomethyl-4,7-dihydro-7-(2,6-difluorobenzyl)-5-isobutyryl-2-(4-isobutyrylaminophenyl)-4-oxothieno[2,3-b]pyridine. From this compound and 3-N-methylaminomethyl-N'-methyl indole, the titled compound is produced. m.p. 170–172° C. (hydrochloride).

REFERENCE EXAMPLE 3:18

Substantially the same procedure as described in Reference Example 3:17 gives compounds set forth in Table 26 and Table 27.

TABLE 26

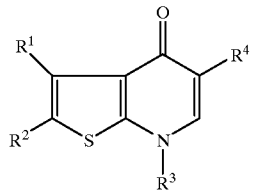

| Ref. Ex. 3:18 Cpd. No. | R¹ | R² | R³ | R⁴ | m.p. (° C.) |
|---|---|---|---|---|---|
| (1) | N-methyl-N-(2-fluorobenzyl)-aminomethyl | 4-isobutyryl-aminophenyl | 2,6-difluorobenzyl | isobutyryl | 135–137 (hydrochloride) |
| (2) | N-methyl-N-(2-bromobenzyl)-aminomethyl | 4-isobutyryl-aminophenyl | 2,6-difluorobenzyl | isobutyryl | 139–141 (hydrochloride) |
| (3) | N-methyl-N-(2-methylthiobenzyl)-aminomethyl | 4-isobutyryl-aminophenyl | 2,6-difluorobenzyl | isobutyryl | amorphous |
| (4) | N-methyl-N-(2-sulfamoylbenzyl)-aminomethyl | 4-isobutyryl-aminophenyl | 2,6-difluorobenzyl | isobutyryl | 240–242 (hydrochloride) |
| (5) | N-methyl-N-(2-pyridylmethyl)-aminomethyl | 4-isobutyryl-aminophenyl | 2,6-difluorobenzyl | isobutyryl | 243–245 (hydrochloride) |

TABLE 27

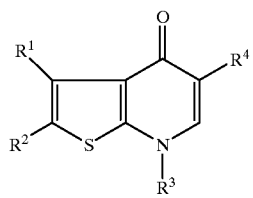

| Ref. Ex. 3:18 Cpd. No. | R¹ | R² | R³ | R⁴ | m.p. (° C.) |
|---|---|---|---|---|---|
| (6) | N-methyl-N-(3-pyridylmethyl)-aminomethyl | 4-isobutyryl-aminophenyl | 2,6-difluorobenzyl | isobutyryl | 181–183 (hydrochloride) |
| (7) | N-methyl-N-butylaminomethyl | 4-isobutyryl-aminophenyl | 2,6-difluorobenzyl | isobutyryl | 239–241 (hydrochloride) |
| (8) | N-methyl-N'-butylcarbamoylmethyl-aminomethyl | 4-isobutyryl-aminophenyl | 2,6-difluorobenzyl | isobutyryl | 156–158 (hydrochloride) |
| (9) | N-methyl-N-(2,6-dinitrobenzyl)-aminomethyl | 4-isobutyryl-aminophenyl | 2,6-difluorobenzyl | isobutyryl | 164–166 (hydrochloride) |
| (10) | hexamethylene tetraammoniummethyl-bromide | 4-isobutyryl-aminophenyl | 2,6-difluorobenzyl | isobutyryl | 184–186 |

REFERENCE EXAMPLE 3:19

Production of 3-(N-benzyl-N-methylaminomethyl)-4,7-dihydro-7-(2,6-difluorobenzyl)-5-benzoyl-2-(4-trifluoroacetylaminophenyl)-4-oxothieno[2,3-b]pyridine:

From the compound which is produced in Reference Example 3:7 and phenyl magnesium chloride in tetrahydrofuran, the titled compound is produced. m.p. 133–135° C.

REFERENCE EXAMPLE 3:20

Employing the compound which is produced in PCT International Publication No. WO95/28405 Working Example 54, substantially the same procedure as described in Reference Example 3:19 is conducted to produce compounds set forth in Table 28 and Table 29.

TABLE 28

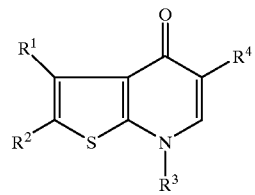

| Ref. Ex. 3:20 Cpd. No. | R¹ | R² | R³ | R⁴ | m.p. (° C.) |
|---|---|---|---|---|---|
| (1) | N-methyl-N-benzylaminomethyl | 4-isobutyryl-aminophenyl | 2,6-difluorobenzyl | 4-methoxy-methoxybenzoyl | 151–153 (hydrochloride) |
| (2) | N-methyl-N-benzylaminomethyl | 4-isobutyryl-aminophenyl | 2,6-difluorobenzyl | 4-dimethylamino-benzoyl | 177–179 (hydrochloride) |
| (3) | N-methyl-N-benzylaminomethyl | 4-isobutyryl-aminophenyl | 2,6-difluorobenzyl | 4-methylthio-benzoyl | 170–172 (hydrochloride) |
| (4) | N-methyl-N-benzylaminomethyl | 4-isobutyryl-aminophenyl | 2,6-difluorobenzyl | 4-methylbenzoyl | 179–181 (hydrochloride) |
| (5) | N-methyl-N-benzylaminomethyl | 4-isobutyryl-aminophenyl | 2,6-difluorobenzyl | 4-methoxybenzoyl | 175–177 (hydrochloride) |
| (6) | N-methyl-N-benzylaminomethyl | 4-isobutyryl-aminophenyl | 2,6-difluorobenzyl | 3-methoxybenzoyl | 169–171 (hydrochloride) |
| (7) | N-methyl-N-benzylaminomethyl | 4-isobutyryl-aminophenyl | 2,6-difluorobenzyl | 2-methoxybenzoyl | 173–175 (hydrochloride) |
| (8) | N-methyl-N-benzylaminomethyl | 4-isobutyryl-aminophenyl | 2,6-difluorobenzyl | 2,4-dimethoxybenzoyl | 170–172 (hydrochloride) |
| (9) | N-methyl-N-benzylaminomethyl | 4-isobutyryl-aminophenyl | 2,6-difluorobenzyl | 2,5-dimethoxybenzoyl | 168–170 (hydrochloride) |
| (10) | N-methyl-N-benzylaminomethyl | 4-isobutyryl-aminophenyl | 2,6-difluorobenzyl | 3,4-dimethoxybenzoyl | 170–172 (hydrochloride) |

TABLE 29

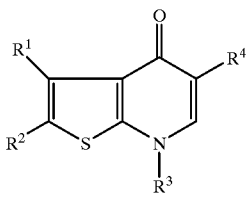

Ref. Ex. 3:20

| Cpd. No. | R¹ | R² | R³ | R⁴ | m.p. (° C.) |
|---|---|---|---|---|---|
| (11) | N-methyl-N-benzylaminomethyl | 4-isobutyryl-aminophenyl | 2,6-difluorobenzyl | 3,4-methylene-dioxybenzoyl | 173–175 (hydrochloride) |
| (12) | N-methyl-N-benzylaminomethyl | 4-isobutyryl-aminophenyl | 2,6-difluorobenzyl | 4-phenoxy-benzoyl | 173–174 (hydrochloride) |
| (13) | N-methyl-N-benzylaminomethyl | 4-propionyl-aminophenyl | 2,6-difluorobenzyl | isovaleryl | 220–224 (hydrochloride) |
| (14) | N-methyl-N-benzylaminomethyl | 4-propionyl-aminophenyl | 2,6-difluorobenzyl | valeryl | 220–224 (hydrochloride) |
| (15) | N-methyl-N-benzylaminomethyl | 4-propionyl-aminophenyl | 2,6-difluorobenzyl | acetyl | 212–217 (hydrochloride) |
| (16) | N-methyl-N-benzylaminomethyl | 4-ethanesulfon-amidephenyl | 2,6-difluorobenzyl | isobutyryl | 177–182 (hydrochloride) |
| (17) | N-methyl-N-benzylaminomethyl | 4-propionyl-aminophenyl | 2,6-difluorobenzyl | propionyl | 233–237 (hydrochloride) |
| (18) | N-methyl-N-benzylaminomethyl | 4-propionyl-aminophenyl | 2,6-difluorobenzyl | butyryl | 228–233 (hydrochloride) |
| (19) | N-methyl-N-benzylaminomethyl | 4-propionyl-aminophenyl | 2,6-difluorobenzyl | 4,4-ethylene-dioxybutyryl | 210–215 (hydrochloride) |
| (20) | N-methyl-N-benzylaminomethyl | 4-propionyl-aminophenyl | 2,6-difluorobenzyl | 2-thenoyl | 229–231 (hydrochloride) |

REFERENCE EXAMPLE 3:21

Production of 3-(N-benzyl-N-methylaminomethyl)-4,7-dihydro-7-(2,6-difluorobenzyl)-5-benzoyl-2-[4-(3-oxobutyl)aminophenyl]-4-oxothieno[2,3-b]pyridine hydrochloride:

From the compound which is produced in PCT International Publication No. WO95/28405 Working Example 54 and methyl vinyl ketone, the titled compound is produced. m.p. 165–168° C. (hydrochloride).

REFERENCE EXAMPLE 3:22

From the compound which is produced in PCT International Publication No. WO95/28405 Working Example 54 and various vinyl compounds or oxirane compounds, compounds set forth in Table 30 are produced.

TABLE 30

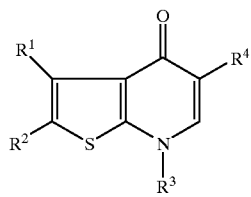

Ref. Ex. 3:22

| Cpd. No. | R¹ | R² | R³ | R⁴ | m.p. (° C.) |
|---|---|---|---|---|---|
| (1) | N-methyl-N-benzylaminomethyl | 4-(3-oxopentyl)-aminophenyl | 2,6-difluorobenzyl | benzoyl | 157–159 (hydrochloride) |
| (2) | N-methyl-N-benzylaminomethyl | 4-(2-hydroxy-cyclohexyl)-aminophenyl | 2,6-difluorobenzyl | benzoyl | 168–170 (hydrochloride) |
| (3) | N-methyl-N-benzylaminomethyl | 4-(2-hydroxypropyl)-aminophenyl | 2,6-difluorobenzyl | benzoyl | 152–154 (hydrochloride) |
| (4) | N-methyl-N-benzylaminomethyl | 4-(2-hydroxybutyl)- | 2,6-difluorobenzyl | benzoyl | 152–154 (hydrochloride) |

TABLE 30-continued

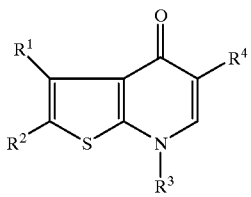

| Ref. Ex. 3:22 Cpd. No. | R¹ | R² | R³ | R⁴ | m.p. (° C.) |
|---|---|---|---|---|---|
| (5) | N-methyl-N-benzylaminomethyl | aminophenyl 4-(2-hydroxy-isobutyl)-aminophenyl | 2,6-difluorobenzyl | benzoyl | 168–170 (hydrochloride) |

REFERENCE EXAMPLE 3:23
Production of 3-(N-benzyl-N-methylaminomethyl)-4,7-dihydro-7-(2,6-difluorobenzyl)-5-benzoyl-2-[4-(2-acetylvinylenephenyl)]-4-oxothieno[2,3-b]pyridine hydrochloride:

The compound which is produced in Reference Example 3:10 is treated with isoamyl nitrite, bis-dibenzylidene acetone palladium and methyl vinyl ketone, and then subjected to a conventional method the titled compound is produced. m.p. 149–151° C. (hydrochlide).

REFERENCE EXAMPLE 3:24

From the compound which is produced in Reference Example 3:10 and various vinyl compounds, compounds set forth in Table 31 are produced.

From the compound which is produced in Reference Example 3:19, ethyl iodide and potassium carbonate, the titled compound is produced.

¹H-NMR (200 MHz, CDCl₃) δ: 1.23(3H,t,J=7.2 Hz), 2.12(3H,s), 3.62(2H,s), 3.83(2H,q,J=7.2 Hz), 4.16(2H,s), 5.31(2H,s), 7.03(2H,t,J=7.8 Hz), 7.12–7.32(7H,m), 7.37–7.47(3H,m), 7.55 (1Hm), 7.89(2H,d,J=7.8 Hz), 7.96 (3H,m). Mass m/z 730(MH)⁺.

REFERENCE EXAMPLE 3:26
Production of 3- (N-benzyl-N-methylaminomethyl)-4,7-dihydro-7- (2,6-difluorobenzyl) -5-benzoyl-2-(4-ethylaminophenyl) -4-oxothieno[2,3-b]pyridine hydrochloride:

From the compound which is produced in Reference Example 3:25 and 5N potassium hydroxide, the titled compound is produced. m.p. 166–168° C. (hydrochloride).

TABLE 31

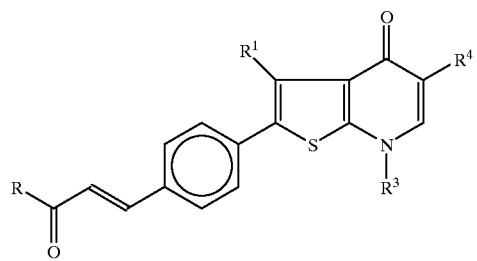

| Ref. Ex. 3:24 Cpd. No. | R¹ | R | R³ | R⁴ | m.p. (° C.) |
|---|---|---|---|---|---|
| (1) | N-methyl-N-benzylaminomethyl | phenyl | 2,6-difluorobenzyl | benzoyl | 137–139 |
| (2) | N-methyl-N-benzylaminomethyl | ethoxy | 2,6-difluorobenzyl | benzoyl | 154–155 (hydrochloride) |
| (3) | N-methyl-N-benzylaminomethyl | methoxy | 2,6-difluorobenzyl | benzoyl | 148–150 (hydrochloride) |
| (4) | N-methyl-N-benzylaminomethyl | hydroxy | 2,6-difluorobenzyl | benzoyl | 159–161 (hydrochloride) |
| (5) | N-methyl-N-benzylaminomethyl | ethyl | 2,6-difluorobenzyl | benzoyl | 168–170 (hydrochloride) |

REFERENCE EXAMPLE 3:25

Production of 3-(N-benzyl-N-methylaminomethyl)-4,7-dihydro-7-(2,6-difluorobenzyl)-5-benzoyl-2-[4-(N-ethyl-N-trifluoroacetylaminophenyl)]-4-oxothieno[2,3-b]pyridine:

REFERENCE EXAMPLE 3:27

From the compounds which are produced in Reference Example 3:19 or Reference Example 3:21 and various halogen compounds, compounds set forth in Table 32 are produced by a similar manner of Reference Example 3:25 or 3:26.

TABLE 32

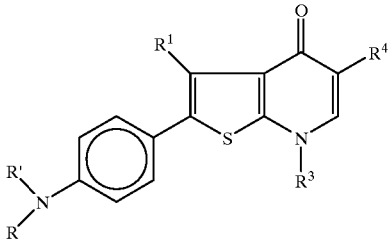

Ref. Ex. 3:27

| Cpd. No. | R¹ | R | R' | R³ | R⁴ | m.p. (° C.) |
|---|---|---|---|---|---|---|
| (1) | N-methyl-N-benzylaminomethyl | ethyl | ethyl | 2,6-difluorobenzyl | benzoyl | 144–146 (hydrochloride) |
| (2) | N-methyl-N-benzylaminomethyl | —(CH$_2$)$_4$— | | 2,6-difluorobenzyl | benzoyl | 154–156 (hydrochloride) |
| (3) | N-methyl-N-benzylaminomethyl | methyl | H | 2,6-difluorobenzyl | benzoyl | 152–154 (hydrochloride) |
| (4) | N-methyl-N-benzylaminomethyl | propyl | H | 2,6-difluorobenzyl | benzoyl | 154–156 (hydrochloride) |
| (5) | N-methyl-N-benzylaminomethyl | butyl | H | 2,6-difluorobenzyl | benzoyl | 145–147 (hydrochloride) |
| (6) | N-methyl-N-benzylaminomethyl | isobutyl | H | 2,6-difluorobenzyl | benzoyl | 157–159 (hydrochloride) |

REFERENCE EXAMPLE 3:28

Production of 3-(N-benzyl-N-methylaminomethyl)-4,7-dihydro-7-(2,6-difluorobenzyl)-5-(4-hydroxybenzoyl)-2-(4-isobutyrylaminophenyl)-4-oxothieno[2,3-b]pyridine hydrochloride:

From the compound which is produced in Reference Example 3:20 (Compound No.1) and 10M hydrogen chloride in ethanol, the titled compound is produced. m.p. 192–194° C. (hydrochloride).

REFERENCE EXAMPLE 3:29

Production of 3-(N-benzyl-N-methylaminomethyl)-4,7-dihydro-7-(2,6-difluorobenzyl)-5-(4-acetoxybenzoyl)-2-(4-isobutyrylaminophenyl)-4-oxothieno[2,3-b]pyridine hydrochloride:

From the compound which is produced in Reference Example 3:28, triethylamine and acetic anhydride, the titled compound is produced. m.p. 167–169° C. (hydrochloride).

REFERENCE EXAMPLE 3:30

Production of 3-(N-benzyl-N-methylaminomethyl)-4,7-dihydro-7-(2,6-difluorobenzyl)-5-(1-hydroxyisobutyl)-2-(4-isobutyrylaminophenyl)-4-oxothieno[2,3-b]pyridine hydrochloride:

From the compound which is produced in Reference Example 3:9 and sodium boronhydride, the titled compound is produced. m.p. 232–234° C. (hydrochloride).

REFERENCE EXAMPLE 3:31

Production of 3-(N-benzyl-N-methylaminomethyl)-4,7-dihydro-7-(2,6-difluorobenzyl)-5-(1-acetoxyisobutyl)- 2-(4-isobutyrylaminophenyl)-4-oxothieno[2,3-b]pyridine hydrochloride:

From the compound which is produced in Reference Example 3:30, pyridine and acetic anhydride, the titled compound is produced. m.p. 166–168° C. (hydrochloride).

REFERENCE EXAMPLE 3:32

Production of 4,7-dihydro-7-(2,6-difluorobenzyl)-2-(4-acetonyloxyphenyl)-5-benzoyl-3-(N-benzyl-N-methylaminomethyl)-4-oxothieno[2,3-b]pyridine hydrochloride:

Employing the compound which is produced in Reference Example 3:15 and chloroacetone, the titled compound is produced.

REFERENCE EXAMPLE 3:33

Production of 4,7-dihydro-7-(2,6-difluorobenzyl)-2-(4-acetonyloxyphenyl)-5-isobutyryl-3-(N-benzyl-N-methylaminomethyl)-4-oxothieno[2,3-b]pyridine hydrochloride:

From the compound which is produced in Reference Example 3:16 and chloroacetone, the titled compound is produced.

The structures of the compounds which are produced in the Reference Examples 3:17, 3:19, 3:21, 3:23, 3:25, 3:26, 3:28 to 3:32 are listed in Table 33.

TABLE 33

| Ref. Ex. No. | R¹ | R² | R⁴ |
|---|---|---|---|
| 3:17 | N-methyl-N-(N-methylindol-3-ylmethyl)-aminomethyl | 4-isobutyryl-aminophenyl | isobutyryl |
| 3:19 | N-benzyl-N-methylamino-methyl | 4-trifluoro-acetylamino-phenyl | benzoyl |
| 3:21 | N-benzyl-N-methylamino-methyl | 4-(3-oxobutyl)-aminophenyl | benzoyl |
| 3:23 | N-benzyl-N-methylamino-methyl | 4-(2-acetyl-vinylenephenyl | benzoyl |

TABLE 33-continued

[Structure diagram showing thieno[2,3-b]pyridine core with R¹, R², R⁴ substituents and N-CH₂-(2,6-difluorophenyl) group]

| Ref. Ex. No. | R¹ | R² | R⁴ |
|---|---|---|---|
| 3:25 | N-benzyl-N-methylamino-methyl | 4-(N-ethyl-N-trifluoroacetyl-aminophenyl) | benzoyl |
| 3:26 | N-benzyl-N-methylamino-methyl | 4-ethylamino-phenyl | benzoyl |
| 3:28 | N-benzyl-N-methylamino-methyl | 4-isobutyryl-aminophenyl | 4-hydroxy-benzoyl |
| 3:29 | N-benzyl-N-methylamino-methyl | 4-isobutyryl-aminophenyl | 4-acetoxy-benzoyl |
| 3:30 | N-benzyl-N-methylamino-methyl | 4-isobutyryl-aminophenyl | 1-hydroxy-isobutyl |
| 3:31 | N-benzyl-N-methylamino-methyl | 4-isobutyryl-aminophenyl | 1-acetoxy-isobutyl |
| 3:32 | N-benzyl-N-methylamino-methyl | 4-acetonyl-oxyphenyl | benzoyl |
| 3:33 | N-benzyl-N-methylamino-methyl | 4-acetonyl-oxyphenyl | isobutyryl |

REFERENCE EXAMPLE 4:1

Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid ethyl ester (hereinafter referred to as Compound 4:B):

From the compound which is produced in Working Example 27 described in PCT International Publication No. WO95/28405 (hereinafter referred to as Compound 4:A) and isobutyl chloride, the titled compound is produced. m.p. 233–235° C.

Compound 4:A and Compound 4:B are shown in the following Table 34.

TABLE 34

[Structure diagram showing thieno[2,3-b]pyridine core with CH₃-N(CH₂-phenyl)-CH₂ group, R², CO-O-C₂H₅ ester and N-CH₂-(2,6-difluorophenyl) group]

| Cpd. No. | R² |
|---|---|
| 4:A | 4-aminophenyl |
| 4:B | 4-isobutyrylaminophenyl |

REFERENCE EXAMPLE 4:2

Production of 4,7-dihydro-7-(2,6-difluorobenzyl)-2-(4-isobutyrylaminophenyl)-3-(N-methyl-N-benzylaminomethyl)-4-oxothieno[2,3-b]pyridine-5-carboxylic acid isopropyl ester hydrochloride (Compound 4:2):

From Compound 4:B, isopropyl alcohol and isopropyl titanate, the titled compound is produced. m.p. 168–170° C.

REFERENCE EXAMPLE 4:3

The compounds set forth in Table 35 are produced in substantially the same manner as described in Reference Example 4:2. (In Table 35, the compounds No. 4:2 are shown inclusively.)

TABLE 35

[Structure diagram showing thieno[2,3-b]pyridine core with CH₃-N(CH₂-phenyl)-CH₂ group, 2-(4-isobutyrylaminophenyl) group, CO-O-R⁴⁶·HCl ester and N-CH₂-(2,6-difluorophenyl) group]

| Cpd. No. | R⁴⁶ | m. p. (hydrochloride) (° C.) |
|---|---|---|
| 4:2 | isopropyl | 168–170 |
| 4:3 (1) | sec-butyl | 171–173 |
| 4:3 (2) | cyclohexyl | 177–179 |
| 4:3 (3) | 3-pentyl | 194–195 |
| 4:4 | H | 212–214 |
| 4:5 | 2,4-dimethyl-3-pentyl | 174–175 |

REFERENCE EXAMPLE 5:1

(1) Production of 4,7-dihydro-4-oxo-7-(2,6-difluorobenzyl)-2-(4-hydroxyphenyl)-3-methyl-thieno[2,3-b]pyridine-5-carboxylic acid ethyl ester:

From the compound which is produced in Working Example 3 (10) of PCT International Publication No. WO95/28405, i.e. 4-oxo-7-(2,6-difluorobenzyl)-2-(4-methoxyphenyl)-3-methyl-thieno[2,3-b]pyridine-5-carboxylic acid ethyl ester, aluminium chloride and dimethyl disulfide, the titled compound is produced. m.p. 244–246° C.

(2) Production of 4,7-dihydro-4-oxo-7-(2,6-difluorobenzyl)-2-(4-methoxymethoxyphenyl)-3-methyl-thieno[2,3-b]pyridine-5-carboxylic acid ethyl ester:

From the compound which is produced in Reference Example 5:1(1), sodium hydride and chloromethyl methyl ether, the titled compound is produced.

$^1$H-NMR (300 MHz, CDCl$_3$) δ: 1.41(3H,t,J=7.2 Hz), 2.65(3H,s), 3.50(3H,s), 4.40(2H,q,J=7.2 Hz), 5.22(2H,s), 5.25(2H,s), 7.00(2H,t,J=8.3 Hz), 7.10(2H,d,J=6.8 Hz), 7.33–7.41(3H,m), 8.37(1H,s).

(3) Production of 4,7-dihydro-4-oxo-7-(2,6-difluorobenzyl)-2-(4-methoxymethoxyphenyl)-3-(N-benzyl-N-methylaminomethyl)-thieno[2,3-b]pyridine-5-carboxylic acid ethyl ester:

The compound, which is produced in Reference Example 5:1(2), is reacted with N-bromosuccinic acid imide and α,α'-azobisisobutyronitrile, thus obtained compound is reacted with ethyl diisopropylamine and N-methyl benzylamine to give the titled compound.

$^1$H-NMR (300 MHz, CDCl$_3$) δ: 1.39(3H,t,J=7.2 Hz), 2.20(3H,s), 3.51(3H,s), 3.93(2H,s), 4.20(2H,s), 4.40(2H,q, J=7.2 Hz), 5.23(2H,s), 5.27(2H,s), 7.00(2H,t,J=8.3 Hz), 7.10(2H,d,J=6.8 Hz), 7.18–7.26(5H,m), 7.36–7.44(1H,m), 7.72–7.75(2H,m), 8.37(1H,s).

(4) Production of 4,7-dihydro-4-oxo-7-(2,6-difluorobenzyl)-2-(4-methoxymethoxyphenyl)-3-(N-benzyl-N-methylaminomethyl)-thieno[2,3-b]pyridine-5-N-methyl-O-methyl hydroxamic acid:

From the compound which is produced in Reference Example 5:1(3), N-methyl-O-methyl hydroxylamine hydrochloride, N-ethyl diisopropylamine and trimethyl ammonium, the titled compound is produced.

$^1$H-NMR (300 MHz, CDCl$_3$) δ: 2.21(3H,s), 3.34(3H,s), 3.54(3H,s), 3.72(2H,s), 3.76(3H,s), 4.19(2H,s), 5.23(2H,s), 5.30(2H,s), 6.95(2H,t,J=8.3 Hz), 7.12(2H,d,J=6.8 Hz), 7.15–7.22(5H,m), 7.33–7.41(1H,m), 7.70–7.74(2H,m), 8.33 (1H,s).

(5) Production of 4,7-dihydro-4-oxo-7-(2,6-difluorobenzyl)-2-(4-hydroxyphenyl)-3-(N-benzyl-N-methylaminomethyl)-5-benzoyl thieno[2,3-b] pyridine:

From the compound which is produced in Reference Example 5:1(4), phenyl magnesium bromide and 6N hydrochloric acid, the titled compound is produced.

$^1$H-NMR (300 MHz, CDCl$_3$) δ: 2.37(3H,s), 3.91(2H,s), 4.30(2H,s), 5.38(2H,s), 6.98–7.05(4H,m), 7.21–7.38(5H,m), 7.43–7.48(5H,m), 7.55–7.59(1H,m), 7.90(2H,d,J=7.1 Hz), 8.06(1H,s).

(6) Production of 4,7-dihydro-4-oxo-7-(2,6-difluorobenzyl)-2-(4-hydroxyphenyl)-3-(N-benzyl-N-methylaminomethyl)-5-isobutyrylthieno [2,3-b] pyridine:

From the compound which is produced in Reference Example 5:1(4), isopropyl magnesium chloride and 6N hydrochloric acid, the titled compound is produced.

$^1$H-NMR (300 MHz, CDCl$_3$) δ: 1.18(6H,d), 2.10(3H,s), 3.61(2H,s), 4.1–4.2(3H,m), 5.26(2H,s), 6.90(2H,d), 6.99 (2H,t), 7.1–7.2(6H,m), 7.40(1H,m), 7.65(2H,d), 8.28(1H,s).

REFERENCE EXAMPLE 5:2

The compound which is produced in Reference Example 5:1(3) is subjected to hydrolysis using 1N sodium hydroxide to thereby convert the compound into one whose substituent at 5-position is carboxyl group. From the carboxylic acid derivative, N,N-dimethylaminopyridine, alcohol (e.g. isopropanol, cyclohexanol, sec-butanol, 3-pentanol or 2,4-dimethyl-3-pentanol) and phosphorus oxychloride to produce a compound whose substituent at 5-position is ester. The ester derivative is subjected to demethylation reaction in substantially the same manner as in Reference Example 5:1(1) to give the compound shown in Table 36.

TABLE 36

[Structure shown]

| $R^{47}$ |
|---|
| isopropoxy |
| cyclohexyloxy |
| sec-butoxy |
| 3-pentoxy |
| 2,4-dimethyl-3-pentoxy |

REFERENCE EXAMPLE 5:3

Production of 3-(N-methyl-N-benzylaminomethyl)-4,7-dihydro-7-(2,6-difluorobenzyl)-2-(4-allyloxyphenyl)-5-benzoyl-4-oxothieno[2,3-b]pyridine hydrochloride:

From the compound which is produced in Reference Example 5:1(5), potassium carbonate and allyl iodide, the titled compound is produced. m.p. 120–122° C.

REFERENCE EXAMPLE 5:4

Employing the compound which is produced in Reference Example 5:1(5), substantially the same procedure as described in Reference Example 5:3 is conducted to give compounds shown in Table 37, including the compound of Reference Example 5:3.

TABLE 37

[Structure shown]

| Cpd. No. | $R^{48}$ |
|---|---|
| 5:3 | allyl |
| 5:4 (1) | cyclopropylmethyl |

TABLE 37-continued

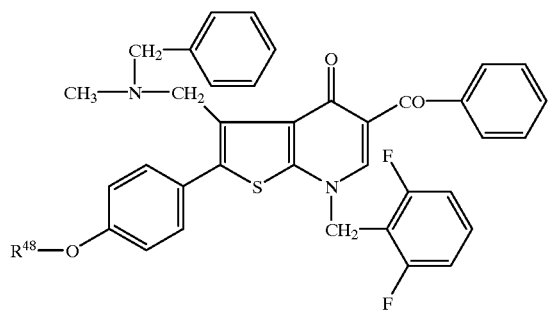

| Cpd. No. | R<sup>48</sup> |
|---|---|
| 5:4 (2) | 2-buten-1-yl |
| 5:4 (3) | 2-methyl-2-propen-1-yl |
| 5:4 (4) | 3-buten-1-yl |

REFERENCE EXAMPLE 5:5

Employing the compound which is produced in Reference Example 5:1(6), substantially the same procedure as described in Reference Example 5:3 is conducted to give compounds shown in Table 38.

TABLE 38

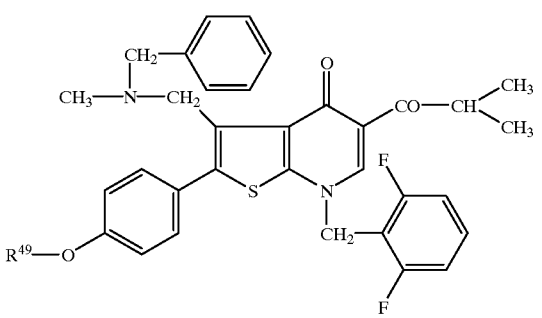

| Cpd. No. | R$^{49}$ | m.p. (hydrochloride) (° C.) |
|---|---|---|
| 5:5 (1) | allyl | 182–184 |
| 5:5 (2) | cyclopropylmethyl | 152–155 |
| 5:5 (3) | 2-buten-1-yl | 126–130 |
| 5:5 (4) | 2-methy1-2-propen-1-yl | 175–177 |
| 5:5 (5) | 3-buten-1-yl | 141–144 |
| 5:5 (6) | 2,2,2-trifluoroethyl | 128–130 |

REFERENCE EXAMPLE 5:6

Employing, the compound which is produced in Reference Example 5:2, substantially the same procedure as described in Reference Example 5:3 is conducted to give compounds shown in Table 39.

TABLE 39

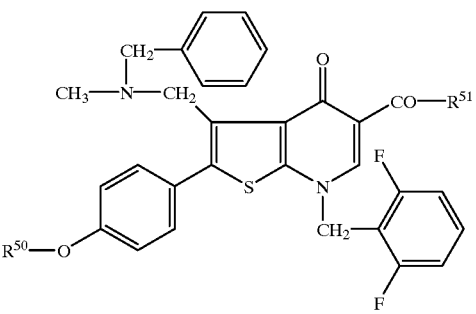

| Cpd. No. | R$^{50}$ | R$^{51}$ |
|---|---|---|
| 5:6 (1) | allyl | isopropoxy |
| 5:6 (2) | cyclopropylmethyl | isopropoxy |
| 5:6 (3) | 2-buten-1-yl | isopropoxy |
| 5:6 (4) | 2-methyl-2-propen-1-yl | isopropoxy |
| 5:6 (5) | 3-buten-1-yl | isopropoxy |
| 5:6 (6) | allyl | cyclohexyloxy |
| 5:6 (7) | cyclopropylmethyl | cyclohexyloxy |
| 5:6 (8) | 2-buten-1-yl | cyclohexyloxy |
| 5:6 (9) | 2-methyl-2-proprn-1-yl | cyclohexyloxy |
| 5:6 (10) | allyl | sec-butoxy |
| 5:6 (11) | cyclopropylmethyl | sec-butoxy |
| 5:6 (12) | 2-buten-1-yl | sec-butoxy |
| 5:6 (13) | 2-methyl-2-propen-1-yl | sec-butoxy |
| 5:6 (14) | allyl | 3-pentoxy |
| 5:6 (15) | cyclopropylmethyl | 3-pentoxy |
| 5:6 (16) | 2-buten-1-yl | 3-pentoxy |
| 5:6 (17) | 2-methyl-2-propen-1-yl | 3-pentoxy |
| 5:6 (18) | allyl | 2,4-dimethyl-3-pentoxy |
| 5:6 (19) | cyclopropylmethyl | 2,4-dimethyl-3-pentoxy |
| 5:6 (20) | 2-buten-1-yl | 2,4-dimethyl-3-pentoxy |
| 5:6 (21) | 2-methyl-2-propen-1-yl | 2,4-dimethyl-3-pentoxy |

REFERENCE EXAMPLE 6:1

Employing an acetone derivative, the compound shown in Table 40 is produced in accordance with substantially the same manner as described in PCT International Publication No. WO95/28405 Reference Example 2.

TABLE 40

$$\underset{R^{4y}}{\overset{R^{3y}}{\diagdown}}\underset{S}{\diagup}\underset{NH_2}{\overset{COOC_2H_5}{\diagup}}$$

| Ref. Ex. Cpd. No. | R$^{3y}$ | R$^{4y}$ |
|---|---|---|
| 6:1 | methyl | bromo |

REFERENCE EXAMPLE 6:2

Employing, the compounds which are produced in PCT International Publicaiton No. WO95/28405 Reference Examples 2, 3 or 19, compounds which are produced in accordance with the method described in PCT International Publicaiton No. WO95/28405 Reference Example 20 are set forth in Table 41.

TABLE 41

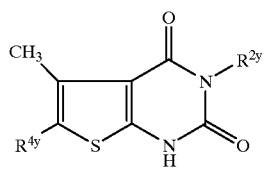

| Ref. Ex. Cpd. No. | $R^{2y}$ | $R^{4y}$ | m.p. (° C.) |
|---|---|---|---|
| 6:2 (1) | 3-methoxyphenyl | bromo | 245–247 |
| 6:2 (2) | 3-isopropoxyphenyl | bromo | |
| 6:2 (3) | 3-isopropoxyphenyl | 4-methoxyphenyl | |
| 6:2 (4) | 3-methoxy-methoxyphenyl | 4-nitrophenyl | 263–267 |

REFERENCE EXAMPLE 6:3

Starting from the compounds which are produced in Reference Example 6:2, compounds which are produced in accordance with the method described in PCT International Publicaiton No. WO95/28405 Reference Example 23 are set forth in Table 42.

TABLE 42

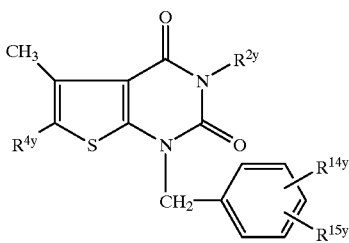

| Ref. Ex. Cpd. No. | $R^{2y}$ | $R^{14y}, R^{15y}$ | $R^{4y}$ | m.p. (° C.) |
|---|---|---|---|---|
| 6:3 (1) | 3-methoxyphenyl | 2,6-difluoro | bromo | 261–262 |
| 6:3 (2) | 3-isopropoxyphenyl | 2,6-difluoro | bromo | |
| 6:3 (3) | 3-isopropoxyphenyl | 2,6-difluoro | 4-methoxy-phenyl | |

REFERENCE EXAMPLE 6:4

The compounds shown in Table 43 are produced from the compounds of Reference Example 6:3 by the method of Reference Example 6:35 mentioned below.

TABLE 43

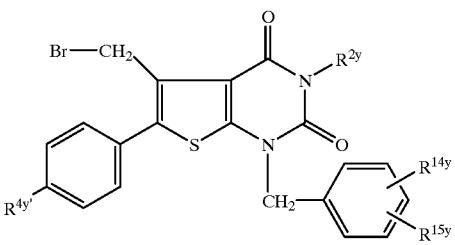

| Ref. Ex. Cpd. No. | $R^{2y}$ | $R^{14y}, R^{15y}$ | $R^{4y'}$ |
|---|---|---|---|
| 6:4 (1) | 3-methoxyphenyl | 2,6-difluoro | propylaminocarbonyl |
| 6:4 (2) | 3-methoxyphenyl | 2,6-difluoro | isopropyl-aminocarbonyl |
| 6:4 (3) | 3-isopropoxyphenyl | 2,6-difluoro | propylaminocarbonyl |
| 6:4 (4) | 3-isopropoxyphenyl | 2,6-difluoro | isopropyl-aminocarbonyl |
| 6:4 (5) | 3-isopropoxyphenyl | 2,6-difluoro | methoxy |

REFERENCE EXAMPLE 6:5

Production of 3-isobutyl-2,4(1H,3H)-dioxo-5-methyl-6-(4-methoxyphenyl)thieno[2,3-d]pyrimidine:

From the compound which is produced in PCT International Publicaiton No. WO95/28405 Reference Example 2, isovaleric acid, diphenylphosphoryl azide and triethylamine, the titled compound is produced. m.p. 215–216° C.

REFERENCE EXAMPLE 6:6

Employing the compounds which are produced in PCT International Publicaiton No. WO95/28405 Reference Example 2 or 19, compounds which are produced in accordance with the method described in Reference Example 6:5 are set forth in Table 44.

TABLE 44

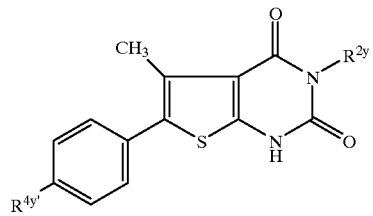

| Ref. Ex. 6:6 Cpd. No. | $R^{2y}$ | $R^{4y'}$ | m.p. (° C.) |
|---|---|---|---|
| 1 | methoxyethyl | methoxy | 131–233 |
| 2 | 3,5-dimethoxyphenyl | methoxy | >300 |
| 3 | 3,5-dimethoxyphenyl | nitro | >300 |

REFERENCE EXAMPLE 6:7

Production of 2-amino-4-methyl-5-(4-methoxyphenyl)thiophene-3-carboxylic acid:

From the compound which is produced in PCT International Publicaiton No. WO95/28405 Reference Example 2 and 2N sodium hydroxide, the titled compound is produced. m.p. 142–145° C.

REFERENCE EXAMPLE 6:8

Production of 2,4(1H)-dioxo-6-(4-methoxyphenyl)-5-methylthieno[2,3-d]oxazine:

From the compound which is produced in Reference Example 6:7 and triphosgene, the titled compound is produced. m.p. 209–210° C.

REFERENCE EXAMPLE 6:9
Production of 2,4(1H)-dioxo-1-(2-fluorobenzyl)-6-(4-methoxyphenyl)-5-methylthieno[2,3-d]oxazine:

From the compound which is produced in Reference Example 6:8, potassium carbonate, potassium iodide and 2-fluorobenzylchloride, the titled compound is produced. m.p. 162–163° C.

REFERENCE EXAMPLE 6:10
Production of 2,4(1H)-dioxo-1-(2,6-difluorobenzyl)-6-(4-methoxyphenyl)-5-methylthieno[2,3-d]oxazine:

From the compound which is obtained in Reference Example 6:9, 2,6-difluorobenzylchloride, potassium carbonate and potassium iodide, the titled compound is produced. m.p. 189–190° C.

REFERENCE EXAMPLE 6:11
Production of 2,4-(1H,3H)-dioxo-1-(2-fluorobenzyl)-6-(4-methoxyphenyl)-3-(3-methoxypropyl)-5-methylthieno[2,3-d]pyrimidine:

From the compound which is obtained in Reference Example 6:9 and 3-methoxypropylamine, the titled compound is produced. m.p. 113–115° C.

REFERENCE EXAMPLE 6:12

Employing the compounds which are produced in Reference Example 6:10, compounds which are produced in accordance with the method described in Reference Example 6:7 are set forth in Table 45.

TABLE 45

| Ref. Ex. Cpd. No. | $R^{14y}, R^{15y}$ | $R^2$ | m.p. (° C.) |
|---|---|---|---|
| 6:12 (1) | 2,6-difluoro | methoxypropyl | 173–174 |
| 6:12 (2) | 2,6-difluoro | 3-methyl-thiophenyl | 243–245 |

REFERENCE EXAMPLE 6:13
Production of 2,4(1H,3H)-dioxo-3-phenyl-5-methyl-6-(4-methoxyphenyl)thieno[2,3-d]pyrimidine:

From the compound which is obtained in PCT International Publicaiton No. WO95/28405 Reference Example 19 and phenylisocyanate, the titled compound is produced. m.p. >300° C.

REFERENCE EXAMPLE 6:14
Production of 2,4(1H,3H)-dioxo-5-methyl-3-(3-methoxyphenyl)-6-(4-methoxyphenyl)thieno[2,3-d]pyrimidine:

In substantially the same procedure as described in Reference Example 6:13, using 3-methoxyphenylisocyanate and the compound which is obtained in PCT International Publicaiton No. WO95/28405 Reference Example 19 and 28% sodium methoxide, the titled compound is produced. m.p. >300° C.

REFERENCE EXAMPLE 6:15
Production of 2,4(1H,3H)-dioxo-1-(2,6-difluorobenzyl)-5-methyl-3-(3-methylsulfinylphenyl)-6-(4-methoxyphenyl)thieno[2,3-d]pyrimidine:

From the compound 6:12(2) which is obtained in Reference Example 6:12 and m-chloroperbenzoic acid, the titled compound is produced. m.p. 267–268° C.

REFERENCE EXAMPLE 6:16
Production of 2,4(1H,3H)-dioxo-1-(2,6-difluorobenzyl)-5-methyl-3-(3-methylsulfonylphenyl)-6-(4-methoxyphenyl)thieno[2,3-d]pyrimidine:

In substantially the same procedures as described in Reference Example 6:15, using m-chloroperbenzoic acid again, from the compound which is obtained in Reference Example 6:15, the titled compound is produced. m.p. 256–257° C.

REFERENCE EXAMPLE 6:17

Employing the compounds which are produced in accordance with the methods of Reference Example 6:5, 6:6, 6:13 or 6:14, compounds which are produced in accordance with the method described in Reference Example 6:9 are set forth in Table 46.

TABLE 46

| Ref. Ex. 6:17 Cpd. No. | $R^{2y}$ | $R^{14y}, R^{15y}$ | $R^{4y'}$ | m.p. (° C.) |
|---|---|---|---|---|
| (1) | isobutyl | 2-fluoro | methoxy | 136–138 |
| (2) | isobutyl | 2,6-difluoro | methoxy | 121–122 |
| (3) | methoxyethyl | 2-fluoro | methoxy | 102–104 |
| (4) | methoxyethyl | 2,6-difluoro | methoxy | 152–153 |
| (5) | 3,5-dimethoxyphenyl | 2-fluoro | methoxy | 250–252 |
| (6) | 3,5-dimethoxyphenyl | 2,6-difluoro | methoxy | 270–272 |
| (7) | 3,5-dimethoxyphenyl | 2,6-difluoro | nitro | 257–258 |
| (8) | phenyl | 2,6-difluoro | nitro | 280–282 |
| (9) | 3-methoxyphenyl | 2,6-difluoro | nitro | 231–234 |
| (10) | 3-isopropoxy-phenyl | 2,6-difluoro | nitro | |
| (11) | 3-methoxy-methoxyphenyl | 2,6-difluoro | nitro | 209–210 |

REFERENCE EXAMPLE 6:18
Production of 2,4(1H,3H)-dioxo-1-(2-fluorobenzyl)-5-bromomethyl-6-(4-methoxyphenyl)-3-(3-methoxypropyl)thieno[2,3-d]pyrimidine:

From the compound which is obtained in Reference Example 6:11, N-bromosuccinimide, α,α'-azobisisobutylonitrile and carbon tetrachloride, the titled compound is produced. m.p. 105–107° C.

REFERENCE EXAMPLE 6:19

Employing the compounds which are produced in Reference Examples 6:11, 6:12, 6:15, 6:16 or 6:17, compounds which are produced in accordance with the method described in Reference Example 6:18 are set forth in Table 47.

TABLE 47

[Structure: BrCH₂ group on thieno[2,3-d]pyrimidine core with R²ʸ, R⁴ʸ', R¹⁴ʸ, R¹⁵ʸ substituents]

Ref. Ex. 6:19

| Cpd. No. | $R^{2y}$ | $R^{14y}, R^{15y}$ | $R^{4y'}$ | m.p. (° C) |
|---|---|---|---|---|
| (1) | methoxypropyl | 2,6-difluoro | methoxy | 166–167 |
| (2) | 3-methyl-mercaptophenyl | 2,6-difluoro | methoxy | 228–230 |
| (3) | 3-methyl-sulfinylphenyl | 2,6-difluoro | methoxy | 272–273 |
| (4) | 3-methyl-sulfonylphenyl | 2,6-difluoro | methoxy | 261–263 |
| (5) | isobutyl | 2-fluoro | methoxy | 125–127 |
| (6) | isobutyl | 2,6-difluoro | methoxy | 155–157 |
| (7) | methoxyethyl | 2-fluoro | methoxy | 152–153 |
| (8) | methoxyethyl | 2,6-difluoro | methoxy | 150–151 |
| (9) | 3,5-dimethoxy-phenyl | 2-fluoro | methoxy | 234–238 |
| (10) | 3,5-dimethoxy-phenyl | 2,6-difluoro | methoxy | 251–253 |
| (11) | 3,5-dimethoxy-phenyl | 2,6-difluoro | nitro | 245–247 |
| (12) | phenyl | 2,6-difluoro | nitro | 228–229 |
| (13) | 3-methoxyphenyl | 2,6-difluoro | nitro | 253–254 |
| (14) | 3-isopropoxy-phenyl | 2,6-difluoro | nitro | |
| (15) | 3-methoxy-methoxyphenyl | 2,6-difluoro | nitro | 207–209 |

REFERENCE EXAMPLE 6:20

Production of 2,4(1H,3H)-dioxo-6-(4-methoxyphenyl)-3-phenyl-1-(2-fluorobenzyl)-5-(N-benzyl-N-methylaminomethyl)thieno[2,3-d]pyrimidine hydrochloride: (Compound 6:A)

From the compound which is produced in PCT International Publicaiton No. WO95/28405 Reference Example 26 (Compound No.5), ethyldiisopropylamine and methylbenzylamine, the titled compound is produced. m.p. 140–143° C.

Starting from the compounds which are produced in PCT International Publicaiton No. WO95/28405 Reference Example 26, Reference Example 6:4, compounds which are produced in accordance with the method described in the above are set forth in Table 48.

TABLE 48

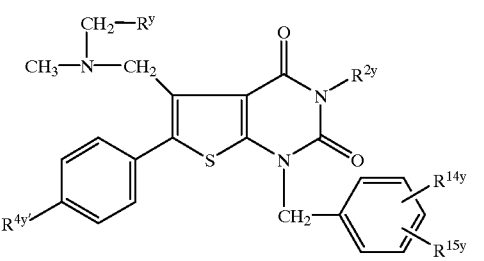

| Compound | $R^{2y}$ | $R^{14y}, R^{15y}$ | $R^{4y'}$ | $R^y$ | m.p. (° C.) |
|---|---|---|---|---|---|
| 6:A | phenyl | 2-fluoro | methoxy | phenyl | 140–143 (hydrochloride) |

Ref. No. 6:20

| Cpd. No. | $R^{2y}$ | $R^{14y}, R^{15y}$ | $R^{4y'}$ | $R^y$ | m.p. (° C.) |
|---|---|---|---|---|---|
| (1) | methyl | 2-methoxy | methoxy | phenyl | 119–122 |
| (2) | methyl | 2-fluoro | methoxy | phenyl | 128–131 |
| (3) | phenyl | 2-methoxy | methoxy | phenyl | 97–105 |
| (4) | phenyl | 2-fluoro | nitro | phenyl | 140–143 |
| (5) | phenyl | 3-fluoro | methoxy | phenyl | 152–156 |
| (6) | phenyl | 4-fluoro | methoxy | phenyl | 165–170 |
| (7) | phenyl | 2,4-difluoro | methoxy | phenyl | 155–160 |
| (8) | phenyl | 2,6-difluoro | methoxy | phenyl | 160–162 |
| (9) | phenyl | 2-chloro, 6-fluoro | methoxy | phenyl | 150–155 |
| (10) | phenyl | 2-methylthio | methoxy | phenyl | 152–158 |
| (11) | benzyl | 2-fluoro | methoxy | phenyl | 128–134 |
| (12) | benzyl | 2,6-difluoro | methoxy | phenyl | 123–127 |
| (13) | 4-methoxy phenyl | 2-fluoro | methoxy | phenyl | 150–155 |
| (14) | 4-methoxy phenyl | 2,6-difluoro | methoxy | phenyl | 153–157 |
| (15) | cyclohexyl | 2-fluoro | methoxy | phenyl | 144–150 |
| (16) | cyclohexyl | 2,6-difluoro | methoxy | phenyl | 145–150 |
| (17) | phenyl | 2,6-difluoro | nitro | phenyl | 155–160 |
| (18) | 2-methoxy-phenyl | 2-fluoro | methoxy | phenyl | 152–153 |
| (19) | 2-methoxy-phenyl | 2,6-difluoro | methoxy | phenyl | 148–150 |
| (20) | 3-methoxy-phenyl | 2-fluoro | methoxy | phenyl | 155–158 |
| (21) | 3-methoxy-phenyl | 2,6-difluoro | methoxy | phenyl | 160–163 |
| (22) | 2-chloro-phenyl | 2-fluoro | methoxy | phenyl | 147–152 |
| (23) | 2-chloro-phenyl | 2,6-difluoro | methoxy | phenyl | 150–155 |
| (24) | 3-chloro-phenyl | 2-fluoro | methoxy | phenyl | 148–153 |
| (25) | 3-chloro-phenyl | 2,6-difluoro | methoxy | phenyl | 152–157 |
| (26) | 4-chloro-phenyl | 2-fluoro | methoxy | phenyl | 161–164 |
| (27) | 4-chloro-phenyl | 2,6-difluoro | methoxy | phenyl | 145–146 |
| (28) | 3-methoxy-phenyl | 2,6-difluoro | propyl-amino-carbonyl | phenyl | |
| (29) | 3-methoxy-phenyl | 2,6-difluoro | isopropyl-amino-carbonyl | phenyl | |
| (30) | 3-isopropoxy-phenyl | 2,6-difluoro | propyl-amino-carbonyl | phenyl | |

TABLE 48-continued

| | | | | | |
|---|---|---|---|---|---|
| (31) | 3-isopropoxyphenyl | 2,6-difluoro | isopropylaminocarbonyl | phenyl | |
| (32) | 3-methoxyphenyl | 2,6-difluoro | methoxy | phenyl | 160–163 |
| (33) | 3-isopropoxyphenyl | 2,6-difluoro | methoxy | phenyl | |
| (34) | 3-methoxyphenyl | 2,6-difluoro | methoxy | 2-methylthiophenyl | |
| (35) | 3-methoxyphenyl | 2,6-difluoro | methoxy | 2-pyridyl | |
| (36) | phenyl | 2,6-difluoro | methoxy | 2-methylthiophenyl | |
| (37) | phenyl | 2,6-difluoro | methoxy | 2-pyridyl | |
| (38) | phenyl | 2,6-difluoro | methoxy | dimethylaminomethyl | |
| (39) | phenyl | 2,6-difluoro | methoxy | diethylaminomethyl | |
| (40) | phenyl | 2,6-difluoro | methoxy | 1-pyrrolidinylmethyl | |

REFERENCE EXAMPLE 6:21

Production of 6-(4-aminophenyl)-2,4-(1H,3H)-dioxo-1-(2,6-difluorobenzyl)-5-(N-methyl-N-benzylaminomethyl)-3-phenylthieno[2,3-d]pyrimidine:

Starting from the compound No. 17 produced in REFERENCE EXAMPLE 6:20, the titled compound is produced in accordance with the method described in PCT International Publicaiton No. WO95/28405 Working Example 60. Structure is shown in Table 49.

$^1$H-NMR (300 MHz, CDCl$_3$) δ: 2.05(3H,s), 3.56(2H,s), 3.81(2H,br s), 3.88(2H,s), 5.36(2H,s), 6.71(2H,d,J=8.7 Hz), 6.91(2H,t,J=8.7 Hz), 7.21–7.53(13H,m).

REFERENCE EXAMPLE 6:22

Production of 6-(4-acetylaminophenyl)-2,4(1H,3H)-dioxo-1-(2-fluorobenzyl)-5-(N-methyl-N-benzylaminomethyl)-3-phenylthieno[2,3-d]pyrimidine:

From the compound which is produced in PCT International Publicaiton No. WO95/28405 Working Example 60 and acetic anhydride, the titled compound is produced. The structure is shown in Table 49.

$^1$H-NMR (300 MHz, CDCl$_3$) δ: 2.06(3H,s), 2.19(3H,s), 3.57(2H,s), 3.90(2H,s), 5.30(2H,s), 7.04–7.57(16H,s), 7.70 (2H,d,J=8.4 Hz).

REFERENCE EXAMPLE 6:23

Employing the compound which is produced in PCT International Publicaiton No. WO95/28405 Working Example 60, in accordance with substantially the same procedure as described in Reference Example 6:22, the following compounds are produced. The structures are shown in Table 49.

Ref.Ex.6:23 No. 1: 2,4(2H,3H)-Dioxo-1-(2-fluorobenzyl)-5-(N-methyl-N-benzylaminomethyl)-3-phenyl-6-(4-propionylaminophenyl)thieno[2,3-d]pyrimidine hydrochloride (m.p. 172–175° C.)

Ref.Ex.6:23 No. 2: 2,4(2H,3H)-Dioxo-1-(2-fluorobenzyl)-6-(4-isobutyrylaminophenyl)-5-(N-methyl-N-benzylaminomethyl)-3-phenylthieno[2,3-d]pyrimidine hydrochloride (m.p. 185–188° C.)

Ref.Ex.6:23 No. 3: 2,4(2H,3H)-Dioxo-1-(2-fluorobenzyl)-6-(4-methoxyacetylaminophenyl)-5-(N-d]pyrimidine hydrochloride (m.p. 157–162° C.)

TABLE 49

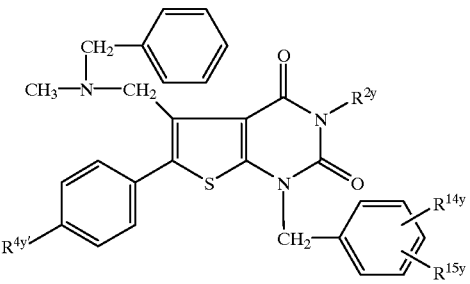

| Ref. Ex. Cpd. No. | R$^{2y}$ | R$^{14y}$, R$^{15y}$ | R$^{4y'}$ |
|---|---|---|---|
| 6:21 | phenyl | 2,6-difluoro | amino |
| 6:22 | phenyl | 2-fluoro | acetylamino |
| 6:23(1) | phenyl | 2-fluoro | propionylamino |
| 6:23(2) | phenyl | 2-fluoro | isobutyrylamino |
| 6:23(3) | phenyl | 2-fluoro | methoxyacetylamino |

REFERENCE EXAMPLE 6:24

Production of 2,4(1H,3H)-dioxo-1-(2-fluorobenzyl)-5-(N-benzyl-N-methylaminomethyl)-6-(4-methoxyphenyl)-3-(3-methoxypropyl)thieno[2,3-d]pyrimidine:

From the compound which is obtained in Reference Example 6:18, ethyldiisopropylamine and methylbenzylamine, the titled compound is produced. The structure is listed in Table 50. m.p. 95–100° C.

REFERENCE EXAMPLE 6:25

Starting from the compounds which are produced in Reference Example 6:19, compounds which are produced in accordance with the method described in Reference Example 6:24 are set forth in Table 50. The compound 19 and 20 are produced by hydrolyzing the compound 21 to produce the compound 22, and by reacting the compound 22 with alkyl halide in the presence of a base.

TABLE 50

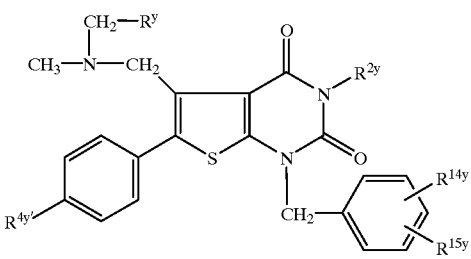

| Ref. Ex. Cpd. No. | $R^{2y}$ | $R^{14y}, R^{15y}$ | $R^{4y'}$ | $R^y$ | m.p. (° C.) |
|---|---|---|---|---|---|
| 6:24 | 3-methoxy-propyl | 2-fluoro | methoxy | phenyl | 95–100 |
| 6:25(1) | methoxypropyl | 2,6-difluoro | methoxy | phenyl | 95–100 |
| 6:25(2) | 3-methyl-thiophenyl | 2,6-difluoro | methoxy | phenyl | 139–144 |
| 6:25(3) | 3-methyl-sulfinylphenyl | 2,6-difluoro | methoxy | phenyl | 153–156 |
| 6:25(4) | 3-methyl-sulfonylphenyl | 2,6-difluoro | methoxy | phenyl | 155–159 |
| 6:25(5) | isobutyl | 2-fluoro | methoxy | phenyl | 150–153 |
| 6:25(6) | isobutyl | 2,6-difluoro | methoxy | phenyl | 165–167 |
| 6:25(7) | methoxyethyl | 2-fluoro | methoxy | phenyl | 154–156 |
| 6:25(8) | methoxyethyl | 2,6-difluoro | methoxy | phenyl | 126–130 |
| 6:25(9) | 3,5-dimethoxy-phenyl | 2-fluoro | methoxy | phenyl | 140–145 |
| 6:25(10) | 3,5-dimethoxy-phenyl | 2,6-difluoro | methoxy | phenyl | 146–148 |
| 6:25(11) | 3,5-dimethoxy-phenyl | 2,6-difluoro | nitro | phenyl | 142–146 |
| 6:25(12) | phenyl | 2,6-difluoro | nitro | phenyl | 152–153 |
| 6:25(13) | 3-methoxy-phenyl | 2,6-difluoro | nitro | phenyl | 142–144 |
| 6:25(14) | 3-isopropoxy-phenyl | 2,6-difluoro | nitro | phenyl | amorphous (80–90) |
| 6:25(15) | 3-isopropoxy-phenyl | 2,6-difluoro | nitro | 2-thiomethyl-phenyl | |
| 6:25(16) | 3-isopropoxy-phenyl | 2,6-difluoro | nitro | 2-pyridyl | |
| 6:25(17) | 3-methoxy-phenyl | 2,6-difluoro | nitro | 2-thiomethyl-phenyl | |
| 6:25(18) | 3-methoxy-phenyl | 2,6-difluoro | nitro | 2-pyridyl | |
| 6:25(19) | 3-ethoxyphenyl | 2,6-difluoro | nitro | phenyl | 171–176 |
| 6:25(20) | 3-propoxy-phenyl | 2,6-difluoro | nitro | phenyl | 149–151 |
| 6:25(21) | 3-methoxy-methoxyphenyl | 2,6-difluoro | nitro | phenyl | 110–120 |
| 6:25(22) | 3-hydroxy-phenyl | 2,6-difluoro | nitro | phenyl | 207–209 |
| 6:25(23) | 3-methoxy-phenyl | 2,6-difluoro | nitro | diethyl-aminomethyl | |
| 6:25(24) | 3-methoxy-phenyl | 2,6-difluoro | nitro | dimethyl-aminomethyl | |
| 6:25(25) | 3-methoxy-phenyl | 2,6-difluoro | nitro | 1-pyrroli-dinylmethyl | |

REFERENCE EXAMPLE 6:26

Production of 6-(4-aminophenyl)-2,4(1H,3H)-dioxo-1-(2,6-difluorobenzyl)-5-(N-benzyl-N-methylaminomethyl)-3-(3-methoxyphenyl)thieno[2,3-d]pyrimidine hydrochloride:

The compound 13 which is produced in Reference Example 6:25 is treated with 50% paradium-carbon powder in a hydrogen atmosphere to give the titled compound. The structure is listed in Table 51. m.p. 162–165° C.

REFERENCE EXAMPLE 6:27

Starting from the compounds which are produced in Reference Example 6:25, compounds which are produced in accordance with the method described in Reference Example 6:26 are set forth in Table 51.

TABLE 51

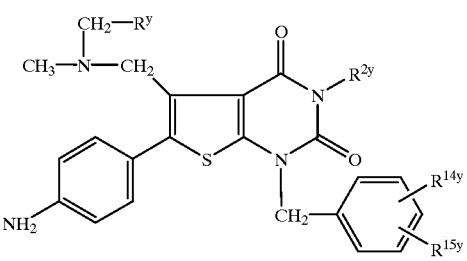

| Ref. Ex. 6:26 Cpd. No. | $R^{2y}$ | $R^{14y}, R^{15y}$ | $R^y$ | m.p. (° C.) |
|---|---|---|---|---|
| 6:26 | phenyl | 2,6-difluoro | methoxyphenyl | 162–165 |

| Ref. Ex. 6:26 Cpd. No. | $R^{2y}$ | $R^{14y}, R^{15y}$ | $R^y$ | m.p. (° C.) |
|---|---|---|---|---|
| (1) | 3,5-dimethoxy-phenyl | 2,6-difluoro | phenyl | 95–100 |
| (2) | phenyl | 2,6-difluoro | phenyl | 139–144 |
| (3) | 3-isopropoxy-phenyl | 2,6-difluoro | phenyl | 138–140 |
| (4) | 3-isopropoxy-phenyl | 2,6-difluoro | 2-methylthio-phenyl | |
| (5) | 3-isopropoxy-phenyl | 2,6-difluoro | 2-pyridyl | |
| (6) | 3-methoxyphenyl | 2,6-difluoro | 2-methylthio-phenyl | |
| (7) | 3-methoxyphenyl | 2,6-difluoro | 2-pyridyl | |
| (8) | 3-ethoxyphenyl | 2,6-difluoro | phenyl | 169–172 |
| (9) | 3-propoxyphenyl | 2,6-difluoro | phenyl | 115–120 |
| (10) | 3-methoxyphenyl | 2,6-difluoro | diethylamino-methyl | |
| (11) | 3-methoxyphenyl | 2,6-difluoro | dimethylamino-methyl | |
| (12) | 3-methoxyphenyl | 2,6-difluoro | 1-pyrroli-dinylmethyl | |

REFERENCE EXAMPLE 6:28

Production of 2,4(1H,3H)-dioxo-1-(2,6-difluorobenzyl)-5-(N-benzyl-N-methylaminomethyl)-6-(4-formamidophenyl)-3-phenylthieno[2,3-d]pyrimidine:

From compound which is obtained in Reference Example 6:27(2), formic acid and acetic anhydride, the titled compound is produced. The structure is shown in Table 52. m.p. 194–196° C.

REFERENCE EXAMPLE 6:29

Starting from the compounds which are produced in Reference Example 6:26 or 6:27, compounds which are produced in accordance with the method described in Reference Example 6:28 are set forth in Table.52.

TABLE 52

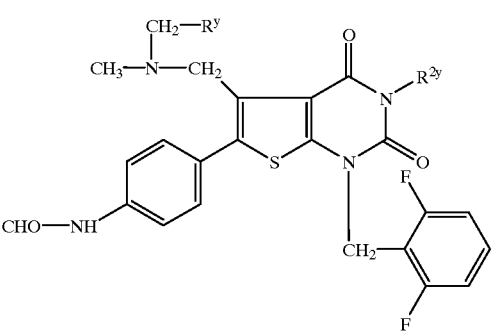

| Ref. Ex. 6:26 Cpd. No. | $R^{2y}$ | $R^y$ | m.p. (° C.) |
|---|---|---|---|
| 6:28 | phenyl | phenyl | 194–196 |
| 6:29(1) | 3,5-dimethoxy-phenyl | phenyl | 239–243 |
| 6:29(2) | 3-methoxyphenyl | phenyl | 213–215 |
| 6:29(3) | 3-isopropoxy-phenyl | phenyl | |
| 6:29(4) | 3-isopropoxy phenyl | 2-methylthio-phenyl | |
| 6:29(5) | 3-isopropoxy phenyl | 2-pyridyl | |
| 6:29(6) | 3-methoxyphenyl | 2-methylthio-phenyl | |
| 6:29(7) | 3-methoxyphenyl | 2-pyridyl | |

REFERENCE EXAMPLE 6:30

Production of 2,4(1H,3H)-dioxo-1-(2,6-difluorobenzyl)-5-(N-benzyl-N-methylaminomethyl)-6-(4-methylaminophenyl)-3-(3-methoxyphenyl)thieno[2,3-d]pyrimidine hydrochloride:

The compound 2 which is obtained in Reference Example 6:29, is treated with dimethylsulfid borane and then hydrochloric acid (pH<2), and thus obtained compound is treated with 1N hydrogen chloride to give the titled compound. The structure is shown in Table 53. m.p. 155–160° C.

REFERENCE EXAMPLE 6:31

Production of 2,4(1H,3H)-dioxo-1-(2,6-difluorobenzyl)-6-(4-propionylaminophenyl)-5-(N-benzyl-N-methylaminomethyl)-3-(3-methoxyphenyl)thieno[2,3-d]pyrimidine hydrochloride:

The compound which is obtained in Reference Example 6:26 is treated with triethylamine and propionyl chloride, and then with 1N hydrogen chloride in ether to give the titled compound. The structure is shown in Table 53. m.p. 218–224° C.

TABLE 53

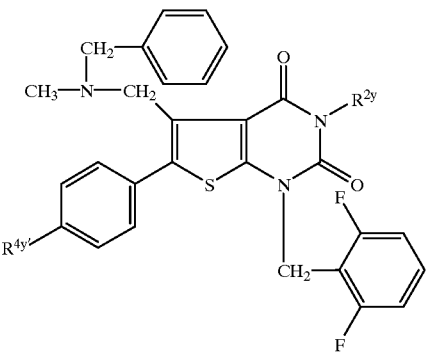

| Ref. Ex. Cpd. No. | R²ʸ | R⁴ʸ' |
|---|---|---|
| 6:30 | methoxyphenyl | methylamino |
| 6:31 | methoxyphenyl | propionylamino |

REFERENCE EXAMPLE 6:32

Starting from the compounds which are produced in Reference Example 6:26 or 6:27, compounds which are produced in accordance with the method described in Reference Example 6:31 are set forth in Table 54.

TABLE 54

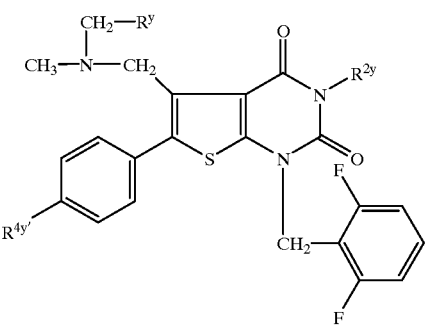

| Ref. Ex. 6:32 Cpd. No. | R²ʸ | R⁴ʸ' | Rʸ | m.p. (° C.) |
|---|---|---|---|---|
| (1) | 3-methoxyphenyl | isobutyryl-amino | phenyl | 170–173 |
| (2) | phenyl | isobutyryl-amino | phenyl | 185–190 |
| (3) | 3,5-dimethoxy-phenyl | propionyl-amino | phenyl | 218–224 |
| (4) | 3,5-dimethoxy-phenyl | isobutynyl-amino | phenyl | 240–245 |
| (5) | 3-methoxyphenyl | N-methyl-N-propionyl-amino | phenyl | 138–143 |
| (6) | 3-methoxyphenyl | N-methyl-N-isobutyryl-amino | phenyl | 146–152 |
| (7) | phenyl | propionyl-amino | phenyl | 197–202 |
| (8) | phenyl | butyryl-amino | phenyl | 169–170 |
| (9) | phenyl | benzoyl-amino | phenyl | 167–169 |
| (10) | 3-methoxyphenyl | propionyl-amino | phenyl | 170–175 |

TABLE 54-continued

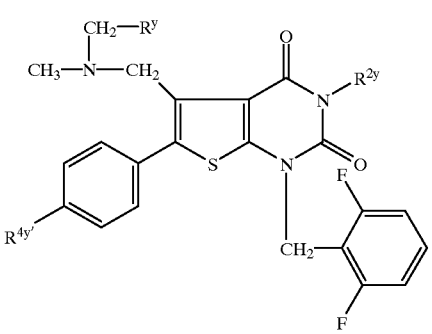

| Ref. Ex. 6:32 Cpd. No. | R²ʸ | R⁴ʸ' | Rʸ | m.p. (° C.) |
|---|---|---|---|---|
| (11) | 3-isopropoxy-phenyl | isobutyryl-amino | phenyl | |
| (12) | 3-isopropoxy-phenyl | isobutyryl-amino | 2-methylthio-phenyl | |
| (13) | 3-isopropoxy-phenyl | isobutyryl-amino | 2-pyridyl | |
| (14) | 3-methoxyphenyl | isobutyryl-amino | 3-methylthio-phenyl | |
| (15) | 3-methoxyphenyl | isobutyryl-amino | 2-pyridyl | |
| (16) | 3-isopropoxy-phenyl | propionyl-amino | phenyl | 179–181 |
| (17) | 3-ethoxyphenyl | propionyl-amino | phenyl | 164–168 |
| (18) | 3-propoxyphenyl | propionyl-amino | phenyl | 165–170 |
| (19) | 3-methoxyphenyl | ethylsul-fonylamino | phenyl | |
| (20) | 3-methoxyphenyl | trifluoro-acetylamino | phenyl | |
| (21) | 3-methoxyphenyl | isobutyryl-amino | diethylamino-methyl | |
| (22) | 3-methoxyphenyl | isobutyryl-amino | dimethylamino-methyl | |
| (23) | 3-methoxyphenyl | isobutyryl-amino | 1-pyrrolidinyl-methyl | |

REFERENCE EXAMPLE 6:33

In substantially the same procedure as described in Reference Example 6:31, using the compound which are obtained in Reference Example 6:26 or 6:27 and anhydrous trifluoro acetic acid, trifluoroacetylamino derivative are obtained. To the derivative is added halogeno derivative (e.g. propyl bromide, isopropyl bromide) in the presence of an appropriate base (e.g. potassium carbonate), and then subjecting to hydrolysis using 2N aqueous sodium hydroxide solution to give compounds set forth in Table 55.

TABLE 55

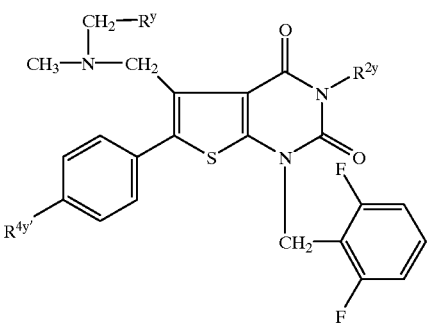

Ref. Ex.
6:33
Cpd. No.

| Cpd. No. | $R^{2y}$ | $R^{4y'}$ | $R^y$ |
|---|---|---|---|
| (1) | 3-methoxyphenyl | propylamino | phenyl |
| (2) | 3-methoxyphenyl | isopropylamino | phenyl |
| (3) | 3-isopropoxy-phenyl | propylamino | phenyl |
| (4) | 3-isopropoxy-phenyl | isopropylamino | phenyl |
| (5) | 3-isopropoxy-phenyl | propylamino | 2-methylthio-phenyl |
| (6) | 3-isopropoxy-phenyl | propylamino | 2-pyridyl |
| (7) | 3-isopropoxy-phenyl | isopropylamino | 2-methylthio-phenyl |
| (8) | 3-isopropoxy-phenyl | isopropylamino | 2-pyridyl |
| (9) | 3-methoxyphenyl | ethylamino | phenyl |
| (10) | 3-isopropoxy-phenyl | ethylamino | phenyl |
| (11) | 3-methoxyphenyl | isopropylamino | 2-methylthio-phenyl |
| (12) | 3-methoxyphenyl | isopropylamino | 2-pyridyl |
| (13) | 3-methoxyphenyl | propylamino | 2-methylthio-phenyl |
| (14) | 3-methoxyphenyl | propylamino | 2-pyridyl |
| (15) | 3-methoxyphenyl | propylamino | diethylamino-methyl |

REFERENCE EXAMPLE 6:34

Employing the compounds which are obtained in Reference Example 6:26 or 6:27, the compounds set forth in Table 56 are produced by reacting the starting compounds with isoamyl nitrite, vinyl compound and palladium compound (e.g. tetrakistri phenylphosphine palladium, dibenzylidene-acetone palladium).

TABLE 56

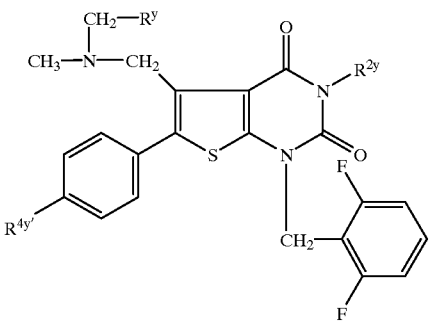

Ref. Ex.
6:34
Cpd. No.

| Cpd. No. | $R^{2y}$ | $R^{4y'}$ | $R^y$ |
|---|---|---|---|
| (1) | 3-methoxyphenyl | ethoxycarbonyl-vinyl | phenyl |
| (2) | 3-methoxyphenyl | ethoxycarbonyl-vinyl | 2-methylthio-phenyl |
| (3) | 3-methoxyphenyl | ethoxycarbonyl-vinyl | 2-pyridyl |
| (4) | 3-methoxyphenyl | propionylvinjyl | phenyl |
| (5) | 3-methoxyphenyl | propionylvinyl | 2-methylthio-phenyl |
| (6) | 3-methoxyphenyl | propionylvinyl | 2-pyridyl |
| (7) | 3-isopropoxy-phenyl | ethoxycarbonyl-vinyl | phenyl |
| (8) | 3-isopropoxy-phenyl | propionylvinyl | phenyl |
| (9) | 3-isopropoxy-phenyl | ethoxycarbonyl-vinyl | 2-methylthio-phenyl |
| (10) | 3-isopropoxy-phenyl | ethoxycarbonyl-vinyl | 2-pyridyl |
| (11) | 3-isopropoxy-phenyl | propionylvinyl | 2-methylthio-phenyl |
| (12) | 3-isopropoxy-phenyl | propionylvinyl | 2-pyridyl |
| (13) | 3-methoxyphenyl | propionylvinyl | dimethyl-aminomethyl |
| (14) | 3-methoxyphenyl | propionylvinyl | 1-pyrrolidinyl-methyl |
| (15) | 3-methoxyphenyl | propionylvinyl | diethylamino-methyl |

REFERENCE EXAMPLE 6:35

The compound 6:3(1) or 6:3(2) which are obtained in Reference Example 6:3, are treated with arylborric acid derivative, 2M aqueous sodium carbonate solution 1,2-dimethoxyethane and tetrakis(triphenylphosphine) palladium(0). To the resulting compound, N-methylbenzylamino group is introduced in accordance with the method described in Reference Example 6:18 and Reference Example 6:20 to give compounds set forth in Table 57.

TABLE 57

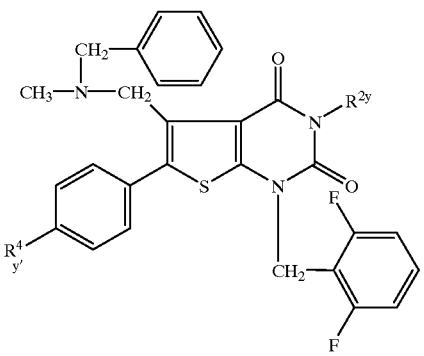

Ref. Ex. 6:35
| Cpd. No. | $R^{2y}$ | $R^{4y'}$ |
|---|---|---|
| (1) | 3-methoxyphenyl | propylaminocarbonyl |
| (2) | 3-isopropoxyphenyl | propylaminocarbonyl |
| (3) | 3-methoxyphenyl | isopropylaminocarbonyl |
| (4) | 3-isopropoxyphenyl | isopropylaminocarbonyl |
| (5) | 3-methoxyphenyl | ethylaminocarbonyl |
| (6) | 3-methoxyphenyl | N-methyl-N-propyl-aminocarbonyl |

REFERENCE EXAMPLE 6:36

From the compounds which are obtained in Reference Example 6:20, dimethylsulfide and aluminium chloride, $R^{4y}$ phenol derivative is produced.

From thus obtained compound, alkyl halide (e.g. chloro acetone) and a base (e.g. potassium carbonate), compounds set forth in Table 58 are produced.

TABLE 58

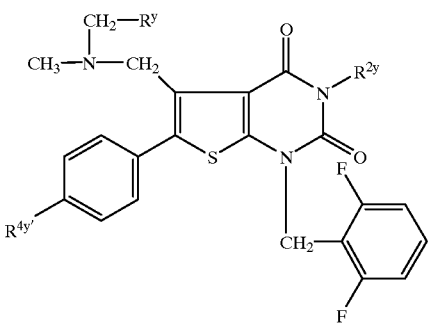

Ref. Ex. 6:36
| Cpd. No. | $R^{2y}$ | $R^{4y'}$ | $R^y$ |
|---|---|---|---|
| (1) | phenyl | acetonyloxy | phenyl |
| (2) | phenyl | acetonyloxy | 2-methylthio-phenyl |
| (3) | phenyl | acetonyloxy | 2-pyridyl |
| (4) | phenyl | acetonyloxy | diethylamino-methyl |
| (5) | phenyl | acetonyloxy | dimethylamino-methyl |
| (6) | phenyl | acetonyloxy | 1-pyrrolidinyl-methyl |
| (7) | phenyl | allyloxy | phenyl |
| (8) | phenyl | propoxy | phenyl |
| (9) | phenyl | isobutoxy | phenyl |
| (10) | phenyl | cyclopropyl methoxy | phenyl |

TABLE 58-continued

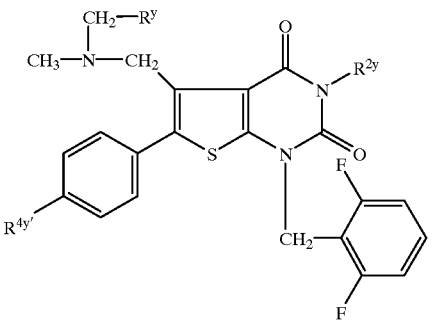

Ref. Ex. 6:36
| Cpd. No. | $R^{2y}$ | $R^{4y'}$ | $R^y$ |
|---|---|---|---|
| (11) | phenyl | allyloxy | diethylamino-methyl |
| (12) | phenyl | propoxy | diethylamino-methyl |

REFERENCE EXAMPLE 7:1

Production of (3-bromo-4-methylphenyl) aminomethylenemalonic acid diethylester:

From 3-bromo-4-methylaniline and ethoxymethylenemalonic acid diethylester, the titled compound is produced. m.p. 66–67° C.

REFERENCE EXAMPLE 7:2

Production of 4-hydroxy-6-methyl-7-bromoquinoline-3-carboxylic acid ethylester:

The compound which is obtained in Reference Example 7:1 is treated with Dowtherm under heating to give the titled compound. m.p. more than 250° C.

REFERENCE EXAMPLE 7:3

Production of 1,4-dihydro-1-(2,6-difluorobenzyl)-6-methyl-7-bromo-4-oxoquinoline-3-carboxylic acid ethylester:

From the compound which is obtained in Reference Example 7:2, potassium carbonate and 2,6-difluorobenzyl chloride, the titled compound is obtained. m.p. 199–200° C.

REFERENCE EXAMPLE 7:4

Production of 1,4-dihydro-1-(2,6-difluorobenzyl)-6-methyl-7-(4-propionylaminophenyl)-4-oxoquinoline-3-carboxylic acid ethyl ester:

From the compound which is obtained in Reference Example 7:3, 2M sodium carbonate, 4-propionylaminophenyl boric acid tetrakistriphenylphosphinepalladium(O), the titled compound is produced. m.p. 263–264° C.

REFERENCE EXAMPLE 7:5

Production of 6-bromomethyl-1,4-dihydro-1-(2,6-difluorobenzyl)-7-(4-propionylaminophenyl)-4-oxoquinoline-3-carboxylic acid ethyl ester:

From the compound which is obtained in Reference Example 7:4, N-bromosuccinimide and α,α'-azobisisobutyronitrile, the titled compound is produced. m.p. 251–253° C.

REFERENCE EXAMPLE 7:6

Production of 6-(N-benzyl-N-methylaminomethyl)-1,4-dihydro-1-(2,6-difluorobenzyl)-7-(4-propionylaminophenyl)-4-oxoquinoline-3-carboxylic acid ethyl ester hydrochloride:

The compound which is obtained in Reference Example 7:5 is reacted with ethyldiisopropylamine and N-benzyl-N-methylamine, and then with 1N hydrogen chloride in ether, whereby the titled compound is obtained. m.p. 165–168° C. (hydrochloride).

The compounds shown in the above Reference Examples 7:4 to 7:6 are listed in the following Table 59.

TABLE 59

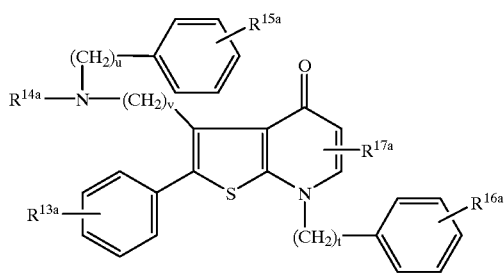

| Ref. Ex. No. | $R^{1z}$ |
|---|---|
| 7:4 | methyl |
| 7:5 | bromomethyl |
| 7:6 | N-benzyl-N-methylaminomethyl |

What we claim is:

1. A method for treating a mammal suffering from galactorrhea, hyperprolactinemic ovulation disturbances, prolactinoma, or interbrain tumor, which comprises administering an effective amount of a composition comprising a condensed cyclic compound, or a salt thereof, and a carrier, excipient or diluent therefor, to the mammal, wherein the condensed cyclic compound is a compound represented by the formula:

wherein $R^{13a}$ stands for 1 to 5 substituents and independently stands for a hydrogen atom, an alkyl group, an alkoxy group, a halogen atom or an alkanoylamino group, $R^{14a}$ stands for a hydrogen atom or an alkyl group; $R^{15a}$ stands for 1 to 5 substituents and independently stands for a hydrogen atom, a halogen atom, an alkyl group, an alkoxy group or an alkylthio group; $R^{16a}$ stands for 1 to 5 substituents and independently stands for a hydrogen atom, an alkyl group, a halogen atom or an alkoxy group; $R^{17a}$ stands for one or two substituents and independently stands for an optionally esterified or amidated carboxyl group, an alkylcarbonyl group, an arylcarbonyl group or an optionally substituted alkyl group; and each of v, t and u denote an integer of 1 to 4.

2. A method for treating a mammal suffering from galactorrhea, hyperprolactinemic ovulation disturbances, prolactinoma, or interbrain tumor, which comprises administering an effective amount of a composition comprising a condensed cyclic compound, or a salt thereof, and a carrier, excipient or diluent therefor, to the mammal, wherein the condensed cyclic compound is a compound represented by the formula:

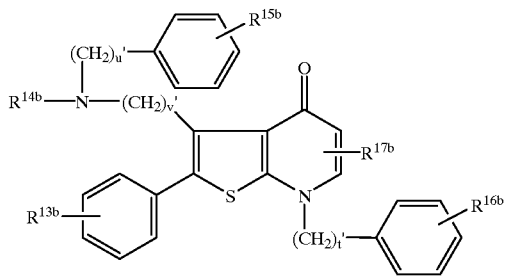

wherein $R^{13b}$ stands for 1 to 3 substituents and independently stands for hydrogen atom, a $C_{1-6}$ alkoxy group or an alkanoylamino group, $R^{14b}$ stands for a hydrogen atom or a $C_{1-6}$ alkyl group, $R^{15b}$ stands for 1 to 3 substituents and independently stands for a hydrogen atom or a halogen atom, $R^{16b}$ stands for 1 to 3 substituents and independently stands for a hydrogen atom, a halogen atom or a $C_{1-6}$ alkoxy group, $R^{17b}$ stands for 1 to 2 substituents and independently stands for a carboxyl group which may optionally be esterified or amidated or an alkylcarbonyl group, and each of v', t' and u' denote an integer of 1 to 3.

3. A method according to claim 1, wherein the condensed cyclic compound is 4,7-dihydro-3-(N-methyl-N-benzylaminomethyl)-7-(2-methoxybenzyl)-2-(4-methoxyphenyl)-4-oxo-thieno[2,3-b]pyridine-5-carboxylic acid ethyl ester or its salt.

4. A method according to claim 1, wherein the condensed cyclic compound is 2-(4-acetylaminophenyl)-4,7-dihydro-3-(N-methyl-N-benzylaminomethyl)-7-(2-methoxybenzyl)-4-oxo-thieno[2,3-b]pyridine-5-carboxylic acid ethyl ester or its salt.

5. A method according to claim 1, wherein the condensed cyclic compound is 5-n-butyryl-4,7-dihydro-3-(N-methyl-N-benzylaminomethyl)-7-(2-fluorobenzyl)-2-(4-methoxyphenyl)-4-oxo-thieno[2,3-b]pyridine or its salt.

6. A method according to claim 1, wherein the condensed cyclic compound is 5-benzoyl-4,7-dihydro-3-(N-methyl-N-benzylaminomethyl)-7-(2-fluorobenzyl)-2-(4-methoxyphenyl)-4-oxo-thieno[2,3-b]pyridine or its salt.

7. A method according to claim 1, wherein the condensed cyclic compound is 7-(2,6-difluorobenzyl)-4,7-dihydro-3-(N-methyl-N-benzylaminomethyl)-2-(4-isobutyrylaminophenyl)-5-isobutyryl-4-oxo-thieno[2,3-b]pyridine or its salt.

8. A method according to claim 1, wherein the condensed cyclic compound is 7-(2,6-difluorobenzyl)-4,7-dihydro-3-(N-methyl-N-benzylaminomethyl)-5-isobutyryl-2-(4-propionylaminophenyl)-4-oxo-thieno[2,3-b]pyridine or its salt.

9. A method according to claim 1, wherein the condensed cyclic compound is 5-benzoyl-7-(2,6-difluorobenzyl)-4,7-dihydro-3-(N-methyl-N-benzylaminomethyl)-2-(4-isobutyrylaminophenyl)-4-oxo-thieno[2,3-b]pyridine or its salt.

10. A method according to claim 1, wherein the composition further comprises a medicine selected from the group consisting of a steroidal or non-steroidal anti-androgenic agent or anti-estrogenic agent, a somatostatin-acceptor agonist and an antitumor agent.

11. A method according to claim 1, wherein the composition is administered as an agent of suppressing puerperal galactorrhea.

* * * * *